US012286618B2

(12) United States Patent
Cochu-Blachére et al.

(10) Patent No.: US 12,286,618 B2
(45) Date of Patent: Apr. 29, 2025

(54) LACTIC ACID BACTERIA

(71) Applicant: International N&H Denmark APS, Kongens Lyngby (DK)

(72) Inventors: Armelle Cochu-Blachére, Dangé-Saint-Romain (FR); Christophe Fremaux, Dangé-Saint-Romain (FR); Thomas Desfougéres, Dangé-Saint-Romain (FR); Anaïs Jedrzejowski, Dangé-Saint-Romain (FR)

(73) Assignee: International N&H Denmark Aps, Kongens Lyngby (DK)

( * ) Notice: Subject to any disclaimer, the term of this patent is extended or adjusted under 35 U.S.C. 154(b) by 682 days.

(21) Appl. No.: 17/415,964

(22) PCT Filed: Dec. 21, 2018

(86) PCT No.: PCT/EP2018/086681
§ 371 (c)(1),
(2) Date: Jun. 18, 2021

(87) PCT Pub. No.: WO2019/197051
PCT Pub. Date: Oct. 17, 2019

(65) Prior Publication Data
US 2022/0017855 A1 Jan. 20, 2022

(51) Int. Cl.
*C12N 1/20* (2006.01)
*A23C 9/123* (2006.01)
*C07K 14/315* (2006.01)
*C12N 9/12* (2006.01)

(52) U.S. Cl.
CPC .............. *C12N 1/20* (2013.01); *A23C 9/1238* (2013.01); *C07K 14/315* (2013.01); *C12N 9/1205* (2013.01); *C12Y 207/01002* (2013.01); *A23V 2400/249* (2023.08)

(58) Field of Classification Search
CPC ........ C12N 1/20; C12N 9/1205; C12N 1/205; C12N 15/01; A23C 9/1238; C07K 14/315; C12Y 207/01002; A23V 2400/249; C12R 2001/46
See application file for complete search history.

(56) References Cited

U.S. PATENT DOCUMENTS

| 11,044,920 B2 * | 6/2021 | Johansen ................. C12N 1/20 |
| 11,725,199 B2 * | 8/2023 | Cochu-Blachere ........................ A23C 9/1238 435/253.4 |
| 2015/0086675 A1 * | 3/2015 | Johansen ................. C12N 1/20 506/10 |

FOREIGN PATENT DOCUMENTS

| WO | 2011026863 A1 | 3/2011 | |
| WO | WO-2013160413 A1 * | 10/2013 | ......... A23C 19/0323 |
| WO | 2015014940 A1 | 2/2015 | |
| WO | 2015140211 A1 | 9/2015 | |
| WO | 2015193459 A1 | 12/2015 | |
| WO | 2017103051 A1 | 6/2017 | |
| WO | 2017167660 A1 | 10/2017 | |

OTHER PUBLICATIONS van den Bogaard, et al. "Control of lactose transport, β-galactosidase activity, and glycolysis by CcpA in Streptococcus thermophilus: evidence for carbon catabolite repression by a non-phosphoenolpyruvate-dependent phosphotransferase system sugar." Journal of bacteriology 182.21 (2000): 5982-5989 (Year: 2000).*
Cochu, et al. "Genetic and biochemical characterization of the phosphoenolpyruvate: glucose/mannose phosphotransferase system of Streptococcus thermophilus." Applied and environmental microbiology 69.9 (2003): 5423-5432. (Year: 2003).*
De Vin, et al. "Molecular and biochemical analysis of the galactose phenotype of dairy Streptococcus thermophilus strains reveals four different fermentation profiles." Applied and Environmental Microbiology 71.7 (2005): 3659-3667. (Year: 2005).*
Pachekrepapol et al., Characterization of the chemical structures and physical properties of exopolysaccharides produced by various Streptococcus thermophilusstrains, Journal of Dairy Science, vol. 100, No. 5, May 2017, 3424-3435.
Pool et al., Natural sweetening of food products by engineering Lactococcus lactis for glucose production, Metabolic Engineering, vol. 8, No. 5, Sep. 2006, 456-464.
Porter et al., Purification and Kinetic Characterization of a Specific Glucokinase from Streptococcus Mutans OMZ70 Cells, Biochimica et Biophysica Acta, 709, Aug. 1982, 178-186.
Sørensen et al., Enhancing the Sweetness of Yoghurt through Metabolic Remodeling of Carbohydrate Metabolism In Streptococcus thermophilus and Lactobacillus delbrueckii subsp. bulgari cus, Applied and Environmental Microbiology, vol. 82, No. 12, Apr. 2016, 3683-3692.
Thompson et al., Lactose Metabolism in Streptococcus-Lactis Studies With a Mutant Lacking Glucokinase EC-2.7.1.2 and Mannose-Phosphotransferase Activities, Journal of Bacteriology, vol. 162, No. 1, Apr. 1985, 217-223.
Van Den Bogaard et al., Control of Lactose Transport, β-Galactosidase Activity, Glycolysis by CcpA in Streptococcus thermophilus: Evidence for Carbon Catabolite Repression by a Non-Phosphoenolypyruvate-Dependent Phosphotransferase System Sugar, Journal of Bacteriology, Nov. 2000, 5982-5989.
International Search Report issued in PCT/EP2018/086681, dated Aug. 22, 2019, 6 pgs.

* cited by examiner

*Primary Examiner* — Aaron J Kosar
*Assistant Examiner* — Andrew T Moehlman

(57) ABSTRACT

The invention relates to a lactose-positive, galactose-negative, Streptococcus thermophilus strain carrying a mutation in 2 or 3 genes selected from the group consisting of 1) a gene encoding a protein of the mannose-glucose-specific PTS and a glcK gene, 2) a gene encoding a protein of the mannose-glucose-specific PTS and a ccpA gene, and 3) a gene encoding a protein of the mannose-glucose-specific PTS, a glcK gene and a ccpA gene, wherein said strain, when used to ferment milk, provides a low lactose fermented milk and/or a fermented milk not undergoing acidification when stored at fermentation temperature.

15 Claims, 10 Drawing Sheets
Specification includes a Sequence Listing.

```
DGCC7710         MSKKLLGIDLGGTTVKFGILTADGEVQEKWAIETNTFENGSHIVPDIVESLKHRLELYG
DSM32587         MSKKLLGIDLGGTTVKFGILTADGEVQEKWAIETNTFENGSHIVPDIVESLKHRLELYG
ST1m-glcK0-gal+  MSKKLLGIDLGGTTVKFGILTADGEVQEKWAIETNTFENGSHIVPDIVESLKHRLELYG LTAEDFIGIGMGSPGAVDRENKTVTGAFNLNWAETQEVGSVIEKELGIPFAIDNDANVAALGERWVGAGAN
LTAEDFIGIGMGSPGAVDRENKTVTGAFNLNWAETQEVGSVIEKELGIPFAIDNDANVAALGERWVGAGAN
LTAEDFIGIGMG[P]PGAVDRENKTVTGAFNLNWAETQEVGSVIEKELGIPFAIDNDANVAALGERWVGAGAN NRNVVFITLGTGVGGGVIADGNLIHGVAGAGGEIGHIIVEPDTGFECTCGNKGCLETVASATGIVRVAHH
NRNVVFITLGTGVGGGVIADGNLIHGVAGAGGEIGHIIVEPDTGFECTCGNKGCLETVASATGIVRVAHH
NRNVVFITLGTGVGGGVIADGNLIHGVAGAGGEIGHIIVEPDTGFECTCGNKGCLETVASATGIVRVAHH LAEKYEGNSSIKAAVDNGEFVTSKDIIVAATEGDKFADSIVDKVSKYLGLATANISNILNPDSVVIGGGV
LAEKYEGNSSIKAAVDNGEFVTSKDIIVAATEGDKFADSIVDKVSKYLGLATANISNILNPDSVVIGGGV
LAEKYEGNSSIKAAVDNGEFVTSKDIIVAATEGDKFADSIVDKVSKYLGLATANISNILNPDSVVIGGGV SAAGEFLRSRVEGYFTRYAFPQVRRTTKVKLAELGNDAGIIGAASLAYSIDK
SAAG[K]FLRSRVEGYFTRYAFPQVRRTTKVKLAELGNDAGIIGAASLAYSIDK
SAAGEFLRSRVEGYFTRYAFPQVRRTTKVKLAELGNDAGIIGAASLAYSIDK
```

Fig 1.

```
                          SEQUENCE LISTING

<160> NUMBER OF SEQ ID NOS: 222

<210> SEQ ID NO 1
<211> LENGTH: 969
<212> TYPE: DNA
<213> ORGANISM: Streptococcus thermophilus

<400> SEQUENCE: 1
atgagtaaga aactcttagg tattgacctt ggtggaacaa ctgttaagtt tggtattttg      60
actgcagatg gtgaagttca agaaaaatgg gctattgaaa caaatacgtt tgaaaatggt     120
agccacattg ttcctgacat tgtagaatct ttgaaacacc gtttggaatt gtatggactt     180
actgctgaag attttattgg aattggtatg ggatctccag gtgcagttga ccgagaaaat     240
aaaacagtaa cgggtgcctt taacttgaac tgggcagaaa ctcaagaagt tggctctgtt     300
attgaaaaag aacttggtat tccattcgct attgataatg atgctaatgt ggctgcactg     360
ggtgaacgtt gggttggtgc tggtgctaac aatcggaatg ttgtctttat aacattgggt     420
acaggtgttg gtggcggtgt tatcgctgat ggtaacttaa ttcatggtgt tgccggtgct     480
ggtggggaaa ttggtcacat tattgttgaa cctgacacag gatttgagtg tacttgcgga     540 aacaagggt gtctggaaac tgtagcttca gcaacaggta ttgtacgtgt agcacatcat     600
ttggcagaaa aatacgaagg aaactcttct attaaagctc tgtagacaa tggtgagttt     660 gtgacaagta aagatattat cgtagctgct actgaaggtg ataagtttgc tgacagcatt     720
gttgataaag tctctaaata cctcggactt gcaacagcaa acatctcaaa cattcttaac     780
ccagattctg tcgttatcgg tggtggtgtt tctgccgcag gagaattctt gcgtagtcgt     840
gttgaaggat actttacacg ttatgcattc ccacaagttc gccgtacaac aaaagtgaaa     900
ttagcggagc ttggaaatga tgcaggaatc attggagctg ctagtcttgc ttatagtatt     960
gacaaataa                                                             969

<210> SEQ ID NO 2
<211> LENGTH: 322
<212> TYPE: PRT
<213> ORGANISM: Streptococcus thermophilus

<400> SEQUENCE: 2

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
```

|       |       |       |       |       |       | 100   |       |       |       |       | 105   |       |       |       |       | 110   |       |
|-------|-------|-------|-------|-------|-------|-------|-------|-------|-------|-------|-------|-------|-------|-------|-------|-------|-------|

Asn Asp Ala Asn Val Ala Ala Leu Gly Glu Arg Trp Val Gly Ala Gly
            115                   120                   125

Ala Asn Arg Asn Val Val Phe Ile Thr Leu Gly Thr Gly Val Gly
130                   135                   140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
             165                   170                 175

Cys Thr Cys Gly Asn Lys Gly Cys Leu Glu Thr Val Ala Ser Ala Thr
         180                   185                 190

Gly Ile Val Arg Val Ala His His Leu Ala Glu Lys Tyr Glu Gly Asn
     195                 200                 205

Ser Ser Ile Lys Ala Ala Val Asp Asn Gly Glu Phe Val Thr Ser Lys
   210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
             245                   250                 255

Asn Ile Leu Asn Pro Asp Ser Val Val Ile Gly Gly Val Ser Ala
         260                   265                 270

Ala Gly Glu Phe Leu Arg Ser Arg Val Glu Gly Tyr Phe Thr Arg Tyr
   275                 280                 285

Ala Phe Pro Gln Val Arg Arg Thr Thr Lys Val Lys Leu Ala Glu Leu
290                 295                 300

Gly Asn Asp Ala Gly Ile Ile Gly Ala Ala Ser Leu Ala Tyr Ser Ile
305                 310                 315                 320

Asp Lys

<210> SEQ ID NO 3
<211> LENGTH: 969
<212> TYPE: DNA
<213> ORGANISM: Streptococcus thermophilus

<400> SEQUENCE: 3

```
atgagtaaga aactcttagg tattgacctt ggtggaacaa ctgttaagtt tggtattttg     60
actgcagatg tgaagttca agaaaaatgg gctattgaaa caaatacgtt tgaaaatggt    120
agccacattg ttcctgacat tgtagaatct ttgaaacacc gtttggaatt gtatggactt    180
actgctgaag attttattgg aattggtatg ggatctccag gtgcagttga ccagaaaaat    240
aaaacagtaa cgggtgcctt taacttgaac tgggcagaaa ctcaagaagt tggctctgtt    300
attgaaaaag aacttggtat tccattcgct attgataatg atgctaatgt ggctgcactg    360
ggtgaacgtt gggttggtgc tggtgctaac aatcggaatg ttgtctttgt aacattgggt    420
acaggtgttg gtgcggttgt tatcgctgat ggtaacttaa ttcatggtgt tgccggtgct    480
ggtggggaaa ttggtcacat tattgttgaa cctgacacag gatttgagtg tacttgcgga    540
aacaagggt gtctggaaac tgtagcttca gcaacaggta ttgtacgtgt agcacatcat    600
ttggcagaaa aatacgaagg aaactcttct attaaagctg ctgtagacaa tggtgagttt    660
gtgacaagta agatattat cgtagctgct actgaaggtg ataagtttgc tgacagcatt    720
gttgataaag tctctaaata cctcggactt gcaacagcaa acatctcaaa cattcttaac    780
ccagattctg tcgttatcgg tggtggtgtt tctgccgcag agaattcttg cgtagtcgt    840
```

```
gttgaaggat actttacacg ttatgcattc ccacaagttc gccgtacaac aaaagtgaaa      900
ttagcggagc ttggaaatga tgcaggaatc attggagctg ctagtcttgc ttatagtatt      960
gacaaataa                                                              969
```

<210> SEQ ID NO 4
<211> LENGTH: 322
<212> TYPE: PRT
<213> ORGANISM: Streptococcus thermophilus

<400> SEQUENCE: 4

```
Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
                20                  25                  30

Glu Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Asp
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Val Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Ile Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys
```

<210> SEQ ID NO 5
<211> LENGTH: 969

```
<212> TYPE: DNA
<213> ORGANISM: Streptococcus thermophilus

<400> SEQUENCE: 5
atgagtaaga aactcttagg tattgacctt ggtggaacaa ctgttaagtt tggtattttg      60
aatgcagatg gtgaagttca agaaaaatgg gctattggaa caaatacgtt tgaaaatggt     120
agccacattg ttcctgacat tgtagaatct ttgaaacacc gtttggaatt gtatggactt     180
actgctgaag attttattgg aattggtatg ggatctccag gtgcagttga ccagaaaaat     240
aaaacagtaa cgggtgcctt taacttgaac tgggcagaaa ctcaagaagt tggctctgtt     300
attgaaaaag aacttggtat tccattcgct attgataatg atgctaatgt ggctgcactg     360
ggtgaacgtt gggttggtgc tggtgctaac aatcggaatg ttgtctttgt aacattgggt     420
acaggtgttg gtggcggtgt catcgttgat ggtaaattaa ttcatggtgt tgccggtgct     480
ggtggggaaa ttggtcacat tattgttgaa cctgacacag gatttgagtg tacttgcgga     540
aacaaggggt gtctggaaac tgtagcttca gcaacaggta ttgtacgtat agcacatcat     600
ttggcagaaa atacgaagg aaactcttct attaaagctg ctgtagacaa tggtgagttt     660
gtgacaagta aagatattct cgtagctgct actgaaggtg ataagtttgc tgacagcatt     720
gttgataaag tctctaaata cctcggactt gcaacagcaa acatctcaaa cattcttaac     780
ccagattctg tcgttatcgg tggtggtgtt tctgccgcag agaattctt gcgtagtcgt     840
gttgaaggat actttacacg ttatgcattc ccacaagttc gccgtacaac aaaagtgaaa     900
ttagcggagc ttggaaatga tgcaggaatc attggagccg ctagtcttgc ttatagtatt     960
gacaaataa                                                              969

<210> SEQ ID NO 6
<211> LENGTH: 322
<212> TYPE: PRT
<213> ORGANISM: Streptococcus thermophilus

<400> SEQUENCE: 6

Met Ser Lys Lys Leu Leu Gly Ile Asp Leu Gly Gly Thr Thr Val Lys
1               5                   10                  15

Phe Gly Ile Leu Asn Ala Asp Gly Glu Val Gln Glu Lys Trp Ala Ile
                20                  25                  30

Gly Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Asp
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Val Thr Leu Gly Thr Gly Val Gly
    130                 135                 140

Gly Gly Val Ile Val Asp Gly Lys Leu Ile His Gly Val Ala Gly Ala
145                 150                 155                 160

Gly Gly Glu Ile Gly His Ile Ile Val Glu Pro Asp Thr Gly Phe Glu
                165                 170                 175
```

```
Cys Thr Cys Gly Asn Lys Gly Cys Leu Glu Thr Val Ala Ser Ala Thr
            180                 185                 190

Gly Ile Val Arg Ile Ala His His Leu Ala Glu Lys Tyr Glu Gly Asn
        195                 200                 205

Ser Ser Ile Lys Ala Ala Val Asp Asn Gly Glu Phe Val Thr Ser Lys
210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
290                 295                 300

Gly Asn Asp Ala Gly Ile Ile Gly Ala Ala Ser Leu Ala Tyr Ser Ile
305                 310                 315                 320

Asp Lys
```

<210> SEQ ID NO 7
<211> LENGTH: 969
<212> TYPE: DNA
<213> ORGANISM: Streptococcus thermophilus

<400> SEQUENCE: 7

```
atgagtaaga aactcttagg tattgacctt ggtggaacaa ctgttaagtt tggtattttg    60
actgcagatg tgaagttca agaaaaatgg gctattgaaa caaatacgtt tgaaaatggt   120
agccacattg ttcctgacat tgtagaatct ttgaaacacc gtttggaatt gtatggactt   180
actgctgaag cttttattgg aattggtatg ggatctccag gtgcagttga ccagaaaaat   240
aaaacagtaa cgggtgcctt taacttgaac tgggcagaaa ctcaagaagt tggctctgtt   300
attgaaaaag aacttggtat tccattcgct attgataatg atgctaatgt agctgcactg   360
ggtgaacgtt gggttggtgc tggtgctaac aatcggaatg ttgtctttat aacattgggt   420
acaggtgttg gtggcggtgt tatcgctgat ggtaacttaa ttcatggtgt tgccggtgct   480
ggtgggaaaa ttggtcacat tattgttgaa cctgacacag gatttgagtg tacttgcgga   540
aacaagggt gtctggaaac tgtagcttca gcaacaggta ttgtacgtgt agcacatcat   600
ttggcagaaa atacgaagg aaactcttct attaaagctg ctgtagacaa tggtgagttt   660
gtgacaagta agatattat cgtagctgct actgaaggtg ataagtttgc tgacagcatt   720
gttgataaag tctctaaata cctcggactt gcaacagcaa acatctcaaa cattcttaac   780
ccagattctg tcgttatcgg tggtggtgtt tctgccgcag agaattctt gcgtagtcgt   840
gttgaaggat actttacacg ttatgcattc ccacaagttc gccgtacaac aaaagtgaaa   900
ttagcggagc ttggaaatga tgcaggaatc attggagctg ctagtcttgc ttatagtatt   960
gacaaataa                                                         969
```

<210> SEQ ID NO 8
<211> LENGTH: 322
<212> TYPE: PRT
<213> ORGANISM: Streptococcus thermophilus

<400> SEQUENCE: 8

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
                20                  25                  30

Glu Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Ala
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Ile Thr Leu Gly Thr Gly Val Gly
130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
290                 295                 300

Gly Asn Asp Ala Gly Ile Gly Ala Ala Ser Leu Ala Tyr Ser Ile
305                 310                 315                 320

Asp Lys

<210> SEQ ID NO 9
<211> LENGTH: 969
<212> TYPE: DNA
<213> ORGANISM: Streptococcus thermophilus

<400> SEQUENCE: 9
atgagtaaga aactcttagg tattgacctt ggtggaacaa ctgttaagtt tggtattttg        60
actgcagatg gtgaagttca agaaaaatgg ctattgaaa caaatacgtt tgaaaatggt       120
agccacattg ttcctgacat tgtagaatct ttgaaacacc gtttggaatt gtatggactt       180
actgctgaag attttattgg aattggtatg ggatctccag gtgcagttga ccgagaaaat       240

-continued

```
aaaacagtaa cgggtgcctt taacttgaac tgggcagaaa ctcaagaagt tggctctgtt      300
attgaaaaag aacttggtat tccattcgct attgataatg atgctaatgt ggctgcactg      360
ggtgaacgtt gggttggtgc tggtgctaac aatcggaatg ttgtctttat aacattgggt      420
acaggtgttg gtggcggtgt tatcgctgat ggtaacttaa ttcatggtgt tgccggtgct      480
ggtggggaaa ttggtcacat tattgttgaa cctgacacag gatttgagtg tacttgcgga      540
aacaagggtg tctggaaac tgcagcttca gcaacaggta ttgtacgtgt agcacatcat      600
ttggcagaaa aatacgaagg aaactcttct attaaagctg ctgtagacaa tggtgagttt      660
gtgacaagta aagatattat cgtagctgct actgaaggtg ataagtttgc tgacagcatt      720
gttgataaag tctctaaata cctcggactt gcaacagcaa acatctcaaa cattcttaac      780
ccagattctg tcgttatcgg tggtggtgtt tctgccgcag gagaattctt gcgtagtcgt      840
gttgaaggat actttacacg ttatgcattc ccacaagttc gccgtacaac aaaagtgaaa      900
ttagcggagc ttggaaatga tgcaggaatc attggagctg ctagtcttgc ttatagtatt      960
gacaaataa                                                               969
```

<210> SEQ ID NO 10
<211> LENGTH: 322
<212> TYPE: PRT
<213> ORGANISM: Streptococcus thermophilus

<400> SEQUENCE: 10

```
Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Ile Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Ala Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240
```

Val Asp Lys Val Ser Lys Tyr Leu Gly Leu Ala Thr Ala Asn Ile Ser
            245                 250                 255

Asn Ile Leu Asn Pro Asp Ser Val Val Ile Gly Gly Val Ser Ala
        260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
        290                 295                 300

Gly Asn Asp Ala Gly Ile Ile Gly Ala Ala Ser Leu Ala Tyr Ser Ile
305                 310                 315                 320

Asp Lys

<210> SEQ ID NO 11
<211> LENGTH: 969
<212> TYPE: DNA
<213> ORGANISM: Streptococcus thermophilus

<400> SEQUENCE: 11

```
atgagtaaga aactcttagg tattgacctt ggtggaacaa ctgttaagtt tggtattttg      60
actgcagatg gtgaagttca agaaaaatgg gctattgaaa caaatacgtt tgaaaatggt     120
agccacattg ttcctgacat tgtagaatct ttgaaacacc gtttggaatt gtatggactt     180
actgctgaag attttattgg aattggtatg ggatctccag gtgcagttga ccgagaaaat     240
aaaacagtaa cgggtgcctt taacttgaac tgggcagaaa ctcaagaagt tggctctgtt     300
attgaaaaag aacttggtat tccattcgct attgataatg atgctaatgt agctgcactg     360
ggtgaacgtt gggttggtgc tggtgctaac aatcggaatg ttgtctttat aacattgggt     420
acaggtgttg gtggcggtgt tatcgctgat ggtaacttaa ttcatggtgt tgccggtgct     480
ggtgggggaaa ttggtcacat tattgttgaa cctgacacag gatttgagtg tacttgcgga     540
aacaatgggt gtctggaaac tgtagcttca gcaacaggta ttgtacgtgt aacacatcat     600
ttggcagaaa aatacgaagg aaactcttct attaaagctg ctgtagacaa tggtgagttt     660
gtgacaagta aagatattat cgtagctgct actgaaggtg ataagtttgc tgacagcatt     720
gttgataaag tctctaaata cctcggactt gcaacagcaa acatctcaaa cattcttaac     780
ccagattctg tcgttatcgg tggtggtgtt tctgccgcag agaattctt gcgtagtcgt     840
gttgaaggat actttacacg ttatgcattc ccacaagttc gccgtacaac aaaagtgaaa     900
ttagcggagc ttggaaatga tgcaggaatc attggagctg ctagtcttgc ttatagtatt     960
gacaaataa                                                             969
```

<210> SEQ ID NO 12
<211> LENGTH: 322
<212> TYPE: PRT
<213> ORGANISM: Streptococcus thermophilus

<400> SEQUENCE: 12

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
 65                  70                  75                  80

Lys Thr Val Thr Gly Ala Phe Asn Leu Asn Trp Ala Glu Thr Gln Glu
                 85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Ile Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Asn Gly Cys Leu Glu Thr Val Ala Ser Ala Thr
            180                 185                 190

Gly Ile Val Arg Val Thr His His Leu Ala Glu Lys Tyr Gly Asn
        195                 200                 205

Ser Ser Ile Lys Ala Ala Val Asp Asn Gly Glu Phe Val Thr Ser Lys
210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Ile Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys

<210> SEQ ID NO 13
<211> LENGTH: 969
<212> TYPE: DNA
<213> ORGANISM: Streptococcus thermophilus

<400> SEQUENCE: 13
atgagtaaga aactcttagg tattgacctt ggtggaacaa ctgttaagtt tggtattttg      60
actgcagatg gtgaagttca agaaaaatgg gctattgaaa caaatacgtt tgaaaatggt     120
agccacattg ttcctgacat tgtagactct ttgaaacacc gtttggaatt gtatggactt     180
actgctgaag attttattgg aattggtatg ggatctccag gtgcagttga ccgagaaaat     240
aaaacagtaa cgggtgcctt taacttgaac tgggcagaaa ctcaagaagt tggctctgtt     300
attgaaaaag aacttggtat tccattcgct attgataatg atgctaatgt ggctgcactg     360
ggtgaacgtt gggttggtgc tggtgctaac aatcggaatg ttgtctttgt aacattgggt     420
acaggtgttg gtggcggtgt tatcgctgat ggtaacttaa ttcatggtgt tgccggtgct     480
ggtggggaaa ttggtcacat tattgttgaa cctgacacag gatttgagtg tacttgcgga     540
aacaaggggt gtctggaaac tgtagcttca gcaacaggta ttgtacgtgt agcacatcat     600
ttggcagaaa aatacgaagg aaactcttct attaaagctg ctgtagacaa tggtgagctt     660

```
gtgacaagta aagatattct cgtagctgct actgaaggtg ataagtttgc tgacagcatt    720
gttgataaag tctctaaata cctcggactt gcaatagcaa acatctcaaa cattcttaac    780
ccagattctg tcgttatcgg tggtggtgtt tctgccgcag agaattcttg cgtagtcgt     840 gttgaaggat actttacacg ttatgcattc ccacaagttc gccgtacaac aaaagtgaaa    900
ttagcggagc ttggaaatga tgcaggaatc attggagctg ctagtcttgc ttatagtatt    960
gacaaataa                                                            969
```

<210> SEQ ID NO 14
<211> LENGTH: 322
<212> TYPE: PRT
<213> ORGANISM: Streptococcus thermophilus

<400> SEQUENCE: 14

```
Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Asp Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Val Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Leu Val Thr Ser Lys
    210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Ile Ala Asn Ile Ser
                245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
```

<210> SEQ ID NO 15
<211> LENGTH: 969
<212> TYPE: DNA
<213> ORGANISM: Streptococcus thermophilus

<400> SEQUENCE: 15

```
atgagtaaga aactcttagg tattgacctt ggtggaacaa ctgttaagtt tggtattttg      60
aatgcagatg gtgaagttca agaaaaatgg gctattggaa caaatacgtt tgaaaatggt     120
agccacattg ttcctgacat tgtagaatct ttgaaacacc gtttggaatt gtatggactt     180
actgctgaag attttattgg aattggtatg ggatctccag gtgcagttga ccgagaaaat     240
aaaacagtaa cgggtgcctt taacttgaac tgggcagaaa ctcaagaagt tggctctgtt     300
attgaaaaag aacttggtat tccattcgct attgataatg atgctaatgt ggctgcactg     360
ggtgaacgtt gggttggtgc tggtgctaac aatcggaatg ttgtctttgt aacattgggt     420
acaggtgttg gtgcggtgt catcgttgat ggtaaattaa ttcatggtgt tgccggtgct     480
ggtgggaaa ttggtcacat tattgttgaa cctgacacag gatttgagtg tacttgcgga     540
aacaaggggt gtctggaaac tgtagcttca gcaacaggta ttgtacgtat agcacatcat     600
ttggcagaaa atacgaagg aaactcttct attaaagctg ctgtagacaa tggtgagttt     660
gtgacaagta aagatattat cgtagctgct actgaaggtg ataagtttgc tgacagcatt     720
gttgataaag tctctaaata cctcggactt gcaacagcaa acatctcaaa cattcttaac     780
ccagattctg tcgttatcgg tggtggtgtt tctgccgcag agaattcttc gcgtagtcgt     840
gttgaaggat actttacacg ttatgcattc ccacaagttc gccgtacaac aaaagtgaaa     900
ttagcggagc ttggaaatga tgcaggaatc attggagctg ctagtcttgc ttatagtatt     960
gacaaataa                                                             969
```

<210> SEQ ID NO 16
<211> LENGTH: 322
<212> TYPE: PRT
<213> ORGANISM: Streptococcus thermophilus

<400> SEQUENCE: 16

Met Ser Lys Lys Leu Leu Gly Ile Asp Leu Gly Gly Thr Thr Val Lys
1               5                   10                  15

Phe Gly Ile Leu Asn Ala Asp Gly Glu Val Gln Glu Lys Trp Ala Ile
            20                  25                  30

Gly Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Val Thr Leu Gly Thr Gly Val Gly

|   |   |   |   |   | 130 |   |   |   |   | 135 |   |   |   |   | 140 |   |   |
|---|---|---|---|---|---|---|---|---|---|---|---|---|---|---|---|---|---|

Gly Gly Val Ile Val Asp Gly Lys Leu Ile His Gly Val Ala Gly Ala
145                  150                  155                  160

Gly Gly Glu Ile Gly His Ile Ile Val Glu Pro Asp Thr Gly Phe Glu
                165                  170                  175

Cys Thr Cys Gly Asn Lys Gly Cys Leu Glu Thr Val Ala Ser Ala Thr
                180                  185                  190

Gly Ile Val Arg Ile Ala His His Leu Ala Glu Lys Tyr Glu Gly Asn
                195                  200                  205

Ser Ser Ile Lys Ala Ala Val Asp Asn Gly Glu Phe Val Thr Ser Lys
210                  215                  220

Asp Ile Ile Val Ala Ala Thr Glu Gly Asp Lys Phe Ala Asp Ser Ile
225                  230                  235                  240

Val Asp Lys Val Ser Lys Tyr Leu Gly Leu Ala Thr Ala Asn Ile Ser
                245                  250                  255

Asn Ile Leu Asn Pro Asp Ser Val Val Ile Gly Gly Gly Val Ser Ala
                260                  265                  270

Ala Gly Glu Phe Leu Arg Ser Arg Val Glu Gly Tyr Phe Thr Arg Tyr
            275                  280                  285

Ala Phe Pro Gln Val Arg Arg Thr Thr Lys Val Lys Leu Ala Glu Leu
290                  295                  300

Gly Asn Asp Ala Gly Ile Ile Gly Ala Ala Ser Leu Ala Tyr Ser Ile
305                  310                  315                  320

Asp Lys

<210> SEQ ID NO 17
<211> LENGTH: 969
<212> TYPE: DNA
<213> ORGANISM: Streptococcus thermophilus

<400> SEQUENCE: 17

```
atgagtaaga aactcttagg tattgacctt ggtggaacaa ctgttaagtt tggtattttg      60
actgcagatg gtgaagttca agaaaaatgg ctattgaaa caaatacgtt tgataatggt     120
agccacattg ttcctgacat tgtagaatct ttgaaacacc gtttggaatt gtatggactt     180
actgctgaag attttattgg aattggtatg ggatctccag gtgcagttga ccgagaaaat     240
aaaacagtaa cgggtgcctt taacttgaac tgggcagaaa ctcaagaagt tggttctgtt     300
attgaaaaag aacttggtat tccattcgct attgataatg atgctaatgt ggctgcactg     360
ggtgaacgtt gggttggtgc tggtgctaac agtcgggatg ttgtctttgt aacattgggt     420
acaggtgttg gtggcggtgt tatcgctgat ggtaacttaa ttcatggtgt tgccggtgct     480
ggtgggaaa ttggtcacat tattgttgaa cctgacacag gatttgagtg tacttgcgga     540
aacaagggt gtctggaaac tgtagcttca gcaacaggta ttgtacgtgt agcacatcat     600
ttggcagaaa aatacgaagg aaactcttct attaaagctg ctgtagacaa tggtgagctt     660
gtgacaagta aagatattct cgtagctgct actgaaggtg ataagtttgc tgacagcatt     720
gttgataaag tctctaaata cctcggactt gcaatagcaa acatctcaaa cattcttaac     780
ccagattctg ttgttatcgg tggtggtgtt tctgccgcag agaattctt gcgtagtcgt     840
gttgaaggat acttacacg ttatgcattc ccacaagttc gccgtacaac aaaagtgaaa     900
ttagcggagc ttggaaatga tgcaggaatc attggagctg ctagtcttgc ttatagtatt     960
gacaaataa                                                            969
```

<210> SEQ ID NO 18
<211> LENGTH: 322
<212> TYPE: PRT
<213> ORGANISM: Streptococcus thermophilus

<400> SEQUENCE: 18

```
Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Asp Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Ser Arg Asp Val Val Phe Val Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Leu Val Thr Ser Lys
    210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Ile Ala Asn Ile Ser
                245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys
```

<210> SEQ ID NO 19
<211> LENGTH: 969
<212> TYPE: DNA
<213> ORGANISM: Streptococcus thermophilus

<400> SEQUENCE: 19
atgagtaaga aactcttagg tattgacctt ggtggaacaa ctgttaagtt tggtattttg    60

```
actgcagatg gtgaagttca agaaaaatgg gctattgaaa caaatacgtt tgataatggt    120
agccacattg ttcctgacat gtagaatct ttgaaacacc gtttggaatt gtatggactt    180
actgctgaag attttattgg aattggtatg ggatctccag gtgcagttga ccgagaaaat    240
aaaacagtaa cggtgcctt taacttgaac tgggcagaaa ctcaagaagt tggctctat     300 attgaaaaag aacttggtat tccattcgct attgataatg atgctaatgt ggctgcactg    360
ggtgaacgtt gggttggtgc tggtgctaac aatcgggatt tgtctttgt aacattgggt     420 acaggtgttg gtggcggtgt tatcgctgat ggtaacttaa ttcatggtgt tgccggtgct    480 ggtgggaa ttggtcacat tattgttgaa cctgacacag gatttgagtg tacttgcgga     540 aacaagggt gtctggaaac tgtagcttca gcaacaggta ttgtacgtgt agcacatcat    600
ttggcagaaa atacgaagg aaactcttct attaaagctg ctgtagacaa tggtgagctt    660
gtgacaagta aagatattct cgtagctgct actgaaggtg ataagtttgc tgacagcatt    720
gttgataaag tctctaaata cctcggactt gcaatagcaa acatctcaaa cattcttaac    780
ccagattctg tcattatcgg tggtggtgtt tctgccgcag gagaattctt gcgtagtcgt    840
gttgaaggat actttacacg ttatgcattc ccacaagttc gccgtacaac aaaagtgaaa    900
ttagcggagc ttggaaatga tgcaggaatc attggagctg ctagtcttgc ttatagtatt    960
gacaaataa                                                           969
```

<210> SEQ ID NO 20
<211> LENGTH: 322
<212> TYPE: PRT
<213> ORGANISM: Streptococcus thermophilus

<400> SEQUENCE: 20

```
Met Ser Lys Lys Leu Leu Gly Ile Asp Leu Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Asp Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Ile Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asp Val Val Phe Val Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205
```

Ser Ser Ile Lys Ala Ala Val Asp Asn Gly Glu Leu Val Thr Ser Lys
    210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Ile Ala Asn Ile Ser
                245                 250                 255

Asn Ile Leu Asn Pro Asp Ser Val Ile Ile Gly Gly Val Ser Ala
                260                 265                 270

Ala Gly Glu Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
            290                 295                 300

Gly Asn Asp Ala Gly Ile Ile Gly Ala Ala Ser Leu Ala Tyr Ser Ile
305                 310                 315                 320

Asp Lys

<210> SEQ ID NO 21
<211> LENGTH: 969
<212> TYPE: DNA
<213> ORGANISM: Streptococcus thermophilus

<400> SEQUENCE: 21
atgagtaaga aactcttagg tattgacctt ggtggaacaa ctgttaagtt tggtattttg      60
actgcagatg gtgaagttca agaaaaatgg gctattgaaa caaatacgtt gaaaatggt     120
agccacattg ttcctgacat tgtagaatct ttgaaacacc gtttggaatt gtatggactt    180
actgctgaag atttttattgg aattggtatg ggatctccag gtgcagttga ccgagaaaat    240
aaaacagtaa cgggtgcctt taacttgaac tgggcagaaa ctcaagaagt tggctctgtt    300
attgaaaaag aacttggtat tccattcgct attgataatg atgctaatgt ggctgcactg    360
ggtgaacgtt gggttggtgc tggtgctaac aatcggaatg ttgtctttat aacattgggt    420
acaggtgttg gtggcggtgt tatcgctgat ggtaacttaa ttcatggtgt tgccggtgct    480
ggtgggaaa ttggtcacat tattgttgaa cctgacacag gatttgagtg tacttgcgga    540
aacaaggggt gtctggaaac tgtagcttca gcaacaggta ttgtacgtgt agcacatcat    600
ttggcagaaa aatacgaagg aaactcttct attaaagctg ctgtagacaa tggtgagttt    660
gtgacaagta aagatattat cgtagctgct actgaaggtg ataagtttgc tgacagcatt    720
gttgataaag tctctaaata cctcggactt gcaacagcaa acatctcaaa cattcttaac    780
ccagattctg tcgttatcgg tggtggtgtt tctgccgcag gaaaattctt gcgtagtcgt    840
gttgaaggat actttacacg ttatgcattc ccacaagttc gccgtacaac aaaagtgaaa    900
ttagcggagc ttggaaatga tgcaggaatc attggagctg ctagtcttgc ttatagtatt    960
gacaaataa                                                            969

<210> SEQ ID NO 22
<211> LENGTH: 322
<212> TYPE: PRT
<213> ORGANISM: Streptococcus thermophilus

<400> SEQUENCE: 22

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Asp
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Ile Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Lys Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys

<210> SEQ ID NO 23
<211> LENGTH: 322
<212> TYPE: PRT
<213> ORGANISM: Streptococcus thermophilus

<400> SEQUENCE: 23

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Pro Pro Gly Ala Val Asp Arg Glu Asn
65                  70                  75                  80

```
Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Ile Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys

<210> SEQ ID NO 24
<211> LENGTH: 147
<212> TYPE: DNA
<213> ORGANISM: Streptococcus thermophilus

<400> SEQUENCE: 24
catagtatcc tcctcatatt tcagtataac ataactttta tttttacct atatttact      60 aaaaaaatag taaaaatatt gattttccat gtgaaagggg ttatgatttc agtataaaca    120
aaaagaataa gtgagataca tcctatg                                       147

<210> SEQ ID NO 25
<211> LENGTH: 322
<212> TYPE: PRT
<213> ORGANISM: Streptococcus thermophilus
<220> FEATURE:
<221> NAME/KEY: MISC_FEATURE
<222> LOCATION: (275)..(275)
<223> OTHER INFORMATION: Xaa can be any naturally occurring amino acid,
      but not Glu

<400> SEQUENCE: 25

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
```

```
                20                  25                  30
Glu Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Asp
 50                  55                  60

Phe Ile Gly Ile Gly Met Gly Ser Pro Gly Ala Val Asp Arg Glu Asn
 65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
            115                 120                 125

Ala Asn Asn Arg Asn Val Val Phe Ile Thr Leu Gly Thr Gly Val Gly
            130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
            195                 200                 205

Ser Ser Ile Lys Ala Ala Val Asp Asn Gly Glu Phe Val Thr Ser Lys
            210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Xaa Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
            290                 295                 300

Gly Asn Asp Ala Gly Ile Ile Gly Ala Ala Ser Leu Ala Tyr Ser Ile
305                 310                 315                 320

Asp Lys

<210> SEQ ID NO 26
<211> LENGTH: 322
<212> TYPE: PRT
<213> ORGANISM: Streptococcus thermophilus
<220> FEATURE:
<221> NAME/KEY: MISC_FEATURE
<222> LOCATION: (275)..(275)
<223> OTHER INFORMATION: Xaa can be any naturally occurring amino acid,
      but not Glu

<400> SEQUENCE: 26

Met Ser Lys Lys Leu Leu Gly Ile Asp Leu Gly Thr Thr Val Lys
 1               5                  10                  15

Phe Gly Ile Leu Thr Ala Asp Gly Glu Val Gln Glu Lys Trp Ala Ile
                20                  25                  30

Glu Thr Asn Thr Phe Glu Asn Gly Ser His Ile Val Pro Asp Ile Val
            35                  40                  45
```

Glu Ser Leu Lys His Arg Leu Glu Leu Tyr Gly Leu Thr Ala Glu Asp
            50                  55                  60

Phe Ile Gly Ile Gly Met Gly Ser Pro Gly Ala Val Asp Arg Glu Asn
 65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
                100                 105                 110

Asn Asp Ala Asn Val Ala Ala Leu Gly Glu Arg Trp Val Gly Ala Gly
                115                 120                 125

Ala Asn Asn Arg Asn Val Val Phe Val Thr Leu Gly Thr Gly Val Gly
            130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
                180                 185                 190

Gly Ile Val Arg Val Ala His His Leu Ala Glu Lys Tyr Glu Gly Asn
                195                 200                 205

Ser Ser Ile Lys Ala Ala Val Asp Asn Gly Glu Phe Val Thr Ser Lys
210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
                260                 265                 270

Ala Gly Xaa Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
            290                 295                 300

Gly Asn Asp Ala Gly Ile Ile Gly Ala Ala Ser Leu Ala Tyr Ser Ile
305                 310                 315                 320

Asp Lys

<210> SEQ ID NO 27
<211> LENGTH: 322
<212> TYPE: PRT
<213> ORGANISM: Streptococcus thermophilus
<220> FEATURE:
<221> NAME/KEY: MISC_FEATURE
<222> LOCATION: (275)..(275)
<223> OTHER INFORMATION: Xaa can be any naturally occurring amino acid,
      but not Glu

<400> SEQUENCE: 27

Met Ser Lys Lys Leu Leu Gly Ile Asp Leu Gly Thr Thr Val Lys
 1               5                  10                  15

Phe Gly Ile Leu Asn Ala Asp Gly Glu Val Gln Glu Lys Trp Ala Ile
                20                  25                  30

Gly Thr Asn Thr Phe Glu Asn Gly Ser His Ile Val Pro Asp Ile Val
                35                  40                  45

Glu Ser Leu Lys His Arg Leu Glu Leu Tyr Gly Leu Thr Ala Glu Asp
            50                  55                  60

```
Phe Ile Gly Ile Gly Met Gly Ser Pro Gly Ala Val Asp Arg Glu Asn
 65                  70                  75                  80

Lys Thr Val Thr Gly Ala Phe Asn Leu Asn Trp Ala Glu Thr Gln Glu
                 85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Val Thr Leu Gly Thr Gly Val Gly
    130                 135                 140

Gly Val Ile Val Asp Gly Lys Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Ile Ala His His Leu Ala Glu Lys Tyr Glu Gly Asn
        195                 200                 205

Ser Ser Ile Lys Ala Ala Val Asp Asn Gly Glu Phe Val Thr Ser Lys
210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Xaa Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys

<210> SEQ ID NO 28
<211> LENGTH: 322
<212> TYPE: PRT
<213> ORGANISM: Streptococcus thermophilus
<220> FEATURE:
<221> NAME/KEY: MISC_FEATURE
<222> LOCATION: (275)..(275)
<223> OTHER INFORMATION: Xaa can be any naturally occurring amino acid,
      but not Glu

<400> SEQUENCE: 28

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
                20                  25                  30

Glu Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Ala
        50                  55                  60

Phe Ile Gly Ile Gly Met Gly Ser Pro Gly Ala Val Asp Arg Glu Asn
 65                 70                  75                  80

Lys Thr Val Thr Gly Ala Phe Asn Leu Asn Trp Ala Glu Thr Gln Glu
```

```
                     85                  90                  95
Val Gly Ser Val Ile Glu Lys Glu Leu Gly Ile Pro Phe Ala Ile Asp
                100                 105                 110

Asn Asp Ala Asn Val Ala Ala Leu Gly Glu Arg Trp Val Gly Ala Gly
            115                 120                 125

Ala Asn Asn Arg Asn Val Val Phe Ile Thr Leu Gly Thr Gly Val Gly
        130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Val Ser Ala
            260                 265                 270

Ala Gly Xaa Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys

<210> SEQ ID NO 29
<211> LENGTH: 322
<212> TYPE: PRT
<213> ORGANISM: Streptococcus thermophilus
<220> FEATURE:
<221> NAME/KEY: MISC_FEATURE
<222> LOCATION: (275)..(275)
<223> OTHER INFORMATION: Xaa can be any naturally occurring amino acid,
      but not Glu

<400> SEQUENCE: 29

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
                100                 105                 110
```

```
Asn Asp Ala Asn Val Ala Ala Leu Gly Glu Arg Trp Val Gly Ala Gly
        115                 120                 125

Ala Asn Asn Arg Asn Val Val Phe Ile Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Ala Ala Ser Ala Thr
                180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
                260                 265                 270

Ala Gly Xaa Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
        290                 295                 300

Gly Asn Asp Ala Gly Ile Ile Gly Ala Ala Ser Leu Ala Tyr Ser Ile
305                 310                 315                 320

Asp Lys

<210> SEQ ID NO 30
<211> LENGTH: 322
<212> TYPE: PRT
<213> ORGANISM: Streptococcus thermophilus
<220> FEATURE:
<221> NAME/KEY: MISC_FEATURE
<222> LOCATION: (275)..(275)
<223> OTHER INFORMATION: Xaa can be any naturally occurring amino acid,
      but not Glu

<400> SEQUENCE: 30

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
                20                  25                  30

Glu Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Asp
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125
```

```
Ala Asn Asn Arg Asn Val Val Phe Ile Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Asn Gly Cys Leu Glu Thr Val Ala Ser Ala Thr
                180                 185                 190

Gly Ile Val Arg Val Thr His His Leu Ala Glu Lys Tyr Glu Gly Asn
                195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
                260                 265                 270

Ala Gly Xaa Phe Leu Arg Ser Arg Val Glu Gly Tyr Phe Thr Arg Tyr
                275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys

<210> SEQ ID NO 31
<211> LENGTH: 322
<212> TYPE: PRT
<213> ORGANISM: Streptococcus thermophilus
<220> FEATURE:
<221> NAME/KEY: MISC_FEATURE
<222> LOCATION: (275)..(275)
<223> OTHER INFORMATION: Xaa can be any naturally occurring amino acid,
      but not Glu

<400> SEQUENCE: 31

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
                20                  25                  30

Glu Thr Asn Thr Phe Glu Asn Gly Ser His Ile Val Pro Asp Ile Val
                35                  40                  45

Asp Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
                100                 105                 110

Asn Asp Ala Asn Val Ala Ala Leu Gly Glu Arg Trp Val Gly Ala Gly
                115                 120                 125

Ala Asn Asn Arg Asn Val Val Phe Val Thr Leu Gly Thr Gly Val Gly
    130                 135                 140

Gly Gly Val Ile Ala Asp Gly Asn Leu Ile His Gly Val Ala Gly Ala
```

```
145                 150                 155                 160
  Gly Gly Glu Ile Gly His Ile Ile Val Glu Pro Asp Thr Gly Phe Glu
                  165                 170                 175

Cys Thr Cys Gly Asn Lys Gly Cys Leu Glu Thr Val Ala Ser Ala Thr
                  180                 185                 190

Gly Ile Val Arg Val Ala His His Leu Ala Glu Lys Tyr Glu Gly Asn
                  195                 200                 205

Ser Ser Ile Lys Ala Ala Val Asp Asn Gly Glu Leu Val Thr Ser Lys
                  210                 215                 220

Asp Ile Leu Val Ala Ala Thr Glu Gly Asp Lys Phe Ala Asp Ser Ile
  225                 230                 235                 240

Val Asp Lys Val Ser Lys Tyr Leu Gly Leu Ala Ile Ala Asn Ile Ser
                  245                 250                 255

Asn Ile Leu Asn Pro Asp Ser Val Val Ile Gly Gly Val Ser Ala
                  260                 265                 270

Ala Gly Xaa Phe Leu Arg Ser Arg Val Glu Gly Tyr Phe Thr Arg Tyr
                  275                 280                 285

Ala Phe Pro Gln Val Arg Arg Thr Thr Lys Val Lys Leu Ala Glu Leu
                  290                 295                 300

Gly Asn Asp Ala Gly Ile Ile Gly Ala Ala Ser Leu Ala Tyr Ser Ile
  305                 310                 315                 320

Asp Lys

<210> SEQ ID NO 32
<211> LENGTH: 322
<212> TYPE: PRT
<213> ORGANISM: Streptococcus thermophilus
<220> FEATURE:
<221> NAME/KEY: MISC_FEATURE
<222> LOCATION: (275)..(275)
<223> OTHER INFORMATION: Xaa can be any naturally occurring amino acid,
      but not Glu

<400> SEQUENCE: 32

Met Ser Lys Lys Leu Leu Gly Ile Asp Leu Gly Gly Thr Thr Val Lys
1               5                   10                  15

Phe Gly Ile Leu Asn Ala Asp Gly Glu Val Gln Glu Lys Trp Ala Ile
                20                  25                  30

Gly Thr Asn Thr Phe Glu Asn Gly Ser His Ile Val Pro Asp Ile Val
                35                  40                  45

Glu Ser Leu Lys His Arg Leu Glu Leu Tyr Gly Leu Thr Ala Glu Asp
                50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
                100                 105                 110

Asn Asp Ala Asn Val Ala Ala Leu Gly Glu Arg Trp Val Gly Ala Gly
                115                 120                 125

Ala Asn Asn Arg Asn Val Val Phe Val Thr Leu Gly Thr Gly Val Gly
                130                 135                 140

Gly Gly Val Ile Val Asp Gly Lys Leu Ile His Gly Val Ala Gly Ala
145                 150                 155                 160

Gly Gly Glu Ile Gly His Ile Ile Val Glu Pro Asp Thr Gly Phe Glu
                165                 170                 175
```

```
Cys Thr Cys Gly Asn Lys Gly Cys Leu Glu Thr Val Ala Ser Ala Thr
            180                 185                 190

Gly Ile Val Arg Ile Ala His His Leu Ala Glu Lys Tyr Glu Gly Asn
            195                 200                 205

Ser Ser Ile Lys Ala Ala Val Asp Asn Gly Glu Phe Val Thr Ser Lys
210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Val Ser Ala
            260                 265                 270

Ala Gly Xaa Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
290                 295                 300

Gly Asn Asp Ala Gly Ile Ile Gly Ala Ala Ser Leu Ala Tyr Ser Ile
305                 310                 315                 320

Asp Lys

<210> SEQ ID NO 33
<211> LENGTH: 322
<212> TYPE: PRT
<213> ORGANISM: Streptococcus thermophilus
<220> FEATURE:
<221> NAME/KEY: MISC_FEATURE
<222> LOCATION: (275)..(275)
<223> OTHER INFORMATION: Xaa can be any naturally occurring amino acid,
      but not Glu

<400> SEQUENCE: 33

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Asp Asn Gly Ser His Ile Val Pro Asp Ile Val
            35                  40                  45

Glu Ser Leu Lys His Arg Leu Glu Leu Tyr Gly Leu Thr Ala Glu Asp
50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
            115                 120                 125

Ala Asn Ser Arg Asp Val Val Phe Val Thr Leu Gly Thr Gly Val Gly
            130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190
```

```
Gly Ile Val Arg Val Ala His His Leu Ala Glu Lys Tyr Glu Gly Asn
            195                 200                 205

Ser Ser Ile Lys Ala Ala Val Asp Asn Gly Glu Leu Val Thr Ser Lys
    210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Ile Ala Asn Ile Ser
                245                 250                 255

Asn Ile Leu Asn Pro Asp Ser Val Val Ile Gly Gly Val Ser Ala
            260                 265                 270

Ala Gly Xaa Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys
```

<210> SEQ ID NO 34
<211> LENGTH: 322
<212> TYPE: PRT
<213> ORGANISM: Streptococcus thermophilus
<220> FEATURE:
<221> NAME/KEY: MISC_FEATURE
<222> LOCATION: (275)..(275)
<223> OTHER INFORMATION: Xaa can be any naturally occurring amino acid, but not Glu

<400> SEQUENCE: 34

```
Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Asp Asn Gly Ser His Ile Val Pro Asp Ile Val
        35                  40                  45

Glu Ser Leu Lys His Arg Leu Glu Leu Tyr Gly Leu Thr Ala Glu Asp
50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Ile Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asp Val Val Phe Val Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Leu Val Thr Ser Lys
```

```
            210                 215                 220
Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Ile Ala Asn Ile Ser
                245                 250                 255

Asn Ile Leu Asn Pro Asp Ser Val Ile Gly Gly Gly Val Ser Ala
            260                 265                 270

Ala Gly Xaa Phe Leu Arg Ser Arg Val Glu Gly Tyr Phe Thr Arg Tyr
                275                 280                 285

Ala Phe Pro Gln Val Arg Arg Thr Thr Lys Val Lys Leu Ala Glu Leu
            290                 295                 300

Gly Asn Asp Ala Gly Ile Ile Gly Ala Ala Ser Leu Ala Tyr Ser Ile
305                 310                 315                 320

Asp Lys

<210> SEQ ID NO 35
<211> LENGTH: 322
<212> TYPE: PRT
<213> ORGANISM: Streptococcus thermophilus

<400> SEQUENCE: 35

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
                20                  25                  30

Glu Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Asp
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Val Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
```

```
                260                 265                 270
Ala Gly Lys Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
        290                 295                 300

Gly Asn Asp Ala Gly Ile Ile Gly Ala Ala Ser Leu Ala Tyr Ser Ile
305                 310                 315                 320

Asp Lys

<210> SEQ ID NO 36
<211> LENGTH: 322
<212> TYPE: PRT
<213> ORGANISM: Streptococcus thermophilus

<400> SEQUENCE: 36

Met Ser Lys Lys Leu Leu Gly Ile Asp Leu Gly Gly Thr Thr Val Lys
1               5                   10                  15

Phe Gly Ile Leu Asn Ala Asp Gly Glu Val Gln Glu Lys Trp Ala Ile
            20                  25                  30

Gly Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Val Thr Leu Gly Thr Gly Val Gly
    130                 135                 140

Gly Gly Val Ile Val Asp Gly Lys Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Ile Ala His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Lys Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
```

```
                 305                 310                 315                 320

Asp Lys

<210> SEQ ID NO 37
<211> LENGTH: 322
<212> TYPE: PRT
<213> ORGANISM: Streptococcus thermophilus

<400> SEQUENCE: 37

Met Ser Lys Lys Leu Leu Gly Ile Asp Leu Gly Thr Thr Val Lys
1               5                   10                  15

Phe Gly Ile Leu Thr Ala Asp Gly Glu Val Gln Glu Lys Trp Ala Ile
                20                  25                  30

Glu Thr Asn Thr Phe Glu Asn Gly Ser His Ile Val Pro Asp Ile Val
                35                  40                  45

Glu Ser Leu Lys His Arg Leu Glu Leu Tyr Gly Leu Thr Ala Glu Ala
            50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
                100                 105                 110

Asn Asp Ala Asn Val Ala Ala Leu Gly Glu Arg Trp Val Gly Ala Gly
            115                 120                 125

Ala Asn Asn Arg Asn Val Val Phe Ile Thr Leu Gly Thr Gly Val Gly
130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
                180                 185                 190

Gly Ile Val Arg Val Ala His His Leu Ala Glu Lys Tyr Glu Gly Asn
            195                 200                 205

Ser Ser Ile Lys Ala Ala Val Asp Asn Gly Glu Phe Val Thr Ser Lys
210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
                260                 265                 270

Ala Gly Lys Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
            290                 295                 300

Gly Asn Asp Ala Gly Ile Ile Gly Ala Ala Ser Leu Ala Tyr Ser Ile
305                 310                 315                 320

Asp Lys

<210> SEQ ID NO 38
<211> LENGTH: 322
<212> TYPE: PRT
<213> ORGANISM: Streptococcus thermophilus
```

<400> SEQUENCE: 38

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Ile Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Ala Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Lys Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys

<210> SEQ ID NO 39
<211> LENGTH: 322
<212> TYPE: PRT
<213> ORGANISM: Streptococcus thermophilus

<400> SEQUENCE: 39

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

```
Glu Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Asp
 50                  55                  60

Phe Ile Gly Ile Gly Met Gly Ser Pro Gly Ala Val Asp Arg Glu Asn
 65                  70                  75                  80

Lys Thr Val Thr Gly Ala Phe Asn Leu Asn Trp Ala Glu Thr Gln Glu
                 85                  90                  95

Val Gly Ser Val Ile Glu Lys Glu Leu Gly Ile Pro Phe Ala Ile Asp
                100                 105                 110

Asn Asp Ala Asn Val Ala Ala Leu Gly Glu Arg Trp Val Gly Ala Gly
            115                 120                 125

Ala Asn Asn Arg Asn Val Val Phe Ile Thr Leu Gly Thr Gly Val Gly
130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Asn Gly Cys Leu Glu Thr Val Ala Ser Ala Thr
            180                 185                 190

Gly Ile Val Arg Val Thr His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
                260                 265                 270

Ala Gly Lys Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
290                 295                 300

Gly Asn Asp Ala Gly Ile Ile Gly Ala Ala Ser Leu Ala Tyr Ser Ile
305                 310                 315                 320

Asp Lys

<210> SEQ ID NO 40
<211> LENGTH: 322
<212> TYPE: PRT
<213> ORGANISM: Streptococcus thermophilus

<400> SEQUENCE: 40

Met Ser Lys Lys Leu Leu Gly Ile Asp Leu Gly Gly Thr Thr Val Lys
 1               5                  10                  15

Phe Gly Ile Leu Thr Ala Asp Gly Glu Val Gln Glu Lys Trp Ala Ile
                 20                  25                  30

Glu Thr Asn Thr Phe Glu Asn Gly Ser His Ile Val Pro Asp Ile Val
            35                  40                  45

Asp Ser Leu Lys His Arg Leu Glu Leu Tyr Gly Leu Thr Ala Glu Asp
 50                  55                  60

Phe Ile Gly Ile Gly Met Gly Ser Pro Gly Ala Val Asp Arg Glu Asn
 65                  70                  75                  80
```

```
Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
            115                 120                 125

Ala Asn Asn Arg Asn Val Val Phe Val Thr Leu Gly Thr Gly Val Gly
        130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
                180                 185                 190

Gly Ile Val Arg Val Ala His His Leu Ala Glu Lys Tyr Glu Gly Asn
                195                 200                 205

Ser Ser Ile Lys Ala Ala Val Asp Asn Gly Glu Leu Val Thr Ser Lys
        210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Ile Ala Asn Ile Ser
                245                 250                 255

Asn Ile Leu Asn Pro Asp Ser Val Val Ile Gly Gly Val Ser Ala
                260                 265                 270

Ala Gly Lys Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
        290                 295                 300

Gly Asn Asp Ala Gly Ile Ile Gly Ala Ala Ser Leu Ala Tyr Ser Ile
305                 310                 315                 320

Asp Lys

<210> SEQ ID NO 41
<211> LENGTH: 322
<212> TYPE: PRT
<213> ORGANISM: Streptococcus thermophilus

<400> SEQUENCE: 41

Met Ser Lys Lys Leu Leu Gly Ile Asp Leu Gly Gly Thr Thr Val Lys
1               5                   10                  15

Phe Gly Ile Leu Asn Ala Asp Gly Glu Val Gln Glu Lys Trp Ala Ile
                20                  25                  30

Gly Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Asp
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
            115                 120                 125
```

```
Ala Asn Asn Arg Asn Val Val Phe Val Thr Leu Gly Thr Gly Val Gly
    130                 135                 140
Gly Gly Val Ile Val Asp Gly Lys Leu Ile His Gly Val Ala Gly Ala
145                 150                 155                 160
Gly Gly Glu Ile Gly His Ile Ile Val Glu Pro Asp Thr Gly Phe Glu
                165                 170                 175
Cys Thr Cys Gly Asn Lys Gly Cys Leu Glu Thr Val Ala Ser Ala Thr
                180                 185                 190
Gly Ile Val Arg Ile Ala His His Leu Ala Glu Lys Tyr Glu Gly Asn
                195                 200                 205
Ser Ser Ile Lys Ala Ala Val Asp Asn Gly Glu Phe Val Thr Ser Lys
210                 215                 220
Asp Ile Ile Val Ala Ala Thr Glu Gly Asp Lys Phe Ala Asp Ser Ile
225                 230                 235                 240
Val Asp Lys Val Ser Lys Tyr Leu Gly Leu Ala Thr Ala Asn Ile Ser
                245                 250                 255
Asn Ile Leu Asn Pro Asp Ser Val Val Ile Gly Gly Val Ser Ala
                260                 265                 270
Ala Gly Lys Phe Leu Arg Ser Arg Val Glu Gly Tyr Phe Thr Arg Tyr
                275                 280                 285
Ala Phe Pro Gln Val Arg Arg Thr Thr Lys Val Lys Leu Ala Glu Leu
                290                 295                 300
Gly Asn Asp Ala Gly Ile Ile Gly Ala Ala Ser Leu Ala Tyr Ser Ile
305                 310                 315                 320
Asp Lys

<210> SEQ ID NO 42
<211> LENGTH: 322
<212> TYPE: PRT
<213> ORGANISM: Streptococcus thermophilus

<400> SEQUENCE: 42

Met Ser Lys Lys Leu Leu Gly Ile Asp Leu Gly Gly Thr Thr Val Lys
1               5                   10                  15
Phe Gly Ile Leu Thr Ala Asp Gly Glu Val Gln Glu Lys Trp Ala Ile
                20                  25                  30
Glu Thr Asn Thr Phe Asp Asn Gly Ser His Ile Val Pro Asp Ile Val
                35                  40                  45
Glu Ser Leu Lys His Arg Leu Glu Leu Tyr Gly Leu Thr Ala Glu Asp
50                  55                  60
Phe Ile Gly Ile Gly Met Gly Ser Pro Gly Ala Val Asp Arg Glu Asn
65                  70                  75                  80
Lys Thr Val Thr Gly Ala Phe Asn Leu Asn Trp Ala Glu Thr Gln Glu
                85                  90                  95
Val Gly Ser Val Ile Glu Lys Glu Leu Gly Ile Pro Phe Ala Ile Asp
                100                 105                 110
Asn Asp Ala Asn Val Ala Ala Leu Gly Glu Arg Trp Val Gly Ala Gly
                115                 120                 125
Ala Asn Ser Arg Asp Val Val Phe Val Thr Leu Gly Thr Gly Val Gly
    130                 135                 140
Gly Gly Val Ile Ala Asp Gly Asn Leu Ile His Gly Val Ala Gly Ala
145                 150                 155                 160
Gly Gly Glu Ile Gly His Ile Ile Val Glu Pro Asp Thr Gly Phe Glu
                165                 170                 175
```

```
Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
            195                 200                 205

Ser Ser Ile Lys Ala Ala Val Asp Asn Gly Glu Leu Val Thr Ser Lys
            210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Ile Ala Asn Ile Ser
            245                 250                 255

Asn Ile Leu Asn Pro Asp Ser Val Val Ile Gly Gly Val Ser Ala
            260                 265                 270

Ala Gly Lys Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
            290                 295                 300

Gly Asn Asp Ala Gly Ile Ile Gly Ala Ala Ser Leu Ala Tyr Ser Ile
305                 310                 315                 320

Asp Lys

<210> SEQ ID NO 43
<211> LENGTH: 322
<212> TYPE: PRT
<213> ORGANISM: Streptococcus thermophilus

<400> SEQUENCE: 43

Met Ser Lys Lys Leu Leu Gly Ile Asp Leu Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Asp Asn Gly Ser His Ile Val Pro Asp Ile Val
            35                  40                  45

Glu Ser Leu Lys His Arg Leu Glu Leu Tyr Gly Leu Thr Ala Glu Asp
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
            85                  90                  95

Val Gly Ser Ile Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
            115                 120                 125

Ala Asn Asn Arg Asp Val Val Phe Val Thr Leu Gly Thr Gly Val Gly
            130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
            165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
            195                 200                 205

Ser Ser Ile Lys Ala Ala Val Asp Asn Gly Glu Leu Val Thr Ser Lys
            210                 215                 220
```

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Ile Ala Asn Ile Ser
            245                 250                 255

Asn Ile Leu Asn Pro Asp Ser Val Ile Ile Gly Gly Val Ser Ala
        260                 265                 270

Ala Gly Lys Phe Leu Arg Ser Arg Val Glu Gly Tyr Phe Thr Arg Tyr
    275                 280                 285

Ala Phe Pro Gln Val Arg Arg Thr Thr Lys Val Lys Leu Ala Glu Leu
        290                 295                 300

Gly Asn Asp Ala Gly Ile Ile Gly Ala Ala Ser Leu Ala Tyr Ser Ile
305                 310                 315                 320

Asp Lys

<210> SEQ ID NO 44
<211> LENGTH: 969
<212> TYPE: DNA
<213> ORGANISM: Streptococcus thermophilus

<400> SEQUENCE: 44

```
atgagtaaga aactcttagg tattgacctt ggtggaacaa ctgttaagtt tggtattttg      60
actgcagatg gtgaagttca agaaaaatgg gctattgaaa caaatacgtt gaaaatggt     120
agccacattg ttcctgacat tgtagaatct ttgaaacacc gtttggaatt gtatggactt    180
actgctgaag attttattgg aattggtatg gatctccag gtgcagttga ccgagaaaat     240
aaaacagtaa cgggtgcctt taacttgaac tgggcagaaa ctcaagaagt tggctctgtt    300
attgaaaaag aacttggtat tccattcgct attgataatg atgctaatgt ggctgcactg    360
ggtgaacgtt gggttggtgc tggtgctaac aatcggaatg ttgtctttat aacattgggt    420
acaggtgtta gtggcggtgt tatcgctgat ggtaacttaa ttcatggtgt tgccggtgct    480
ggtggggaaa ttggtcacat tattgttgaa cctgacacag gatttgagtg tacttgcgga    540
aacaaggggt gtctggaaac tgtagcttca gcaacaggta ttgtacgtgt agcacatcat    600
ttggcagaaa aatacgaagg aaactcttct attaaagctg ctgtagacaa tggtgagttt    660
gtgacaagta agatattat cgtagctgct actgaaggtg ataagtttgc tgacagcatt     720
gttgataaag tctctaaata cctcggactt gcaacagcaa acatctcaaa cattcttaac    780
ccagattctg tcgttatcgg tggtggtgtt tctgccgcag gagaattctt gcgtagtcgt    840
gttgaaggat actttacacg ttatgcattc ccacaagttc gccgtacaac aaaagtgaaa    900
ttagcggagc ttggaaatga tgcaggaatc attggagctg ctagtcttgc ttatagtatt    960
gacaaataa                                                            969
```

<210> SEQ ID NO 45
<211> LENGTH: 322
<212> TYPE: PRT
<213> ORGANISM: Streptococcus thermophilus

<400> SEQUENCE: 45

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

```
Glu Ser Leu Lys His Arg Leu Glu Leu Tyr Gly Leu Thr Ala Glu Asp
 50                  55                  60

Phe Ile Gly Ile Gly Met Gly Ser Pro Gly Ala Val Asp Arg Glu Asn
 65                  70                  75                  80

Lys Thr Val Thr Gly Ala Phe Asn Leu Asn Trp Ala Glu Thr Gln Glu
                 85                  90                  95

Val Gly Ser Val Ile Glu Lys Glu Leu Gly Ile Pro Phe Ala Ile Asp
                100                 105                 110

Asn Asp Ala Asn Val Ala Ala Leu Gly Glu Arg Trp Val Gly Ala Gly
                115                 120                 125

Ala Asn Asn Arg Asn Val Val Phe Ile Thr Leu Gly Thr Gly Val Ser
130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
                180                 185                 190

Gly Ile Val Arg Val Ala His His Leu Ala Glu Lys Tyr Glu Gly Asn
                195                 200                 205

Ser Ser Ile Lys Ala Ala Val Asp Asn Gly Glu Phe Val Thr Ser Lys
210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
                260                 265                 270

Ala Gly Glu Phe Leu Arg Ser Arg Val Glu Gly Tyr Phe Thr Arg Tyr
                275                 280                 285

Ala Phe Pro Gln Val Arg Arg Thr Thr Lys Val Lys Leu Ala Glu Leu
                290                 295                 300

Gly Asn Asp Ala Gly Ile Ile Gly Ala Ala Ser Leu Ala Tyr Ser Ile
305                 310                 315                 320

Asp Lys

<210> SEQ ID NO 46
<211> LENGTH: 322
<212> TYPE: PRT
<213> ORGANISM: Streptococcus thermophilus
<220> FEATURE:
<221> NAME/KEY: MISC_FEATURE
<222> LOCATION: (144)..(144)
<223> OTHER INFORMATION: Xaa can be any naturally occurring amino acid,
      but not Gly

<400> SEQUENCE: 46

Met Ser Lys Lys Leu Leu Gly Ile Asp Leu Gly Thr Thr Val Lys
 1                   5                  10                  15

Phe Gly Ile Leu Thr Ala Asp Gly Glu Val Gln Glu Lys Trp Ala Ile
                 20                  25                  30

Glu Thr Asn Thr Phe Glu Asn Gly Ser His Ile Val Pro Asp Ile Val
                 35                  40                  45

Glu Ser Leu Lys His Arg Leu Glu Leu Tyr Gly Leu Thr Ala Glu Asp
 50                  55                  60

Phe Ile Gly Ile Gly Met Gly Ser Pro Gly Ala Val Asp Arg Glu Asn
```

```
            65                  70                  75                  80
Lys Thr Val Thr Gly Ala Phe Asn Leu Asn Trp Ala Glu Thr Gln Glu
                    85                  90                  95

Val Gly Ser Val Ile Glu Lys Glu Leu Gly Ile Pro Phe Ala Ile Asp
                100                 105                 110

Asn Asp Ala Asn Val Ala Ala Leu Gly Glu Arg Trp Val Gly Ala Gly
                115                 120                 125

Ala Asn Asn Arg Asn Val Val Phe Ile Thr Leu Gly Thr Gly Val Xaa
            130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
            195                 200                 205

Ser Ser Ile Lys Ala Ala Val Asp Asn Gly Glu Phe Val Thr Ser Lys
210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
            290                 295                 300

Gly Asn Asp Ala Gly Ile Ile Gly Ala Ala Ser Leu Ala Tyr Ser Ile
305                 310                 315                 320

Asp Lys

<210> SEQ ID NO 47
<211> LENGTH: 322
<212> TYPE: PRT
<213> ORGANISM: Streptococcus thermophilus
<220> FEATURE:
<221> NAME/KEY: MISC_FEATURE
<222> LOCATION: (144)..(144)
<223> OTHER INFORMATION: Xaa can be any naturally occurring amino acid,
      but not Gly

<400> SEQUENCE: 47

Met Ser Lys Lys Leu Leu Gly Ile Asp Leu Gly Thr Thr Val Lys
1               5                   10                  15

Phe Gly Ile Leu Thr Ala Asp Gly Glu Val Gln Glu Lys Trp Ala Ile
                20                  25                  30

Glu Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Asp
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95
```

```
Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
            115                 120                 125

Ala Asn Asn Arg Asn Val Val Phe Val Thr Leu Gly Thr Gly Val Xaa
        130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
            195                 200                 205

Ser Ser Ile Lys Ala Ala Val Asp Asn Gly Glu Phe Val Thr Ser Lys
            210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
            290                 295                 300

Gly Asn Asp Ala Gly Ile Ile Gly Ala Ala Ser Leu Ala Tyr Ser Ile
305                 310                 315                 320

Asp Lys

<210> SEQ ID NO 48
<211> LENGTH: 322
<212> TYPE: PRT
<213> ORGANISM: Streptococcus thermophilus
<220> FEATURE:
<221> NAME/KEY: MISC_FEATURE
<222> LOCATION: (144)..(144)
<223> OTHER INFORMATION: Xaa can be any naturally occurring amino acid,
      but not Gly

<400> SEQUENCE: 48

Met Ser Lys Lys Leu Leu Gly Ile Asp Leu Gly Gly Thr Thr Val Lys
1               5                   10                  15

Phe Gly Ile Leu Asn Ala Asp Gly Glu Val Gln Glu Lys Trp Ala Ile
            20                  25                  30

Gly Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110
```

```
Asn Asp Ala Asn Val Ala Ala Leu Gly Glu Arg Trp Val Gly Ala Gly
            115                 120                 125

Ala Asn Asn Arg Asn Val Val Phe Val Thr Leu Gly Thr Gly Val Xaa
130                 135                 140

Gly Gly Val Ile Val Asp Gly Lys Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Ile Ala His His Leu Ala Glu Lys Tyr Glu Gly Asn
        195                 200                 205

Ser Ser Ile Lys Ala Ala Val Asp Asn Gly Glu Phe Val Thr Ser Lys
210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
290                 295                 300

Gly Asn Asp Ala Gly Ile Ile Gly Ala Ala Ser Leu Ala Tyr Ser Ile
305                 310                 315                 320

Asp Lys

<210> SEQ ID NO 49
<211> LENGTH: 322
<212> TYPE: PRT
<213> ORGANISM: Streptococcus thermophilus
<220> FEATURE:
<221> NAME/KEY: MISC_FEATURE
<222> LOCATION: (144)..(144)
<223> OTHER INFORMATION: Xaa can be any naturally occurring amino acid,
      but not Gly

<400> SEQUENCE: 49

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Ala
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Ile Thr Leu Gly Thr Gly Val Xaa
130                 135                 140
```

```
        130                 135                 140
Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
                180                 185                 190

Gly Ile Val Arg Val Ala His His Leu Ala Glu Lys Tyr Glu Gly Asn
                195                 200                 205

Ser Ser Ile Lys Ala Ala Val Asp Asn Gly Glu Phe Val Thr Ser Lys
210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
                260                 265                 270

Ala Gly Glu Phe Leu Arg Ser Arg Val Glu Gly Tyr Phe Thr Arg Tyr
                275                 280                 285

Ala Phe Pro Gln Val Arg Arg Thr Thr Lys Val Lys Leu Ala Glu Leu
                290                 295                 300

Gly Asn Asp Ala Gly Ile Ile Gly Ala Ala Ser Leu Ala Tyr Ser Ile
305                 310                 315                 320

Asp Lys

<210> SEQ ID NO 50
<211> LENGTH: 322
<212> TYPE: PRT
<213> ORGANISM: Streptococcus thermophilus
<220> FEATURE:
<221> NAME/KEY: MISC_FEATURE
<222> LOCATION: (144)..(144)
<223> OTHER INFORMATION: Xaa can be any naturally occurring amino acid,
      but not Gly

<400> SEQUENCE: 50

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
                20                  25                  30

Glu Thr Asn Thr Phe Glu Asn Gly Ser His Ile Val Pro Asp Ile Val
                35                  40                  45

Glu Ser Leu Lys His Arg Leu Glu Leu Tyr Gly Leu Thr Ala Glu Asp
50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
                100                 105                 110

Asn Asp Ala Asn Val Ala Ala Leu Gly Glu Arg Trp Val Gly Ala Gly
                115                 120                 125

Ala Asn Asn Arg Asn Val Val Phe Ile Thr Leu Gly Thr Gly Val Xaa
                130                 135                 140

Gly Gly Val Ile Ala Asp Gly Asn Leu Ile His Gly Val Ala Gly Ala
145                 150                 155                 160
```

```
Gly Gly Glu Ile Gly His Ile Ile Val Glu Pro Asp Thr Gly Phe Glu
            165                 170                 175

Cys Thr Cys Gly Asn Lys Gly Cys Leu Glu Thr Ala Ala Ser Ala Thr
            180                 185                 190

Gly Ile Val Arg Val Ala His His Leu Ala Glu Lys Tyr Glu Gly Asn
            195                 200                 205

Ser Ser Ile Lys Ala Ala Val Asp Asn Gly Glu Phe Val Thr Ser Lys
210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
            245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
            290                 295                 300

Gly Asn Asp Ala Gly Ile Ile Gly Ala Ala Ser Leu Ala Tyr Ser Ile
305                 310                 315                 320

Asp Lys

<210> SEQ ID NO 51
<211> LENGTH: 322
<212> TYPE: PRT
<213> ORGANISM: Streptococcus thermophilus
<220> FEATURE:
<221> NAME/KEY: MISC_FEATURE
<222> LOCATION: (144)..(144)
<223> OTHER INFORMATION: Xaa can be any naturally occurring amino acid,
      but not Gly

<400> SEQUENCE: 51

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
            115                 120                 125

Ala Asn Asn Arg Asn Val Val Phe Ile Thr Leu Gly Thr Gly Val Xaa
            130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
            165                 170                 175
```

```
Cys Thr Cys Gly Asn Asn Gly Cys Leu Glu Thr Val Ala Ser Ala Thr
                180                 185                 190

Gly Ile Val Arg Val Thr His His Leu Ala Glu Lys Tyr Glu Gly Asn
            195                 200                 205

Ser Ser Ile Lys Ala Ala Val Asp Asn Gly Glu Phe Val Thr Ser Lys
        210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
                260                 265                 270

Ala Gly Glu Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
        290                 295                 300

Gly Asn Asp Ala Gly Ile Ile Gly Ala Ala Ser Leu Ala Tyr Ser Ile
305                 310                 315                 320

Asp Lys

<210> SEQ ID NO 52
<211> LENGTH: 322
<212> TYPE: PRT
<213> ORGANISM: Streptococcus thermophilus
<220> FEATURE:
<221> NAME/KEY: MISC_FEATURE
<222> LOCATION: (144)..(144)
<223> OTHER INFORMATION: Xaa can be any naturally occurring amino acid,
      but not Gly

<400> SEQUENCE: 52

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Asp Ser Leu Lys His Arg Leu Glu Leu Tyr Gly Leu Thr Ala Glu Asp
50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Val Thr Leu Gly Thr Gly Val Xaa
        130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
                180                 185                 190

Gly Ile Val Arg Val Ala His His Leu Ala Glu Lys Tyr Glu Gly Asn
```

```
                195                 200                 205
Ser Ser Ile Lys Ala Ala Val Asp Asn Gly Glu Leu Val Thr Ser Lys
    210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Ile Ala Asn Ile Ser
                245                 250                 255

Asn Ile Leu Asn Pro Asp Ser Val Val Ile Gly Gly Val Ser Ala
    260                 265                 270

Ala Gly Glu Phe Leu Arg Ser Arg Val Glu Gly Tyr Phe Thr Arg Tyr
    275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys

<210> SEQ ID NO 53
<211> LENGTH: 322
<212> TYPE: PRT
<213> ORGANISM: Streptococcus thermophilus
<220> FEATURE:
<221> NAME/KEY: MISC_FEATURE
<222> LOCATION: (144)..(144)
<223> OTHER INFORMATION: Xaa can be any naturally occurring amino acid,
      but not Gly

<400> SEQUENCE: 53

Met Ser Lys Lys Leu Leu Gly Ile Asp Leu Gly Gly Thr Thr Val Lys
1               5                   10                  15

Phe Gly Ile Leu Asn Ala Asp Gly Glu Val Gln Glu Lys Trp Ala Ile
                20                  25                  30

Gly Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
    115                 120                 125

Ala Asn Asn Arg Asn Val Val Phe Val Thr Leu Gly Thr Gly Val Xaa
    130                 135                 140

Gly Gly Val Ile Val Asp Gly Lys Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Ile Ala His His Leu Ala Glu Lys Tyr Glu Gly Asn
    195                 200                 205

Ser Ser Ile Lys Ala Ala Val Asp Asn Gly Glu Phe Val Thr Ser Lys
    210                 215                 220
```

```
Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
            245                 250                 255

Asn Ile Leu Asn Pro Asp Ser Val Val Ile Gly Gly Val Ser Ala
        260                 265                 270

Ala Gly Glu Phe Leu Arg Ser Arg Val Glu Gly Tyr Phe Thr Arg Tyr
    275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys

<210> SEQ ID NO 54
<211> LENGTH: 322
<212> TYPE: PRT
<213> ORGANISM: Streptococcus thermophilus
<220> FEATURE:
<221> NAME/KEY: MISC_FEATURE
<222> LOCATION: (144)..(144)
<223> OTHER INFORMATION: Xaa can be any naturally occurring amino acid,
      but not Gly

<400> SEQUENCE: 54

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Asp Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Ser Arg Asp Val Val Phe Val Thr Leu Gly Thr Gly Val Xaa
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Leu Val Thr Ser Lys
    210                 215                 220

Asp Ile Leu Val Ala Ala Thr Glu Gly Asp Lys Phe Ala Asp Ser Ile
225                 230                 235                 240
```

```
Val Asp Lys Val Ser Lys Tyr Leu Gly Leu Ala Ile Ala Asn Ile Ser
            245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
            290                 295                 300

Gly Asn Asp Ala Gly Ile Ile Gly Ala Ala Ser Leu Ala Tyr Ser Ile
305                 310                 315                 320

Asp Lys

<210> SEQ ID NO 55
<211> LENGTH: 322
<212> TYPE: PRT
<213> ORGANISM: Streptococcus thermophilus
<220> FEATURE:
<221> NAME/KEY: MISC_FEATURE
<222> LOCATION: (144)..(144)
<223> OTHER INFORMATION: Xaa can be any naturally occurring amino acid,
      but not Gly

<400> SEQUENCE: 55

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Asp Asn Gly Ser His Ile Val Pro Asp Ile Val
            35                  40                  45

Glu Ser Leu Lys His Arg Leu Glu Leu Tyr Gly Leu Thr Ala Glu Asp
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Ile Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
            115                 120                 125

Ala Asn Asn Arg Asp Val Val Phe Val Thr Leu Gly Thr Gly Val Xaa
130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
            195                 200                 205

Ser Ser Ile Lys Ala Ala Val Asp Asn Gly Glu Leu Val Thr Ser Lys
210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Ile Ala Asn Ile Ser
            245                 250                 255

Asn Ile Leu Asn Pro Asp Ser Val Ile Ile Gly Gly Gly Val Ser Ala
```

```
            260                 265                 270
Ala Gly Glu Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
            290                 295                 300

Gly Asn Asp Ala Gly Ile Ile Gly Ala Ala Ser Leu Ala Tyr Ser Ile
305                 310                 315                 320

Asp Lys

<210> SEQ ID NO 56
<211> LENGTH: 322
<212> TYPE: PRT
<213> ORGANISM: Streptococcus thermophilus

<400> SEQUENCE: 56

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Val Thr Leu Gly Thr Gly Val Ser
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
```

```
305                 310                 315                 320

Asp Lys

<210> SEQ ID NO 57
<211> LENGTH: 322
<212> TYPE: PRT
<213> ORGANISM: Streptococcus thermophilus

<400> SEQUENCE: 57

Met Ser Lys Lys Leu Leu Gly Ile Asp Leu Gly Gly Thr Thr Val Lys
1               5                   10                  15

Phe Gly Ile Leu Asn Ala Asp Gly Glu Val Gln Glu Lys Trp Ala Ile
                20                  25                  30

Gly Thr Asn Thr Phe Glu Asn Gly Ser His Ile Val Pro Asp Ile Val
            35                  40                  45

Glu Ser Leu Lys His Arg Leu Glu Leu Tyr Gly Leu Thr Ala Glu Asp
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Val Thr Leu Gly Thr Gly Val Ser
130                 135                 140

Gly Gly Val Ile Val Asp Gly Lys Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Ile Ala His His Leu Ala Glu Lys Tyr Glu Gly Asn
        195                 200                 205

Ser Ser Ile Lys Ala Ala Val Asp Asn Gly Glu Phe Val Thr Ser Lys
210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
290                 295                 300

Gly Asn Asp Ala Gly Ile Ile Gly Ala Ala Ser Leu Ala Tyr Ser Ile
305                 310                 315                 320

Asp Lys

<210> SEQ ID NO 58
<211> LENGTH: 322
<212> TYPE: PRT
<213> ORGANISM: Streptococcus thermophilus
```

<400> SEQUENCE: 58

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Ala
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Ile Thr Leu Gly Thr Gly Val Ser
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys

<210> SEQ ID NO 59
<211> LENGTH: 322
<212> TYPE: PRT
<213> ORGANISM: Streptococcus thermophilus

<400> SEQUENCE: 59

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

```
Glu Thr Asn Thr Phe Glu Asn Gly Ser His Ile Val Pro Asp Ile Val
             35                  40                  45

Glu Ser Leu Lys His Arg Leu Glu Leu Tyr Gly Leu Thr Ala Glu Asp
 50                  55                  60

Phe Ile Gly Ile Gly Met Gly Ser Pro Gly Ala Val Asp Arg Glu Asn
 65                  70                  75                  80

Lys Thr Val Thr Gly Ala Phe Asn Leu Asn Trp Ala Glu Thr Gln Glu
                 85                  90                  95

Val Gly Ser Val Ile Glu Lys Glu Leu Gly Ile Pro Phe Ala Ile Asp
                100                 105                 110

Asn Asp Ala Asn Val Ala Ala Leu Gly Glu Arg Trp Val Gly Ala Gly
                115                 120                 125

Ala Asn Asn Arg Asn Val Val Phe Ile Thr Leu Gly Thr Gly Val Ser
130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Ala Ala Ser Ala Thr
                180                 185                 190

Gly Ile Val Arg Val Ala His His Leu Ala Glu Lys Tyr Glu Gly Asn
                195                 200                 205

Ser Ser Ile Lys Ala Ala Val Asp Asn Gly Glu Phe Val Thr Ser Lys
                210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Val Ser Ala
                260                 265                 270

Ala Gly Glu Phe Leu Arg Ser Arg Val Glu Gly Tyr Phe Thr Arg Tyr
                275                 280                 285

Ala Phe Pro Gln Val Arg Arg Thr Thr Lys Val Lys Leu Ala Glu Leu
                290                 295                 300

Gly Asn Asp Ala Gly Ile Ile Gly Ala Ala Ser Leu Ala Tyr Ser Ile
305                 310                 315                 320

Asp Lys

<210> SEQ ID NO 60
<211> LENGTH: 322
<212> TYPE: PRT
<213> ORGANISM: Streptococcus thermophilus

<400> SEQUENCE: 60

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
                20                  25                  30

Glu Thr Asn Thr Phe Glu Asn Gly Ser His Ile Val Pro Asp Ile Val
             35                  40                  45

Glu Ser Leu Lys His Arg Leu Glu Leu Tyr Gly Leu Thr Ala Glu Asp
 50                  55                  60

Phe Ile Gly Ile Gly Met Gly Ser Pro Gly Ala Val Asp Arg Glu Asn
 65                  70                  75                  80
```

-continued

```
Lys Thr Val Thr Gly Ala Phe Asn Leu Asn Trp Ala Glu Thr Gln Glu
             85                  90                  95

Val Gly Ser Val Ile Glu Lys Glu Leu Gly Ile Pro Phe Ala Ile Asp
         100                 105                 110

Asn Asp Ala Asn Val Ala Ala Leu Gly Glu Arg Trp Val Gly Ala Gly
         115                 120                 125

Ala Asn Asn Arg Asn Val Val Phe Ile Thr Leu Gly Thr Gly Val Ser
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Asn Gly Cys Leu Glu Thr Val Ala Ser Ala Thr
            180                 185                 190

Gly Ile Val Arg Val Thr His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Gly Leu Ala Thr Ala Asn Ile Ser
                245                 250                 255

Asn Ile Leu Asn Pro Asp Ser Val Val Ile Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys
```

<210> SEQ ID NO 61
<211> LENGTH: 322
<212> TYPE: PRT
<213> ORGANISM: Streptococcus thermophilus

<400> SEQUENCE: 61

```
Met Ser Lys Lys Leu Leu Gly Ile Asp Leu Gly Gly Thr Thr Val Lys
1               5                  10                  15

Phe Gly Ile Leu Thr Ala Asp Gly Glu Val Gln Glu Lys Trp Ala Ile
             20                  25                  30

Glu Thr Asn Thr Phe Glu Asn Gly Ser His Ile Val Pro Asp Ile Val
         35                  40                  45

Asp Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
             85                  90                  95

Val Gly Ser Val Ile Glu Lys Glu Leu Gly Ile Pro Phe Ala Ile Asp
         100                 105                 110

Asn Asp Ala Asn Val Ala Ala Leu Gly Glu Arg Trp Val Gly Ala Gly
    115                 120                 125
```

```
Ala Asn Asn Arg Asn Val Val Phe Val Thr Leu Gly Thr Gly Val Ser
    130                 135                 140
Gly Gly Val Ile Ala Asp Gly Asn Leu Ile His Gly Val Ala Gly Ala
145                 150                 155                 160
Gly Gly Glu Ile Gly His Ile Ile Val Glu Pro Asp Thr Gly Phe Glu
                165                 170                 175
Cys Thr Cys Gly Asn Lys Gly Cys Leu Glu Thr Val Ala Ser Ala Thr
                180                 185                 190
Gly Ile Val Arg Val Ala His His Leu Ala Glu Lys Tyr Glu Gly Asn
                195                 200                 205
Ser Ser Ile Lys Ala Ala Val Asp Asn Gly Glu Leu Val Thr Ser Lys
    210                 215                 220
Asp Ile Leu Val Ala Ala Thr Glu Gly Asp Lys Phe Ala Asp Ser Ile
225                 230                 235                 240
Val Asp Lys Val Ser Lys Tyr Leu Gly Leu Ala Ile Ala Asn Ile Ser
                245                 250                 255
Asn Ile Leu Asn Pro Asp Ser Val Val Ile Gly Gly Gly Val Ser Ala
                260                 265                 270
Ala Gly Glu Phe Leu Arg Ser Arg Val Glu Gly Tyr Phe Thr Arg Tyr
    275                 280                 285
Ala Phe Pro Gln Val Arg Arg Thr Thr Lys Val Lys Leu Ala Glu Leu
    290                 295                 300
Gly Asn Asp Ala Gly Ile Ile Gly Ala Ala Ser Leu Ala Tyr Ser Ile
305                 310                 315                 320
Asp Lys

<210> SEQ ID NO 62
<211> LENGTH: 322
<212> TYPE: PRT
<213> ORGANISM: Streptococcus thermophilus

<400> SEQUENCE: 62

Met Ser Lys Lys Leu Leu Gly Ile Asp Leu Gly Gly Thr Thr Val Lys
1               5                   10                  15
Phe Gly Ile Leu Asn Ala Asp Gly Glu Val Gln Glu Lys Trp Ala Ile
                20                  25                  30
Gly Thr Asn Thr Phe Glu Asn Gly Ser His Ile Val Pro Asp Ile Val
                35                  40                  45
Glu Ser Leu Lys His Arg Leu Glu Leu Tyr Gly Leu Thr Ala Glu Asp
    50                  55                  60
Phe Ile Gly Ile Gly Met Gly Ser Pro Gly Ala Val Asp Arg Glu Asn
65                  70                  75                  80
Lys Thr Val Thr Gly Ala Phe Asn Leu Asn Trp Ala Glu Thr Gln Glu
                85                  90                  95
Val Gly Ser Val Ile Glu Lys Glu Leu Gly Ile Pro Phe Ala Ile Asp
                100                 105                 110
Asn Asp Ala Asn Val Ala Ala Leu Gly Glu Arg Trp Val Gly Ala Gly
                115                 120                 125
Ala Asn Asn Arg Asn Val Val Phe Val Thr Leu Gly Thr Gly Val Ser
    130                 135                 140
Gly Gly Val Ile Val Asp Gly Lys Leu Ile His Gly Val Ala Gly Ala
145                 150                 155                 160
Gly Gly Glu Ile Gly His Ile Ile Val Glu Pro Asp Thr Gly Phe Glu
                165                 170                 175
```

-continued

```
Cys Thr Cys Gly Asn Lys Gly Cys Leu Glu Thr Val Ala Ser Ala Thr
                180                 185                 190
Gly Ile Val Arg Ile Ala His His Leu Ala Glu Lys Tyr Glu Gly Asn
            195                 200                 205
Ser Ser Ile Lys Ala Ala Val Asp Asn Gly Glu Phe Val Thr Ser Lys
210                 215                 220
Asp Ile Ile Val Ala Ala Thr Glu Gly Asp Lys Phe Ala Asp Ser Ile
225                 230                 235                 240
Val Asp Lys Val Ser Lys Tyr Leu Gly Leu Ala Thr Ala Asn Ile Ser
                245                 250                 255
Asn Ile Leu Asn Pro Asp Ser Val Val Ile Gly Gly Gly Val Ser Ala
                260                 265                 270
Ala Gly Glu Phe Leu Arg Ser Arg Val Glu Gly Tyr Phe Thr Arg Tyr
            275                 280                 285
Ala Phe Pro Gln Val Arg Arg Thr Thr Lys Val Lys Leu Ala Glu Leu
            290                 295                 300
Gly Asn Asp Ala Gly Ile Ile Gly Ala Ala Ser Leu Ala Tyr Ser Ile
305                 310                 315                 320
Asp Lys

<210> SEQ ID NO 63
<211> LENGTH: 322
<212> TYPE: PRT
<213> ORGANISM: Streptococcus thermophilus

<400> SEQUENCE: 63

Met Ser Lys Lys Leu Leu Gly Ile Asp Leu Gly Thr Thr Val Lys
1               5                   10                  15
Phe Gly Ile Leu Thr Ala Asp Gly Glu Val Gln Glu Lys Trp Ala Ile
                20                  25                  30
Glu Thr Asn Thr Phe Asp Asn Gly Ser His Ile Val Pro Asp Ile Val
            35                  40                  45
Glu Ser Leu Lys His Arg Leu Glu Leu Tyr Gly Leu Thr Ala Glu Asp
        50                  55                  60
Phe Ile Gly Ile Gly Met Gly Ser Pro Gly Ala Val Asp Arg Glu Asn
65                  70                  75                  80
Lys Thr Val Thr Gly Ala Phe Asn Leu Asn Trp Ala Glu Thr Gln Glu
                85                  90                  95
Val Gly Ser Val Ile Glu Lys Glu Leu Gly Ile Pro Phe Ala Ile Asp
            100                 105                 110
Asn Asp Ala Asn Val Ala Ala Leu Gly Glu Arg Trp Val Gly Ala Gly
        115                 120                 125
Ala Asn Ser Arg Asp Val Val Phe Val Thr Leu Gly Thr Gly Val Ser
130                 135                 140
Gly Gly Val Ile Ala Asp Gly Asn Leu Ile His Gly Val Ala Gly Ala
145                 150                 155                 160
Gly Gly Glu Ile Gly His Ile Ile Val Glu Pro Asp Thr Gly Phe Glu
                165                 170                 175
Cys Thr Cys Gly Asn Lys Gly Cys Leu Glu Thr Val Ala Ser Ala Thr
            180                 185                 190
Gly Ile Val Arg Val Ala His His Leu Ala Glu Lys Tyr Glu Gly Asn
        195                 200                 205
Ser Ser Ile Lys Ala Ala Val Asp Asn Gly Glu Leu Val Thr Ser Lys
210                 215                 220
```

```
Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Ile Ala Asn Ile Ser
                245                 250                 255

Asn Ile Leu Asn Pro Asp Ser Val Val Ile Gly Gly Val Ser Ala
            260                 265                 270

Ala Gly Glu Phe Leu Arg Ser Arg Val Glu Gly Tyr Phe Thr Arg Tyr
        275                 280                 285

Ala Phe Pro Gln Val Arg Arg Thr Thr Lys Val Lys Leu Ala Glu Leu
        290                 295                 300

Gly Asn Asp Ala Gly Ile Ile Gly Ala Ala Ser Leu Ala Tyr Ser Ile
305                 310                 315                 320

Asp Lys

<210> SEQ ID NO 64
<211> LENGTH: 322
<212> TYPE: PRT
<213> ORGANISM: Streptococcus thermophilus

<400> SEQUENCE: 64

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
                20                  25                  30

Glu Thr Asn Thr Phe Asp Asn Gly Ser His Ile Val Pro Asp Ile Val
            35                  40                  45

Glu Ser Leu Lys His Arg Leu Glu Leu Tyr Gly Leu Thr Ala Glu Asp
        50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Ile Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asp Val Val Phe Val Thr Leu Gly Thr Gly Val Ser
130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Leu Val Thr Ser Lys
210                 215                 220

Asp Ile Leu Val Ala Ala Thr Glu Gly Asp Lys Phe Ala Asp Ser Ile
225                 230                 235                 240

Val Asp Lys Val Ser Lys Tyr Leu Gly Leu Ala Ile Ala Asn Ile Ser
                245                 250                 255

Asn Ile Leu Asn Pro Asp Ser Val Ile Ile Gly Gly Val Ser Ala
            260                 265                 270
```

Ala Gly Glu Phe Leu Arg Ser Arg Val Glu Gly Tyr Phe Thr Arg Tyr
         275                 280                 285
Ala Phe Pro Gln Val Arg Arg Thr Thr Lys Val Lys Leu Ala Glu Leu
         290                 295                 300
Gly Asn Asp Ala Gly Ile Ile Gly Ala Ala Ser Leu Ala Tyr Ser Ile
305                 310                 315                 320
Asp Lys

<210> SEQ ID NO 65
<211> LENGTH: 1002
<212> TYPE: DNA
<213> ORGANISM: Streptococcus thermophilus

<400> SEQUENCE: 65

| | | | | | |
|---|---|---|---|---|---|
| atgaatactg | atgaaacaat | cacaatttat | gatgtagcgc | gtgaagctgg | agtatcgatg | 60 |
| gcaactgttt | ctcgtgttgt | aaatggtaac | aaaaacgtaa | agaaaacac | ccgaaaaaaa | 120 |
| gtgctcgaag | tcattgatcg | tttggattac | cgtccaaatg | cggttgcgcg | tggcttggca | 180 |
| agtaaaaaaa | caactactgt | aggagttgtc | attccaaata | ttgtaaatag | ctattttgct | 240 |
| actctagcta | aggtattga | tgacattgca | accatgtata | agtataatat | tgttcttgct | 300 |
| tccagtgatg | ataatgagga | tcatgaagtt | acagtcattc | attctctaat | ttctaaacaa | 360 |
| gttgatggta | ttatttttat | gggacaccat | ctgacagaaa | aaatccgtgc | agaattctct | 420 |
| cgtacccgta | caccgattgt | tctagcagga | acagttgatc | tcgaacacca | attaccaagt | 480 |
| gttaacatcg | actataaagc | tgccgttgag | gattgtgtaa | cgcaacttgc | taaaaataat | 540 |
| gaaaaggttg | cctttgtatc | aggaccacta | attgatgata | ttaatggcaa | actacgtttg | 600 |
| gccgggtata | agtctggact | tgaaaagaat | aatttgagct | acaacgaagg | acttgtcttt | 660 |
| gaagctaaat | atagctataa | agacggcttt | gagttagcac | aacgtgtctt | gaactctggt | 720 |
| gccactgctg | cctatgttgg | ggaagatgaa | ttggctgcag | gtctcttgaa | tggcctcttt | 780 |
| gctgcaggca | aatcagttcc | agaagatttc | gaaatcatca | caagcaatga | ttcaccggtt | 840 |
| acaagctaca | cacgtccaaa | cctttctagt | ataaaccatc | ctctctatga | tttaggggca | 900 |
| gttagcatgc | gtatgttgac | taaaattatg | cataaggaag | aacttgaaga | taaagacgtt | 960 |
| attcttaatc | atggtctaac | tttacgccag | tcaacaaaat | aa | | 1002 |

<210> SEQ ID NO 66
<211> LENGTH: 1002
<212> TYPE: DNA
<213> ORGANISM: Streptococcus thermophilus

<400> SEQUENCE: 66

| | | | | | |
|---|---|---|---|---|---|
| atgaatactg | atgaaacaat | cacaatttat | gatgtagcgc | gtgaagctgg | agtatcgatg | 60 |
| gcaactgttt | ctcgtgttgt | aaatggtaac | aaaaacgtaa | agaaaacac | ccgaaaaaaa | 120 |
| gtgctcgaag | tcattgatcg | tttggattac | cgtccaaatg | cggttgcgcg | tggcttggca | 180 |
| agtaaaaaaa | caactactgt | aggagttgtc | attccaaata | ttgtaaatag | ctattttgct | 240 |
| actctagcta | aggtattga | tgacattgca | accatgtata | agtataatat | tgttcttgct | 300 |
| tccagtgatg | ataatgagga | tcatgaagtt | acagtcattc | attctctaat | ttctaaacaa | 360 |
| gttgatggta | ttatttttat | gggacaccat | ctgacagaaa | aaatccgtgc | agaattctct | 420 |
| cgtacccgta | caccgattgt | tctagcagga | acagttgatc | tcgaacacca | attaccaagt | 480 |
| gttaacatcg | actataaagc | tgccgttgag | gattgtgtaa | cgcaacttgc | taaaaataat | 540 |

```
gaaaaggttg cctttgtatc aggaccacta attgatgata ttaatggcaa actacgtttg    600
gctgggtata agtctggact tgaaaagaat aatttgagct acaacgaagg acttgtcttt    660
gaagctaaat atagctataa agacggcttt gatttagcac aacgtgtctt gaactctggt    720
gccactgctg cctatgttgg ggaagatgaa ttggctgcag gtctcttgaa tggcctcttt    780
gctgcaggca aatcagttcc agaagatttc gaaatcatca caagcaatga ttcaccggtt    840
acaagctaca cacgtccaaa cctttctagt ataaaccatc ctctctatga tttaggggca    900
gttagcatgc gtatgttgac taaaattatg cataaggaag aacttgaaga taaagacgtt    960
attcttaatc atggtctaac tttacgccag tcaacaaaat aa                      1002
```

<210> SEQ ID NO 67
<211> LENGTH: 1002
<212> TYPE: DNA
<213> ORGANISM: Streptococcus thermophilus

<400> SEQUENCE: 67

```
atgaatactg atgaaacaat cacaatttat gatgtagcgc gtgaagctgg agtatcgatg     60
gcaactgttt ctcgtgttgt aaatggtaac aaaaacgtaa agaaaacac ccaaaaaaaa    120 gtgctcgaag tcattgatcg tttggattac cgtccaaatg cggttgcgcg tggcttggca    180
agtaaaaaaa caactactgt aggagttgtc attccaaata ttgtaaatag ctattttgct    240
actctagcta aaggtattga tgacattgca accatgtata agtataatat tgttcttgct    300
tccagtgatg ataatgagga tcatgaagtt acagtcattc attctctaat ttctaaacaa    360
gttgatggta ttattttat gggacaccat ctgacagaaa aaatccgtgc agaattctct    420
cgtacccgta caccgattgt tctagcagga acagttgatc tcgaacacca attaccaagt    480
gttaacatcg actataaagc tgccgttgag gattgtgtaa cgcaacttgc taaaaataat    540
gaaaaggttg cctttgtatc aggaccacta attgatgata ttaatggcaa actacgtttg    600
gctgggtata agtctggact tgaaaagaat aatttgagct acaacgaagg acttgtcttt    660
gaagctaaat atagctataa agacggcttt gagttagcac aacgtgtctt gaactctggt    720
gccactgctg cctatgttgg ggaagatgaa ttggctgcag gtctcttgaa tggcctcttt    780
gctgcaggca aatcagttcc agaagatttc gaaatcatca caagcaatga ttcaccggtt    840
acaagctaca cacgtccaaa cctttctagt ataaaccatc ctctctatga tttaggggca    900
gttagcatgc gtatgttgac taaaattatg cataaggaag aacttgaaga taaagacgtt    960
attcttaatc atggtctaac tttacgccag tcaacaaaat aa                      1002
```

<210> SEQ ID NO 68
<211> LENGTH: 1002
<212> TYPE: DNA
<213> ORGANISM: Streptococcus thermophilus

<400> SEQUENCE: 68

```
atgaatactg atgaaacaat cacaatttat gatgtagcgc gtgaagctgg agtatcgatg     60
gcaactgttt ctcgtgttgt aaatggtaac aaaaacgtaa agaaaacac ccgaaaaaaa    120 gtgctcgaag tcattgatcg tttggattac cgtccaaatg cggttgcgcg tggcttggca    180
agtaaaaaaa caactactgt aggagttgtc attccaaata ttgtaaatag ctattttgct    240
actctagcta aaggtattga tgacattgca accatgtata agtataatat tgttcttgct    300
tccagtgatg ataatgagga tcatgaagtt acagtcattc attctctaat ttctaaacaa    360
gttgatggta ttattttat gggacaccat ctgacagaaa aaatccgtgc agaattctct    420
```

| | |
|---|---|
| cgtacccgta caccgattgt tctagcagga acagttgatc tcgaacacca aatacccaagt | 480 |
| gttaacatcg actataaagc tgccgttgag gattgtgtaa cgcaacttgc taaaaataat | 540 |
| gaaaaggttg cctttgtatc aggaccacta attgatgata ttaatggcaa actacgtttg | 600 |
| gctgggtata agtctggact tgaaaagaat aatttgagct acaacgaagg acttgtcttt | 660 |
| gaagctaaat atagctataa agacggcttt gagttagcac aacgtgtctt gaactctggt | 720 |
| gccactgctg cctatgttgg ggaagatgaa ttggctgcag gtctcttgaa tggcctcttt | 780 |
| gctgcaggca aatcagttcc agaagatttc gaaatcatca caagcaatga ttcaccggtt | 840 |
| acaagctaca cacgtccaaa cctttctagt ataaaccatc ctctctatga tttaggggca | 900 |
| gttagcatgc gtatgttgac taaaattatg cataaggaag aacttgaaga gaaagacgtt | 960 |
| attcttaatc atggtctaac tttacgccag tcaacaaaat aa | 1002 |

<210> SEQ ID NO 69
<211> LENGTH: 1002
<212> TYPE: DNA
<213> ORGANISM: Streptococcus thermophilus

<400> SEQUENCE: 69

| | |
|---|---|
| atgaatactg atgaaacaat cacaatttat gatgtagcgc gtgaagctgg agtatcgatg | 60 |
| gcaactgttt ctcgtgttgt aaatggtaac aaaaacgtaa aagaaaacac ccgaaaaaaa | 120 |
| gtgctcgaag tcattgatcg tttggattac cgtccaaatg cggttgcgcg tggcttggca | 180 |
| agtaaaaaaa caactactgt aggagttgtc attccaaata ttgtaaatag ctattttgct | 240 |
| actctagcta aaggtattga tgacattgca accatgtata agtataatat tgttcttgct | 300 |
| tccagtgatg ataatgagga tcatgaagtt acagtcattc attctctaat ttctaaacaa | 360 |
| gttgatggta ttatttttat gggacaccat ctgacagaaa aaatccgtgc agaattctct | 420 |
| cgtacccgta caccgattgt tctagcagga acagttgatc tcgaacacca aatacccaagt | 480 |
| gttaacatcg actataaagc tgccgttgag gattgtgtaa cgcaacttgc taaaaataat | 540 |
| gaaaaggttg cctttgtatc aggaccacta attgatgata ttaatggcaa actacgtttg | 600 |
| gctgggtata agtctggact tgaaaagaat aatttgagct acaacgaagg acttgtcttt | 660 |
| gaagctaaat atagctataa agacggcttt gagttagcac aacgtgtctt gaactctggt | 720 |
| gccactgctg cctatgttgg ggaagatgaa ttggctgcag gtctcttgaa tggcctcttt | 780 |
| gctgcaggca aatcagttcc agaagatttc gaaatcatca caagcaatga ttcaccggtt | 840 |
| acaagctaca cacgtccaaa cctttctagt ataaaccatc ctctctatga tttaggggca | 900 |
| gttagcatgc gtatgttgac taaaattatg cataaggaag aacttgaaga taaagacgtt | 960 |
| attcttaatc atggtctaac tttacgccag tcaacaaaat aa | 1002 |

<210> SEQ ID NO 70
<211> LENGTH: 1002
<212> TYPE: DNA
<213> ORGANISM: Streptococcus thermophilus

<400> SEQUENCE: 70

| | |
|---|---|
| atgaatactg atgaaacaat cacaatttat gatgtagcgc gtgaagctgg agtatcgatg | 60 |
| gcaactgttt ctcgtgttgt aaatggtaac aaaaacgtaa aagaaaacac ccgaaaaaaa | 120 |
| gtgctcgaag tcattgatcg tttggattac cgtccaaatg cggttgcgcg tggcttggca | 180 |
| agtaaaaaaa caactactgt aggagttgtc attccaaata ttgtaaatag ctattttgct | 240 |

```
actctagcta aaggtattga tgacattgca accatgtata agtataatat tgttcttgct    300
tccagtgatg ataatgagga tcatgaagtt acagtcattc attctctaat ttctaaacaa    360
gttgatggta ttattttat gggacaccat ctgacagaaa aaatccgtgc agaattctct    420
cgtacccgta caccgattgt tctagcagga acagttgatc tcgaacacca attaccaagt    480
gttaacatcg actataaagc tgccgttgag gattgtgtaa tgcaacttgc taaaaataat    540
gaaaaggttg cctttgtatc aggaccacta attgatgata ttaatggcaa actacgtttg    600
gctgggtata agtctggact tgaaaagaat aatttgagct acaacgaagg acttgtcttt    660
gaagctaaat atagctataa agacggcttt gagttagcac aacgtgtctt gaactctggt    720
gccactgctg cctatgttgg ggaagatgaa ttggctgcag gtctcttgaa tggcctcttt    780
gctgcaggca atcagttcc agaagatttc gaaatcatca aagcaatga ttcaccggtt    840 acaagctaca cacgtccaaa cctttctagt ataaaccatc ctctctatga tttaggggca    900
gttagcatgc gtatgttgac taaaattatg cataaggaag aacttgaaga gaaagacgtt    960
attcttaatc atggtctaac tttacgccag tcaacaaaat aa                      1002

<210> SEQ ID NO 71
<211> LENGTH: 1001
<212> TYPE: DNA
<213> ORGANISM: Streptococcus thermophilus

<400> SEQUENCE: 71
atgaatactg atgaaacaat cacaatttat gatgtagcgc gtgaagctgg agtatcgatg     60
gcaactgttt ctcgtgttgt aaatggtaac aaaaacgtaa agaaaacac ccgaaaaaag    120 tgctcgaagt cattgatcgt ttggattacc gtccaaatgc ggttgcgcgt ggcttggcaa    180
gtaaaaaaac aactactgta ggagttgtca ttccaaatat tgtaaatagc tattttgcta    240
ctctagctaa aggtattgat gacattgcaa ccatgtataa gtataatatt gttcttgctt    300
ccagtgatga taatgaggat catgaagtta cagtcattca ttctctaatt tctaaacaag    360
ttgatggtat tatttttatg ggacaccatc tgacagaaaa aatccgtgca gaattctctc    420
gtacccgtac accgattgtt ctagcaggaa cagttgatct cgaacaccaa ttaccaagtg    480
ttaacatcga ctataaagct gccgttgagg attgtgtaac gcaacttgct aaaaataatg    540
aaaaggttgc ctttgtatca ggaccactaa ttgatgatat taatggcaaa ctacgtttgg    600
ccgggtataa gtctggactt gaaaagaata atttgagcta caacgaagga cttgtctttg    660
aagctaaata tagctataaa gacggctttg agttagcaca acgtgtcttg aactctggtg    720
ccactgctgc ctatgttggg gaagatgaat tggctgcagg tctcttgaat ggcctctttg    780
ctgcaggcaa atcagttcca gaagatttcg aaatcatcac aagcaatgat tcaccggtta    840
caagctacac acgtccaaac ctttctagta taaaccatcc tctctatgat ttaggggcag    900
ttagcatgcg tatgttgact aaaattatgc ataaggaaga acttgaagat aaagacgtta    960
ttcttaatca tggtctaact ttacgccagt caacaaaata a                       1001

<210> SEQ ID NO 72
<211> LENGTH: 1001
<212> TYPE: DNA
<213> ORGANISM: Streptococcus thermophilus

<400> SEQUENCE: 72
atgaatactg atgaaacaat cacaatttat gatgtagcgc gtgaagctgg agtatcgatg     60
gcaactgttt ctcgtgttgt aaatggtaac aaaaacgtaa agaaaacac ccgaaaaaag    120
```

```
tgctcgaagt cattgatcgt ttggattacc gtccaaatgc ggttgcgcgt ggcttggcaa      180
gtaaaaaaac aactactgta ggagttgtca ttccaaatat tgtaaatagc tattttgcta      240
ctctagctaa aggtattgat gacattgcaa ccatgtataa gtataatatt gttcttgctt      300
ccagtgatga taatgaggat catgaagtta cagtcattca ttctctaatt tctaaacaag      360
ttgatggtat tattttatg ggacaccatc tgacagaaaa aatccgtgca gaattctctc       420
gtacccgtac accgattgtt ctagcaggaa cagttgatct cgaacaccaa ttaccaagtg      480
ttaacatcga ctataaagct gccgttgagg attgtgtaac gcaacttgct aaaaataatg      540
aaaaggttgc ctttgtatca ggaccactaa ttgatgatat taatggcaaa ctacgtttgg      600
ctgggtataa gtctggactt gaaaagaata atttgagcta caacgaagga cttgtctttg      660
aagctaaata tagctataaa gacggctttg atttagcaca acgtgtcttg aactctggtg      720
ccactgctgc ctatgttggg gaagatgaat tggctgcagg tctcttgaat ggcctctttg      780
ctgcaggcaa atcagttcca gaagatttcg aaatcatcac aagcaatgat tcaccggtta      840
caagctacac acgtccaaac ctttctagta taaaccatcc tctctatgat ttaggggcag      900
ttagcatgcg tatgttgact aaaattatgc ataaggaaga acttgaagat aaagacgtta      960
ttcttaatca tggtctaact ttacgccagt caacaaaata a                          1001
```

<210> SEQ ID NO 73
<211> LENGTH: 1001
<212> TYPE: DNA
<213> ORGANISM: Streptococcus thermophilus

<400> SEQUENCE: 73

```
atgaatactg atgaaacaat cacaatttat gatgtagcgc gtgaagctgg agtatcgatg       60
gcaactgttt ctcgtgttgt aaatggtaac aaaaacgtaa aagaaaacac ccaaaaaaag      120
tgctcgaagt cattgatcgt ttggattacc gtccaaatgc ggttgcgcgt ggcttggcaa      180
gtaaaaaaac aactactgta ggagttgtca ttccaaatat tgtaaatagc tattttgcta      240
ctctagctaa aggtattgat gacattgcaa ccatgtataa gtataatatt gttcttgctt      300
ccagtgatga taatgaggat catgaagtta cagtcattca ttctctaatt tctaaacaag      360
ttgatggtat tattttatg ggacaccatc tgacagaaaa aatccgtgca gaattctctc       420
gtacccgtac accgattgtt ctagcaggaa cagttgatct cgaacaccaa ttaccaagtg      480
ttaacatcga ctataaagct gccgttgagg attgtgtaac gcaacttgct aaaaataatg      540
aaaaggttgc ctttgtatca ggaccactaa ttgatgatat taatggcaaa ctacgtttgg      600
ctgggtataa gtctggactt gaaaagaata atttgagcta caacgaagga cttgtctttg      660
aagctaaata tagctataaa gacggctttg agttagcaca acgtgtcttg aactctggtg      720
ccactgctgc ctatgttggg gaagatgaat tggctgcagg tctcttgaat ggcctctttg      780
ctgcaggcaa atcagttcca gaagatttcg aaatcatcac aagcaatgat tcaccggtta      840
caagctacac acgtccaaac ctttctagta taaaccatcc tctctatgat ttaggggcag      900
ttagcatgcg tatgttgact aaaattatgc ataaggaaga acttgaagat aaagacgtta      960
ttcttaatca tggtctaact ttacgccagt caacaaaata a                          1001
```

<210> SEQ ID NO 74
<211> LENGTH: 1001
<212> TYPE: DNA
<213> ORGANISM: Streptococcus thermophilus

<400> SEQUENCE: 74

```
atgaatactg atgaaacaat cacaatttat gatgtagcgc gtgaagctgg agtatcgatg      60
gcaactgttt ctcgtgttgt aaatggtaac aaaaacgtaa agaaaacac ccgaaaaaag     120
tgctcgaagt cattgatcgt ttggattacc gtccaaatgc ggttgcgcgt ggcttggcaa    180
gtaaaaaaac aactactgta ggagttgtca ttccaaatat tgtaaatagc tattttgcta    240
ctctagctaa aggtattgat gacattgcaa ccatgtataa gtataatatt gttcttgctt    300
ccagtgatga taatgaggat catgaagtta cagtcattca ttctctaatt tctaaacaag    360
ttgatggtat tattttatg ggacaccatc tgacagaaaa aatccgtgca gaattctctc     420
gtacccgtac accgattgtt ctagcaggaa cagttgatct cgaacaccaa ataccaagtg    480
ttaacatcga ctataaagct gccgttgagg attgtgtaac gcaacttgct aaaaataatg    540
aaaaggttgc ctttgtatca ggaccactaa ttgatgatat taatggcaaa ctacgtttgg    600
ctgggtataa gtctggactt gaaaagaata atttgagcta caacgaagga cttgtctttg    660
aagctaaata tagctataaa gacggctttg agttagcaca acgtgtcttg aactctggtg    720
ccactgctgc ctatgttggg gaagatgaat tggctgcagg tctcttgaat ggcctctttg    780
ctgcaggcaa atcagttcca gaagatttcg aaatcatcac aagcaatgat tcaccggtta    840
caagctacac acgtccaaac cttcctagta taaaccatcc tctctatgat ttaggggcag    900
ttagcatgcg tatgttgact aaaattatgc ataaggaaga acttgaagag aaagacgtta    960
ttcttaatca tggtctaact ttacgccagt caacaaaata a                       1001
```

<210> SEQ ID NO 75
<211> LENGTH: 1001
<212> TYPE: DNA
<213> ORGANISM: Streptococcus thermophilus

<400> SEQUENCE: 75

```
atgaatactg atgaaacaat cacaatttat gatgtagcgc gtgaagctgg agtatcgatg      60
gcaactgttt ctcgtgttgt aaatggtaac aaaaacgtaa agaaaacac ccgaaaaaag     120
tgctcgaagt cattgatcgt ttggattacc gtccaaatgc ggttgcgcgt ggcttggcaa    180
gtaaaaaaac aactactgta ggagttgtca ttccaaatat tgtaaatagc tattttgcta    240
ctctagctaa aggtattgat gacattgcaa ccatgtataa gtataatatt gttcttgctt    300
ccagtgatga taatgaggat catgaagtta cagtcattca ttctctaatt tctaaacaag    360
ttgatggtat tattttatg ggacaccatc tgacagaaaa aatccgtgca gaattctctc     420
gtacccgtac accgattgtt ctagcaggaa cagttgatct cgaacaccaa ataccaagtg    480
ttaacatcga ctataaagct gccgttgagg attgtgtaac gcaacttgct aaaaataatg    540
aaaaggttgc ctttgtatca ggaccactaa ttgatgatat taatggcaaa ctacgtttgg    600
ctgggtataa gtctggactt gaaaagaata atttgagcta caacgaagga cttgtctttg    660
aagctaaata tagctataaa gacggctttg agttagcaca acgtgtcttg aactctggtg    720
ccactgctgc ctatgttggg gaagatgaat tggctgcagg tctcttgaat ggcctctttg    780
ctgcaggcaa atcagttcca gaagatttcg aaatcatcac aagcaatgat tcaccggtta    840
caagctacac acgtccaaac cttcctagta taaaccatcc tctctatgat ttaggggcag    900
ttagcatgcg tatgttgact aaaattatgc ataaggaaga acttgaagat aaagacgtta    960
ttcttaatca tggtctaact ttacgccagt caacaaaata a                       1001
```

<210> SEQ ID NO 76
<211> LENGTH: 1001
<212> TYPE: DNA
<213> ORGANISM: Streptococcus thermophilus

<400> SEQUENCE: 76

```
atgaatactg atgaaacaat cacaatttat gatgtagcgc gtgaagctgg agtatcgatg      60
gcaactgttt ctcgtgttgt aaatggtaac aaaaacgtaa agaaaacac  ccgaaaaaag    120
tgctcgaagt cattgatcgt ttggattacc gtccaaatgc ggttgcgcgt ggcttggcaa    180
gtaaaaaaac aactactgta ggagttgtca ttccaaatat tgtaaatagc tattttgcta    240
ctctagctaa aggtattgat gacattgcaa ccatgtataa gtataatatt gttcttgctt    300
ccagtgatga taatgaggat catgaagtta cagtcattca ttctctaatt tctaaacaag    360
ttgatggtat tatttttatg ggacaccatc tgacagaaaa aatccgtgca gaattctctc    420
gtacccgtac accgattgtt ctagcaggaa cagttgatct cgaacaccaa ttaccaagtg    480
ttaacatcga ctataaagct gccgttgagg attgtgtaat gcaacttgct aaaaataatg    540
aaaaggttgc ctttgtatca ggaccactaa ttgatgatat taatggcaaa ctacgtttgg    600
ctgggtataa gtctggactt gaaaagaata atttgagcta caacgaagga cttgtctttg    660
aagctaaata tagctataaa gacggctttg agttagcaca acgtgtcttg aactctggtg    720
ccactgctgc ctatgttggg gaagatgaat tggctgcagg tctcttgaat ggcctctttg    780
ctgcaggcaa atcagttcca gaagatttcg aaatcatcac aagcaatgat tcaccggtta    840
caagctacac acgtccaaac ctttctagta taaaccatcc tctctatgat ttaggggcag    900
ttagcatgcg tatgttgact aaaattatgc ataaggaaga acttgaagag aaagacgtta    960
ttcttaatca tggtctaact ttacgccagt caacaaaata a                      1001
```

<210> SEQ ID NO 77
<211> LENGTH: 993
<212> TYPE: DNA
<213> ORGANISM: Streptococcus thermophilus

<400> SEQUENCE: 77

```
atgggtatcg gtattattat tgccagccat ggtaggttcg ctgaaggaat ccaccaatca      60
ggctctatga ttttggggga ccaagagaaa gttcaagttg tgactttcat gccaagtgaa    120
ggtcctgatg atttgtacgc tcacttcaac aacgccattg cacaattcga tgttgatgat    180
gaaattcttg ttttggctga cctttggagt ggttcaccat ttaaccaagc tagtcgaatc    240
gctagggaaa atccagatcg caagattgct atcatcacag acttaacttg gccaatgcta    300
atccaagcat acactgaacg tatgatggat gctaacgcta ctgtagagca agttgctgct    360
aatatcatca aggaagctaa gggtggtatc aaggcacttc cagaagagct aaatccagct    420
gaggaaacaa ctgcagctcc tgtagaagct gcagcacctc aaggagctat ccctgaagga    480
acagtcatcg gagatggtaa actcaagatt aacttggcac gtttggacac acgtctcttg    540
catggtcaag tagtaactaa ctgggtacct tattctaaag cagaccgtat tattgttgct    600
tcggatgacg ttgccaaaga tgagcttcgt aaggaattga tcaaacaggc tgcaccaaac    660
ggtattaaag taaacgttgt tccgattcaa aaattaattg atgcttctaa agacccacgt    720
tttggaaata cacatgcgct tgtcttgttc gaaactgttc aagacgcact tcgtgctatc    780
gaaggtggcg tgccaataaa agaacttaac gttggttcta tggctcactc aactggtaaa    840
acaatggtta acaacgtttt gtctatggat aaagatgatg ttgcttgttt tgaaaaatta    900
```

```
cgtgaccttg gcgttgaatt tgacgtccgt aaggttccaa acgattctaa gaaagatttg    960
tttgagctta tcaagaaagc taacgttcaa taa                                 993
```

<210> SEQ ID NO 78
<211> LENGTH: 330
<212> TYPE: PRT
<213> ORGANISM: Streptococcus thermophilus

<400> SEQUENCE: 78

```
Met Gly Ile Gly Ile Ile Ala Ser His Gly Arg Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Asn Ala Ile Ala Gln Phe Asp Val Asp Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Gly
        115                 120                 125

Gly Ile Lys Ala Leu Pro Glu Glu Leu Asn Pro Ala Glu Glu Thr Thr
    130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Asp Val Ala Lys Asp Glu
        195                 200                 205

Leu Arg Lys Glu Leu Ile Lys Gln Ala Ala Pro Asn Gly Ile Lys Val
    210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
    290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330
```

<210> SEQ ID NO 79
<211> LENGTH: 993
<212> TYPE: DNA

<213> ORGANISM: Streptococcus thermophilus

<400> SEQUENCE: 79

```
atgggtatcg gtattattat tgccagccat ggtaagttcg ctgaaggaat ccaccaatca      60
ggctctatga tttttgggga ccaagagaaa gttcaagttg tgactttcat gccaagtgaa     120
ggtcctgatg atttgtacgc tcacttcaac aacgccattg cacaattcga tgttgatgat     180
gaaattcttg ttttggctga cctttggagt ggttcaccat taaccaagc tagtcgaatc     240
gctagggaaa acccagatcg caagattgct atcatcacag acttaactt gccaatgcta     300
atccaagcat acactgaacg tatgatggat gctaacgcta ctgtagagca agttgctgct     360
aatatcatca aggaagctaa ggctggtatc aaggcacttc cagaggcgct aaatccagct     420
gaggaaacaa ctgcagctcc tgtagaagct gcagcacctc aaggagctat ccctgaagga     480
acagtcatcg gagatggtaa actcaagatt aacttggcac gtttggacac acgtctcttg     540
catggtcaag tagtaactaa ctgggtacct tattctaaag cagaccgtat tattgttgct     600
tcggatgacg ttgccaaaga tgagcttcgt aaggaattga tcaaacaggc tgcaccaaac     660
ggtattaaag taacgttgt tccgattcaa aaattaattg atgcttctaa agacccacgt     720
tttggaaata cacatgcgct tgtcttgttc gaaactgttc aagacgcact tcgtgctatc     780
gaaggtggcg tgccaataaa agaacttaac gttggttcta tggctcactc aactggtaaa     840
acaatggtta caacgttttt gtctatggat aaagatgatg ttgcttgttt tgaaaaatta     900
cgtgaccttg gcgttgaatt tgacgtccgt aaggttccaa acgattctaa gaaagacttg     960
tttgagctta tcaagaaagc taacgttcaa taa                                   993
```

<210> SEQ ID NO 80
<211> LENGTH: 330
<212> TYPE: PRT
<213> ORGANISM: Streptococcus thermophilus

<400> SEQUENCE: 80

```
Met Gly Ile Gly Ile Ile Ile Ala Ser His Gly Lys Phe Ala Glu Gly
  1               5                  10                  15

Ile His Gln Ser Gly Ser Met Ile Phe Gly Asp Gln Glu Lys Val Gln
             20                  25                  30

Val Val Thr Phe Met Pro Ser Glu Gly Pro Asp Asp Leu Tyr Ala His
         35                  40                  45

Phe Asn Asn Ala Ile Ala Gln Phe Asp Val Asp Glu Ile Leu Val
     50                  55                  60

Leu Ala Asp Leu Trp Ser Gly Ser Pro Phe Asn Gln Ala Ser Arg Ile
 65                  70                  75                  80

Ala Arg Glu Asn Pro Asp Arg Lys Ile Ala Ile Ile Thr Gly Leu Asn
                 85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Ala
        115                 120                 125

Gly Ile Lys Ala Leu Pro Glu Ala Leu Asn Pro Ala Glu Glu Thr Thr
    130                 135                 140

Ala Ala Pro Val Glu Ala Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175
```

```
Thr Arg Leu Leu His Gly Gln Val Val Thr Asn Trp Val Pro Tyr Ser
            180                 185                 190

Lys Ala Asp Arg Ile Ile Val Ala Ser Asp Asp Val Ala Lys Asp Glu
            195                 200                 205

Leu Arg Lys Glu Leu Ile Lys Gln Ala Ala Pro Asn Gly Ile Lys Val
            210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
            275                 280                 285

Met Asp Lys Asp Asp Val Ala Cys Phe Glu Lys Leu Arg Asp Leu Gly
            290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
            325                 330
```

<210> SEQ ID NO 81
<211> LENGTH: 993
<212> TYPE: DNA
<213> ORGANISM: Streptococcus thermophilus

<400> SEQUENCE: 81

```
atgggtatcg gtattattat tgccagccat ggtaagttcg ctgaaggaat ccaccaatca    60
ggctctatga tttttgggga ccaagagaaa gttcaagttg tgactttcat gccaagtgaa   120
ggtcctgatg atttgtacgc tcacttcaac aacgccattg cacaattcga tgttgatgat   180
gaaattcttg ttttggctga ccttggagt ggttcaccat ttaaccaagc tagtcgaatc    240
gctagggaaa atccagatcg caagattgct atcatcacag gacttaactt gccaatgcta   300
atccaagcat acactgaacg tatgatggat gctaacgcta ctgtagagca agttgctgct   360
aatatcatca aggaagctaa gggtggtatc aaggcacttc agaagagct aaatccagct    420
gaggaaacaa ctgcagctcc tgtagaagct gcagcacctc aaggagctat ccctgaagga   480
acagtcatcg gagatggtaa actcaagatt aacttggcac gtttggacac acgtctcttg   540
catggtcaag tagtaactaa ctgggtacct tattctaaag cagaccgtat tattgttgct   600
tcggatgacg ttgccaaaga tgagcttcgt aaggaattga tcaaacaggc tgcaccaaac   660
ggtattaaag taacgttgt tccgattcaa aaattaattg atgcttctaa agacccacgt    720
tttggaaata cacatgcgct tgtcttgttc gaaactgttc aagacgcact tcgtgctatc   780
gaaggtggcg tgccaataaa agaacttaac gttggttcta tggctcactc aactggtaaa   840
acaatggtta caacgttttt gtctatggat aaagatgatg ttgcttgttt tgaaaaatta   900
cgtgacctttg gcgttgaatt tgacgtccgt aaggttccaa acgattctaa gaaagatttg   960
tttgagctta tcaagaaagc taacgttcaa taa                                993
```

<210> SEQ ID NO 82
<211> LENGTH: 330
<212> TYPE: PRT
<213> ORGANISM: Streptococcus thermophilus

<400> SEQUENCE: 82

```
Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
                20                  25                  30

Val Val Thr Phe Met Pro Ser Glu Gly Pro Asp Asp Leu Tyr Ala His
            35                  40                  45

Phe Asn Asn Ala Ile Ala Gln Phe Asp Val Asp Glu Ile Leu Val
50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Asn Ile Ile Lys Glu Ala Lys Gly
        115                 120                 125

Gly Ile Lys Ala Leu Pro Glu Glu Leu Asn Pro Ala Glu Thr Thr
130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205

Leu Arg Lys Glu Leu Ile Lys Gln Ala Ala Pro Asn Gly Ile Lys Val
210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Leu Arg Asp Leu Gly
290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330

<210> SEQ ID NO 83
<211> LENGTH: 993
<212> TYPE: DNA
<213> ORGANISM: Streptococcus thermophilus

<400> SEQUENCE: 83
atgggtatcg gtattattat tgccagccat ggtaagttcg ctgaaggaat ccaccaatca      60
ggctctatga ttttgggga ccaagagaaa gttcaagttg tgactttcat gccaagtgaa     120
ggtcctgatg atttgtacgc tcacttcaac aaagccattg cacaattcga tgttgatgat     180
gaaattcttg ttttggctga cctttggagt ggttcaccat taaccaagc tagtcgaatc      240
```

-continued

```
gctagggaaa atccagatcg caagattgct atcatcacag gacttaactt gccaatgcta      300
atccaagcat acactgaacg tatgatggat gctaacgcta ctgtagagca agttgctgct      360
aatatcatca aggaagctaa gggtggtatc aaggcacttc cagaggagct aaatccagct      420
gaggaaacaa ctgcagctcc tgtagaagct gcagcacctc aaggagctat ccctgaagga      480
acagtcatcg gagatggtaa actcaagatt aacttggcac gtttggacac acgtctcttg      540
catggtcaag tagtaactaa ctgggtacct tattctaaag cagaccgtat tattgttgct      600
tcggatgacg ttgccaaaga tgagcttcgt aaggaattga tcaaacaggc tgcaccaaac      660
ggtattaaag taaacgttgt tccgattcaa aaattaattg atgcttctaa agacccacgt      720
tttggaaata cacatgcact tgtcttgttc gaaactgttc aagacgtact tcgtgctgtc      780
gaaggtggcg tgccaataaa agaacttaac gttggttcta tggctcactc aactggtaaa      840
acaatggtta acaacgtttt gtctatggat aaagatgatg ttgcttgttt tgaaaaatta      900
cgtgaccttg gcgttgaatt tgacgtccgt aaggttccaa acgattctaa gaaagacttg      960
tttgagctta tcaagaaagc taacgttcaa taa                                   993
```

<210> SEQ ID NO 84
<211> LENGTH: 330
<212> TYPE: PRT
<213> ORGANISM: Streptococcus thermophilus

<400> SEQUENCE: 84

```
Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
                20                  25                  30

Val Val Thr Phe Met Pro Ser Glu Gly Pro Asp Asp Leu Tyr Ala His
                35                  40                  45

Phe Asn Lys Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
                100                 105                 110

Ala Thr Val Glu Gln Val Ala Ala Asn Ile Ile Lys Glu Ala Lys Gly
            115                 120                 125

Gly Ile Lys Ala Leu Pro Glu Glu Leu Asn Pro Ala Glu Glu Thr Thr
        130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205

Leu Arg Lys Glu Leu Ile Lys Gln Ala Ala Pro Asn Gly Ile Lys Val
    210                 215                 220

Asn Val Val Pro Ile Gln Lys Leu Ile Asp Ala Ser Lys Asp Pro Arg
225                 230                 235                 240
```

```
Phe Gly Asn Thr His Ala Leu Val Leu Phe Glu Thr Val Gln Asp Val
                245                 250                 255

Leu Arg Ala Val Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330

<210> SEQ ID NO 85
<211> LENGTH: 993
<212> TYPE: DNA
<213> ORGANISM: Streptococcus thermophilus

<400> SEQUENCE: 85
atgggtatcg gtattattat tgccagccat ggtaagttcg ctgaaggaat ccaccaatca    60
ggctctatga ttttggggga ccaagagaaa gttcaagttg tgactttcat gccaagtgaa   120
ggtcctgatg atttgtacgc tcacttcaac aacgccattg cacaattcga tgttgatgat   180
gaaattcttg ttttggctga cctttggagt ggttcaccat taaccaagc tagtcgaatc    240 gctagggaaa acccagatcg caagattgct atcatcacag acttaacttg ccaatgcta    300 atccaagcat acactgaacg tatgatggat gctaacgcta ctatagagca gttgctgct    360 aatatcatca aggaagctaa gggtggtatc aaggcacttc cagaggcgct aaatccagct   420
gaggaaacaa ctgcagctcc tgtagaagct gcagcacctc aaggagctat ccctgaagga   480
acagtcatcg agatggtaa actcaagatt aacttggcac gtttggacac acgtctcttg    540
catggtcaag tagtaactaa ctgggtacct tattctaaag cagaccgtgt tattgttgct   600
tcggatgacg ttgccaaaga tgagcttcgt aaggaattga tcaaacaggc tgcaccaaac   660
ggtattaaag taaacgttgt tccgattcaa aaattaattg atgcttctaa agacccacgt   720
tttggaaata cacatgcgct tgtcttgttc gaaactgttc aagacgcact tcgtgctatc   780
gaaggtggcg tgccaataaa agaacttaac gttggttcta ggctcactc aactggtaaa    840 acaatggtta caacgttttt gtctatggat aaagatgatg ttgcttgttt tgaaaaatta   900
cgtgaccttg gcgttgaatt tgacgtccgt aaggttccaa acgattctaa gaaagacttg   960
tttgagctta tcaagaaagc taacgttcaa taa                                993

<210> SEQ ID NO 86
<211> LENGTH: 330
<212> TYPE: PRT
<213> ORGANISM: Streptococcus thermophilus

<400> SEQUENCE: 86

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
                20                  25                  30

Val Val Thr Phe Met Pro Ser Glu Gly Pro Asp Asp Leu Tyr Ala His
            35                  40                  45

Phe Asn Asn Ala Ile Ala Gln Phe Asp Val Asp Asp Glu Ile Leu Val
```

|     |     |     |     | 50  |     |     |     |     | 55  |     |     |     |     | 60  |     |     |
| --- | --- | --- | --- | --- | --- | --- | --- | --- | --- | --- | --- | --- | --- | --- | --- | --- |

Leu Ala Asp Leu Trp Ser Gly Ser Pro Phe Asn Gln Ala Ser Arg Ile
65                  70                          75                      80

Ala Arg Glu Asn Pro Asp Arg Lys Ile Ala Ile Ile Thr Gly Leu Asn
                        85                          90                          95

Leu Pro Met Leu Ile Gln Ala Tyr Thr Glu Arg Met Met Asp Ala Asn
                100                         105                         110

Ala Thr Ile Glu Gln Val Ala Ala Asn Ile Ile Lys Glu Ala Lys Gly
            115                         120                         125

Gly Ile Lys Ala Leu Pro Glu Ala Leu Asn Pro Ala Glu Glu Thr Thr
        130                         135                         140

Ala Ala Pro Val Glu Ala Ala Pro Gln Gly Ala Ile Pro Glu Gly
145                         150                         155                         160

Thr Val Ile Gly Asp Gly Lys Leu Lys Ile Asn Leu Ala Arg Leu Asp
                    165                         170                         175

Thr Arg Leu Leu His Gly Gln Val Val Thr Asn Trp Val Pro Tyr Ser
                180                         185                         190

Lys Ala Asp Arg Val Ile Val Ala Ser Asp Asp Val Ala Lys Asp Glu
            195                         200                         205

Leu Arg Lys Glu Leu Ile Lys Gln Ala Ala Pro Asn Gly Ile Lys Val
210                         215                         220

Asn Val Pro Ile Gln Lys Leu Ile Asp Ala Ser Lys Asp Pro Arg
225                         230                         235                         240

Phe Gly Asn Thr His Ala Leu Val Leu Phe Glu Thr Val Gln Asp Ala
                    245                         250                         255

Leu Arg Ala Ile Glu Gly Gly Val Pro Ile Lys Glu Leu Asn Val Gly
                260                         265                         270

Ser Met Ala His Ser Thr Gly Lys Thr Met Val Asn Asn Val Leu Ser
                275                         280                         285

Met Asp Lys Asp Asp Val Ala Cys Phe Glu Lys Leu Arg Asp Leu Gly
        290                         295                         300

Val Glu Phe Asp Val Arg Lys Val Pro Asn Asp Ser Lys Lys Asp Leu
305                         310                         315                         320

Phe Glu Leu Ile Lys Lys Ala Asn Val Gln
                325                         330

<210> SEQ ID NO 87
<211> LENGTH: 993
<212> TYPE: DNA
<213> ORGANISM: Streptococcus thermophilus

<400> SEQUENCE: 87

| | |
|---|---|
| atgggtatcg gtattattat cgccagccat ggtaagttcg ctgaaggaat ccaccaatca | 60 |
| ggctctatga tttttgggga ccaagagaaa gttcgagttg tgactttcat gccaagtgaa | 120 |
| ggtcctgatg atttgtacgc tcacttcaac aacgccattg cacaattcga tgttgatgat | 180 |
| gaaattcttg ttttggctga cctttggagt ggttcaccat ttaaccaagc tagtcgaatc | 240 |
| gctagggaaa acccagatcg caagattgct atcatcacag acttaacttt gccaatgcta | 300 |
| atccaagcat acactgaacg tatgatggat gctaacgcta ctgtagagca agttgctgct | 360 |
| aatatcatca aggaagctaa ggctggtatc aaggcacttc cagaggcgct aaatccagct | 420 |
| gaggaaacaa ctgcagctcc tgtagaagct gcagcacctc aaggagctat ccctgaagga | 480 |
| acagtcatcg gagatggtaa actcaagatt aacttggcac gtttggacac acgtctcttg | 540 |

```
catggtcaag tagtaactaa ctgggtacct tattctaaag cagaccgtat tattgttgct    600
tcggatgacg ttgccaaaga tgagcttcgt aaggaattga tcaaacaggc tgccaccaaac   660 ggtattaaag taaacgttgt tccgattcaa aaattaattg atgcttctaa agacccacgt    720
tttggaaata cacatgcgct tgtcttgttc gaaactgttc aagacgcgct tcgtgctatc    780
gaaggtggcg tgccaataaa agaacttaac gttggttcta tggctcactc aactggtaaa    840
acaatggtta acaacgtttt gtctatggat aaagatgatg ttgcttgttt tgaaaaatta    900
cgtgaccttg gcgttgaatt tgacgtccgt aaggttccaa acgattctaa gaaagacttg    960
tttgagctta tcaagaaagc taacgttcaa taa                                 993
```

<210> SEQ ID NO 88
<211> LENGTH: 330
<212> TYPE: PRT
<213> ORGANISM: Streptococcus thermophilus

<400> SEQUENCE: 88

```
Met Gly Ile Gly Ile Ile Ala Ser His Gly Lys Phe Ala Glu Gly
1               5                   10                  15

Ile His Gln Ser Gly Ser Met Ile Phe Gly Asp Gln Glu Lys Val Arg
            20                  25                  30

Val Val Thr Phe Met Pro Ser Glu Gly Pro Asp Asp Leu Tyr Ala His
        35                  40                  45

Phe Asn Asn Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Ala
        115                 120                 125

Gly Ile Lys Ala Leu Pro Glu Ala Leu Asn Pro Ala Glu Glu Thr Thr
    130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Pro Val Ala Lys Asp Glu
        195                 200                 205

Leu Arg Lys Glu Leu Ile Lys Gln Ala Ala Pro Asn Gly Ile Lys Val
    210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
```

```
             290                 295                 300
Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330

<210> SEQ ID NO 89
<211> LENGTH: 993
<212> TYPE: DNA
<213> ORGANISM: Streptococcus thermophilus

<400> SEQUENCE: 89
atgggtatcg gtattattat tgccagccat ggtaagttcg ctgaaggaat ccaccaatca    60
ggctctatga tttttgggga ccaagagaaa gttcaagttg tgactttcat gccaagtgaa   120
ggtcctgatg atttgtacgc tcacttcaac aacgccattg cacaattcga tgttgatgat   180
gaaattcttg ttttggctga cctttggagt ggttcaccat taaccaagc tagtcgaatc    240 gctagggaaa acccagatcg caagattgct atcatcacag acttaactt gccaatgcta    300 atccaagcat acactgaacg tatgatggat gctaacgcta ctgtagagca agttgctgct   360
aatatcatca aggaagctaa gggtggtatc aaggcacttc cagaggcgct aaatccagct   420
gaggaaacaa ctgcagctcc tgtagaagct gcagcacctc aaggagctat ccctgaagga   480
acagtcatcg agatggtaa actcaagatt aacttggcac gtttggacac acgtctcttg    540
catggtcaag tagtaactaa ctgggtacct tattctaaag cagaccgtat tattgttgct   600
tcggatgacg ttgccaaaga tgagcttcgt aaggaattga tcaaacaggc tgcaccaaac   660
ggtattaaag taacgttgt tccgattcaa aaattaattg atgcttctaa agaccccacgt   720 tttggaaata cacatgcgct tgtcttgttc gaaactgttc aagacgcact tcgtgctatc   780
gaaggtggcg tgccaataaa agaacttaac gttggttcta tggctcactc aactggtaaa   840
acaatggtta caacgttttt gtctatggat aaagatgatg ttgcttgttt tgaaaaatta   900
cgtgaccttg gcgttgaatt tgacgtccgt aaggttccaa acgattctaa gaaagacttg   960
tttgagctta tcaagaaagc taacgttcaa taa                                993

<210> SEQ ID NO 90
<211> LENGTH: 330
<212> TYPE: PRT
<213> ORGANISM: Streptococcus thermophilus

<400> SEQUENCE: 90

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
                20                  25                  30

Val Val Thr Phe Met Pro Ser Glu Gly Pro Asp Asp Leu Tyr Ala His
            35                  40                  45

Phe Asn Asn Ala Ile Ala Gln Phe Asp Val Asp Asp Glu Ile Leu Val
        50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Ile Thr Gly Leu Asn
                85                  90                  95

Leu Pro Met Leu Ile Gln Ala Tyr Thr Glu Arg Met Met Asp Ala Asn
                100                 105                 110
```

```
Ala Thr Val Glu Gln Val Ala Asn Ile Ile Lys Glu Ala Lys Gly
            115                 120                 125

Gly Ile Lys Ala Leu Pro Glu Ala Leu Asn Pro Ala Glu Glu Thr Thr
130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
                195                 200                 205

Leu Arg Lys Glu Leu Ile Lys Gln Ala Ala Pro Asn Gly Ile Lys Val
210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
275                 280                 285

Met Asp Lys Asp Asp Val Ala Cys Phe Glu Lys Leu Arg Asp Leu Gly
            290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330

<210> SEQ ID NO 91
<211> LENGTH: 993
<212> TYPE: DNA
<213> ORGANISM: Streptococcus thermophilus

<400> SEQUENCE: 91
atgggtatcg gtattattat tgccagccat ggtaagttcg ctgaaggaat ccaccaatca      60
ggctctatga ttttggggga ccaagagaaa gttcaagttg tgactttcat gccaagtgaa     120
ggtcctgatg atttgtacgc tcacttcaac aacgccattg cacaattcga tgttgatgat     180
gaaattcttg ttttggctga cctttggagt ggttcaccat taaccaagc tagtcgaatc      240 gctagggaaa acccagatcg caagattgct atcatcacag gacttaactt gccaatgcta     300
atccaagcat acactgaacg tatgatggat gctaacgcta ctgtagagca gttgctgct      360 aatatcatca aggaagctaa ggctggtatc aaggcacttc cagaggagct aaatccagct     420
gaggaaacaa ctgcagctcc tgtagaagct gcagcacctc aaggagctat ccctgaagga     480
acagtcatcg gagatggtaa actcaagatt aacttggcac gtttggacac acgtctcttg     540
catggtcaag tagtaactaa ctgggtacct tattctaaag cagaccgtat tattgttgct     600
tcggatgacg ttgccaaaga tgagcttcgt aaggaattga tcaaacaggc tgcaccaaac     660
ggtattaaag taacgttgt tccgattcaa aaattaattg atgcttctaa agacccacgt     720
tttggaaata cacatgcgct tgtcttgttc gaaactgttc aagacgcact tcgtgctatc     780
gaaggtggcg tgccaataaa agaacttaac gttggttcta tggctcactc aactggtaaa     840
acaatggtta caacgttttt gtctatggat aaagatgatg ttgcttgttt tgaaaaatta     900
```

```
cgtgaccttg gcgttgaatt tgacgtccgt aaggttccaa acgattctaa gaaagacttg      960
tttgagctta tcaagaaagc taacgttcaa taa                                   993
```

<210> SEQ ID NO 92
<211> LENGTH: 330
<212> TYPE: PRT
<213> ORGANISM: Streptococcus thermophilus

<400> SEQUENCE: 92

```
Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Asn Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Ala
        115                 120                 125

Gly Ile Lys Ala Leu Pro Glu Glu Leu Asn Pro Ala Glu Glu Thr Thr
    130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205

Leu Arg Lys Glu Leu Ile Lys Gln Ala Ala Pro Asn Gly Ile Lys Val
    210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
    290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330
```

<210> SEQ ID NO 93
<211> LENGTH: 993

<212> TYPE: DNA
<213> ORGANISM: Streptococcus thermophilus

<400> SEQUENCE: 93

```
atgggtatcg gtattattat tgccagccat ggtaagttcg ctgaaggaat ccaccaatca    60
ggctctatga ttttggggga ccaagagaaa gttcaagttg tgactttcat gccaagtgaa   120
ggtcctgatg atttgtacgc tcacttcaac aacgccattg cacaattcga tgttgatgat   180
gaaattcttg ttttggctga cctttggagt ggttcaccat ttaaccaagc tagtcgaatc   240
gctagggaaa acccagatcg caagattgct atcatcacag gacttaactt gccaatgcta   300
atccaagcat acactgaacg tatgatggat gctaacgcta ctatagagca agttgctgct   360
aatatcatca aggaagctaa gggtggtatc aaggcacttc cagaggcgct aaatccagct   420
gaggaaacaa ctgcagctcc tgtagaagct gcagcacctc aaggagctat ccctgaagga   480
acagtcatcg gagatggtaa actcaagatt aacttggcac gtttggacac acgtctcttg   540
catggtcaag tagtaactaa ctgggtacct tattctaaag cagaccgtat tattgttgct   600
tcggatgacg ttgccaaaga tgagcttcgt aaggaattga tcaaacaggc tgcaccaaac   660
ggtattaaag taaacgttgt tccgattcaa aaattaattg atgcttctaa agacccacgt   720
tttgaaaata cacatgcgct tgtcttgttc gaaactgttc aagacgcact tcgtgctatc   780
gaaggtggcg tgccaataaa agaacttaac gttggttcta tggctcactc aactggtaaa   840
acaatggtta caacgttttt gtctatggat aaagatgatg ttgcttgttt tgaaaaatta   900
cgtgaccttg gcgttgaatt tgacgtccgt aaggttccaa acgattctaa gaaagacttg   960
tttgagctta tcaagaaagc taacgttcaa taa                                993
```

<210> SEQ ID NO 94
<211> LENGTH: 330
<212> TYPE: PRT
<213> ORGANISM: Streptococcus thermophilus

<400> SEQUENCE: 94

```
Met Gly Ile Gly Ile Ile Ile Ala Ser His Gly Lys Phe Ala Glu Gly
1               5                   10                  15
Ile His Gln Ser Gly Ser Met Ile Phe Gly Asp Gln Glu Lys Val Gln
            20                  25                  30
Val Val Thr Phe Met Pro Ser Glu Gly Pro Asp Asp Leu Tyr Ala His
        35                  40                  45
Phe Asn Asn Ala Ile Ala Gln Phe Asp Val Asp Asp Glu Ile Leu Val
    50                  55                  60
Leu Ala Asp Leu Trp Ser Gly Ser Pro Phe Asn Gln Ala Ser Arg Ile
65                  70                  75                  80
Ala Arg Glu Asn Pro Asp Arg Lys Ile Ala Ile Thr Gly Leu Asn
                85                  90                  95
Leu Pro Met Leu Ile Gln Ala Tyr Thr Glu Arg Met Met Asp Ala Asn
            100                 105                 110
Ala Thr Ile Glu Gln Val Ala Ala Asn Ile Ile Lys Glu Ala Lys Gly
        115                 120                 125
Gly Ile Lys Ala Leu Pro Glu Ala Leu Asn Pro Ala Glu Glu Thr Thr
    130                 135                 140
Ala Ala Pro Val Glu Ala Ala Pro Gln Gly Ala Ile Pro Glu Gly
145                 150                 155                 160
Thr Val Ile Gly Asp Gly Lys Leu Lys Ile Asn Leu Ala Arg Leu Asp
                165                 170                 175
```

```
Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205

Leu Arg Lys Glu Leu Ile Lys Gln Ala Ala Pro Asn Gly Ile Lys Val
210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
        260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330

<210> SEQ ID NO 95
<211> LENGTH: 993
<212> TYPE: DNA
<213> ORGANISM: Streptococcus thermophilus

<400> SEQUENCE: 95
atgggtatcg gtattattat tgccagccat ggtaagttcg ctgaaggaat ccaccaatca    60
ggctctatga ttttttggga ccaagagaaa gttcaagttg tgactttcat gccaagtgaa   120
ggtcctgatg atttgtacgc tcacttcaac aacgccattg cacaattcga tgttgatgat   180
gaaattcttg ttttggctga ccttttggagt ggttcaccat taaccaagc tagtcgaatc   240 gctagggaaa acccagatcg caagattgct atcatcacag gacttaactt gccaatgcta   300
atccaagcat acactgaacg tatgatggat gctaacgcta ctgtagagca agttgttgct   360
aatatcatca aggaagctaa gggtggtatc aaggcacttc cagaggcgct aaatccagct   420
gaggaaacaa ctgcagctcc tgtagaagct gcagcacttc aaggagctat ccctgaagga   480
acagtcatcg agatggtaa actcaagatt aacttggcac gtttggacac acgtctcttg   540
catggtcaag tagtaactaa ctgggtacct tattctaaag cagaccgtat tattgttgct   600
tcggatgacg ttgccaaaga tgagcttcgt aaggaattga tcaaacaggc tgcaccaaac   660
ggtattaaag taaacgttgt tccgattcaa aaattaattg atgcttctaa agacccacgt   720
tttggaaata cacatgcgct tgtcttgttc gaaactgttc aagacgcact tcgtgctatc   780
gaaggtggcg tgccaataaa agaacttaac gttggttcta tggctcactc aactggtaaa   840
acaatggtta caacgttttt gtctatggat aaagatgatg ttgcttgttt tgaaaaatta   900
cgtgaccttg gcgttgaatt tgacgtccgt aaggttccaa acgattctaa gaaagacttg   960
tttgagctta tcaagaaagc taacgttcaa taa                                993

<210> SEQ ID NO 96
<211> LENGTH: 330
<212> TYPE: PRT
<213> ORGANISM: Streptococcus thermophilus
```

<400> SEQUENCE: 96

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Asn Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65              70                  75                  80

Ala Arg Glu Asn Pro Asp Arg Lys Ile Ala Ile Thr Gly Leu Asn
            85                  90                  95

Leu Pro Met Leu Ile Gln Ala Tyr Thr Glu Arg Met Met Asp Ala Asn
            100                 105                 110

Ala Thr Val Glu Gln Val Val Ala Asn Ile Ile Lys Glu Ala Lys Gly
        115                 120                 125

Gly Ile Lys Ala Leu Pro Glu Ala Leu Asn Pro Ala Glu Glu Thr Thr
130                 135                 140

Ala Ala Pro Val Glu Ala Ala Leu Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Asp Val Ala Lys Asp Glu
        195                 200                 205

Leu Arg Lys Glu Leu Ile Lys Gln Ala Ala Pro Asn Gly Ile Lys Val
210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330

<210> SEQ ID NO 97
<211> LENGTH: 993
<212> TYPE: DNA
<213> ORGANISM: Streptococcus thermophilus

<400> SEQUENCE: 97
atgggtatcg gtattattat tgccagccat ggtaagttcg ctgaaggaat ccaccaatca      60
ggctctatga ttttggggga ccaagagaaa gttcaagttg tgactttcat gccaagtgaa     120
ggtcctgatg atttgtacgc tcacttcaac aaagccattg cacaattcga tgttgatgat     180

-continued

```
gaaattcttg ttttggctga cctttggagt ggttcaccat ttaaccaagc tagtcgaatc    240
gctagggaaa atccagatcg caagattgct atcatcacag gacttaactt gccaatgcta    300
atccaagcat acactgaacg tatgatggat gctaacgcta ctgtagagca agttgctgct    360
aatatcatca aggaagctaa gggtggtatc aaggcacttc cagaggagct aaatccagct    420
gaggaaacaa ctgcagctcc tgtagaagct gcagcacctc aaggagctat ccctgaagga    480
acagtcatcg gagatggtaa actcaagatt aacttggcac gtttggacac acgtctcttg    540
catggtcaag tagtaactaa ctgggtacct tattctaaag cagaccgtat tattgttgct    600
tcggatgacg ttgccaaaga tgagcttcgt aaggaattga tcaaacaggc tgcaccaaac    660
ggtattaaag taaacgttgt tccgattcaa aaattagttg atgcttctaa agacccacgt    720
tttggaaata cacatgcact tgtcttgttc gaaactgttc aagacgtact tcgtgctgtc    780
gaaggtggcg tgccaataaa agaacttaac gttggttcta tggctcactc aactggtaaa    840
acaatggtta acaacgtttt gtctatggat aaagatgatg ttgcttgttt tgaaaaatta    900
cgtgaccttg gcgttgaatt tgacgtccgt aaggttccaa acgattctaa gaaagacttg    960
tttgagctta tcaagaaagc taacgttcaa taa                                 993
```

<210> SEQ ID NO 98
<211> LENGTH: 330
<212> TYPE: PRT
<213> ORGANISM: Streptococcus thermophilus

<400> SEQUENCE: 98

```
Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Lys Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Gly
        115                 120                 125

Gly Ile Lys Ala Leu Pro Glu Glu Leu Asn Pro Ala Glu Glu Thr Thr
    130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205

Leu Arg Lys Glu Leu Ile Lys Gln Ala Ala Pro Asn Gly Ile Lys Val
    210                 215                 220

Asn Val Val Pro Ile Gln Lys Leu Val Asp Ala Ser Lys Asp Pro Arg
```

```
                225                 230                 235                 240

Phe Gly Asn Thr His Ala Leu Val Leu Phe Glu Thr Val Gln Asp Val
                245                 250                 255

Leu Arg Ala Val Glu Gly Gly Val Pro Ile Lys Glu Leu Asn Val Gly
                260                 265                 270

Ser Met Ala His Ser Thr Gly Lys Thr Met Val Asn Asn Val Leu Ser
                275                 280                 285

Met Asp Lys Asp Val Ala Cys Phe Glu Lys Leu Arg Asp Leu Gly
        290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330

<210> SEQ ID NO 99
<211> LENGTH: 993
<212> TYPE: DNA
<213> ORGANISM: Streptococcus thermophilus

<400> SEQUENCE: 99
atgggtatcg gtattattat tgccagccat ggtaagttcg ctgaaggaat ccaccaatca      60
ggctctatga tttttgggga ccaagagaaa gttcaagttg tgactttcat gccaagtgaa     120
ggtcctgatg atttgtacgc tcacttcaac aacgccattg cacaattcga tgttgatgat     180
gaaattcttg ttttggctga cctttggagt ggttcaccat taaccaagc tagtcgaatc      240 gctagggaaa acccagatcg caagattgct atcatcacag acttaactt gccaatgcta      300 atccaagcat acactgaacg tatgatggat gctaacgcta ctgtagagca agttgctgct     360
aatatcatca aggaagctaa ggctggtatc aaggcacttc cagaggcgct aaatccagct     420
gaggaaacaa ctgcagctcc tgtagaagct gcagcacctc aaggagctat ccctgaagga     480
acagtcatcg agatggtaa actcaagatt aacttggcac gtttggacac acgtctcttg      540
catggtcaag tagtaactaa ctgggtacct tattctaaag cagaccgtat tattgttgct     600
tcggatgacg ttgccaaaga tgagcttcgt aaggaattga tcaaacaggc tgcaccaaac     660
ggtattaaag taaacgtttt tccgattcaa aaattaattg atgcttctaa agacccacgt     720
tttggaaata cacatgcgct tgtcttgttc gaaactgttc aagacgcgct tcgtgctatc     780
gaaggtggcg tgccaataaa agaacttaac gttggttcta tggctcactc aactggtaaa     840
acaatggtta caacgttttt gtctatggat aaagatgatg ttgcttgttt tgaaaaatta     900
cgtgaccttg gcgttgaatt tgacgtccgt aaggttccaa acgattctaa gaaagacttg     960
tttgagctta tcaagaaagc taacgttcaa taa                                  993

<210> SEQ ID NO 100
<211> LENGTH: 330
<212> TYPE: PRT
<213> ORGANISM: Streptococcus thermophilus

<400> SEQUENCE: 100

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
                20                  25                  30

Val Val Thr Phe Met Pro Ser Glu Gly Pro Asp Asp Leu Tyr Ala His
            35                  40                  45
```

```
Phe Asn Asn Ala Ile Ala Gln Phe Asp Val Asp Glu Ile Leu Val
        50                  55                  60

Leu Ala Asp Leu Trp Ser Gly Ser Pro Phe Asn Gln Ala Ser Arg Ile
 65                  70                  75                  80

Ala Arg Glu Asn Pro Asp Arg Lys Ile Ala Ile Thr Gly Leu Asn
                 85                  90                  95

Leu Pro Met Leu Ile Gln Ala Tyr Thr Glu Arg Met Met Asp Ala Asn
                100                 105                 110

Ala Thr Val Glu Gln Val Ala Asn Ile Ile Lys Glu Ala Lys Ala
                115                 120                 125

Gly Ile Lys Ala Leu Pro Glu Ala Leu Asn Pro Ala Glu Glu Thr Thr
130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                    165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Asp Val Ala Lys Asp Glu
                195                 200                 205

Leu Arg Lys Glu Leu Ile Lys Gln Ala Ala Pro Asn Gly Ile Lys Val
210                 215                 220

Asn Val Phe Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
                260                 265                 270

Ser Met Ala His Ser Thr Gly Lys Thr Met Val Asn Asn Val Leu Ser
                275                 280                 285

Met Asp Lys Asp Asp Val Ala Cys Phe Glu Lys Leu Arg Asp Leu Gly
290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330

<210> SEQ ID NO 101
<211> LENGTH: 993
<212> TYPE: DNA
<213> ORGANISM: Streptococcus thermophilus

<400> SEQUENCE: 101
atgggtatcg gtattattat tgccagccat ggtaagttcg ctgaaggaat ccaccaatca      60
ggctctatga ttttggggga ccaagagaaa gttcaagttg tgactttcat gccaagtgaa     120
ggtcctgatg atttgtacgc tcacttcaat aacgccattg cacaattcga tgttgatgat     180
gaaattcttg ttttggctga cctttggagt ggttcaccat taaccaagc tagtcgaatc      240 gctagggaaa atccagatcg caagattgct atcatcacag acttaactt gccaatgcta      300 atccaagcat acactgaacg tatgatggat gctaacgcta ctgtagagca aattgctgct     360
aatatcatca aggaagctaa gggtggtatc aaggcacttc cagaggagct aaatccagct     420
gaggaaacaa ctgcagctcc tgtagaagct gcagcacctc aaggagctat ccctgaagga     480
acagtcatcg gagatggtaa actcaagatt aacttggcac gtttggactc acgtctcttg     540
```

```
catggtcaag tagtaactaa ctgggtacct tattctaaag cagaccgtat tattgttgct    600
tcggatgacg ttgccaaaga tgagcttcgt aaggaattga tcaaacaggc tgcaccaaac    660
ggtattaaag taaacgttgt tccgattcaa aaattaattg atgcttctaa agacccacgt    720
tttggaaata cacatgcgct tgtcttgttc gaaactgttc aagacgcact tcgtgctatc    780
gaaggtggcg tgccaataaa agaacttaac gttggttcta tggctcactc aactggtaaa    840
acaatggtta caacgttttt gtctatggat aaagatgatg ttgcttgttt tgaaaaatta    900
cgtgaccttg gcgtcgaatt tgacgtccgt aaggttccaa acgattctaa gaaagacttg    960
tttgagctta tcaagaaagc taacgttcaa taa                                  993
```

<210> SEQ ID NO 102
<211> LENGTH: 330
<212> TYPE: PRT
<213> ORGANISM: Streptococcus thermophilus

<400> SEQUENCE: 102

```
Met Gly Ile Gly Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Asn Ala Ile Ala Gln Phe Asp Val Asp Glu Ile Leu Val
50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Ile Ala Ala Asn Ile Ile Lys Glu Ala Lys Gly
        115                 120                 125

Gly Ile Lys Ala Leu Pro Glu Glu Leu Asn Pro Ala Glu Glu Thr Thr
    130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Ser Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205

Leu Arg Lys Glu Leu Ile Lys Gln Ala Ala Pro Asn Gly Ile Lys Val
    210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285
```

Met Asp Lys Asp Asp Val Ala Cys Phe Glu Lys Leu Arg Asp Leu Gly
    290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330

<210> SEQ ID NO 103
<211> LENGTH: 993
<212> TYPE: DNA
<213> ORGANISM: Streptococcus thermophilus

<400> SEQUENCE: 103

```
atgggtatcg gtattattat tgccagccat ggtaagttcg ctgaaggaat ccaccaatca     60
ggctctatga tttttgggga ccaagagaaa gttcaagttg tgactttcat gccaagtgaa    120
ggtcctgatg atttgtacgc tcacttcaac aacgccattg cacaattcga tgttgatgat    180
gaaattcttg ttttggctga cctttggagt ggttcaccat taaccaagc tagtcgaatc    240
gctagggaaa acccagatcg caagattgct atcatcacag acttaactt gccaatgcta    300
atccaagcat acactgaacg tatgatggat gctaacgcta ctgtagagca agttactgct    360
aatatcatca aggaagctaa ggctggtatc aaggcacttc agaggcgct aaatccagct    420
gaggaaacaa ctgcagctcc tgtagaagct gcagcacctc aaggagctat ccctgaagga    480
acagtcatcg gagatggtaa actcaagatt aacttggcac gtttggacac acgtctcttg    540
catggtcaag tagtaactaa ctgggtacct tattctaaag cagaccgtat tattgttgct    600
tcggatgacg ttgccaaaga tgagcttcgt aaggaattga tcaaacaggc tgcaccaaac    660
ggtattaaag taaacgttgt tccgattcaa aaattaattg atgcttctaa agacccacgt    720
tttggaaata cacatgcgct tgtcttgttc gaaactgttc aagacgcact tcgtgctatc    780
gaaggtggcg tgccaataaa agaacttaac gttggttcta tggctcactc aactggtaaa    840
acaatggtta caacgttttt gtctatggat aaagatgatg ttgcttgttt tgaaaaatta    900
cgtgaccttg gcgttgaatt tgacgtccgt aaggttccaa acgattctaa gaaagacttg    960
tttgagctta tcaagaaagc taacgttcaa taa                                 993
```

<210> SEQ ID NO 104
<211> LENGTH: 330
<212> TYPE: PRT
<213> ORGANISM: Streptococcus thermophilus

<400> SEQUENCE: 104

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
                20                  25                  30

Val Val Thr Phe Met Pro Ser Glu Gly Pro Asp Asp Leu Tyr Ala His
            35                  40                  45

Phe Asn Asn Ala Ile Ala Gln Phe Asp Val Asp Glu Ile Leu Val
        50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Thr Ala Asn Ile Ile Lys Glu Ala Lys Ala
            115                 120                 125

Gly Ile Lys Ala Leu Pro Glu Ala Leu Asn Pro Ala Glu Glu Thr Thr
        130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
            195                 200                 205

Leu Arg Lys Glu Leu Ile Lys Gln Ala Ala Pro Asn Gly Ile Lys Val
        210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
        290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330

<210> SEQ ID NO 105
<211> LENGTH: 993
<212> TYPE: DNA
<213> ORGANISM: Streptococcus thermophilus

<400> SEQUENCE: 105
atgggtatcg gtattattat tgccagccat ggtaagttcg ctgaaggaat ccaccaatca    60
ggctctatga tttttgggga ccaagagaaa gttcaagttg tgactttcat gccaagtgaa   120
ggtcctgatg atttgtacgc tcacttcaac aaagccattg cacaattcga tgttgatgat   180
gaaattcttg ttttggctga cctttggagt ggttcaccat taaccaagc tagtcgaatc    240 gctagggaaa atccagatcg caagattgct atcatcacag gacttaactt gccaatgcta   300
atccaagcat acactgaacg tatgatggat gctaacgcta ctgtagagca agttgctgct   360
aatatcatca aggaagctaa gggtggtatc aaggcacttc cagaggagct aaatccagct   420
gaggaaacaa ctgcagctcc tgtagaagct gcagcacctc aaggagctat ccctgaagga   480
acagtcatcg gagatggtaa actcaagatt aacttggcac gtttggacac acgtctcttg   540
catggtcaag tagtaactaa ctgggtacct tattctaaag cagaccgtat tattgttgct   600
tcggatgacg ttgccaaaga tgagcttcgt aaggaattga tcaaacaggc tgcaccaaac   660
ggtattaaag taaacgttgt tccgattcaa aaattaattg atgcttctaa agacccacgt   720
tttggaaata cacatgcgct tgtcttgttc gaaactgttc aagacgcgct tcgtgctatc   780
gaaggtggcg tgccaataaa agaacttaac gttggttcta tggctcactc aactggtaaa   840

```
acaatggtta acaacgtttt gtctatggat aaagatgatg ttgcttgttt tgaaaaatta    900
cgtgaccttg gcgttgaatt tgacgtccgt aaggttccaa acgattctaa gaaagacttg    960
tttgagctta tcaagaaagc taacgttcaa taa                                 993
```

```
<210> SEQ ID NO 106
<211> LENGTH: 330
<212> TYPE: PRT
<213> ORGANISM: Streptococcus thermophilus

<400> SEQUENCE: 106
```

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Lys Ala Ile Ala Gln Phe Asp Val Asp Glu Ile Leu Val
50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Gly
        115                 120                 125

Gly Ile Lys Ala Leu Pro Glu Glu Leu Asn Pro Ala Glu Glu Thr Thr
130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Pro Val Ala Lys Asp Glu
        195                 200                 205

Leu Arg Lys Glu Leu Ile Lys Gln Ala Pro Asn Gly Ile Lys Val
210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
290                 295                 300

Val Glu Phe Asp Val Arg Lys Val Pro Asn Asp Ser Lys Asp Leu
305                 310                 315                 320

Phe Glu Leu Ile Lys Lys Ala Asn Val Gln
                325                 330

```
<210> SEQ ID NO 107
```

```
<211> LENGTH: 993
<212> TYPE: DNA
<213> ORGANISM: Streptococcus thermophilus

<400> SEQUENCE: 107
atgggtatcg gtattattat tgccagccat ggtaagttcg ctgaaggaat ccaccaatca     60
ggctctatga ttttggggga ccaagagaaa gttcaagttg tgactttcat gccaagtgaa    120
ggtcctgatg atttgtacgc tcacttcaac aacgccattg cacaattcga tgttgatgat    180
gaaattcttg ttttggctga cctttggagt ggttcaccat taaccaagc tagtcgaatc     240
gctagggaaa acccagatcg caagattgct atcatcacag gacttaactt gccaatgcta    300
atccaagcat acactgaacg tatgatggat gctaacgcta ctgtagagca agttgctgct    360
aatatcatca aggaagctaa ggctggtatc aaggcacttc cagaggcgct aaatccagct    420
gaggaaacaa ctgcagctcc tgtagaagct gcagcacctc aaggagctat ccctgaagga    480
acagtcatcg gagatggtaa actcaagatt aacttggcac gtttggacac acgtctcttg    540
catggtcaag tagtaactaa ctgggtacct tattctaaag cagaccgtat tattgttgct    600
tcggatgacg ttgccaaaga tgagcttcgt aaggaattga tcaaacaggc tgcaccaaac    660
ggtattaaag taacgttgt tccgattcaa aaattaattg atgcttctaa agacccacgt    720
tttggaaata cacatgcact tgtcttgttc gaaactgttc aagacgtact tcgtgctgtc    780
gaaggtggcg tgccaataaa agaacttaac gttggttcta tggctcactc aactggtaaa    840
acaatggtta caacgtttt gtctatggat aaagatgatg ttgcttgttt tgaaaaatta    900
cgtgaccttg gcgttgaatt tgacgtccgt aaggttccaa acgattctaa gaaagacttg    960
tttgagctta tcaagaaagc taacgttcaa taa                                 993

<210> SEQ ID NO 108
<211> LENGTH: 330
<212> TYPE: PRT
<213> ORGANISM: Streptococcus thermophilus

<400> SEQUENCE: 108

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Asn Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Ala
        115                 120                 125

Gly Ile Lys Ala Leu Pro Glu Ala Leu Asn Pro Ala Glu Glu Thr Thr
    130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
```

```
              165                 170                 175
Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205

Leu Arg Lys Glu Leu Ile Lys Gln Ala Ala Pro Asn Gly Ile Lys Val
    210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Val
                245                 250                 255

Leu Arg Ala Val Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
    290                 295                 300

Val Glu Phe Asp Val Arg Lys Val Pro Asn Asp Ser Lys Lys Asp Leu
305                 310                 315                 320

Phe Glu Leu Ile Lys Lys Ala Asn Val Gln
                325                 330
```

<210> SEQ ID NO 109
<211> LENGTH: 993
<212> TYPE: DNA
<213> ORGANISM: Streptococcus thermophilus

<400> SEQUENCE: 109

```
atgggtatcg gtattattat tgccagccat ggtaagttcg ctgaaggaat ccaccaatca    60
ggctctatga tttttgggga ccaagagaaa gttcaagttg tgactttcat gccaagtgaa   120
ggtcctgatg atttgtacgc tcacttcaac aacgccattg cacaattcga tgttgatgat   180
gaaattcttg ttttggctga ccttgggagt ggttcaccat taaccaagc tagtcgaatc    240
gctagggaaa acccagatcg caagattgct atcatcacag acttaactt accaatgcta    300
atccaagcat acactgaacg tatgatggat gctaacgcta ctgtagagca agttgctgct   360
aatatcatca aggaagctaa ggcaggtatc aaggcacttc agaggcgct aaatccagct    420
gaggaaacaa ctgcagctcc tgtagaagct acagcacctc aaggagctat ccctgaagga   480
acagtcatcg agatggtaa actcaagatt aacttggcac gtttggacac acgtctcttg    540
catggtcaag tagtaactaa ctgggtacct tattctaaag cagaccgtat tattgttgct   600
tcggatgacg ttgccaaaga tgagcttcgt aaggaattga tcaaacaggc tgcaccaaac   660
ggtattaaag taacgttgt tccgattcaa aaattaattg atgcttctaa agacccacgt    720
tttggaaata cacatgcgct tgtcttgttc gaaactgttc aagacgcact tcgtgctatc   780
gaaggtggcg tgccaataaa agaacttaac gttggttcta tggctcactc aactggtaaa   840
acaatggtta caacgttttt gtctatggat aaagatgatg ttgcttgttt tgaaaaatta   900
cgtgaccttg gcgttgaatt tgacgtccgt aaggttccaa acgattctaa gaaagacttg   960
tttgagctta tcaagaaagc taacgttcaa taa                                993
```

<210> SEQ ID NO 110
<211> LENGTH: 330
<212> TYPE: PRT
<213> ORGANISM: Streptococcus thermophilus

<400> SEQUENCE: 110

| | | | | | | | | | | | | | | |
|---|---|---|---|---|---|---|---|---|---|---|---|---|---|---|
|Met|Gly|Ile|Gly|Ile|Ile|Ala|Ser|His|Gly|Lys|Phe|Ala|Glu|Gly|
|1| | | |5| | | | |10| | | | |15|
|Ile|His|Gln|Ser|Gly|Ser|Met|Ile|Phe|Gly|Asp|Gln|Glu|Lys|Val|Gln|
| | | |20| | | | |25| | | | |30| | |
|Val|Val|Thr|Phe|Met|Pro|Ser|Glu|Gly|Pro|Asp|Asp|Leu|Tyr|Ala|His|
| | | | |35| | | | |40| | | | |45| |
|Phe|Asn|Asn|Ala|Ile|Ala|Gln|Phe|Asp|Val|Asp|Glu|Ile|Leu|Val|
|50| | | | |55| | | | |60| | | | |
|Leu|Ala|Asp|Leu|Trp|Ser|Gly|Ser|Pro|Phe|Asn|Gln|Ala|Ser|Arg|Ile|
|65| | | | |70| | | | |75| | | | |80|
|Ala|Arg|Glu|Asn|Pro|Asp|Arg|Lys|Ile|Ala|Ile|Thr|Gly|Leu|Asn|
| | | | |85| | | | |90| | | | |95|
|Leu|Pro|Met|Leu|Ile|Gln|Ala|Tyr|Thr|Glu|Arg|Met|Met|Asp|Ala|Asn|
| | | | |100| | | | |105| | | | |110| |
|Ala|Thr|Val|Glu|Gln|Val|Ala|Ala|Asn|Ile|Ile|Lys|Glu|Ala|Lys|Ala|
| | | | |115| | | | |120| | | | |125| |
|Gly|Ile|Lys|Ala|Leu|Pro|Glu|Ala|Leu|Asn|Pro|Ala|Glu|Glu|Thr|Thr|
|130| | | | |135| | | | |140| | | | | |
|Ala|Ala|Pro|Val|Glu|Ala|Thr|Ala|Pro|Gln|Gly|Ala|Ile|Pro|Glu|Gly|
|145| | | | |150| | | | |155| | | | |160|
|Thr|Val|Ile|Gly|Asp|Gly|Lys|Leu|Lys|Ile|Asn|Leu|Ala|Arg|Leu|Asp|
| | | | |165| | | | |170| | | | |175| |
|Thr|Arg|Leu|Leu|His|Gly|Gln|Val|Val|Thr|Asn|Trp|Val|Pro|Tyr|Ser|
| | | |180| | | | |185| | | | |190| | |
|Lys|Ala|Asp|Arg|Ile|Ile|Val|Ala|Ser|Asp|Asp|Val|Ala|Lys|Asp|Glu|
| | | |195| | | | |200| | | | |205| | |
|Leu|Arg|Lys|Glu|Leu|Ile|Lys|Gln|Ala|Ala|Pro|Asn|Gly|Ile|Lys|Val|
| | |210| | | | |215| | | | |220| | | |
|Asn|Val|Val|Pro|Ile|Gln|Lys|Leu|Ile|Asp|Ala|Ser|Lys|Asp|Pro|Arg|
|225| | | | |230| | | | |235| | | | |240|
|Phe|Gly|Asn|Thr|His|Ala|Leu|Val|Leu|Phe|Glu|Thr|Val|Gln|Asp|Ala|
| | | | |245| | | | |250| | | | |255| |
|Leu|Arg|Ala|Ile|Glu|Gly|Gly|Val|Pro|Ile|Lys|Glu|Leu|Asn|Val|Gly|
| | | |260| | | | |265| | | | |270| | |
|Ser|Met|Ala|His|Ser|Thr|Gly|Lys|Thr|Met|Val|Asn|Asn|Val|Leu|Ser|
| | |275| | | | |280| | | | |285| | | |
|Met|Asp|Lys|Asp|Val|Ala|Cys|Phe|Glu|Lys|Leu|Arg|Asp|Leu|Gly|
|290| | | | |295| | | | |300| | | | | |
|Val|Glu|Phe|Asp|Val|Arg|Lys|Val|Pro|Asn|Asp|Ser|Lys|Lys|Asp|Leu|
|305| | | | |310| | | | |315| | | | |320|
|Phe|Glu|Leu|Ile|Lys|Lys|Ala|Asn|Val|Gln|
| | | | |325| | | | |330|

<210> SEQ ID NO 111
<211> LENGTH: 993
<212> TYPE: DNA
<213> ORGANISM: Streptococcus thermophilus

<400> SEQUENCE: 111

```
atgggtatcg gtattattat tgccagccat ggtaggttcg ctgaaggaat ccaccaatca    60
ggctctatga ttttggggga ccaagagaaa gttcaagttg tgactttcat gccaagtgaa   120
ggtcctgatg atttgtacgc tcacttcaac aacgccattg cacaattcga tgttgatgat   180
```

```
gaaattcttg ttttggctga cctttggagt ggttcaccat ttaaccaagc tagtcgaatc    240
gctagggaaa atccagatcg caagattgct atcatcacag gacttaactt gccaatgcta    300
atccaagcat acactgaacg tatgatggat gctaacgcta ctgtagagca agttgctgct    360
aatatcatca aggaagctaa gggtggtatc aaggcacttc cagaagagct aaatccagct    420
gaggaaacaa ctgcagctcc tgtagaagct gcagcacctc aaggagctat ccctgaagga    480
acagtcatcg gagatggtaa actcaagatt aacttggcac gtttggacac acgtctcttg    540
catggtcaag tagtaactaa ctgggtacct tattctaaag cagaccgtat tattgttgct    600
tcggatgacg ttgccaaaga tgagcttcgt aaggaattga tcaaacaggc tgccaccaaac   660 ggtattaaag taaacgttgt tccgattcaa aaattaattg atgcttctaa agacccacgt    720
tttggaaata cacatgcgct tgtcttgttc gaaactgttc aagacgcact tcgtgctatc    780
gaaggtggcg tgccaataaa agaacttaac gttggttcta tggctcactc aactggtaaa    840
acaatggtta acaacgtttt gtctatggat aaagatgatg ttgcttgttt tgaaaaatta    900
cgtgaccttg gcgtttaatt tgacgtccgt aaggttccaa acgattctaa gaaagatttg    960
tttgagctta tcaagaaagc taacgttcaa taa                                 993
```

```
<210> SEQ ID NO 112
<211> LENGTH: 305
<212> TYPE: PRT
<213> ORGANISM: Streptococcus thermophilus

<400> SEQUENCE: 112

Met Gly Ile Gly Ile Ile Ala Ser His Gly Arg Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Asn Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Gly
        115                 120                 125

Gly Ile Lys Ala Leu Pro Glu Glu Leu Asn Pro Ala Glu Glu Thr Thr
    130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Asp Val Ala Lys Asp Glu
        195                 200                 205

Leu Arg Lys Glu Leu Ile Lys Gln Ala Ala Pro Asn Gly Ile Lys Val
    210                 215                 220
```

```
Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
            245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
            275                 280                 285

Met Asp Lys Asp Asp Val Ala Cys Phe Glu Lys Leu Arg Asp Leu Gly
            290                 295                 300

Val
305

<210> SEQ ID NO 113
<211> LENGTH: 305
<212> TYPE: PRT
<213> ORGANISM: Streptococcus thermophilus

<400> SEQUENCE: 113

Met Gly Ile Gly Ile Ile Ala Ser His Gly Lys Phe Ala Glu Gly
1               5                   10                  15

Ile His Gln Ser Gly Ser Met Ile Phe Gly Asp Gln Glu Lys Val Gln
                20                  25                  30

Val Val Thr Phe Met Pro Ser Glu Gly Pro Asp Leu Tyr Ala His
                35                  40                  45

Phe Asn Asn Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Ala
            115                 120                 125

Gly Ile Lys Ala Leu Pro Glu Ala Leu Asn Pro Ala Glu Glu Thr Thr
130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
            165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
            195                 200                 205

Leu Arg Lys Glu Leu Ile Lys Gln Ala Ala Pro Asn Gly Ile Lys Val
            210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
            245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
            275                 280                 285
```

```
Met Asp Lys Asp Asp Val Ala Cys Phe Glu Lys Leu Arg Asp Leu Gly
    290                 295                 300

Val
305

<210> SEQ ID NO 114
<211> LENGTH: 305
<212> TYPE: PRT
<213> ORGANISM: Streptococcus thermophilus

<400> SEQUENCE: 114

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Asn Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65              70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Gly
        115                 120                 125

Gly Ile Lys Ala Leu Pro Glu Glu Leu Asn Pro Ala Glu Glu Thr Thr
    130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Asp Val Ala Lys Asp Glu
        195                 200                 205

Leu Arg Lys Glu Leu Ile Lys Gln Ala Ala Pro Asn Gly Ile Lys Val
    210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
    290                 295                 300

Val
305

<210> SEQ ID NO 115
<211> LENGTH: 305
<212> TYPE: PRT
```

<213> ORGANISM: Streptococcus thermophilus

<400> SEQUENCE: 115

Met Gly Ile Gly Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Lys Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Gly
        115                 120                 125

Gly Ile Lys Ala Leu Pro Glu Glu Leu Asn Pro Ala Glu Glu Thr Thr
130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205

Leu Arg Lys Glu Leu Ile Lys Gln Ala Ala Pro Asn Gly Ile Lys Val
210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Val
                245                 250                 255

Leu Arg Ala Val Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
290                 295                 300

Val
305

<210> SEQ ID NO 116
<211> LENGTH: 305
<212> TYPE: PRT
<213> ORGANISM: Streptococcus thermophilus

<400> SEQUENCE: 116

Met Gly Ile Gly Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His

```
                35                  40                  45
Phe Asn Asn Ala Ile Ala Gln Phe Asp Val Asp Glu Ile Leu Val
 50                  55                  60
Leu Ala Asp Leu Trp Ser Gly Ser Pro Phe Asn Gln Ala Ser Arg Ile
 65                  70                  75                  80
Ala Arg Glu Asn Pro Asp Arg Lys Ile Ala Ile Thr Gly Leu Asn
                 85                  90                  95
Leu Pro Met Leu Ile Gln Ala Tyr Thr Glu Arg Met Met Asp Ala Asn
                100                 105                 110
Ala Thr Ile Glu Gln Val Ala Ala Asn Ile Ile Lys Glu Ala Lys Gly
                115                 120                 125
Gly Ile Lys Ala Leu Pro Glu Ala Leu Asn Pro Ala Glu Glu Thr Thr
                130                 135                 140
Ala Ala Pro Val Glu Ala Ala Pro Gln Gly Ala Ile Pro Glu Gly
145                 150                 155                 160
Thr Val Ile Gly Asp Gly Lys Leu Lys Ile Asn Leu Ala Arg Leu Asp
                165                 170                 175
Thr Arg Leu Leu His Gly Gln Val Val Thr Asn Trp Val Pro Tyr Ser
                180                 185                 190
Lys Ala Asp Arg Val Ile Val Ala Ser Asp Val Ala Lys Asp Glu
                195                 200                 205
Leu Arg Lys Glu Leu Ile Lys Gln Ala Ala Pro Asn Gly Ile Lys Val
210                 215                 220
Asn Val Val Pro Ile Gln Lys Leu Ile Asp Ala Ser Lys Asp Pro Arg
225                 230                 235                 240
Phe Gly Asn Thr His Ala Leu Val Leu Phe Glu Thr Val Gln Asp Ala
                245                 250                 255
Leu Arg Ala Ile Glu Gly Gly Val Pro Ile Lys Glu Leu Asn Val Gly
                260                 265                 270
Ser Met Ala His Ser Thr Gly Lys Thr Met Val Asn Asn Val Leu Ser
                275                 280                 285
Met Asp Lys Asp Asp Val Ala Cys Phe Glu Lys Leu Arg Asp Leu Gly
                290                 295                 300
Val
305

<210> SEQ ID NO 117
<211> LENGTH: 305
<212> TYPE: PRT
<213> ORGANISM: Streptococcus thermophilus

<400> SEQUENCE: 117

Met Gly Ile Gly Ile Ile Ala Ser His Gly Lys Phe Ala Glu Gly
 1                   5                  10                  15
Ile His Gln Ser Gly Ser Met Ile Phe Gly Asp Gln Glu Lys Val Arg
                 20                  25                  30
Val Val Thr Phe Met Pro Ser Glu Gly Pro Asp Asp Leu Tyr Ala His
                 35                  40                  45
Phe Asn Asn Ala Ile Ala Gln Phe Asp Val Asp Asp Glu Ile Leu Val
 50                  55                  60
Leu Ala Asp Leu Trp Ser Gly Ser Pro Phe Asn Gln Ala Ser Arg Ile
 65                  70                  75                  80
Ala Arg Glu Asn Pro Asp Arg Lys Ile Ala Ile Ile Thr Gly Leu Asn
                 85                  90                  95
```

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Ala
        115                 120                 125

Gly Ile Lys Ala Leu Pro Glu Ala Leu Asn Pro Ala Glu Glu Thr Thr
    130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Asp Val Ala Lys Asp Glu
        195                 200                 205

Leu Arg Lys Glu Leu Ile Lys Gln Ala Ala Pro Asn Gly Ile Lys Val
    210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
    290                 295                 300

Val
305

<210> SEQ ID NO 118
<211> LENGTH: 305
<212> TYPE: PRT
<213> ORGANISM: Streptococcus thermophilus

<400> SEQUENCE: 118

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Asn Ala Ile Ala Gln Phe Asp Val Asp Glu Ile Leu Val
    50                  55                  60

Leu Ala Asp Leu Trp Ser Gly Ser Pro Phe Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Gly
        115                 120                 125

Gly Ile Lys Ala Leu Pro Glu Ala Leu Asn Pro Ala Glu Glu Thr Thr
    130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
            165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
            195                 200                 205

Leu Arg Lys Glu Leu Ile Lys Gln Ala Ala Pro Asn Gly Ile Lys Val
210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
            245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
            275                 280                 285

Met Asp Lys Asp Asp Val Ala Cys Phe Glu Lys Leu Arg Asp Leu Gly
            290                 295                 300

Val
305

<210> SEQ ID NO 119
<211> LENGTH: 305
<212> TYPE: PRT
<213> ORGANISM: Streptococcus thermophilus

<400> SEQUENCE: 119

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Leu Tyr Ala His
            35                  40                  45

Phe Asn Asn Ala Ile Ala Gln Phe Asp Val Asp Asp Glu Ile Leu Val
50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
            85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Ala
            115                 120                 125

Gly Ile Lys Ala Leu Pro Glu Glu Leu Asn Pro Ala Glu Glu Thr Thr
130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
            165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
            195                 200                 205

Leu Arg Lys Glu Leu Ile Lys Gln Ala Ala Pro Asn Gly Ile Lys Val

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
            275                 280                 285

Met Asp Lys Asp Asp Val Ala Cys Phe Glu Lys Leu Arg Asp Leu Gly
            290                 295                 300

Val
305

<210> SEQ ID NO 120
<211> LENGTH: 305
<212> TYPE: PRT
<213> ORGANISM: Streptococcus thermophilus

<400> SEQUENCE: 120

Met Gly Ile Gly Ile Ile Ala Ser His Gly Lys Phe Ala Glu Gly
1               5                   10                  15

Ile His Gln Ser Gly Ser Met Ile Phe Gly Asp Gln Glu Lys Val Gln
                20                  25                  30

Val Val Thr Phe Met Pro Ser Glu Gly Pro Asp Asp Leu Tyr Ala His
            35                  40                  45

Phe Asn Asn Ala Ile Ala Gln Phe Asp Val Asp Asp Glu Ile Leu Val
50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Ile Glu Gln Val Ala Ala Asn Ile Ile Lys Glu Ala Lys Gly
            115                 120                 125

Gly Ile Lys Ala Leu Pro Glu Ala Leu Asn Pro Ala Glu Glu Thr Thr
130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
            165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Asp Val Ala Lys Asp Glu
            195                 200                 205

Leu Arg Lys Glu Leu Ile Lys Gln Ala Ala Pro Asn Gly Ile Lys Val
            210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
            275                 280                 285

Met Asp Lys Asp Asp Val Ala Cys Phe Glu Lys Leu Arg Asp Leu Gly
    290                 295                 300

Val
305

<210> SEQ ID NO 121
<211> LENGTH: 305
<212> TYPE: PRT
<213> ORGANISM: Streptococcus thermophilus

<400> SEQUENCE: 121

Met Gly Ile Gly Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Asn Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Val Ala Asn Ile Ile Lys Glu Ala Lys Gly
        115                 120                 125

Gly Ile Lys Ala Leu Pro Glu Ala Leu Asn Pro Ala Glu Glu Thr Thr
    130                 135                 140

Ala Ala Pro Val Glu Ala Ala Leu Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205

Leu Arg Lys Glu Leu Ile Lys Gln Ala Ala Pro Asn Gly Ile Lys Val
    210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
    290                 295                 300

Val
305

<210> SEQ ID NO 122

<211> LENGTH: 305
<212> TYPE: PRT
<213> ORGANISM: Streptococcus thermophilus

<400> SEQUENCE: 122

```
Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Lys Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Gly
        115                 120                 125

Gly Ile Lys Ala Leu Pro Glu Glu Leu Asn Pro Ala Glu Glu Thr Thr
    130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Asp Val Ala Lys Asp Glu
        195                 200                 205

Leu Arg Lys Glu Leu Ile Lys Gln Ala Ala Pro Asn Gly Ile Lys Val
    210                 215                 220

Asn Val Val Pro Ile Gln Lys Leu Val Asp Ala Ser Lys Asp Pro Arg
225                 230                 235                 240

Phe Gly Asn Thr His Ala Leu Val Leu Phe Glu Thr Val Gln Asp Val
                245                 250                 255

Leu Arg Ala Val Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
    290                 295                 300

Val
305
```

<210> SEQ ID NO 123
<211> LENGTH: 305
<212> TYPE: PRT
<213> ORGANISM: Streptococcus thermophilus

<400> SEQUENCE: 123

```
Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30
```

```
Val Val Thr Phe Met Pro Ser Glu Gly Pro Asp Asp Leu Tyr Ala His
            35                  40                  45

Phe Asn Asn Ala Ile Ala Gln Phe Asp Val Asp Glu Ile Leu Val
 50                  55                  60

Leu Ala Asp Leu Trp Ser Gly Ser Pro Phe Asn Gln Ala Ser Arg Ile
 65                  70                  75                  80

Ala Arg Glu Asn Pro Asp Arg Lys Ile Ala Ile Ile Thr Gly Leu Asn
                 85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Ala
            115                 120                 125

Gly Ile Lys Ala Leu Pro Glu Ala Leu Asn Pro Ala Glu Glu Thr Thr
130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
            195                 200                 205

Leu Arg Lys Glu Leu Ile Lys Gln Ala Ala Pro Asn Gly Ile Lys Val
            210                 215                 220

Asn Val Phe Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
            275                 280                 285

Met Asp Lys Asp Asp Val Ala Cys Phe Glu Lys Leu Arg Asp Leu Gly
    290                 295                 300

Val
305

<210> SEQ ID NO 124
<211> LENGTH: 305
<212> TYPE: PRT
<213> ORGANISM: Streptococcus thermophilus

<400> SEQUENCE: 124

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
                20                  25                  30

Val Val Thr Phe Met Pro Ser Glu Gly Pro Asp Asp Leu Tyr Ala His
            35                  40                  45

Phe Asn Asn Ala Ile Ala Gln Phe Asp Val Asp Glu Ile Leu Val
 50                  55                  60

Leu Ala Asp Leu Trp Ser Gly Ser Pro Phe Asn Gln Ala Ser Arg Ile
 65                  70                  75                  80

Ala Arg Glu Asn Pro Asp Arg Lys Ile Ala Ile Ile Thr Gly Leu Asn
```

```
             85                  90                  95
Leu Pro Met Leu Ile Gln Ala Tyr Thr Glu Arg Met Met Asp Ala Asn
            100                 105                 110

Ala Thr Val Glu Gln Ile Ala Ala Asn Ile Ile Lys Glu Ala Lys Gly
            115                 120                 125

Gly Ile Lys Ala Leu Pro Glu Leu Asn Pro Ala Glu Glu Thr Thr
            130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
            165                 170                 175

Ser Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
            195                 200                 205

Leu Arg Lys Glu Leu Ile Lys Gln Ala Ala Pro Asn Gly Ile Lys Val
            210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
            245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
            275                 280                 285

Met Asp Lys Asp Asp Val Ala Cys Phe Glu Lys Leu Arg Asp Leu Gly
            290                 295                 300

Val
305

<210> SEQ ID NO 125
<211> LENGTH: 305
<212> TYPE: PRT
<213> ORGANISM: Streptococcus thermophilus

<400> SEQUENCE: 125

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
            35                  40                  45

Phe Asn Asn Ala Ile Ala Gln Phe Asp Val Asp Glu Ile Leu Val
            50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Ile Thr Gly Leu Asn
            85                  90                  95

Leu Pro Met Leu Ile Gln Ala Tyr Thr Glu Arg Met Met Asp Ala Asn
            100                 105                 110

Ala Thr Val Glu Gln Val Thr Ala Asn Ile Ile Lys Glu Ala Lys Ala
            115                 120                 125

Gly Ile Lys Ala Leu Pro Glu Ala Leu Asn Pro Ala Glu Glu Thr Thr
            130                 135                 140
```

```
Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205

Leu Arg Lys Glu Leu Ile Lys Gln Ala Ala Pro Asn Gly Ile Lys Val
    210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
    290                 295                 300

Val
305

<210> SEQ ID NO 126
<211> LENGTH: 305
<212> TYPE: PRT
<213> ORGANISM: Streptococcus thermophilus

<400> SEQUENCE: 126

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
                20                  25                  30

Val Val Thr Phe Met Pro Ser Glu Gly Pro Asp Asp Leu Tyr Ala His
            35                  40                  45

Phe Asn Lys Ala Ile Ala Gln Phe Asp Val Asp Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Asn Ile Ile Lys Glu Ala Lys Gly
        115                 120                 125

Gly Ile Lys Ala Leu Pro Glu Glu Leu Asn Pro Ala Glu Glu Thr Thr
    130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205
```

```
Leu Arg Lys Glu Leu Ile Lys Gln Ala Ala Pro Asn Gly Ile Lys Val
            210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
290                 295                 300

Val
305

<210> SEQ ID NO 127
<211> LENGTH: 305
<212> TYPE: PRT
<213> ORGANISM: Streptococcus thermophilus

<400> SEQUENCE: 127

Met Gly Ile Gly Ile Ile Ile Ala Ser His Gly Lys Phe Ala Glu Gly
1               5                   10                  15

Ile His Gln Ser Gly Ser Met Ile Phe Gly Asp Gln Glu Lys Val Gln
            20                  25                  30

Val Val Thr Phe Met Pro Ser Glu Gly Pro Asp Asp Leu Tyr Ala His
        35                  40                  45

Phe Asn Asn Ala Ile Ala Gln Phe Asp Val Asp Glu Ile Leu Val
50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Ala
        115                 120                 125

Gly Ile Lys Ala Leu Pro Glu Ala Leu Asn Pro Ala Glu Glu Thr Thr
130                 135                 140

Ala Ala Pro Val Glu Ala Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205

Leu Arg Lys Glu Leu Ile Lys Gln Ala Ala Pro Asn Gly Ile Lys Val
            210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Val
                245                 250                 255

Leu Arg Ala Val Glu Gly Gly Val Pro Ile Lys Glu Leu Asn Val Gly
```

```
                260                 265                 270
Ser Met Ala His Ser Thr Gly Lys Thr Met Val Asn Asn Val Leu Ser
                275                 280                 285

Met Asp Lys Asp Asp Val Ala Cys Phe Glu Lys Leu Arg Asp Leu Gly
        290                 295                 300

Val
305
```

<210> SEQ ID NO 128
<211> LENGTH: 305
<212> TYPE: PRT
<213> ORGANISM: Streptococcus thermophilus

<400> SEQUENCE: 128

```
Met Gly Ile Gly Ile Ile Ala Ser His Gly Lys Phe Ala Glu Gly
1               5                   10                  15

Ile His Gln Ser Gly Ser Met Ile Phe Gly Asp Gln Glu Lys Val Gln
                20                  25                  30

Val Val Thr Phe Met Pro Ser Glu Gly Pro Asp Asp Leu Tyr Ala His
            35                  40                  45

Phe Asn Asn Ala Ile Ala Gln Phe Asp Val Asp Glu Ile Leu Val
    50                  55                  60

Leu Ala Asp Leu Trp Ser Gly Ser Pro Phe Asn Gln Ala Ser Arg Ile
65                  70                  75                  80

Ala Arg Glu Asn Pro Asp Arg Lys Ile Ala Ile Thr Gly Leu Asn
                85                  90                  95

Leu Pro Met Leu Ile Gln Ala Tyr Thr Glu Arg Met Met Asp Ala Asn
            100                 105                 110

Ala Thr Val Glu Gln Val Ala Ala Asn Ile Ile Lys Glu Ala Lys Ala
        115                 120                 125

Gly Ile Lys Ala Leu Pro Glu Ala Leu Asn Pro Ala Glu Glu Thr Thr
130                 135                 140

Ala Ala Pro Val Glu Ala Thr Ala Pro Gln Gly Ala Ile Pro Glu Gly
145                 150                 155                 160

Thr Val Ile Gly Asp Gly Lys Leu Lys Ile Asn Leu Ala Arg Leu Asp
                165                 170                 175

Thr Arg Leu Leu His Gly Gln Val Val Thr Asn Trp Val Pro Tyr Ser
            180                 185                 190

Lys Ala Asp Arg Ile Ile Val Ala Ser Asp Val Ala Lys Asp Glu
        195                 200                 205

Leu Arg Lys Glu Leu Ile Lys Gln Ala Ala Pro Asn Gly Ile Lys Val
210                 215                 220

Asn Val Val Pro Ile Gln Lys Leu Ile Asp Ala Ser Lys Asp Pro Arg
225                 230                 235                 240

Phe Gly Asn Thr His Ala Leu Val Leu Phe Glu Thr Val Gln Asp Ala
                245                 250                 255

Leu Arg Ala Ile Glu Gly Gly Val Pro Ile Lys Glu Leu Asn Val Gly
            260                 265                 270

Ser Met Ala His Ser Thr Gly Lys Thr Met Val Asn Asn Val Leu Ser
        275                 280                 285

Met Asp Lys Asp Asp Val Ala Cys Phe Glu Lys Leu Arg Asp Leu Gly
        290                 295                 300

Val
305
```

<210> SEQ ID NO 129
<211> LENGTH: 828
<212> TYPE: DNA
<213> ORGANISM: Streptococcus thermophilus

<400> SEQUENCE: 129

```
atgtcagata tgtcaattat ttctgcgatt ttggtcgtag ctgttgcctt ccttgctggt      60
cttgaaagta tccttgacca attccaattc caccaaccac ttgttgcatg taccctcatc     120
ggtgctgcca caggtaacct cactgcaggt atcatgcttg gtggttctct tcaaatgatt     180
acccttgctt gggcaaacat cggtgctgcc gtagctcctg acgttgccct tgcatctgtt     240
gccgctgcca tcattttggt taaaggtggt aaatttacag ctgaaggtat cggtgttgcg     300
attgcaatag ctatcctgct tgcagttgca ggtctcttcc taactatgcc tgttcgtaca     360
gcatctattg cctttgttca tgctgcagat aaagctgcag aacacggaaa catcgctggt     420
gttgaacgtg catactacct cgctctcctt cttcaaggtt tgcgtattgc tgtgccagca     480
gcccttcttc ttgccatccc ggcccaatct gttcaacatg cccttggctt gatgcctgac     540
tggctcaccc atggttttggt tgtcggtggt ggtatggtcg tagccgttgg ttacgccatg     600
attatcaata tgatggctac tcgtgaagtt tggccattct tcgccattgg ttttgctttg     660
gcagcaatta gccaattgac acttatcgct cttagtacca ttggtgttgc catcgccttc     720
atctacctca acctttctaa acaaggtggc ggaaatggtg gcgaaatgg tggcggaact     780
tcatctggtt caggcgaccc aatcggcgat atcttggaag actactag                 828
```

<210> SEQ ID NO 130
<211> LENGTH: 275
<212> TYPE: PRT
<213> ORGANISM: Streptococcus thermophilus

<400> SEQUENCE: 130

```
Met Ser Asp Met Ser Ile Ile Ser Ala Ile Leu Val Val Ala Val Ala
1               5                   10                  15

Phe Leu Ala Gly Leu Glu Ser Ile Leu Asp Gln Phe Gln Phe His Gln
                20                  25                  30

Pro Leu Val Ala Cys Thr Leu Ile Gly Ala Ala Thr Gly Asn Leu Thr
            35                  40                  45

Ala Gly Ile Met Leu Gly Gly Ser Leu Gln Met Ile Thr Leu Ala Trp
        50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala
    130                 135                 140

Tyr Tyr Leu Ala Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
            180                 185                 190
```

```
Val Val Ala Val Gly Tyr Ala Met Ile Ile Asn Met Met Ala Thr Arg
        195                 200                 205

Glu Val Trp Pro Phe Phe Ala Ile Gly Phe Ala Leu Ala Ala Ile Ser
        210                 215                 220

Gln Leu Thr Leu Ile Ala Leu Ser Thr Ile Gly Val Ala Ile Ala Phe
225                 230                 235                 240

Ile Tyr Leu Asn Leu Ser Lys Gln Gly Gly Asn Gly Gly Asn
                245                 250                 255

Gly Gly Gly Thr Ser Ser Gly Ser Gly Asp Pro Ile Gly Asp Ile Leu
                260                 265                 270

Glu Asp Tyr
        275

<210> SEQ ID NO 131
<211> LENGTH: 828
<212> TYPE: DNA
<213> ORGANISM: Streptococcus thermophilus

<400> SEQUENCE: 131
atgtcagata tgtcaattat ttctgcgatt ttggtcgtag ctgttgcctt ccttgctggt    60
cttgaaagta tccttgacca attccaattc caccaaccac ttgttgcatg taccctcatc   120
ggtgctgcca caggtaacct cactgcaggt atcatgcttg gtggttctct tcaaatgatt   180
acccttgctt gggcaaacat cggtgctgcc gtagctcctg acgttgccct tgcatctgtt   240
gccgctgcca tcattttggt taaaggtggt aaatttacag ctgaaggtat cggtgttgcg   300
attgcaatag ctatcctgct tgcagttgca ggtctcttcc taactatgcc tgttcgtaca   360
gcatctattg cctttgttca tgctgcagat aaagctgcag aacacggaaa catcgctggt   420
gttgaacgtg catactacct ctctctcctt cttcaaggtt tgcgtattgc tgtgccagca   480
gcccttcttc ttgccatccc ggcccaatct gttcaacatg cccttggctt gatgcctgac   540
tggctcaccc atggtttggt tgtcggtggt ggtatggtcg tagccgttgg ttacgccatg   600
attatcaata tgatggctac tcgtgaagtt tggccattct cgccatcgg ttttgctttg   660 gcagcaatta gccaattgac acttatcgct cttagtacca ttggtgttgc catcgccttc   720
atctacctca acctttctaa acaaggtggc ggaaatggtg cggaaatgg tggcggaact   780 tcatctggtt caggcgaccc aatcggcgat atcttggaag actactag              828

<210> SEQ ID NO 132
<211> LENGTH: 275
<212> TYPE: PRT
<213> ORGANISM: Streptococcus thermophilus

<400> SEQUENCE: 132

Met Ser Asp Met Ser Ile Ile Ser Ala Ile Leu Val Val Ala Val Ala
1               5                   10                  15

Phe Leu Ala Gly Leu Glu Ser Ile Leu Asp Gln Phe Gln Phe His Gln
                20                  25                  30

Pro Leu Val Ala Cys Thr Leu Ile Gly Ala Ala Thr Gly Asn Leu Thr
            35                  40                  45

Ala Gly Ile Met Leu Gly Gly Ser Leu Gln Met Ile Thr Leu Ala Trp
        50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
```

```
                     85                  90                  95
Ile Gly Val Ala Ile Ala Ile Leu Leu Ala Val Ala Gly Leu
                    100                 105                 110
Phe Leu Thr Met Pro Val Arg Thr Ala Ser Ile Ala Phe Val His Ala
                    115                 120                 125
Ala Asp Lys Ala Ala Glu His Gly Asn Ile Ala Gly Val Glu Arg Ala
                    130                 135                 140
Tyr Tyr Leu Ser Leu Leu Leu Gln Gly Leu Arg Ile Ala Val Pro Ala
145                 150                 155                 160
Ala Leu Leu Leu Ala Ile Pro Ala Gln Ser Val Gln His Ala Leu Gly
                    165                 170                 175
Leu Met Pro Asp Trp Leu Thr His Gly Leu Val Val Gly Gly Gly Met
                    180                 185                 190
Val Val Ala Val Gly Tyr Ala Met Ile Ile Asn Met Met Ala Thr Arg
                    195                 200                 205
Glu Val Trp Pro Phe Phe Ala Ile Gly Phe Ala Leu Ala Ala Ile Ser
                    210                 215                 220
Gln Leu Thr Leu Ile Ala Leu Ser Thr Ile Gly Val Ala Ile Ala Phe
225                 230                 235                 240
Ile Tyr Leu Asn Leu Ser Lys Gln Gly Gly Asn Gly Gly Asn
                    245                 250                 255
Gly Gly Gly Thr Ser Ser Gly Ser Gly Asp Pro Ile Gly Asp Ile Leu
                    260                 265                 270
Glu Asp Tyr
            275

<210> SEQ ID NO 133
<211> LENGTH: 828
<212> TYPE: DNA
<213> ORGANISM: Streptococcus thermophilus

<400> SEQUENCE: 133
atgtcagata tgtcaattat ttctgcgatt ttggtcgtag ctgttgcctt ccttgctggt    60
cttgaaggta tccttgacca attccaattc caccaaccac ttgttgcatg taccctcatc   120
ggtgctgcca caggtaacct cactgcaggt atcatgcttg gtggttctct tcaaatgatt   180
acccttgctt gggcaaacat cggtgctgcc gtagctcctg acgttgccct tgcatctgtt   240
gctgctgcca tcattttggt taaaggtggt aaatttacag ctgaaggtat cggtgttgcg   300
attgcaatag ctatcctgct tgcagttgca ggtctcttcc taactatgcc tgttcgtaca   360
gcatctattg cctttgttca tgctgcagat aaagctgcag aacacggaaa catcgctggt   420
gttgaacgtg catactacct cgctctcctt cttcaaggtt tgcgtattgc tgtgccagca   480
gcccttcttc ttgccatccc ggcccaatct gttcaacatg cccttggctt gatgcctgac   540
tggctcaccc atggtttggt tgtcggtggt ggtatggtcg tagccgttgg ttacgccatg   600
attatcaata tgatggctac tcgtgaagtt tggccattct tcgccatcgg ttttgctttg   660
gcagcaatta gccaattgac acttatcgct cttagtacca ttggtgttgc catcgccttc   720
atctacctca acctttctaa acaaggtggc ggaaatggtg gcggaaatgg tggcggaact   780
tcatctggtt caggcgaccc aatcggcgat atcttggaag actactag              828

<210> SEQ ID NO 134
<211> LENGTH: 275
<212> TYPE: PRT
<213> ORGANISM: Streptococcus thermophilus
```

<400> SEQUENCE: 134

Met Ser Asp Met Ser Ile Ile Ser Ala Ile Leu Val Val Ala Val Ala
1               5                   10                  15

Phe Leu Ala Gly Leu Glu Gly Ile Leu Asp Gln Phe Gln Phe His Gln
            20                  25                  30

Pro Leu Val Ala Cys Thr Leu Ile Gly Ala Ala Thr Gly Asn Leu Thr
                35                  40                  45

Ala Gly Ile Met Leu Gly Gly Ser Leu Gln Met Ile Thr Leu Ala Trp
50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala
130                 135                 140

Tyr Tyr Leu Ala Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
            180                 185                 190

Val Val Ala Val Gly Tyr Ala Met Ile Ile Asn Met Met Ala Thr Arg
        195                 200                 205

Glu Val Trp Pro Phe Phe Ala Ile Gly Phe Ala Leu Ala Ala Ile Ser
    210                 215                 220

Gln Leu Thr Leu Ile Ala Leu Ser Thr Ile Gly Val Ala Ile Ala Phe
225                 230                 235                 240

Ile Tyr Leu Asn Leu Ser Lys Gln Gly Gly Gly Asn Gly Gly Gly Asn
                245                 250                 255

Gly Gly Gly Thr Ser Ser Gly Ser Gly Asp Pro Ile Gly Asp Ile Leu
            260                 265                 270

Glu Asp Tyr
        275

<210> SEQ ID NO 135
<211> LENGTH: 828
<212> TYPE: DNA
<213> ORGANISM: Streptococcus thermophilus

<400> SEQUENCE: 135
atgtcagata tgtcaattat ttctgcgatt ttggtcgtag ctgttgcctt ccttgctggt      60
cttgaaagta tccttgacca attccaattc caccaaccac ttgttgcatg taccctcatc     120
ggtgctgcca caggtaatct cactgcaggt atcatgcttg gtggttctct tcaaatgatt     180
acccttgctt gggcaaacat cggtgctgcc gtagctcctg acgttgccct tgcatctgtt     240
gccgctgcca tcattttggt taaaggtggt aaatttacag ctgaaggtat cggtgttgcg     300
attgcaatag ctatcctgct tgcagttgca ggtctcttcc taactatgcc tgttcgtaca     360
gcatctattg cctttgttca tgctgcagat aaagctgcag aacacggaaa catcgctggt     420

```
gttgaacgtg catactacct ctctctcctt cttcaaggtt tgcgtattgc tgtgccagca    480
gcccttcttc ttgccatccc ggcccaatct gttcaacatg cccttggctt gatgcctgac    540
tggctcaccc atggtttggt tgtcggtggt ggtatggtcg tagccgttgg ttacgccatg    600
attatcaata tgatggctac tcgtgaagtt tggccattct tcgccattgg ttttgctttg    660
gcagcaatta gccaattgac acttatcgct ctttgtgcca ttggtgttgc catcgccttc    720
atctacctca acctttctaa acaaggtggc ggaaatggcg gcggaaatgg tggcggaact    780
tcatctggtt caggcgaccc aatcggcgat atcttggaag actactag                 828
```

<210> SEQ ID NO 136
<211> LENGTH: 275
<212> TYPE: PRT
<213> ORGANISM: Streptococcus thermophilus

<400> SEQUENCE: 136

```
Met Ser Asp Met Ser Ile Ile Ser Ala Ile Leu Val Val Ala Val Ala
1               5                   10                  15

Phe Leu Ala Gly Leu Glu Ser Ile Leu Asp Gln Phe Gln His Gln
            20                  25                  30

Pro Leu Val Ala Cys Thr Leu Ile Gly Ala Ala Thr Gly Asn Leu Thr
        35                  40                  45

Ala Gly Ile Met Leu Gly Gly Ser Leu Gln Met Ile Thr Leu Ala Trp
    50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Leu Leu Ala Val Ala Gly Leu
            100                 105                 110

Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala
    130                 135                 140

Tyr Tyr Leu Ser Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Met
            180                 185                 190

Val Val Ala Val Gly Tyr Ala Met Ile Ile Asn Met Met Ala Thr Arg
    195                 200                 205

Glu Val Trp Pro Phe Phe Ala Ile Gly Phe Ala Leu Ala Ala Ile Ser
210                 215                 220

Gln Leu Thr Leu Ile Ala Leu Cys Ala Ile Gly Val Ala Ile Ala Phe
225                 230                 235                 240

Ile Tyr Leu Asn Leu Ser Lys Gln Gly Gly Gly Asn Gly Gly Gly Asn
                245                 250                 255

Gly Gly Gly Thr Ser Ser Gly Ser Gly Asp Pro Ile Gly Asp Ile Leu
            260                 265                 270

Glu Asp Tyr
275
```

<210> SEQ ID NO 137
<211> LENGTH: 828

<212> TYPE: DNA
<213> ORGANISM: Streptococcus thermophilus

<400> SEQUENCE: 137

```
atgtcagata tgtcaattat ttctgcgatt ttggtcgtag ctgttgcctt ccttgctggt      60
cttgaaagta tccttgacca attccaattc caccaaccac ttgttgcatg taccctcatc     120
ggtgctgcca caggtaacct cactgcaggt atcatgcttg gtggttctct tcaaatgatt     180
acccttgctt gggcaaacat cggtgctgcc gtagctcctg acgttgccct tgcatctgtt     240
gccgctgcca tcattttggt taaaggtggt aaatttacag ctgaaggtat cggtgttgcg     300
attgcaatag ctatcctgct tgcagttgca ggtctcttcc taactatgcc tgttcgtaca     360
gcatctattg cctttgttca tgctgcagat aaagctgcag aacacggaaa catcgctggt     420
gttgaacgtg catactacct ctctctcctt cttcaaggtt tgcgtattgc tgtgccagca     480
gcccttcttc ttgccatccc ggcccaatct gttcaacatg cccttggctt gatgcctgac     540
tggctcaccc atggtttggt tgtcggtagt ggtatggtcg tagccgttgg ttacgccatg     600
attatcaata tgatggctac tcgtgaagtt tggccattct tcgccattgg ttttgctttg     660
gcagcaatta gccaattgac acttatcgct ctttgtgcca ttggtgttgc catcgccttc     720
atctacctca accttttctaa acaaggtggc ggaaatggtg gcggaaatgg tggcggaact     780
tcatctggtt caggcgaccc aatcggcgat atcttggaag actactag               828
```

<210> SEQ ID NO 138
<211> LENGTH: 275
<212> TYPE: PRT
<213> ORGANISM: Streptococcus thermophilus

<400> SEQUENCE: 138

```
Met Ser Asp Met Ser Ile Ile Ser Ala Ile Leu Val Val Ala Val Ala
  1               5                  10                  15

Phe Leu Ala Gly Leu Glu Ser Ile Leu Asp Gln Phe Gln Phe His Gln
                 20                  25                  30

Pro Leu Val Ala Cys Thr Leu Ile Gly Ala Ala Thr Gly Asn Leu Thr
             35                  40                  45

Ala Gly Ile Met Leu Gly Gly Ser Leu Gln Met Ile Thr Leu Ala Trp
         50                  55                  60

Ala Asn Ile Gly Ala Ala Val Ala Pro Asp Val Ala Leu Ala Ser Val
 65                  70                  75                  80

Ala Ala Ala Ile Ile Leu Val Lys Gly Gly Lys Phe Thr Ala Glu Gly
                 85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala
    130                 135                 140

Tyr Tyr Leu Ser Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Ser Gly Met
            180                 185                 190

Val Val Ala Val Gly Tyr Ala Met Ile Ile Asn Met Met Ala Thr Arg
        195                 200                 205
```

Glu Val Trp Pro Phe Phe Ala Ile Gly Phe Ala Leu Ala Ala Ile Ser
    210                 215                 220
Gln Leu Thr Leu Ile Ala Leu Cys Ala Ile Gly Val Ala Ile Ala Phe
225                 230                 235                 240
Ile Tyr Leu Asn Leu Ser Lys Gln Gly Gly Asn Gly Gly Asn
            245                 250                 255
Gly Gly Gly Thr Ser Ser Gly Ser Gly Asp Pro Ile Gly Asp Ile Leu
            260                 265                 270
Glu Asp Tyr
        275

<210> SEQ ID NO 139
<211> LENGTH: 828
<212> TYPE: DNA
<213> ORGANISM: Streptococcus thermophilus

<400> SEQUENCE: 139
atgtcagata tgtcaattat ttctgcgatt ttggtcgtag ctgttgcctt ccttgctggt    60
cttgaaagta tccttgacca attccaattc caccaaccac ttgttgcatg taccctcatc   120
ggtgctgcca caggtaacct cactgcaggt atcatgcttg gtggttctct tcaaatgatt   180
acccttgctt gggcaaacat cggtgctgcc gtagctcctg acgttgccct tgcatctgtt   240
gccgctgcca tcattttggt taaaggtggt aaatttacag ctgaaggtat cggtgttgcg   300
attgcaatag ctatcctgct tgcagttgca ggtctcttcc taactatgcc tgttcgtaca   360
gcatctattg cctttgttca tgctgcagat aaagctgcag aacacggaaa catcgctggt   420
gttgaacgtg catactacct cgctctcctt cttcaaggtt tgcgtattgc tgtgccagca   480
gcccttcttc ttgccatccc ggcccaatct gttcaacatg cccttggctt gatgcctgac   540
tggctcaccc atggtttggt tgtcggtggt ggtatggtcg tagccgttgg ttacgccatg   600
attatcaata tgatggctac tcgtgaagtt tggccattct tcgccatcgg ttttgctttg   660
gcagcaatta gccaattgac acttatcgct cttggtacca ttggtgttgc catcgccttc   720
atctacctca acctttctaa acaaggtggc ggaaatggtg gcggaaatgg tggcggaact   780
tcatctggtt caggcgaccc aatcggcgat atcttggaag actactag               828

<210> SEQ ID NO 140
<211> LENGTH: 275
<212> TYPE: PRT
<213> ORGANISM: Streptococcus thermophilus

<400> SEQUENCE: 140

Met Ser Asp Met Ser Ile Ile Ser Ala Ile Leu Val Val Ala Val Ala
1               5                   10                  15
Phe Leu Ala Gly Leu Glu Ser Ile Leu Asp Gln Phe Gln Phe His Gln
            20                  25                  30
Pro Leu Val Ala Cys Thr Leu Ile Gly Ala Ala Thr Gly Asn Leu Thr
        35                  40                  45
Ala Gly Ile Met Leu Gly Gly Ser Leu Gln Met Ile Thr Leu Ala Trp
    50                  55                  60
Ala Asn Ile Gly Ala Ala Val Ala Pro Asp Val Ala Leu Ala Ser Val
65                  70                  75                  80
Ala Ala Ala Ile Ile Leu Val Lys Gly Gly Lys Phe Thr Ala Glu Gly
            85                  90                  95
Ile Gly Val Ala Ile Ala Ile Ala Ile Leu Leu Ala Val Ala Gly Leu

```
            100                 105                 110
Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala
130                 135                 140

Tyr Tyr Leu Ala Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Met
            180                 185                 190

Val Val Ala Val Gly Tyr Ala Met Ile Ile Asn Met Met Ala Thr Arg
        195                 200                 205

Glu Val Trp Pro Phe Phe Ala Ile Gly Phe Ala Leu Ala Ala Ile Ser
    210                 215                 220

Gln Leu Thr Leu Ile Ala Leu Gly Thr Ile Gly Val Ala Ile Ala Phe
225                 230                 235                 240

Ile Tyr Leu Asn Leu Ser Lys Gln Gly Gly Asn Gly Gly Asn
                245                 250                 255

Gly Gly Gly Thr Ser Ser Gly Ser Gly Asp Pro Ile Gly Asp Ile Leu
            260                 265                 270

Glu Asp Tyr
        275

<210> SEQ ID NO 141
<211> LENGTH: 828
<212> TYPE: DNA
<213> ORGANISM: Streptococcus thermophilus

<400> SEQUENCE: 141
atgtcagata tgtcaattat ttctgcgatt ttggtcgtag ctgttgcctt ccttgctggt      60
cttgaaggta tccttgacca attccaattc caccaaccac ttgttgcatg taccctcatc    120
ggtgctgcca caggtaacct cactgcaggt atcatgcttg gtggttctct tcaaatgatt    180
acccttgctt gggcaaacat cggtgctgcc gtagctcctg acgttgccct tgcatctgtt    240
gctgctgcca tcattttggt taaaggtggt aaatttacag ctgaaggtat cggtgttgcg    300
attgcaatag ctatcctgct tgcagttgca ggtctcttcc taactatgcc tgttcgtaca    360
gcatctattg cctttgttca tgctgcagat aaagctgcag aacacggaaa catcgctggt    420
gttgaacgtg catactacct cgctctcctt cttcaaggtt tgcgtattgc tgtgccagca    480
gcccttcttc ttgccatccc ggcccaatct gttcaacatg cccttggctt gatgcctgac    540
tggctcaccc atggtttggt tgtcggtggt ggtatggtcg tagccgttgg ttacgccatg    600
attatcaata tgatggctac tcgtgaagtt tggccattct tcgccatcgg ttttgctttg    660
gcagcaatta gccaattgac acttatcgct cttggtacca ttggtgttgc catcgccttc    720
atctacctca acctttctaa acaaggtggc ggaaatggtg gcggaaatgg tggcggaact    780
tcatctggtt caggcgaccc aatcggcgat atcttggaag actactag              828

<210> SEQ ID NO 142
<211> LENGTH: 275
<212> TYPE: PRT
<213> ORGANISM: Streptococcus thermophilus

<400> SEQUENCE: 142
```

Met Ser Asp Met Ser Ile Ile Ser Ala Ile Leu Val Val Ala Val Ala
1               5                   10                  15

Phe Leu Ala Gly Leu Glu Gly Ile Leu Asp Gln Phe Gln Phe His Gln
            20                  25                  30

Pro Leu Val Ala Cys Thr Leu Ile Gly Ala Ala Thr Gly Asn Leu Thr
                35                  40                  45

Ala Gly Ile Met Leu Gly Gly Ser Leu Gln Met Ile Thr Leu Ala Trp
50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Lys Phe Thr Ala Glu Gly
                85                  90                  95

Ile Gly Val Ala Ile Ala Ile Ala Ile Leu Leu Ala Val Ala Gly Leu
                100                 105                 110

Phe Leu Thr Met Pro Val Arg Thr Ala Ser Ile Ala Phe Val His Ala
            115                 120                 125

Ala Asp Lys Ala Ala Glu His Gly Asn Ile Ala Gly Val Glu Arg Ala
        130                 135                 140

Tyr Tyr Leu Ala Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
            180                 185                 190

Val Val Ala Val Gly Tyr Ala Met Ile Ile Asn Met Met Ala Thr Arg
                195                 200                 205

Glu Val Trp Pro Phe Phe Ala Ile Gly Phe Ala Leu Ala Ala Ile Ser
210                 215                 220

Gln Leu Thr Leu Ile Ala Leu Gly Thr Ile Gly Val Ala Ile Ala Phe
225                 230                 235                 240

Ile Tyr Leu Asn Leu Ser Lys Gln Gly Gly Asn Gly Gly Asn
                245                 250                 255

Gly Gly Gly Thr Ser Ser Gly Ser Gly Asp Pro Ile Gly Asp Ile Leu
            260                 265                 270

Glu Asp Tyr
275

<210> SEQ ID NO 143
<211> LENGTH: 828
<212> TYPE: DNA
<213> ORGANISM: Streptococcus thermophilus

<400> SEQUENCE: 143
atgtcagata tgtcaattat ttctgcgatt tggtcgtag ctgttgcctt ccttgctggt    60
cttgaaagta tccttgacca attccaattc caccaaccac ttgttgcatg tactctcatc   120
ggtgctgcca caggtaacct cactgcaggt atcatgcttg gtggttctct tcaaatgatt   180
acccttgctt gggcaaacat cggtgctgcc gtagctcctg acgttgccct tgcatctgtt   240
gccgctgcca tcatttttggt taaaggtggt aaatttacag ctgaaggtat cggtgttgcg   300
attgcaatag ctatcctgct tgcagttgca ggtctcttcc taactatgcc tgttcgtaca   360
gcatctattg cctttgttca tgctgcagat aaagctgcag aacacggaaa catcgctggt   420
gttgaacgtg catactacct ctctctcctt cttcaaggtt tgcgtattgc tgtgccagca   480
gcccttcttc ttgccatccc ggcccaatct gttcaacatg cccttggctt gatgcctgac   540

```
tggctcaccc atggtttggt tgtcggtggt ggtatggtcg tagccgttgg ttacgccatg    600
attatcaata tgatggctac tcgtgaagtt tggccattct tcgccatcgg ttttgctttg    660
gcagcaatta gccaattgac acttatcgct cttggtgcca ttggtgttgc catcgccttc    720
atctacctca accttttctaa acaaggtggc ggaaatggtg gcggaaatgg tggcggaact    780
tcatctggtt caggcgaccc aatcggcgat atcttggaag actactag                 828
```

<210> SEQ ID NO 144
<211> LENGTH: 275
<212> TYPE: PRT
<213> ORGANISM: Streptococcus thermophilus

<400> SEQUENCE: 144

```
Met Ser Asp Met Ser Ile Ile Ser Ala Ile Leu Val Ala Val Ala
1               5                   10                  15

Phe Leu Ala Gly Leu Glu Ser Ile Leu Asp Gln Phe Gln Phe His Gln
            20                  25                  30

Pro Leu Val Ala Cys Thr Leu Ile Gly Ala Ala Thr Gly Asn Leu Thr
        35                  40                  45

Ala Gly Ile Met Leu Gly Gly Ser Leu Gln Met Ile Thr Leu Ala Trp
    50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Leu Leu Ala Val Ala Gly Leu
            100                 105                 110

Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala
    130                 135                 140

Tyr Tyr Leu Ser Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Met
            180                 185                 190

Val Val Ala Val Gly Tyr Ala Met Ile Ile Asn Met Met Ala Thr Arg
        195                 200                 205

Glu Val Trp Pro Phe Phe Ala Ile Gly Phe Ala Leu Ala Ala Ile Ser
    210                 215                 220

Gln Leu Thr Leu Ile Ala Leu Gly Ala Ile Gly Val Ala Ile Ala Phe
225                 230                 235                 240

Ile Tyr Leu Asn Leu Ser Lys Gln Gly Gly Gly Asn Gly Gly Asn
                245                 250                 255

Gly Gly Gly Thr Ser Ser Gly Ser Gly Asp Pro Ile Gly Asp Ile Leu
            260                 265                 270

Glu Asp Tyr
        275
```

<210> SEQ ID NO 145
<211> LENGTH: 828
<212> TYPE: DNA
<213> ORGANISM: Streptococcus thermophilus

<400> SEQUENCE: 145

```
atgtcagata tgtcaattat ttctgcgatt ttggtcgtag ctgttgcctt ccttgctggt    60
cttgaaggta tccttgacca attccaattc caccaaccac ttgttgcata taccctcatc   120
ggtgctgcca caggtaacct cactgcaggt atcatgcttg gtggttctct tcaaatgatt   180
acccttgctt gggcaaacat cggtgctgcc gtagctcctg acgttgccct tgcatctgtt   240
gctgctgcca tcattttggt taaaggtggt aaatttacag ctgaaggtat cggtgttgcg   300
attgcaatag ctatcctgct tgcagttgca ggtctcttcc taactatgcc tgttcgtaca   360
gcatctattg cctttgttca tgctgcagat aaagctgcag aacacggaaa catcgctggt   420
gttgaacgtg catactacct cgctctcctt cttcaaggtt tgcgtattgc tgtgccagca   480
gcccttcttc ttgccatccc ggcccaatct gttcaacatg cccttggctt gatgcctgac   540
tggctcaccc atggtttggt tgtcggtggt ggtatggtcg tagccgttgg ttacgccatg   600
attatcaata tgatggctac tcgtgaagtt tggccattct tcgccatcgg ttttgctttg   660
gcagcaatta gccaattgac acttatcgct cttagtacca ttggtgttgc catcgccttc   720
atctacctca acctttctaa acaaggtggc ggaaatggtg gcggaaatgg tggcggaact   780
tcatctggtt caggcgaccc aatcggcgat atcttggaag actactag               828
```

<210> SEQ ID NO 146
<211> LENGTH: 275
<212> TYPE: PRT
<213> ORGANISM: Streptococcus thermophilus

<400> SEQUENCE: 146

```
Met Ser Asp Met Ser Ile Ile Ser Ala Ile Leu Val Val Ala Val Ala
1               5                   10                  15

Phe Leu Ala Gly Leu Glu Gly Ile Leu Asp Gln Phe Gln Phe His Gln
            20                  25                  30

Pro Leu Val Ala Tyr Thr Leu Ile Gly Ala Ala Thr Gly Asn Leu Thr
        35                  40                  45

Ala Gly Ile Met Leu Gly Gly Ser Leu Gln Met Ile Thr Leu Ala Trp
    50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala
    130                 135                 140

Tyr Tyr Leu Ala Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
            180                 185                 190

Val Val Ala Val Gly Tyr Ala Met Ile Ile Asn Met Met Ala Thr Arg
        195                 200                 205

Glu Val Trp Pro Phe Phe Ala Ile Gly Phe Ala Leu Ala Ala Ile Ser
    210                 215                 220
```

Gln Leu Thr Leu Ile Ala Leu Ser Thr Ile Gly Val Ala Ile Ala Phe
225                 230                 235                 240

Ile Tyr Leu Asn Leu Ser Lys Gln Gly Gly Asn Gly Gly Asn
                245                 250                 255

Gly Gly Gly Thr Ser Ser Gly Ser Gly Asp Pro Ile Gly Asp Ile Leu
            260                 265                 270

Glu Asp Tyr
    275

<210> SEQ ID NO 147
<211> LENGTH: 828
<212> TYPE: DNA
<213> ORGANISM: Streptococcus thermophilus

<400> SEQUENCE: 147

```
atgtcagata tgtcaattat ttctgcgatt ttggtcgtag ctgttgcctt ccttgctggt      60
cttgaaagta tccttgacca attccaattc caccaaccac ttgttgcatg taccctcatc     120
ggtgctgcca caggtaacct cactgcaggt atcatgcttg gtggttctct tcaaatgatt     180
acccttgctt gggcaaacat cggtgctgcc gtagctcctg acgttgccct tgcatctgtt     240
gccgctgcca tcattttggt taaaggtggt aaatttacag ctgaaggtat cggtgttgcg     300
attgcaatag ctatcctgct tgcagttgca ggtctcttcc taactatgcc tgttcgtaca     360
gcatctattg cctttgttca tgctgcagat aaagctgcag aacacggaaa catcgctggt     420
gttgaacgtg catactacct cgctctcctt cttcaaggtt gcgtattgc tgtgccagca     480
gcccttcttc ttgccatccc ggcccaatct gttcaacatg cccttggctt gatgcctgac     540
tggctcaccc atggtttggt tgtcggtagt ggtatggtcg tagccgttgg ttacgccatg     600
attatcaata tgatggctac tcgtgaagtt tggccattct tcgccatcgg ttttgctttg     660
gcagcaatta gccaattgac acttatcgct cttggtgcca ttggtgttgc catcgccttc     720
atctacctca acctttctaa acaaggtggc ggaaatagtg gcggaaatgg tggcggaact     780
tcatctggtt caggcgaccc aatcggcgat atcttggaag actactag                  828
```

<210> SEQ ID NO 148
<211> LENGTH: 275
<212> TYPE: PRT
<213> ORGANISM: Streptococcus thermophilus

<400> SEQUENCE: 148

Met Ser Asp Met Ser Ile Ile Ser Ala Ile Leu Val Val Ala Val Ala
1               5                   10                  15

Phe Leu Ala Gly Leu Glu Ser Ile Leu Asp Gln Phe Gln Phe His Gln
            20                  25                  30

Pro Leu Val Ala Cys Thr Leu Ile Gly Ala Ala Thr Gly Asn Leu Thr
        35                  40                  45

Ala Gly Ile Met Leu Gly Gly Ser Leu Gln Met Ile Thr Leu Ala Trp
    50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Leu Leu Ala Val Ala Gly Leu
            100                 105                 110

Phe Leu Thr Met Pro Val Arg Thr Ala Ser Ile Ala Phe Val His Ala

```
                    115                 120                 125
Ala Asp Lys Ala Ala Glu His Gly Asn Ile Ala Gly Val Glu Arg Ala
        130                 135                 140

Tyr Tyr Leu Ala Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Ser Gly Met
            180                 185                 190

Val Val Ala Val Gly Tyr Ala Met Ile Ile Asn Met Met Ala Thr Arg
        195                 200                 205

Glu Val Trp Pro Phe Phe Ala Ile Gly Phe Ala Leu Ala Ala Ile Ser
    210                 215                 220

Gln Leu Thr Leu Ile Ala Leu Gly Ala Ile Gly Val Ala Ile Ala Phe
225                 230                 235                 240

Ile Tyr Leu Asn Leu Ser Lys Gln Gly Gly Gly Asn Ser Gly Gly Asn
                245                 250                 255

Gly Gly Gly Thr Ser Ser Gly Ser Gly Asp Pro Ile Gly Asp Ile Leu
            260                 265                 270

Glu Asp Tyr
        275
```

<210> SEQ ID NO 149
<211> LENGTH: 828
<212> TYPE: DNA
<213> ORGANISM: Streptococcus thermophilus

<400> SEQUENCE: 149

```
atgtcagata tgtcaattat ttctgcgatt ttggtcgtag ctgttgcctt ccttgctggt    60
cttgaaagta tccttgacca attccaattc caccaaccac ttgttgcatg taccctcatc   120
ggtgctgcca caggtaacct cactgcaggt atcatgcttg gtggttctct tcaaatgatt   180
acccttgctt gggcaaacat cggtgctgcc gtagctcctg acgttgccct tgcatctgtt   240
gccgctgcca tcattttggt taaaggtggt aaatttacag ctgaaggtat cggtgttgcg   300
attgcaatag ctatcctgct tgcagttgca ggtctcttcc taactatgcc tgttcgtaca   360
gcatctatta cctttgttca tgctgcagat aaagctgcag aacacggaaa catcgctggt   420
gttgaacgtg catactacct ctctctcctt cttcaaggtt tgcgtattgc tgtgccagca   480
gcccttcttc ttgccatccc ggcccaatct gttcaacatg cccttggctt gatgcctgac   540
tggctcaccc atggtttggt tgtcggtggt ggtatggtcg tagccgttgg ttacgccatg   600
attatcaata tgatggctac tcgtgaagtt tggccattct cgccattggt ttttgctttg   660
gcagcaatta gccaattgac acttatcgct ctttgtgcca ttggtgttgc catcgccttc   720
atctacctca acctttctaa acaaggtggc ggaaatggtg cggaaatgg tggcggaact   780
tcatctggtt caggcgaccc aatcggcgat atcttggaag actactag              828
```

<210> SEQ ID NO 150
<211> LENGTH: 275
<212> TYPE: PRT
<213> ORGANISM: Streptococcus thermophilus

<400> SEQUENCE: 150

```
Met Ser Asp Met Ser Ile Ile Ser Ala Ile Leu Val Val Ala Val Ala
1               5                   10                  15
```

```
Phe Leu Ala Gly Leu Glu Ser Ile Leu Asp Gln Phe Gln Phe His Gln
             20                  25                  30

Pro Leu Val Ala Cys Thr Leu Ile Gly Ala Ala Thr Gly Asn Leu Thr
         35                  40                  45

Ala Gly Ile Met Leu Gly Gly Ser Leu Gln Met Ile Thr Leu Ala Trp
     50                  55                  60

Ala Asn Ile Gly Ala Ala Val Ala Pro Asp Val Ala Leu Ala Ser Val
 65                  70                  75                  80

Ala Ala Ala Ile Ile Leu Val Lys Gly Gly Lys Phe Thr Ala Glu Gly
                 85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Thr Phe Val His Ala
        115                 120                 125

Ala Asp Lys Ala Ala Glu His Gly Asn Ile Ala Gly Val Glu Arg Ala
130                 135                 140

Tyr Tyr Leu Ser Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
            180                 185                 190

Val Val Ala Val Gly Tyr Ala Met Ile Ile Asn Met Met Ala Thr Arg
        195                 200                 205

Glu Val Trp Pro Phe Phe Ala Ile Gly Phe Ala Leu Ala Ala Ile Ser
210                 215                 220

Gln Leu Thr Leu Ile Ala Leu Cys Ala Ile Gly Val Ala Ile Ala Phe
225                 230                 235                 240

Ile Tyr Leu Asn Leu Ser Lys Gln Gly Gly Asn Gly Gly Gly Asn
                245                 250                 255

Gly Gly Gly Thr Ser Ser Gly Ser Gly Asp Pro Ile Gly Asp Ile Leu
            260                 265                 270

Glu Asp Tyr
        275

<210> SEQ ID NO 151
<211> LENGTH: 828
<212> TYPE: DNA
<213> ORGANISM: Streptococcus thermophilus

<400> SEQUENCE: 151
atgtcagata tgtcaattat ttctgcgatt ttggtcgtag ctgttgcctt ccttgctggt      60
cttgaaagta tccttgacca attccaattc caccaaccac ttgttgcatg taccctcatc     120
ggtgctgcca caggtaacct cactgcaggt atcatgcttg gtggttctct tcaaatgatt     180
acccttgctt gggcaaacat cggtgctgcc gtagctcctg acgttgccct tgcatctgtt     240
gccgctgcca tcattttggt taaaggtggt aaatttacag ctgaaggtat cggtgttgcg     300
attgcaatag ctatcctgct tgcagttgca ggtctcttcc taactatgcc tgttcgtaca     360
gcatctattg cctttgttca tgctgcagat aaagctgcag aacacggaaa catcgctggt     420
gttgaacgtg catactacct ctctctcctt cttcaaggtt tgcgtattgc tgtgccagca     480
gcccttcttc ttgccatccc ggcccaatct gttcaacatg cccttggctt gatgcctgac     540
tggctcaccc atggtttggt tgtcggtggt ggtatggtcg tagccgttgg ttacgccatg     600
```

```
attatcaata tgatggctac tcgtgaagtt tggccattct tcgccattgg ttttgctttg    660
gcagcaatta gccaattgac acttatcgct cttggtgcca ttggtgttgc catcgccttc    720
atctacctca accttctaa acatggtggc ggaaatggtg gcggaaatgg tggcggaact    780
tcatctggtt caggcgaccc aatcggcgat atcttggaag actactag                828
```

<210> SEQ ID NO 152
<211> LENGTH: 275
<212> TYPE: PRT
<213> ORGANISM: Streptococcus thermophilus

<400> SEQUENCE: 152

```
Met Ser Asp Met Ser Ile Ile Ser Ala Ile Leu Val Val Ala Val Ala
1               5                   10                  15

Phe Leu Ala Gly Leu Glu Ser Ile Leu Asp Gln Phe Gln Phe His Gln
            20                  25                  30

Pro Leu Val Ala Cys Thr Leu Ile Gly Ala Ala Thr Gly Asn Leu Thr
        35                  40                  45

Ala Gly Ile Met Leu Gly Gly Ser Leu Gln Met Ile Thr Leu Ala Trp
    50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala
    130                 135                 140

Tyr Tyr Leu Ser Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
            180                 185                 190

Val Val Ala Val Gly Tyr Ala Met Ile Ile Asn Met Met Ala Thr Arg
        195                 200                 205

Glu Val Trp Pro Phe Phe Ala Ile Gly Phe Ala Leu Ala Ala Ile Ser
    210                 215                 220

Gln Leu Thr Leu Ile Ala Leu Gly Ala Ile Gly Val Ala Ile Ala Phe
225                 230                 235                 240

Ile Tyr Leu Asn Leu Ser Lys His Gly Gly Gly Asn Gly Gly Gly Asn
                245                 250                 255

Gly Gly Gly Thr Ser Ser Gly Ser Gly Asp Pro Ile Gly Asp Ile Leu
            260                 265                 270

Glu Asp Tyr
        275
```

<210> SEQ ID NO 153
<211> LENGTH: 828
<212> TYPE: DNA
<213> ORGANISM: Streptococcus thermophilus

<400> SEQUENCE: 153

```
atgtcagata tgtcaattat ttctgcgatt ttggtcgtag ctgttacctt ccttgctggt     60
```

```
cttgaaagta tccttgacca attccaattc caccaaccac ttgttgcatg taccctcatc    120
ggtgctgcca caggtaacct cactgcaggt atcatgcttg gtggttctct tcaaatgatt    180
acccttgctt gggcaaacat cggtgctgcc gtagctcctg acgttgccct tgcatctgtt    240
gccgctgcca tcattttggt taaaggtggt aaatttacag ctgaaggtat cggtgttgcg    300
attgcaatag ctatcctgct tgcagttgca ggtctcttcc taactatgcc tgttcgtaca    360
gcatctattg cctttgttca tgctgcagat aaagctgcag aacacggaaa catcgctggt    420
gttgaacgtg catactacct cgctctcctt cttcaaggtt tgcgtattgc tgtgccagca    480
gcccttcttc ttgccatccc ggcccaatct gttcaacatg cccttggctt gatgcctgac    540
tggctcaccc atggtttggt tgtcggtagt ggtatggtcg tagccgttgg ttacgccatg    600
attatcaata tgatggctac tcgtgaagtt tggccattct cgccatcgg ttttgctttg    660 gcagcaatta gccaattgac acttatcgct cttggtgcca ttggtgttgc catcgccttc    720
atctacctca acctttctaa acaaggtggt ggaaatggtg gcggaaatgg tggcggaact    780
tcatctggtt caggcgaccc aatcggcgat atcttggaag actactag              828
```

<210> SEQ ID NO 154
<211> LENGTH: 275
<212> TYPE: PRT
<213> ORGANISM: Streptococcus thermophilus

<400> SEQUENCE: 154

```
Met Ser Asp Met Ser Ile Ile Ser Ala Ile Leu Val Val Ala Val Thr
1               5                   10                  15

Phe Leu Ala Gly Leu Glu Ser Ile Leu Asp Gln Phe Gln Phe His Gln
                20                  25                  30

Pro Leu Val Ala Cys Thr Leu Ile Gly Ala Ala Thr Gly Asn Leu Thr
            35                  40                  45

Ala Gly Ile Met Leu Gly Gly Ser Leu Gln Met Ile Thr Leu Ala Trp
        50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala
    130                 135                 140

Tyr Tyr Leu Ala Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Gly Ser Gly Met
        180                 185                 190

Val Val Ala Val Gly Tyr Ala Met Ile Ile Asn Met Met Ala Thr Arg
    195                 200                 205

Glu Val Trp Pro Phe Phe Ala Ile Gly Phe Ala Leu Ala Ala Ile Ser
    210                 215                 220

Gln Leu Thr Leu Ile Ala Leu Gly Ala Ile Gly Val Ala Ile Ala Phe
225                 230                 235                 240
```

Ile Tyr Leu Asn Leu Ser Lys Gln Gly Gly Asn Gly Gly Gly Asn
                245                 250                 255

Gly Gly Gly Thr Ser Ser Gly Ser Gly Asp Pro Ile Gly Asp Ile Leu
            260                 265                 270

Glu Asp Tyr
        275

<210> SEQ ID NO 155
<211> LENGTH: 828
<212> TYPE: DNA
<213> ORGANISM: Streptococcus thermophilus

<400> SEQUENCE: 155
atgtcagata tgtcaattat ttctgcgatt ttggtcgtag ctgttgcctt ccttgctggt      60
cttgaaagta tccttgacca attccaattc caccaaccac ttgttgcatg taccctcatc     120
ggtgctgcca caggtaacct cactgcaggt atcatgcttg gtggttctct tcaaatgatt     180
acccttgctt gggcaaacat cggtgctgcc gtagctcctg acgttgccct tgcatctgtt     240
gccgctgcca tcattttggt taaaggtggt aaatttacag ctgaaggtat cggtgttgcg     300
attgcaatag ctatcctgct tgcagttgca ggtctcttcc taactatgcc tgttcgtaca     360
gcatctattg cctttgttca tgctgcagat aaagctgcag aacacggaaa catcgctggt     420
gttgaacgtg catactacct cgctctcctt cttcaaggtt tgcgtattgc tgtgccagca     480
gcccttcttc ttgccatccc ggcccaatct gttcaacatg cccttggctt gatgcctgac     540
tggctcaccc atggtttggt tgtcggtagt ggtatggtcg tagccgttgg ttacgccatg     600
attatcaata tgatggctac tcgtgaagtt tggccattct tcgccatcgg ttttgctttg     660
gcagcaatta gccaattgac acttatcgct cttggtgcca ttggtgttgc catcgccttc     720
atctacctca acctttctaa acaaggtggc ggaaatggtg gcggaaatgg tggcggaact     780
tcatctggtt caggcgaccc aatcggcgat atcttggaag actactag               828

<210> SEQ ID NO 156
<211> LENGTH: 275
<212> TYPE: PRT
<213> ORGANISM: Streptococcus thermophilus

<400> SEQUENCE: 156

Met Ser Asp Met Ser Ile Ile Ser Ala Ile Leu Val Val Ala Val Ala
1               5                   10                  15

Phe Leu Ala Gly Leu Glu Ser Ile Leu Asp Gln Phe Gln Phe His Gln
            20                  25                  30

Pro Leu Val Ala Cys Thr Leu Ile Gly Ala Ala Thr Gly Asn Leu Thr
        35                  40                  45

Ala Gly Ile Met Leu Gly Gly Ser Leu Gln Met Ile Thr Leu Ala Trp
    50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala

```
            130                 135                 140
Tyr Tyr Leu Ala Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Ser Gly Met
            180                 185                 190

Val Val Ala Val Gly Tyr Ala Met Ile Ile Asn Met Met Ala Thr Arg
        195                 200                 205

Glu Val Trp Pro Phe Phe Ala Ile Gly Phe Ala Leu Ala Ala Ile Ser
    210                 215                 220

Gln Leu Thr Leu Ile Ala Leu Gly Ala Ile Gly Val Ala Ile Ala Phe
225                 230                 235                 240

Ile Tyr Leu Asn Leu Ser Lys Gln Gly Gly Asn Gly Gly Asn
                245                 250                 255

Gly Gly Gly Thr Ser Ser Gly Ser Gly Asp Pro Ile Gly Asp Ile Leu
            260                 265                 270

Glu Asp Tyr
        275

<210> SEQ ID NO 157
<211> LENGTH: 828
<212> TYPE: DNA
<213> ORGANISM: Streptococcus thermophilus

<400> SEQUENCE: 157
atgtcagata tgtcaattat ttctgcgatt ttggtcgtag ctgttgcctt ccttgctggt     60
cttgaaagta tccttgacca attccaattc caccaaccac ttgttgcatg taccctcatc    120
ggtgctgcca caggtaacct cactgcaggt atcatgcttg gtggttctct tcaaatgatt    180
acccttgctt gggcaaacat cggtgctgcc gtagctcctg acgttgccct tgcatctgtt    240
gccgctgcca tcattttggt taaaggtggt aaatttacag ctgaaggtat cggtgttgcg    300
attgcaatag ctatcctgct tgcagttgca ggtctcttcc taactatgcc tgttcgtaca    360
gcatctattg cctttgttca tgctgcagat aaagctgcag aacacggaaa catcgctggt    420
gttgaacgtg catactacct cgctctcctt cttcaaggtt gcgtattgc tgtgccagca     480 gcccttcttc ttgccatccc ggcccaatct gttcaacatg cccttggctt gatgcctgac    540
tggctcaccc atggtttggt tgtcggtggt ggtatggtcg tagccgttgg ttacgccatg    600
attatcaata tgatggctac tcgttaagtt tggccattct tcgccattgg ttttgctttg    660
gcagcaatta gccaattgac acttatcgct cttagtacca ttggtgttgc catcgccttc    720
atctacctca accttttctaa acaaggtggc ggaaatggtg gcggaaatgg tggcggaact    780
tcatctggtt caggcgaccc aatcggcgat atcttggaag actactag               828

<210> SEQ ID NO 158
<211> LENGTH: 208
<212> TYPE: PRT
<213> ORGANISM: Streptococcus thermophilus

<400> SEQUENCE: 158

Met Ser Asp Met Ser Ile Ile Ser Ala Ile Leu Val Val Ala Val Ala
1               5                   10                  15

Phe Leu Ala Gly Leu Glu Ser Ile Leu Asp Gln Phe Gln Phe His Gln
            20                  25                  30
```

```
Pro Leu Val Ala Cys Thr Leu Ile Gly Ala Ala Thr Gly Asn Leu Thr
         35                  40                  45

Ala Gly Ile Met Leu Gly Gly Ser Leu Gln Met Ile Thr Leu Ala Trp
 50                  55                  60

Ala Asn Ile Gly Ala Ala Val Ala Pro Asp Val Ala Leu Ala Ser Val
 65                  70                  75                  80

Ala Ala Ala Ile Ile Leu Val Lys Gly Gly Lys Phe Thr Ala Glu Gly
                 85                  90                  95

Ile Gly Val Ala Ile Ala Ile Ala Ile Leu Leu Ala Val Ala Gly Leu
                100                 105                 110

Phe Leu Thr Met Pro Val Arg Thr Ala Ser Ile Ala Phe Val His Ala
            115                 120                 125

Ala Asp Lys Ala Ala Glu His Gly Asn Ile Ala Gly Val Glu Arg Ala
        130                 135                 140

Tyr Tyr Leu Ala Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
            180                 185                 190

Val Val Ala Val Gly Tyr Ala Met Ile Ile Asn Met Met Ala Thr Arg
        195                 200                 205
```

<210> SEQ ID NO 159
<211> LENGTH: 208
<212> TYPE: PRT
<213> ORGANISM: Streptococcus thermophilus

<400> SEQUENCE: 159

```
Met Ser Asp Met Ser Ile Ile Ser Ala Ile Leu Val Val Ala Val Ala
 1               5                  10                  15

Phe Leu Ala Gly Leu Glu Ser Ile Leu Asp Gln Phe Gln Phe His Gln
            20                  25                  30

Pro Leu Val Ala Cys Thr Leu Ile Gly Ala Ala Thr Gly Asn Leu Thr
         35                  40                  45

Ala Gly Ile Met Leu Gly Gly Ser Leu Gln Met Ile Thr Leu Ala Trp
 50                  55                  60

Ala Asn Ile Gly Ala Ala Val Ala Pro Asp Val Ala Leu Ala Ser Val
 65                  70                  75                  80

Ala Ala Ala Ile Ile Leu Val Lys Gly Gly Lys Phe Thr Ala Glu Gly
                 85                  90                  95

Ile Gly Val Ala Ile Ala Ile Ala Ile Leu Leu Ala Val Ala Gly Leu
                100                 105                 110

Phe Leu Thr Met Pro Val Arg Thr Ala Ser Ile Ala Phe Val His Ala
            115                 120                 125

Ala Asp Lys Ala Ala Glu His Gly Asn Ile Ala Gly Val Glu Arg Ala
        130                 135                 140

Tyr Tyr Leu Ser Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
            180                 185                 190

Val Val Ala Val Gly Tyr Ala Met Ile Ile Asn Met Met Ala Thr Arg
        195                 200                 205
```

<210> SEQ ID NO 160
<211> LENGTH: 208
<212> TYPE: PRT
<213> ORGANISM: Streptococcus thermophilus

<400> SEQUENCE: 160

Met Ser Asp Met Ser Ile Ile Ser Ala Ile Leu Val Val Ala Val Ala
1               5                   10                  15

Phe Leu Ala Gly Leu Glu Gly Ile Leu Asp Gln Phe Gln Phe His Gln
            20                  25                  30

Pro Leu Val Ala Cys Thr Leu Ile Gly Ala Ala Thr Gly Asn Leu Thr
        35                  40                  45

Ala Gly Ile Met Leu Gly Gly Ser Leu Gln Met Ile Thr Leu Ala Trp
    50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala
    130                 135                 140

Tyr Tyr Leu Ala Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
            180                 185                 190

Val Val Ala Val Gly Tyr Ala Met Ile Ile Asn Met Met Ala Thr Arg
        195                 200                 205

<210> SEQ ID NO 161
<211> LENGTH: 208
<212> TYPE: PRT
<213> ORGANISM: Streptococcus thermophilus

<400> SEQUENCE: 161

Met Ser Asp Met Ser Ile Ile Ser Ala Ile Leu Val Val Ala Val Ala
1               5                   10                  15

Phe Leu Ala Gly Leu Glu Ser Ile Leu Asp Gln Phe Gln Phe His Gln
            20                  25                  30

Pro Leu Val Ala Cys Thr Leu Ile Gly Ala Ala Thr Gly Asn Leu Thr
        35                  40                  45

Ala Gly Ile Met Leu Gly Gly Ser Leu Gln Met Ile Thr Leu Ala Trp
    50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Ala Phe Val His Ala
        115                 120                 125

```
Ala Asp Lys Ala Ala Glu His Gly Asn Ile Ala Gly Val Glu Arg Ala
        130                 135                 140

Tyr Tyr Leu Ser Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Ser Gly Met
                180                 185                 190

Val Val Ala Val Gly Tyr Ala Met Ile Ile Asn Met Met Ala Thr Arg
                195                 200                 205

<210> SEQ ID NO 162
<211> LENGTH: 208
<212> TYPE: PRT
<213> ORGANISM: Streptococcus thermophilus

<400> SEQUENCE: 162

Met Ser Asp Met Ser Ile Ile Ser Ala Ile Leu Val Val Ala Val Ala
1               5                   10                  15

Phe Leu Ala Gly Leu Glu Gly Ile Leu Asp Gln Phe Gln Phe His Gln
                20                  25                  30

Pro Leu Val Ala Tyr Thr Leu Ile Gly Ala Ala Thr Gly Asn Leu Thr
                35                  40                  45

Ala Gly Ile Met Leu Gly Gly Ser Leu Gln Met Ile Thr Leu Ala Trp
        50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Ile Leu Leu Ala Val Ala Gly Leu
                100                 105                 110

Phe Leu Thr Met Pro Val Arg Thr Ala Ser Ile Ala Phe Val His Ala
                115                 120                 125

Ala Asp Lys Ala Ala Glu His Gly Asn Ile Ala Gly Val Glu Arg Ala
        130                 135                 140

Tyr Tyr Leu Ala Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
                180                 185                 190

Val Val Ala Val Gly Tyr Ala Met Ile Ile Asn Met Met Ala Thr Arg
                195                 200                 205

<210> SEQ ID NO 163
<211> LENGTH: 208
<212> TYPE: PRT
<213> ORGANISM: Streptococcus thermophilus

<400> SEQUENCE: 163

Met Ser Asp Met Ser Ile Ile Ser Ala Ile Leu Val Val Ala Val Ala
1               5                   10                  15

Phe Leu Ala Gly Leu Glu Ser Ile Leu Asp Gln Phe Gln Phe His Gln
                20                  25                  30

Pro Leu Val Ala Cys Thr Leu Ile Gly Ala Ala Thr Gly Asn Leu Thr
                35                  40                  45
```

```
Ala Gly Ile Met Leu Gly Gly Ser Leu Gln Met Ile Thr Leu Ala Trp
         50                  55                  60

Ala Asn Ile Gly Ala Ala Val Ala Pro Asp Val Ala Leu Ala Ser Val
 65                  70                  75                  80

Ala Ala Ala Ile Ile Leu Val Lys Gly Gly Lys Phe Thr Ala Glu Gly
                 85                  90                  95

Ile Gly Val Ala Ile Ala Ile Ala Ile Leu Leu Ala Val Ala Gly Leu
                100                 105                 110

Phe Leu Thr Met Pro Val Arg Thr Ala Ser Ile Ala Phe Val His Ala
                115                 120                 125

Ala Asp Lys Ala Ala Glu His Gly Asn Ile Ala Gly Val Glu Arg Ala
    130                 135                 140

Tyr Tyr Leu Ala Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Ser Gly Met
                180                 185                 190

Val Val Ala Val Gly Tyr Ala Met Ile Ile Asn Met Met Ala Thr Arg
                195                 200                 205

<210> SEQ ID NO 164
<211> LENGTH: 208
<212> TYPE: PRT
<213> ORGANISM: Streptococcus thermophilus

<400> SEQUENCE: 164

Met Ser Asp Met Ser Ile Ile Ser Ala Ile Leu Val Val Ala Val Ala
1               5                   10                  15

Phe Leu Ala Gly Leu Glu Ser Ile Leu Asp Gln Phe Gln Phe His Gln
                20                  25                  30

Pro Leu Val Ala Cys Thr Leu Ile Gly Ala Ala Thr Gly Asn Leu Thr
                35                  40                  45

Ala Gly Ile Met Leu Gly Gly Ser Leu Gln Met Ile Thr Leu Ala Trp
         50                  55                  60

Ala Asn Ile Gly Ala Ala Val Ala Pro Asp Val Ala Leu Ala Ser Val
 65                  70                  75                  80

Ala Ala Ala Ile Ile Leu Val Lys Gly Gly Lys Phe Thr Ala Glu Gly
                 85                  90                  95

Ile Gly Val Ala Ile Ala Ile Ala Ile Leu Leu Ala Val Ala Gly Leu
                100                 105                 110

Phe Leu Thr Met Pro Val Arg Thr Ala Ser Ile Thr Phe Val His Ala
                115                 120                 125

Ala Asp Lys Ala Ala Glu His Gly Asn Ile Ala Gly Val Glu Arg Ala
    130                 135                 140

Tyr Tyr Leu Ser Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
                180                 185                 190

Val Val Ala Val Gly Tyr Ala Met Ile Ile Asn Met Met Ala Thr Arg
                195                 200                 205
```

<210> SEQ ID NO 165
<211> LENGTH: 208
<212> TYPE: PRT
<213> ORGANISM: Streptococcus thermophilus

<400> SEQUENCE: 165

```
Met Ser Asp Met Ser Ile Ile Ser Ala Ile Leu Val Val Ala Val Thr
1               5                   10                  15

Phe Leu Ala Gly Leu Glu Ser Ile Leu Asp Gln Phe Gln Phe His Gln
            20                  25                  30

Pro Leu Val Ala Cys Thr Leu Ile Gly Ala Ala Thr Gly Asn Leu Thr
        35                  40                  45

Ala Gly Ile Met Leu Gly Gly Ser Leu Gln Met Ile Thr Leu Ala Trp
    50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala
    130                 135                 140

Tyr Tyr Leu Ala Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Ser Gly Met
            180                 185                 190

Val Val Ala Val Gly Tyr Ala Met Ile Ile Asn Met Met Ala Thr Arg
        195                 200                 205
```

<210> SEQ ID NO 166
<211> LENGTH: 912
<212> TYPE: DNA
<213> ORGANISM: Streptococcus thermophilus

<400> SEQUENCE: 166

| | | |
|---|---|---|
| atggctgaaa aaattcaatt atctcaagcg gatcgtaaaa aggtttggtg gcgctcacaa | 60 |
| ttcttgcaag gtcatggaa ctatgaacgt atgcaaaact tgggttgggc ttactcactc | 120 |
| attcctgcta tcaaaaaact ttatactaac aaagaggacc aagccgcagc tcttaaacgt | 180 |
| cacttggaat tcttcaacac tcacccttac gtagctgctc ctatcatagg ggttaccttca | 240 |
| gctcttgaag aagaaaaagc taatggtact gaaatcgaag atgcggctat ccaagggtt | 300 |
| aaaatcggta tgatgggtcc acttgccggt atcggtgacc ctgtcttctg gttcacaatt | 360 |
| cgtccaattc ttggtgccct tggtgcatca ttggcacaag ctggtaacat tgctggtcca | 420 |
| cttatcttct tcattggttg gaaccttatc cgcatggcct tcttgtggta cactcaagaa | 480 |
| cttggttaca agcaggttc agaaatcact aagacatat ctggtggtat cttgaaagat | 540 |
| attactaaag gggcatcaat acttggtatg ttcatcttgg ccgtcctcgt tgaacgttgg | 600 |
| gtatctgtcg tcttcactgt aaagcttcca ggtaaagttt tgcctaaagg tgcttatatt | 660 |
| gaatggccaa aggatatgt tactggtgac caactaaaaa ctatccttgg tcaagtcaac | 720 |
| gataagctta gctttgataa gattcaagtc gataccctac aaaaacaatt ggattcatta | 780 |

-continued

```
attccaggtt tgacgggact tctccttact tttgcatgta tgtggttgct taagaagaaa      840
gtttcaccaa tcacaatcat catcggactc tttgtagttg gtattgttgc aagcttcttc      900
ggaatcatgt aa                                                          912
```

<210> SEQ ID NO 167
<211> LENGTH: 303
<212> TYPE: PRT
<213> ORGANISM: Streptococcus thermophilus

<400> SEQUENCE: 167

Met Ala Glu Lys Ile Gln Leu Ser Gln Ala Asp Arg Lys Lys Val Trp
1               5                   10                  15

Trp Arg Ser Gln Phe Leu Gln Gly Ala Trp Asn Tyr Glu Arg Met Gln
                20                  25                  30

Asn Leu Gly Trp Ala Tyr Ser Leu Ile Pro Ala Ile Lys Lys Leu Tyr
            35                  40                  45

Thr Asn Lys Glu Asp Gln Ala Ala Ala Leu Lys Arg His Leu Glu Phe
        50                  55                  60

Phe Asn Thr His Pro Tyr Val Ala Ala Pro Ile Ile Gly Val Thr Leu
65                  70                  75                  80

Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Leu Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Ile Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Phe Thr Val Lys
        195                 200                 205

Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Thr Phe Ala
            260                 265                 270

Cys Met Trp Leu Leu Lys Lys Lys Val Ser Pro Ile Thr Ile Ile Ile
        275                 280                 285

Gly Leu Phe Val Val Gly Ile Val Ala Ser Phe Phe Gly Ile Met
    290                 295                 300

<210> SEQ ID NO 168
<211> LENGTH: 912
<212> TYPE: DNA
<213> ORGANISM: Streptococcus thermophilus

<400> SEQUENCE: 168

```
atggctgaaa aaattcaatt atctcaagcg atcgtaaaa aggtttggtg gcgctcacaa    60
ttcttgcaag gttcatggaa ctatgaacgt atgcaaaact tgggttgggc ttactcactc   120
attcctgcta tcaaaaaact ttatactaac aaagaggacc aagccgcagc tcttaaacgt   180
cacttgaaat tcttcaacac tcaccctac gtagctgctc ctatcatggg ggttacctta   240
gctcttgaag aagaaaaagc taatggtact gaaatcgaag atgcggctat ccaaggggtt   300
aaaatcggta tgatgggtcc acttgccggt atcggtgacc ctgttttctg gttcacaatt   360
cgtccaattc ttggtgccat tggtgcttca ttggcacaag ctggtaacat tgctggtcca   420
cttatcttct tcattggttg gaaccttatc cgcatggcct tcttgtggta cactcaagaa   480
cttggttaca agcaggttc agaaatcact aaagacatgt ctggtggtat cttgaaagat   540
attactaaag gggcatcaat acttggtatg ttcatcttgg ccgtcctcgt tgaacgttgg   600
gtatctgtcg tcttcactgt aaagcttcca ggtaaagttt tgcctaaagg tgcttatatt   660
gaatggccaa aaggatatgt tactggtgat caactaaaaa ctattcttgg tcaagtcaac   720
gataagctta gctttgataa gattcaagtc gatacccta aaaaacaatt ggattcatta   780
attccaggtt tgacgggact tctccttact tttgcatgta tgtggttgct taagaagaaa   840
gtttcaccaa tcacaatcat catcggactc tttgtagttg gtattgttgc aagcttcttc   900
ggaatcatgt aa                                                       912
```

<210> SEQ ID NO 169
<211> LENGTH: 303
<212> TYPE: PRT
<213> ORGANISM: Streptococcus thermophilus

<400> SEQUENCE: 169

```
Met Ala Glu Lys Ile Gln Leu Ser Gln Ala Asp Arg Lys Lys Val Trp
1               5                   10                  15

Trp Arg Ser Gln Phe Leu Gln Gly Ser Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Leu Lys Arg His Leu Lys Phe
    50                  55                  60

Phe Asn Thr His Pro Tyr Val Ala Ala Pro Ile Met Gly Val Thr Leu
65                  70                  75                  80

Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Ile Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Val Phe Thr Val Lys
        195                 200                 205
```

```
Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Thr Phe Ala
                260                 265                 270

Cys Met Trp Leu Leu Lys Lys Val Ser Pro Ile Thr Ile Ile Ile
            275                 280                 285

Gly Leu Phe Val Val Gly Ile Val Ala Ser Phe Phe Gly Ile Met
    290                 295                 300
```

<210> SEQ ID NO 170
<211> LENGTH: 912
<212> TYPE: DNA
<213> ORGANISM: Streptococcus thermophilus

<400> SEQUENCE: 170

```
atggctgaaa aaattcaatt atctcaagcg gatcgtaaaa aggtttggtg gcgctcacaa      60
ttcttgcaag gtgcatggaa ctatgaacgt atgcaaaact gggttgggc ttactcactc     120
attcctgcta tcaaaaaact ttatactaac aaagaggacc aagccgcagc tcttaaacgt    180
cacttggaat tcttcaacac tcaccctta gtagctgctc ctatcatagg ggttacctta    240
gctcttgaag aagaaaaagc taatggtact gaaatcgaag atgcggctat ccaagggt    300
aaaatcggta tgatgggtcc acttgccggt atcggtgacc ctgtcttctg gttcacaatt    360
cgtccaattc ttggtgccct tggtgcatca ttggcacaag ctggtaacat tgctggtcca    420
cttatcttct tcattggttg gaaccttatc cgcatggcct tcttgtggta cactcaagaa    480
cttggttaca agcaggttc agaaatcact aaagacatat ctggtggtat cttgaaagat    540
attactaaag gggcatcaat acttggtatg ttcatcttgg ccgtcctcgt tgaacgttgg    600
gtatctgtcg tcttcactgt aaagcttcca ggtaaagttt tgcctaaagg tgcttatatt    660
gaatggccaa aggatatgt tactggtgac caactaaaaa ctatccttgg tcaagtcaac    720
gataagctta gctttgataa gattcaagtc gataccctac aaaaacaatt ggattcatta    780
attccaggtt tgacgggact ctccttact tttgcatgta tgtggttgct aagaagaaa    840
gtttcaccaa tcacaatcat catcggactc tttgtagttg gtattattgc aagcttcttc    900
ggaatcatgt aa                                                         912
```

<210> SEQ ID NO 171
<211> LENGTH: 303
<212> TYPE: PRT
<213> ORGANISM: Streptococcus thermophilus

<400> SEQUENCE: 171

```
Met Ala Glu Lys Ile Gln Leu Ser Gln Ala Asp Arg Lys Lys Val Trp
1               5                   10                  15

Trp Arg Ser Gln Phe Leu Gln Gly Ala Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60
```

| Phe | Asn | Thr | His | Pro | Tyr | Val | Ala | Ala | Pro | Ile | Ile | Gly | Val | Thr | Leu |
| 65  |     |     |     | 70  |     |     |     |     | 75  |     |     |     |     | 80  |     |

| Ala | Leu | Glu | Glu | Glu | Lys | Ala | Asn | Gly | Thr | Glu | Ile | Glu | Asp | Ala | Ala |
|     |     |     |     | 85  |     |     |     |     | 90  |     |     |     |     | 95  |     |

| Ile | Gln | Gly | Val | Lys | Ile | Gly | Met | Met | Gly | Pro | Leu | Ala | Gly | Ile | Gly |
|     |     |     | 100 |     |     |     |     | 105 |     |     |     |     | 110 |     |     |

| Asp | Pro | Val | Phe | Trp | Phe | Thr | Ile | Arg | Pro | Ile | Leu | Gly | Ala | Leu | Gly |
|     |     |     | 115 |     |     |     |     | 120 |     |     |     |     | 125 |     |     |

| Ala | Ser | Leu | Ala | Gln | Ala | Gly | Asn | Ile | Ala | Gly | Pro | Leu | Ile | Phe | Phe |
|     |     | 130 |     |     |     |     | 135 |     |     |     |     | 140 |     |     |     |

| Ile | Gly | Trp | Asn | Leu | Ile | Arg | Met | Ala | Phe | Leu | Trp | Tyr | Thr | Gln | Glu |
| 145 |     |     |     |     | 150 |     |     |     |     | 155 |     |     |     |     | 160 |

| Leu | Gly | Tyr | Lys | Ala | Gly | Ser | Glu | Ile | Thr | Lys | Asp | Ile | Ser | Gly | Gly |
|     |     |     |     | 165 |     |     |     |     | 170 |     |     |     |     | 175 |     |

| Ile | Leu | Lys | Asp | Ile | Thr | Lys | Gly | Ala | Ser | Ile | Leu | Gly | Met | Phe | Ile |
|     |     |     | 180 |     |     |     |     | 185 |     |     |     |     | 190 |     |     |

| Leu | Ala | Val | Leu | Val | Glu | Arg | Trp | Val | Ser | Val | Phe | Thr | Val | Lys |     |
|     |     |     | 195 |     |     |     |     | 200 |     |     |     |     | 205 |     |     |

| Leu | Pro | Gly | Lys | Val | Leu | Pro | Lys | Gly | Ala | Tyr | Ile | Glu | Trp | Pro | Lys |
|     |     | 210 |     |     |     |     | 215 |     |     |     |     | 220 |     |     |     |

| Gly | Tyr | Val | Thr | Gly | Asp | Gln | Leu | Lys | Thr | Ile | Leu | Gly | Gln | Val | Asn |
| 225 |     |     |     |     | 230 |     |     |     |     | 235 |     |     |     |     | 240 |

| Asp | Lys | Leu | Ser | Phe | Asp | Lys | Ile | Gln | Val | Asp | Thr | Leu | Gln | Lys | Gln |
|     |     |     |     | 245 |     |     |     |     | 250 |     |     |     |     | 255 |     |

| Leu | Asp | Ser | Leu | Ile | Pro | Gly | Leu | Thr | Gly | Leu | Leu | Leu | Thr | Phe | Ala |
|     |     |     | 260 |     |     |     |     | 265 |     |     |     |     | 270 |     |     |

| Cys | Met | Trp | Leu | Leu | Lys | Lys | Lys | Val | Ser | Pro | Ile | Thr | Ile | Ile | Ile |
|     |     | 275 |     |     |     |     | 280 |     |     |     |     | 285 |     |     |     |

| Gly | Leu | Phe | Val | Val | Gly | Ile | Ile | Ala | Ser | Phe | Phe | Gly | Ile | Met |     |
|     | 290 |     |     |     |     | 295 |     |     |     |     | 300 |     |     |     |     |

<210> SEQ ID NO 172
<211> LENGTH: 912
<212> TYPE: DNA
<213> ORGANISM: Streptococcus thermophilus

<400> SEQUENCE: 172

| atgtctgaaa | aaattcaatt | atctcaagcg | gatcgtaaaa | aggtttggtg | gcgctcacaa | 60  |
| ttcttgcaag | ttcatggaa  | ctatgaacgt | atgcaaaact | ggggttgggc | ttactcactc | 120 |
| attcctgcta | tcaaaaaact | ttatactaac | aaagaggacc | aagccgcagc | tcttaaacgt | 180 |
| cacttggaat | tcttcaacac | tcaccgttac | gtagctgctc | ctatcatggg | ggttacctta | 240 |
| gctcttgaag | aagaaaaagc | taatggtact | gaaatcgaag | atgcggctat | ccaagggggtt | 300 |
| aaaatcggta | tgatgggtcc | acttgccggt | atcggtgacc | ctgtcttctg | gttcacaatt | 360 |
| cgtccaattc | ttggtgccct | tggtgcatca | ttggcacaat | ctggtaacat | tgctggtcca | 420 |
| cttatcttct | tcattggttg | gaaccttatc | cgcatgacct | tcttgtggta | cactcaagaa | 480 |
| cttggttaca | agcaggttc  | agaaatcact | aaagacatgt | ctggtggtat | cttgaaagat | 540 |
| attactaaag | gggcatcaat | acttggtatg | ttcatcttgg | ccgtcctcgt | tgaacgttgg | 600 |
| gtatctgtcg | tcttcactgt | aaagcttcca | ggtaaagttt | tgcctaaagg | tgcttatatt | 660 |
| gaatggccaa | aaggatatgt | tactggtgac | caactaaaaa | ctatccttgg | tcaagtcaac | 720 |
| gataagctta | gctttgataa | gattcaagtc | gataccctac | aaaaacaatt | ggattcatta | 780 |

```
attccaggtt tgacgggact ctccttact  tttgcatgta tgtggttgct taagaagaaa    840
gtttcaccaa tcacaatcat catcggactc tttgtagttg gtattgttgc aagcttcttc    900
ggaatcatgt aa                                                        912
```

<210> SEQ ID NO 173
<211> LENGTH: 303
<212> TYPE: PRT
<213> ORGANISM: Streptococcus thermophilus

<400> SEQUENCE: 173

```
Met Ser Glu Lys Ile Gln Leu Ser Gln Ala Asp Arg Lys Lys Val Trp
1               5                   10                  15

Trp Arg Ser Gln Phe Leu Gln Gly Ser Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60

Phe Asn Thr His Pro Tyr Val Ala Ala Pro Ile Met Gly Val Thr Leu
65                  70                  75                  80

Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Leu Gly
        115                 120                 125

Ala Ser Leu Ala Gln Ser Gly Asn Ile Ala Gly Pro Leu Ile Phe Phe
    130                 135                 140

Ile Gly Trp Asn Leu Ile Arg Met Thr Phe Leu Trp Tyr Thr Gln Glu
145                 150                 155                 160

Leu Gly Tyr Lys Ala Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Phe Thr Val Lys
        195                 200                 205

Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Leu Thr Phe Ala
            260                 265                 270

Cys Met Trp Leu Leu Lys Lys Lys Val Ser Pro Ile Thr Ile Ile Ile
        275                 280                 285

Gly Leu Phe Val Val Gly Ile Val Ala Ser Phe Phe Gly Ile Met
    290                 295                 300
```

<210> SEQ ID NO 174
<211> LENGTH: 912
<212> TYPE: DNA
<213> ORGANISM: Streptococcus thermophilus

<400> SEQUENCE: 174

```
atggctgaaa aaattcaatt atctcaagcg atcgtaaaa aggtttggtg gcgctcacaa      60
ttcttgcaag gttcatggaa ctatgaacgt atgcaaaact tgggttgggc ttactcactc     120
attcccgcta tcaaaaaact ttatactaac aaagaggacc aagccgcagc tcttaaacgt     180
cacttgaaat tcttcaacac tcacccttac gtagctgctc ctatcatggg ggttaccta     240
gctcttgaag aagaaaaagc taatggtact gaaatcgaag atgcagctat ccaagggtt     300
aaaatcggta tgatgggtcc acttgccggt atcggtgacc ctgtcttctg gttcacaatt     360
cgtccaattc ttggtgccat tggtgcttca ttggcacaag ctggtaacat tgctggtcca     420
cttatcttct tcattggttg gaaccttatc cgcatggcct tcttgtgtta cactcaagaa     480
cttggttaca agcaggttc agaaatcact aaagacatgt ctggtggtat cttgaaagat     540
attactaaag gggcatcaat acttggtatg ttcatcttgg ccgtcctcgt tgaacgttgg     600
gtatctgtcg tcttcactgt aaagcttcca ggtaaagttt tgcctaaaag tgcttatatt     660
gaatggccaa aaggatatgt tactggtgat caactaaaaa ctatccttgg tcaagtcaac     720
gataagctta gctttgataa gattcaagtc gatacctac aaaaacaatt ggattcatta     780
attccaggtt tgacgggact tctccttact tttgcatgta tgtggttgct taagaagaaa     840
gtttcaccaa ttcaatcat catcggactc tttgtagttg gtattgttgc aagcttcttc     900
ggaatcatgt aa                                                          912
```

<210> SEQ ID NO 175
<211> LENGTH: 303
<212> TYPE: PRT
<213> ORGANISM: Streptococcus thermophilus

<400> SEQUENCE: 175

```
Met Ala Glu Lys Ile Gln Leu Ser Gln Ala Asp Arg Lys Lys Val Trp
1               5                   10                  15

Trp Arg Ser Gln Phe Leu Gln Gly Ser Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Lys Phe
    50                  55                  60

Phe Asn Thr His Pro Tyr Val Ala Ala Pro Ile Met Gly Val Thr Leu
65                  70                  75                  80

Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Ile Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Val Phe Thr Val Lys
        195                 200                 205
```

```
Leu Pro Gly Lys Val Leu Pro Lys Ser Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Thr Phe Ala
            260                 265                 270

Cys Met Trp Leu Leu Lys Lys Val Ser Pro Ile Thr Ile Ile
            275                 280                 285

Gly Leu Phe Val Val Gly Ile Val Ala Ser Phe Gly Ile Met
    290                 295                 300
```

<210> SEQ ID NO 176
<211> LENGTH: 912
<212> TYPE: DNA
<213> ORGANISM: Streptococcus thermophilus

<400> SEQUENCE: 176

```
atggctgaaa aaattcaatt atctcaagcg gatcgtaaaa aggtttggtg gcgctcacaa      60
ttcttgcaag gtgcatggaa ctatgaacgt atgcaaaact ggggttgggc ttactcactc     120
attcctgcta tcaaaaaact ttatactaac aaagaggacc aagccgcagc tcttaaacgt     180
cacttggaat tcttcaacac tcacccttac gtagctgctc ctatcatggg ggttacctta     240
gctcttgaag aagaaaaagc taatggtact gaaatcgaag atgcggctat ccaaggggtt     300
aaaatcggta tgatgggtcc acttgccggt attggtgacc ctgtcttctg gttcacaatt     360
cgtccaattc ttggtgccct tggtgcatca ttggcacaag ctggtaacat tgctggtcca     420
cttatcttct tcattggttg gaaccttatc cgcatggcct tcttgtggta cactcaagaa     480
cttggttaca agcaggttc agaaatcact aaagacatgt ctggtggtat cttgaaagat     540
attactaaag gggcatcaat acttggtatg ttcatcttgg ccgtcctcgt tgaacgttgg     600
gtatctgtcg tcttcactgt aaagcttcca ggtaaagttt tgcctaaagg tgcttatatt     660
gaatggccaa aggatatgt tactggtgat caactaaaaa ctatccttgg tcaagtcaac     720
gataagctta gctttgataa gattcaagtc gatacactac aaaaacaatt ggattcatta     780
attccaggtt tgacgggact tctccttact tttgcatgta tgtggttgct taagaagaaa     840
gtttcaccaa tcacaatcat catcggactc tttgtagttg gtattgttgc aagcttcttc     900
ggaatcatgt aa                                                         912
```

<210> SEQ ID NO 177
<211> LENGTH: 303
<212> TYPE: PRT
<213> ORGANISM: Streptococcus thermophilus

<400> SEQUENCE: 177

```
Met Ala Glu Lys Ile Gln Leu Ser Gln Ala Asp Arg Lys Lys Val Trp
1               5                   10                  15

Trp Arg Ser Gln Phe Leu Gln Gly Ala Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60

Phe Asn Thr His Pro Tyr Val Ala Ala Pro Ile Met Gly Val Thr Leu
```

```
                65                  70                  75                  80
Ala Leu Glu Glu Glu Lys Ala Asn Gly Thr Glu Ile Glu Asp Ala Ala
                        85                  90                  95

Ile Gln Gly Val Lys Ile Gly Met Met Gly Pro Leu Ala Gly Ile Gly
                        100                 105                 110

Asp Pro Val Phe Trp Phe Thr Ile Arg Pro Ile Leu Gly Ala Leu Gly
                        115                 120                 125

Ala Ser Leu Ala Gln Ala Gly Asn Ile Ala Gly Pro Leu Ile Phe Phe
        130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Met Ser Gly Gly
                        165                 170                 175

Ile Leu Lys Asp Ile Thr Lys Gly Ala Ser Ile Leu Gly Met Phe Ile
                        180                 185                 190

Leu Ala Val Leu Val Glu Arg Trp Val Ser Val Val Phe Thr Val Lys
                        195                 200                 205

Leu Pro Gly Lys Val Leu Pro Lys Gly Ala Tyr Ile Glu Trp Pro Lys
        210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                        245                 250                 255

Leu Asp Ser Leu Ile Pro Gly Leu Thr Gly Leu Leu Thr Phe Ala
                        260                 265                 270

Cys Met Trp Leu Leu Lys Lys Lys Val Ser Pro Ile Thr Ile Ile Ile
        275                 280                 285

Gly Leu Phe Val Val Gly Ile Val Ala Ser Phe Phe Gly Ile Met
                        290                 295                 300
```

<210> SEQ ID NO 178
<211> LENGTH: 912
<212> TYPE: DNA
<213> ORGANISM: Streptococcus thermophilus

<400> SEQUENCE: 178

```
atggctgaaa aaattcaatt atctcaagcg gatcgtaaaa aggtttggtg gcgctcacaa      60
ttcttgcaag gttcatggaa ctatgaacgt atgcaaaact tgggttgggc ttactcactc     120
attcctgcta tcaaaaaact ttatactaac aaagaggacc aagccgcagc tcttaaacgt     180
cacttgaaat tcttcaacac tcaccttac gtagctgctc ctatcatggg ggttacctta     240
gctcttgaag aagaaaaagc taatggtact gaaatcgaag atgcggctat ccaagggtt     300
aaaatcggta tgatgggtcc acttgccggt atcggtgacc ctgtcttctg gttcacaatt     360
cgtccaattc ttggtgccat tggtgcttca ttggcacaag ctggtaacat tgctggtcca     420
cttatcttct tcattggttg gaaccttatc cgcatggtct tcttgtggta cactcaagaa     480
cttggttaca agcaggttc agaaatcact aaagacatgt ctggtggtat cttgaaagat     540
attactaaag gggcatcaat acttggtatg ttcatcttgg ccgtcctcgt tgaacgttgg     600
gtatctgtcg tcttcactgt aaagcttcca ggtaaagttt tgcctaaagg tgcttatatt     660
gaatggccaa aaggatatgt tactggtgat caactaaaaa ctatccttgg tcaagtcaac     720
gataagctta gctttgataa tattcaagtc gataccctac aaaaacaatt ggattcatta     780
attccaggtt tgacgggact tctccttact tttgcatgta tgtggttgct taagaagaaa     840
```

```
gtttcaccaa tcacaatcat catcggactc tttgtagttg gtattgttgc aagcttcttc      900
ggaatcatgt aa                                                          912
```

<210> SEQ ID NO 179
<211> LENGTH: 303
<212> TYPE: PRT
<213> ORGANISM: Streptococcus thermophilus

<400> SEQUENCE: 179

```
Met Ala Glu Lys Ile Gln Leu Ser Gln Ala Asp Arg Lys Lys Val Trp
1               5                   10                  15

Trp Arg Ser Gln Phe Leu Gln Gly Ser Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Leu Lys Arg His Leu Lys Phe
    50                  55                  60

Phe Asn Thr His Pro Tyr Val Ala Ala Pro Ile Met Gly Val Thr Leu
65              70                  75                  80

Ala Leu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Ile Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Val Phe Leu Trp Tyr Thr Gln Glu
145                 150                 155                 160

Leu Gly Tyr Lys Ala Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Phe Thr Val Lys
        195                 200                 205

Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240

Asp Lys Leu Ser Phe Asp Asn Ile Gln Val Asp Thr Leu Gln Lys Gln
                245                 250                 255

Leu Asp Ser Leu Ile Pro Gly Leu Thr Gly Leu Leu Thr Phe Ala
            260                 265                 270

Cys Met Trp Leu Leu Lys Lys Lys Val Ser Pro Ile Thr Ile Ile Ile
        275                 280                 285

Gly Leu Phe Val Val Gly Ile Val Ala Ser Phe Phe Gly Ile Met
    290                 295                 300
```

<210> SEQ ID NO 180
<211> LENGTH: 912
<212> TYPE: DNA
<213> ORGANISM: Streptococcus thermophilus

<400> SEQUENCE: 180

```
atggctgaaa aaattcaatt atctcaagcg gatcgtaaaa aggtttggtg gcgctcacaa      60
```

```
ttcttgcaag gtgcatggaa ctatgaacgt atgcaaaact tgggttgggc ttactcactc    120
attcctgcta tcaaaaaact ttatactaac aaagaggacc aagccgcagc tcttaaacgt    180
cacttggaat tcttcaacac tcaccccttac gtagctgctc ctatcatggg ggttaccta    240
gctcttgaag aagaaaaagc taatggtact gaaatcgaag atgcggctat ccaaggggtt    300
aaaatcggta tgatgggtcc acttgccggt atcggtgacc ctgtcttctg gttcacaatt    360
cgtccaattc ttggtgccct tggtgcatca ttggcacaag ctggtaacat tgctggtcca    420
cttatcttct tcattggttg gaaccttatc cgcatggcct tcttgtggta cactcaagaa    480
cttggttaca agcaggttc agaaatcact aaagacatat ctggtggtat cttgaaagat    540
attactaaag gggcatcaat acttggtatg ttcatcttgg ccgtcctcgt gaacgttgg    600
gtatctgtcg tcttcactgt aaagcttcca ggtaaagttt tgcctaaagg tgcttatatt    660
gaatggccaa aaggatatgt tactggtgac caactaaaaa ctatccttgg tcaagtcaac    720
gataagctta gctttgataa gattcaagtc gataccctac aaaaacaatt ggattcatta    780
attccaggtt tgacgggact tctccttact tttgcatgta tgtggttgct taagaagaaa    840
gtttcaccaa tcacaatcat catcggactc tttgtagttg gtattgttgc aagtttcttc    900
ggaatcatgt aa                                                       912
```

<210> SEQ ID NO 181  
<211> LENGTH: 303  
<212> TYPE: PRT  
<213> ORGANISM: Streptococcus thermophilus

<400> SEQUENCE: 181

```
Met Ala Glu Lys Ile Gln Leu Ser Gln Ala Asp Arg Lys Lys Val Trp
1               5                   10                  15

Trp Arg Ser Gln Phe Leu Gln Gly Ala Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60

Phe Asn Thr His Pro Tyr Val Ala Ala Pro Ile Met Gly Val Thr Leu
65                  70                  75                  80

Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Leu Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Ile Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Val Phe Thr Val Lys
        195                 200                 205

Leu Pro Gly Lys Val Leu Pro Lys Gly Ala Tyr Ile Glu Trp Pro Lys
```

```
                 210                 215                 220
Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Thr Phe Ala
            260                 265                 270

Cys Met Trp Leu Leu Lys Lys Lys Val Ser Pro Ile Thr Ile Ile Ile
            275                 280                 285

Gly Leu Phe Val Val Gly Ile Val Ala Ser Phe Phe Gly Ile Met
290                 295                 300
```

<210> SEQ ID NO 182
<211> LENGTH: 912
<212> TYPE: DNA
<213> ORGANISM: Streptococcus thermophilus

<400> SEQUENCE: 182

```
atgtctgaaa aaattcaatt atctcaagcg gatcgtaaaa aggtttggtg gcgctcacaa      60
ttcttgcaag gttcatggaa ctatgaacgt atgcaaaact ggggttgggc ttactcactc     120
attcctgcta tcaaaaaact ttatactaac aaagaggacc aagccgcagc tcttaaacgt     180
cacttggaat tcttcaacac tcacccttac gtagctgctc ctatcatggg ggttaccttac    240
gctcttgaag aagaaaaagc taatggtact gaaatcgaag atgcggctat ccaaggggtt     300
aaaatcggta tgatgggtcc acttgccggt atcggtgacc ctgtcttctg gttcacaatt     360
cgtccaattc ttggtgccct tggtgcatca ttggcacaag ctggtaacat tgctggtcca     420
cttatcttct tcattggttg gaaccttatc cgcatgacct tcttgtgtac actcaagaa      480
cttggttaca agcaggttc agaaatcact aaagacatgt ctggtggtat cttgaaagat     540
attactaaag gggcatcaat acttggtatg ttcatcttgg ccgtcctcgt tgaacgttgg     600
gtatctgtcg tcttcactgt aaagcttcca ggtaaagttt tgcctaaagg tgcttatatt     660
gaatggccaa aaggatatgt tactggtgat caactaaaaa ctatccttgg tcaagtcaac     720
gataagctta gctttgataa gattcaagtc gataccctac aaaaacaatt ggattcatta     780
attccaggtt tgacgggact ctccttact tttgcatgta tgtggttgct taagaagaaa     840
gtttcaccaa tcacaatcat catcggactc tttgtagttg gtattgttgc aagcttcttc     900
ggaatcatgt aa                                                         912
```

<210> SEQ ID NO 183
<211> LENGTH: 303
<212> TYPE: PRT
<213> ORGANISM: Streptococcus thermophilus

<400> SEQUENCE: 183

```
Met Ser Glu Lys Ile Gln Leu Ser Gln Ala Asp Arg Lys Lys Val Trp
1               5                   10                  15

Trp Arg Ser Gln Phe Leu Gln Gly Ser Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60

Phe Asn Thr His Pro Tyr Val Ala Ala Pro Ile Met Gly Val Thr Leu
65                  70                  75                  80
```

```
Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Leu Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Thr Phe Leu Trp Tyr Thr Gln Glu
145                 150                 155                 160

Leu Gly Tyr Lys Ala Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Phe Thr Val Lys
        195                 200                 205

Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Thr Phe Ala
            260                 265                 270

Cys Met Trp Leu Leu Lys Lys Lys Val Ser Pro Ile Thr Ile Ile
        275                 280                 285

Gly Leu Phe Val Val Gly Ile Val Ala Ser Phe Phe Gly Ile Met
    290                 295                 300
```

<210> SEQ ID NO 184
<211> LENGTH: 912
<212> TYPE: DNA
<213> ORGANISM: Streptococcus thermophilus

<400> SEQUENCE: 184

```
atggctgaaa aaattcaatt atctcaagcg gatcgtagaa aggtttggtg gcgctcacaa    60
ttcttgcaag gttcatggaa ctatgaacgt atgcaaaact tgggttgggc ttactcactc   120
attcctgcta tcaaaaaact ttatactaac aaagaggacc aagccgcagc tcttaaacgt   180
cacttggaat tcttcaacac tcacccttac gtagctgctc ctatcatggg agttaccta    240
gctcttgaag aagaaaaagc taatggtact gaaatcgaag atgcggctat ccaaggggtt   300
aaaatcggta tgatgggtcc acttgccggt atcggtgacc ctgtcttctg gttcacaatt   360
cgtccaattc ttggtgccct tggtgcatca ttggcacaag ctggtaacat tactggtcca   420
cttatcttct tcattggttg gaaccttatc cgcatggcct tcttgtggta cactcaagaa   480
cttggttaca agcaggttc agaaatcact aaagacatgt ctggtggtat cttgaaagat   540
attactaaag gggcatcaat acttggtatg ttcatcttgg ccgtcctcgt tgaacgttgg   600
gtatctgtcg tcttcactgt aaagcttcca ggtaaagttt tgcctaaagg tgcttatatt   660
gaatggccaa aaggatatgt tactggtgat caactaaaaa ctatccttgg tcaagtcaac   720
gataagctta gctttgataa gattcaagtc gatacccctac aaaaacaatt ggattcatta   780
attccaggtt tgacgggact tctccttact tttgcatgta tgtggttgct taagaagaaa   840
```

```
gtttcaccaa tcacaatcat catcggactc tttgtagttg gtattgttgc aagcttcttc    900
ggaatcatgt aa                                                        912
```

<210> SEQ ID NO 185
<211> LENGTH: 303
<212> TYPE: PRT
<213> ORGANISM: Streptococcus thermophilus

<400> SEQUENCE: 185

```
Met Ala Glu Lys Ile Gln Leu Ser Gln Ala Asp Arg Arg Lys Val Trp
1               5                   10                  15

Trp Arg Ser Gln Phe Leu Gln Gly Ser Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Leu Lys Arg His Leu Glu Phe
    50                  55                  60

Phe Asn Thr His Pro Tyr Val Ala Pro Ile Met Gly Val Thr Leu
65                  70                  75                  80

Ala Leu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
                100                 105                 110

Asp Pro Val Phe Trp Phe Thr Ile Arg Pro Ile Leu Gly Ala Leu Gly
            115                 120                 125

Ala Ser Leu Ala Gln Ala Gly Asn Ile Thr Gly Pro Leu Ile Phe Phe
    130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Val Phe Thr Val Lys
    195                 200                 205

Leu Pro Gly Lys Val Leu Pro Lys Gly Ala Tyr Ile Glu Trp Pro Lys
210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Leu Thr Phe Ala
            260                 265                 270

Cys Met Trp Leu Leu Lys Lys Lys Val Ser Pro Ile Thr Ile Ile Ile
    275                 280                 285

Gly Leu Phe Val Val Gly Ile Val Ala Ser Phe Phe Gly Ile Met
290                 295                 300
```

<210> SEQ ID NO 186
<211> LENGTH: 912
<212> TYPE: DNA
<213> ORGANISM: Streptococcus thermophilus

<400> SEQUENCE: 186

```
atggctgaaa aaattcaatt atctcaagcg gatcgtagaa aggtttggtg gcgcttacaa    60
```

-continued

```
ttcttgcaag gttcatggaa ctatgaacgt atgcaaaact tgggttgggc ttactcactc    120
attcctgcta tcaaaaaact ttatactaac aaagaggacc aagccgcagc tcttaaacgt    180
cacttggaat tcttcaacac tcaccttac gtagctgctc ctatcatggg ggttacctta     240
gctcttgaag aagaaaaagc taatggtact gaaatcgaag atgcggctat ccaaggggtt    300
aaaatcggta tgatgggtcc acttgccggt atcggtgacc ctgtcttctg gttcacaatt    360
cgtccaattc ttggtgccct tggtgcatca ttggcacaag ctggtaacat tgctggtcca    420
cttatcttct tcattggttg gaaccttatc cgcatggcct tcttgtggta cactctagaa    480
cttggttaca agaaggttc agaaatcact aaagacatgt ctggtggtat cttgaaagat    540
attactaaag gggcatcaat acttggtatg ttcttcttgg ccgtcctcgt tgaacgttgg    600
gtatctgtcg tcttcactgt aaagcttcca ggtaaagttt tgcctaaagg tgcttatatt    660
gaatggccaa aaggatatgt tactggtgac caactaaaaa ctatccttgg tcaagtcaac    720
gataagctta gctttgataa gattcaagtc gataccctac aaaaacaatt ggattcatta    780
attccaggtt tgacgggact tctccttact tttgcatgta tgtggttgct taagaagaaa    840
gtttcaccaa tcacaatcat catcggactc tttgtagttg gtattgttgc aagcttcttc    900
ggaatcatgt aa                                                       912
```

<210> SEQ ID NO 187
<211> LENGTH: 303
<212> TYPE: PRT
<213> ORGANISM: Streptococcus thermophilus

<400> SEQUENCE: 187

```
Met Ala Glu Lys Ile Gln Leu Ser Gln Ala Asp Arg Arg Lys Val Trp
1               5                   10                  15

Trp Arg Leu Gln Phe Leu Gln Gly Ser Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60

Phe Asn Thr His Pro Tyr Val Ala Ala Pro Ile Met Gly Val Thr Leu
65                  70                  75                  80

Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Leu Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Ala Phe Leu Trp Tyr Thr Leu Glu
145                 150                 155                 160

Leu Gly Tyr Lys Glu Gly Ser Glu Ile Thr Lys Asp Met Ser Gly Gly
                165                 170                 175

Ile Leu Lys Asp Ile Thr Lys Gly Ala Ser Ile Leu Gly Met Phe Phe
            180                 185                 190

Leu Ala Val Leu Val Glu Arg Trp Val Ser Val Val Phe Thr Val Lys
        195                 200                 205

Leu Pro Gly Lys Val Leu Pro Lys Gly Ala Tyr Ile Glu Trp Pro Lys
    210                 215                 220
```

```
Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
            245                 250                 255

Leu Asp Ser Leu Ile Pro Gly Leu Thr Gly Leu Leu Leu Thr Phe Ala
        260                 265                 270

Cys Met Trp Leu Leu Lys Lys Lys Val Ser Pro Ile Thr Ile Ile Ile
    275                 280                 285

Gly Leu Phe Val Val Gly Ile Val Ala Ser Phe Phe Gly Ile Met
        290                 295                 300

<210> SEQ ID NO 188
<211> LENGTH: 912
<212> TYPE: DNA
<213> ORGANISM: Streptococcus thermophilus

<400> SEQUENCE: 188
atggctgaaa aaattcaatt atctcaagcg atcgtaaaa aggtttggtg gcgctcacaa      60
ttcttgcaag gttcatggaa ctatgaacgt atgcaaaact ggggttgggc ttactcactc     120
attcctgcta tcaaaaaact ttatactaac aaagaggacc aagccgcagc tcttaaacgt     180
cacttgaaat tcttcaacac tcacccttac gtagctgctc ctatcatggg ggttacctta     240
gctcttgaag aagaaaaagc taatggtact gaaatcgaag atgcggctat ccaaggggtt     300
aaaatcggta tgatgggtcc acttgccggt atcggtgacc ctgtcttctg gttcacaatt     360
cgtccaattc ttggtgccat ggtgcttca ttggcacaag ctggtaacat tgctggtcca     420
cttatcttct tcattggttg aaccttatc cgcatggcct tcttgtggta cactcaagaa     480
cttggttaca agcaggttc agaaatcact aaagacatgt ctggtggtat cttgaaagat     540
attactaaag gggcatcaat acttggtatg ttcatcttgg ccttcctcgt gaacgttgg     600 gtatctgtcg tcttcactgt aaagcttcca ggtaaagttt tgcctaaagg tgcttatatt     660
gaatggccaa aaggatatgt tactggtgat caactaaaaa ctatccttgg tcaagtcaac     720
gataagctta gctttgataa gattcaagtc gataccctac aaaaacaatt ggattcatta     780
attccaggtt tgacgggact tctccttact tttgcatgta tgtggttgct aagaagaaa      840 gtttcaccaa tcacaatcat catcggactc tttgtagttg gtattgttgc aagcttcttc     900
ggaatcatgt aa                                                        912

<210> SEQ ID NO 189
<211> LENGTH: 303
<212> TYPE: PRT
<213> ORGANISM: Streptococcus thermophilus

<400> SEQUENCE: 189

Met Ala Glu Lys Ile Gln Leu Ser Gln Ala Asp Arg Lys Lys Val Trp
1               5                   10                  15

Trp Arg Ser Gln Phe Leu Gln Gly Ser Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Lys Phe
    50                  55                  60

Phe Asn Thr His Pro Tyr Val Ala Ala Pro Ile Met Gly Val Thr Leu
65                  70                  75                  80
```

```
Ala Leu Glu Glu Glu Lys Ala Asn Gly Thr Glu Ile Glu Asp Ala Ala
                 85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Ile Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
            180                 185                 190

Leu Ala Phe Leu Val Glu Arg Trp Val Ser Val Phe Thr Val Lys
        195                 200                 205

Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Thr Phe Ala
            260                 265                 270

Cys Met Trp Leu Leu Lys Lys Lys Val Ser Pro Ile Thr Ile Ile Ile
        275                 280                 285

Gly Leu Phe Val Val Gly Ile Val Ala Ser Phe Phe Gly Ile Met
    290                 295                 300

<210> SEQ ID NO 190
<211> LENGTH: 912
<212> TYPE: DNA
<213> ORGANISM: Streptococcus thermophilus

<400> SEQUENCE: 190
atggctgaaa aaattcaatt atctcaagcg atcgtaaaa  aggtttggtg gcgctcacaa       60
ttcttgcaag ttcatggaa  ctatgaacgt atgcaaaact tgggttgggc ttactcactc      120
attcctgcta tcaaaaaact ttatactaac aaagaggacc aagccgcagc tcttaaacgt      180
cacttgaaat tcttcaacac tcaccttac  gtagctgctc ctatcatggg gattaccta      240 gctcttgaag aagaaaaagc taatggtact gaaatcgaag atgcggctat ccaagggtt      300 aaaatcggta tgatgggtcc acttgccggt atcggtgacc ctgtcttctg gttcacaatt      360
cgtccaattc taggtgccat tggtgcttca ttggcacaag ctggtaacat tgctggtcca      420
cttatcttct tcattggttg gaaccttatc cgcatggcct tcttgtggta cactcaagaa      480
cttggttaca agcaggttc  agaaatcact aaagacatgt ctggtggtat cttgaaagat      540
attactaaag gggcatcaat acttggtatg ttcatcttgg ccgtcctcgt gaacgttgg       600 gtatctgtcg tcttcactgt aaagcttcca ggtaaagttt tgcctaaagg tgcttatatt      660
gaatggccaa aaggatatgt tactggtgac caactaaaaa ctatccttgg tcaagtcaac      720
gataagctta gctttgataa gattcaagtc gataccctac aaaaacaatt ggattcatta      780
attccaggtt tgacgggact tctccttact tttgcatgta tgtggttgct taagaagaaa      840
gtttcactaa tcacaatcat catcggactc tttgtagttg gtattgttgc aagcttcttc      900
```
ggaatcatgt aa 912

<210> SEQ ID NO 191
<211> LENGTH: 303
<212> TYPE: PRT
<213> ORGANISM: Streptococcus thermophilus

<400> SEQUENCE: 191

Met Ala Glu Lys Ile Gln Leu Ser Gln Ala Asp Arg Lys Lys Val Trp
1               5                   10                  15

Trp Arg Ser Gln Phe Leu Gln Gly Ser Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Leu Lys Arg His Leu Lys Phe
    50                  55                  60

Phe Asn Thr His Pro Tyr Val Ala Ala Pro Ile Met Gly Ile Thr Leu
65                  70                  75                  80

Ala Leu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Ile Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Val Phe Thr Val Lys
        195                 200                 205

Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Leu Thr Phe Ala
            260                 265                 270

Cys Met Trp Leu Leu Lys Lys Lys Val Ser Leu Ile Thr Ile Ile
        275                 280                 285

Gly Leu Phe Val Val Gly Ile Val Ala Ser Phe Phe Gly Ile Met
    290                 295                 300

<210> SEQ ID NO 192
<211> LENGTH: 912
<212> TYPE: DNA
<213> ORGANISM: Streptococcus thermophilus

<400> SEQUENCE: 192
atggctgaaa aaattcaatt atctcaagcg gatcgtagaa aggtttggtg gcgctcacaa      60
ttcttgcaag gttcatggaa ctatgaacgt atgcaaaact tgggttgggc ttactcactc     120

-continued

```
attcctgcta tcaaaaaact ttatactaac aaagaggatc aagccgcagc tcttaaacgt    180
cacttggaat tcttcaacac tcaccctTac gtagctgctc ctatcatggg ggttaccTta    240
gctcttgaag aagaaaaagc taatggtact gaaatcgaag atgcggctat ccaaggggtt    300
aaaatcggta tgatgggtcc ccttgcaggt atcggtgacc ctgtcttctg gttcacaatt    360
cgtccaattc ttggtgccct tggtgcatca ttggcacaag ctggtaacat tactggtcca    420
cttatcttct tcattggttg gaaccttatc cgcatggcct tcttgtgtta cactcaagaa    480
cttggttaca aatcaggttc agaaatcact aaagacatgt ctggtggtat cttgaaagat    540
attactaaag gggcatcaat acttggtatg ttcatcttgg ccgtcctcgt tgaacgttgg    600
gtatctgtcg tcttcactgt aaagcttcca ggtaaagttt tgcctaaagg tgcttatatt    660
gaatggccaa aaggatatgt tactggtgac caactaaaaa ctatccttgg tcaagtcaac    720
gataagctta gctttgataa gattcaagtc gatacCctac aaaaacaatt ggattcatta    780
attccaggtt tgacgggact ctccttact tttgcatgta tgtggttgct taagaagaaa    840
gtttcaccaa tcacaatcat catcggactc tttgtagttg gtattgttgc aagcttcttc    900
ggaatcatgt aa                                                       912
```

<210> SEQ ID NO 193
<211> LENGTH: 303
<212> TYPE: PRT
<213> ORGANISM: Streptococcus thermophilus

<400> SEQUENCE: 193

```
Met Ala Glu Lys Ile Gln Leu Ser Gln Ala Asp Arg Arg Lys Val Trp
1               5                   10                  15

Trp Arg Ser Gln Phe Leu Gln Gly Ser Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Leu Lys Arg His Leu Glu Phe
    50                  55                  60

Phe Asn Thr His Pro Tyr Val Ala Pro Ile Met Gly Val Thr Leu
65                  70                  75                  80

Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Leu Gly
        115                 120                 125

Ala Ser Leu Ala Gln Ala Gly Asn Ile Thr Gly Pro Leu Ile Phe Phe
    130                 135                 140

Ile Gly Trp Asn Leu Ile Arg Met Ala Phe Leu Trp Tyr Thr Gln Glu
145                 150                 155                 160

Leu Gly Tyr Lys Ser Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Val Phe Thr Val Lys
        195                 200                 205

Leu Pro Gly Lys Val Leu Pro Lys Gly Ala Tyr Ile Glu Trp Pro Lys
    210                 215                 220
```

```
Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Thr Phe Ala
            260                 265                 270

Cys Met Trp Leu Leu Lys Lys Val Ser Pro Ile Thr Ile Ile Ile
        275                 280                 285

Gly Leu Phe Val Val Gly Ile Val Ala Ser Phe Phe Gly Ile Met
    290                 295                 300

<210> SEQ ID NO 194
<211> LENGTH: 912
<212> TYPE: DNA
<213> ORGANISM: Streptococcus thermophilus

<400> SEQUENCE: 194
atggctgaaa aaattcaatt atctcaagcg atcgtaaaa aggtttggtg gcgctcacaa       60 ttccttgcaag gtgcatggaa ctatgaacgt atgcaaaact ggggttgggc ttactcactc      120
attcctgcta tcaaaaaact ttatactaac aaagaggacc aagccgcagc tcttaaacgt      180
cacttggaat tcttcaacac tcacccttac gtagctgctc ctatcatagg ggttacctta      240
gctcttgaag aagaaaaagc taatggtact gaaatcgaag atgcggctat ccaaggggtt      300
aaaatcggta tgatgggtcc acttgccggt atcggtgacc ctgtcttctg gttcacaatt      360
cgtccaattc ttggtgccct tggtgcatca ttggcacaat ctggtaacat tgctggtcca      420
cttatcttct tcattggttg gaaccttatc cgcatgacct tcttgtggta cactcaagaa      480
cttggttaca agcaggttc agaaatcact aaagacatgt ctggtggtat cttgaaagat      540
attactaaag gggcatcaat acttggtatg ttcatcttgg ccgtcctcgt tgaacgttgg      600
gtatctgtcg tcttcactgt aaagcttcca ggtaaagttt tgcctaaagg tgcttatatt      660
gaatggccaa aaggatatgt tactggtgac caactaaaaa ctatccttgg tcaagtcaac      720
gataagctta gctttgataa gattcaagtc gataccctac aaaaacaatt ggattcatta      780
attccaggtt tgacgggact tctccttact tttgcatgta tgtggttgct aagaagaaa       840 gtttcaccaa tcacaatcat catcggactc tttgtagttg gtattgttgc aagcttcttc      900
ggaatcatgt aa                                                          912

<210> SEQ ID NO 195
<211> LENGTH: 303
<212> TYPE: PRT
<213> ORGANISM: Streptococcus thermophilus

<400> SEQUENCE: 195

Met Ala Glu Lys Ile Gln Leu Ser Gln Ala Asp Arg Lys Lys Val Trp
1               5                   10                  15

Trp Arg Ser Gln Phe Leu Gln Gly Ala Trp Asn Tyr Glu Arg Met Gln
                20                  25                  30

Asn Leu Gly Trp Ala Tyr Ser Leu Ile Pro Ala Ile Lys Lys Leu Tyr
            35                  40                  45

Thr Asn Lys Glu Asp Gln Ala Ala Ala Leu Lys Arg His Leu Glu Phe
        50                  55                  60

Phe Asn Thr His Pro Tyr Val Ala Ala Pro Ile Ile Gly Val Thr Leu
65                  70                  75                  80

Ala Leu Glu Glu Glu Lys Ala Asn Gly Thr Glu Ile Glu Asp Ala Ala
```

```
                     85                  90                  95
Ile Gln Gly Val Lys Ile Gly Met Met Gly Pro Leu Ala Gly Ile Gly
                100                 105                 110

Asp Pro Val Phe Trp Phe Thr Ile Arg Pro Ile Leu Gly Ala Leu Gly
                115                 120                 125

Ala Ser Leu Ala Gln Ser Gly Asn Ile Ala Gly Pro Leu Ile Phe Phe
            130                 135                 140

Ile Gly Trp Asn Leu Ile Arg Met Thr Phe Leu Trp Tyr Thr Gln Glu
145                 150                 155                 160

Leu Gly Tyr Lys Ala Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
                180                 185                 190

Leu Ala Val Leu Val Glu Arg Trp Val Ser Val Phe Thr Val Lys
                195                 200                 205

Leu Pro Gly Lys Val Leu Pro Lys Gly Ala Tyr Ile Glu Trp Pro Lys
            210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Leu Thr Phe Ala
            260                 265                 270

Cys Met Trp Leu Leu Lys Lys Lys Val Ser Pro Ile Thr Ile Ile Ile
                275                 280                 285

Gly Leu Phe Val Val Gly Ile Val Ala Ser Phe Phe Gly Ile Met
            290                 295                 300
```

<210> SEQ ID NO 196
<211> LENGTH: 912
<212> TYPE: DNA
<213> ORGANISM: Streptococcus thermophilus

<400> SEQUENCE: 196

```
atgtctgaaa aaattcaatt atctcaagcg gatcataaaa aggtttggtg gcgctcacaa      60
ttcttgcaag ttcatggaa ctatgaacgt atgcaaaact tgggttgggc ttactcactc     120
attcctgcta tcaaaaaact ttatactaac aaagaggacc aagccgcagc tcttaaacgt     180
cacttggaat tcttcaacac tcaccttac gtagctgctc ctatcatggg ggttacctta     240
gctcttgaag aagaaaaagc taatggtact gaaatcgaag atgcggctat ccaagggtt      300
aaaatcggta tgatgggtcc acttgccggt atcggtgacc ctgtcttctg gttcacaatt     360
cgtccaattc ttggtgccct tggtgcatca ttggcacaat ctggtaacat tgctggtcca     420
cttatcttct tcattggttg gaaccttatc cgcatgacct tcttgtggta cactcaagaa     480
cttggttaca agcaggttc agaaatcact aaagacatgt ctggtggtat cttgaaagat     540
attactaaag gggcatcaat acttggtatg ttcatcttgg ccgtcctcgt tgaacgttgg     600
gtatctgtcg tcttcactgt aaagcttcca ggtaaagttt tgcctaaagg tgcttatatt     660
gaatggccaa aaggatatgt tactggtgac caactaaaaa ctatccttgg tcaagtcaac     720
gataagctta gctttgataa gattcaagtc gataccctac aaaaacaatt ggattcatta     780
attccaggtt tgacgggact tctccttact tttgcatgta tgtggttgct taagaagaaa     840
gtttcaccaa tcacaatcat catcggactc tttgtagttg gtattgttgc aagcttcttc     900
```
ggaatcatgt aa    912

<210> SEQ ID NO 197
<211> LENGTH: 303
<212> TYPE: PRT
<213> ORGANISM: Streptococcus thermophilus

<400> SEQUENCE: 197

Met Ser Glu Lys Ile Gln Leu Ser Gln Ala Asp His Lys Lys Val Trp
1               5                   10                  15

Trp Arg Ser Gln Phe Leu Gln Gly Ser Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60

Phe Asn Thr His Pro Tyr Val Ala Ala Pro Ile Met Gly Val Thr Leu
65              70                  75                  80

Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Leu Gly
        115                 120                 125

Ala Ser Leu Ala Gln Ser Gly Asn Ile Ala Gly Pro Leu Ile Phe Phe
    130                 135                 140

Ile Gly Trp Asn Leu Ile Arg Met Thr Phe Leu Trp Tyr Thr Gln Glu
145                 150                 155                 160

Leu Gly Tyr Lys Ala Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Val Phe Thr Val Lys
        195                 200                 205

Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Leu Thr Phe Ala
            260                 265                 270

Cys Met Trp Leu Leu Lys Lys Lys Val Ser Pro Ile Thr Ile Ile Ile
        275                 280                 285

Gly Leu Phe Val Val Gly Ile Val Ala Ser Phe Phe Gly Ile Met
    290                 295                 300

<210> SEQ ID NO 198
<211> LENGTH: 912
<212> TYPE: DNA
<213> ORGANISM: Streptococcus thermophilus

<400> SEQUENCE: 198
atggctgaaa aaattcaatt atctcaagcg gatcgtaaaa aggtttggtg gcgctcacaa    60
ttcttgcaag gtgcatggaa ctatgaacgt atgcaaaact gggttgggc ttactcactc    120

```
attcctgcta tcaaaaaact ttatactaac aaagaggacc aagccgcagc tcttaaacgt    180
cacttggaat tcttcaacac tcacccttac gtagctgctc ctatcataga ggttacctta    240
gctcttgaag aagaaaaagc taatggtact gaaatcgaag atgcggctat ccaaggggtt    300
aaaatcggta tgatgggtcc acttgccggt atcggtgacc ctgtcttctg gttcacaatt    360
cgtccaattc ttggtgccct ggtgcatca ttggcacaag ctggtaacat tgctggtcca     420
cttatcttct tcattggttg gaaccttatc cgcatggcct tcttgtggta cactcaagaa    480
cttggttaca agcaggttc agaaatcact aaagacatat ctggtggtat cttgaaagat     540
attactaaag gggcatcaat acttggtatg ttcatcttgg ccgtcctcgt tgaacgttgg    600
gtatctgtcg tcttcactgt aaagcttcca ggtaaagttt tgcctaaagg tgcttatatt    660
gaatggccaa aaggatatgt tactggtgac caactaaaaa ctatccttgg tcaagtcaac    720
gataagctta gctttgataa gattcaagtc gataccctac aaaaacaatt ggattcatta    780
attccaggtt tgacgggact tctccttact tttgcatgta tgtggttgct taagaagaaa    840
gtttcaccaa tcacaatcat catcggactc tttgtagttg gtattgttgc aagcttcttc    900
ggaatcatgt aa                                                        912
```

<210> SEQ ID NO 199
<211> LENGTH: 303
<212> TYPE: PRT
<213> ORGANISM: Streptococcus thermophilus

<400> SEQUENCE: 199

```
Met Ala Glu Lys Ile Gln Leu Ser Gln Ala Asp Arg Lys Lys Val Trp
1               5                   10                  15

Trp Arg Ser Gln Phe Leu Gln Gly Ala Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60

Phe Asn Thr His Pro Tyr Val Ala Ala Pro Ile Ile Glu Val Thr Leu
65                  70                  75                  80

Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Leu Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Ile Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Phe Thr Val Lys
        195                 200                 205

Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
```

```
                   225                 230                 235                 240
Asp Lys Leu Ser Phe Asp Lys Ile Gln Val Asp Thr Leu Gln Lys Gln
                        245                 250                 255

Leu Asp Ser Leu Ile Pro Gly Leu Thr Gly Leu Leu Leu Thr Phe Ala
            260                 265                 270

Cys Met Trp Leu Leu Lys Lys Lys Val Ser Pro Ile Thr Ile Ile Ile
        275                 280                 285

Gly Leu Phe Val Val Gly Ile Val Ala Ser Phe Phe Gly Ile Met
    290                 295                 300
```

<210> SEQ ID NO 200
<211> LENGTH: 912
<212> TYPE: DNA
<213> ORGANISM: Streptococcus thermophilus

<400> SEQUENCE: 200

```
atggctgaaa aaattcaatt atctcaagcg gatcgtaaaa aggtttggtg gcgctcacaa      60
ttcttgcaag gtgcatggaa ctatgaacgt atgcaaaact ggggttgggc ttactcactc     120
attcctgcta tcaaaaaact ttatactaac aaagaggacc aagccgcagc tcttaaacgt     180
cacttggaat tcttcaacac tcaccccttac gtagatgctc ctatcatggg ggttacctta    240
gctcttgaag aagaaaaagc taatggtact gaaatcgaag atgcggctat ccaaggggtt     300
aaaatcggta tgatgggtcc acttgccggt atcggtgacc ctgtcttctg gttcacaatt     360
cgtccaattc ttggtgccct tggtgcatca ttggcacaag ctggtaacat tgctggtcca     420
cttatcttct tcattggttg gaaccttatc cgcatggcct tcttgtgtga cactcaagaa     480
cttggttaca agcaggttc agaaatcact aagacatat ctggtggtat cttgaaagat      540
attactaaag gggcatcaat acttggtatg ttcatcttgg ccgtcctcgt tgaacgttgg     600
gtatctgtcg tcttcactgt aaagcttcca ggtaaagttt tgcctaaagg tgcttatatt     660
gaatggccaa aaggatatgt tactggtgac caactaaaaa ctatccttgg tcaagtcaac     720
gataagctta gctttgataa gattcaagtc gataccctac aaaaacaatt ggattcatta    780
attccaggtt tgacgggact ctctccttact tttgcatgta tgtggttgct taagaagaaa   840
gtttcaccaa tcacaatcat catcggactc tttgtagttg gtattgttgc aagtttcttc   900
ggaatcatgt aa                                                          912
```

<210> SEQ ID NO 201
<211> LENGTH: 303
<212> TYPE: PRT
<213> ORGANISM: Streptococcus thermophilus

<400> SEQUENCE: 201

```
Met Ala Glu Lys Ile Gln Leu Ser Gln Ala Asp Arg Lys Lys Val Trp
1               5                   10                  15

Trp Arg Ser Gln Phe Leu Gln Gly Ala Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60

Phe Asn Thr His Pro Tyr Val Asp Ala Pro Ile Met Gly Val Thr Leu
65                  70                  75                  80

Ala Leu Glu Glu Glu Lys Ala Asn Gly Thr Glu Ile Glu Asp Ala Ala
                85                  90                  95
```

```
Ile Gln Gly Val Lys Ile Gly Met Met Gly Pro Leu Ala Gly Ile Gly
                100                 105                 110

Asp Pro Val Phe Trp Phe Thr Ile Arg Pro Ile Leu Gly Ala Leu Gly
            115                 120                 125

Ala Ser Leu Ala Gln Ala Gly Asn Ile Ala Gly Pro Leu Ile Phe Phe
        130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Ile Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Val Phe Thr Val Lys
        195                 200                 205

Leu Pro Gly Lys Val Leu Pro Lys Gly Ala Tyr Ile Glu Trp Pro Lys
210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Leu Thr Phe Ala
            260                 265                 270

Cys Met Trp Leu Leu Lys Lys Lys Val Ser Pro Ile Thr Ile Ile Ile
        275                 280                 285

Gly Leu Phe Val Val Gly Ile Val Ala Ser Phe Phe Gly Ile Met
    290                 295                 300
```

<210> SEQ ID NO 202
<211> LENGTH: 912
<212> TYPE: DNA
<213> ORGANISM: Streptococcus thermophilus

<400> SEQUENCE: 202

```
atggctgaaa aaattcaatt atctcaagcg gatcgtaaaa aggtttggtg gcgctcacaa    60
ttcttgcaag gtgcatggaa ctatgaacgt atgcaaaact tgggttgggc ttactcactc   120
attcctgcta tcaaaaaact ttatactaac aaagaggacc aagccgcagc tcttaaacgt   180
cacttggaat tcttcaacac tcacccttac gtagctgctc ctatcatagg ggttacctta   240
gctcttgaag aagaaaaagc taatggtact gaaatcgaag atgcggctat ccaaggggtt   300
aaaatcggta tgatgggtcc acttgccggt atcggtgacc ctgtcttctg gttcacaatt   360
cgtccaattc ttggtgccct tggtgcatca ttggcacaag ctggtaacat tgctggtcca   420
cttatcttct tcattggttg gaaccttatc cgcatggcct tcttgtggta cactcaagaa   480
cttggttaca agcaggttc agaaatcact aaagacatgt ctggtggtat cttgaaagat   540
attactaaag gggcatcaat acttggtatg ttcatcttgg ccgtcctcgt tgaacgttgg   600
gtatctgtcg tcttcactgt aaagcttcca ggtaaagttt tgcctaaagg tgcttatatt   660
gaatggccaa aaggatatgt tactggtgac caactaaaaa ctatccttgg tcaagtcaac   720
gataagctta gctttgataa gattcaagtc gataccctac aaaaacaatt ggattcatta   780
attccaggtt tgacgggact tctccttact tttgcatgta tgtggttgct taagaagaaa   840
gtttcaccaa tcacaatcat catcggactc tttgtagttg gtattgttgc aagcttcttc   900
ggaatcatgt aa                                                        912
```

<210> SEQ ID NO 203
<211> LENGTH: 303
<212> TYPE: PRT
<213> ORGANISM: Streptococcus thermophilus

<400> SEQUENCE: 203

```
Met Ala Glu Lys Ile Gln Leu Ser Gln Ala Asp Arg Lys Lys Val Trp
1               5                   10                  15

Trp Arg Ser Gln Phe Leu Gln Gly Ala Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60

Phe Asn Thr His Pro Tyr Val Ala Ala Pro Ile Ile Gly Val Thr Leu
65                  70                  75                  80

Ala Leu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Leu Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Phe Thr Val Lys
        195                 200                 205

Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Leu Thr Phe Ala
            260                 265                 270

Cys Met Trp Leu Leu Lys Lys Lys Val Ser Pro Ile Thr Ile Ile Ile
        275                 280                 285

Gly Leu Phe Val Val Gly Ile Val Ala Ser Phe Phe Gly Ile Met
    290                 295                 300
```

<210> SEQ ID NO 204
<211> LENGTH: 912
<212> TYPE: DNA
<213> ORGANISM: Streptococcus thermophilus

<400> SEQUENCE: 204

```
atggctgaaa aaattcaatt atctcaagcg gatcgtagaa aggtttggtg gcgctcacaa      60
ttcttgcaag gttcatggaa ctatgaacgt atgcaaaact gggttgggc ttactcactc     120 attcctgcta tcaaaaaact ttatactaac aaagaggatc aagccgcagc tcttaaacgt     180
```

```
cacttggaat tcttcaacac tcaccettac gtagctgctc ctatcatggg ggttaccetta    240 gctcttgaag aagaaaaagc taatggtact gaaatcgaag atgcggctat ccaagggggtt   300 aaaatcggta tgatgggtcc acttgcaggt atcggtgacc ctgtcttctg gttcacaatt   360
cgtccaattc ttggtgccat tggtgcttca ttggcacaag ctggtaacat tgctggtcca   420
cttatcttct tcattggttg gaaccttatc cgcatggcct tcttgtggta cactcaagaa   480
cttggttaca aatcaggttc agaaatcact aaagacatgt ctggtggtat cttgaaagat   540
attactaaag gggcatcaat acttggtatg ttcatcttgg ccgtcctcgt gaacgttgg    600 gtatctgtcg tcttcactgt aaagcttcca ggtaaagttt tgcctaaagg tgcttatatt   660
gaatggccaa aaggatatgt tactggtgat caactaaaaa ctatccttgg tcaagtcaac   720
gataagctta gctttgataa gattcaagtc gataccctac aaaaacaatt ggattcatta   780
attccaggtt tgacgggact tctccttact tttgcatgta tgtggttgct taagaagaaa   840
gtttcaccaa tcacaatcat catcggactc tttgtagttg gtattgttgc aagcttcttc   900
ggaatcatgt aa                                                        912
```

<210> SEQ ID NO 205
<211> LENGTH: 303
<212> TYPE: PRT
<213> ORGANISM: Streptococcus thermophilus

<400> SEQUENCE: 205

```
Met Ala Glu Lys Ile Gln Leu Ser Gln Ala Asp Arg Arg Lys Val Trp
1               5                   10                  15

Trp Arg Ser Gln Phe Leu Gln Gly Ser Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60

Phe Asn Thr His Pro Tyr Val Ala Ala Pro Ile Met Gly Val Thr Leu
65                  70                  75                  80

Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Ile Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Ala Phe Leu Trp Tyr Thr Gln Glu
145                 150                 155                 160

Leu Gly Tyr Lys Ser Gly Ser Glu Ile Thr Lys Asp Met Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Phe Thr Val Lys
        195                 200                 205

Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240
```

```
Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Thr Phe Ala
            260                 265                 270

Cys Met Trp Leu Leu Lys Lys Lys Val Ser Pro Ile Thr Ile Ile Ile
        275                 280                 285

Gly Leu Phe Val Val Gly Ile Val Ala Ser Phe Phe Gly Ile Met
        290                 295                 300
```

<210> SEQ ID NO 206
<211> LENGTH: 913
<212> TYPE: DNA
<213> ORGANISM: Streptococcus thermophilus

<400> SEQUENCE: 206

```
atggctgaaa aaattcaatt atctcaagcg gatcgtaaaa aaggtttggt ggcgctcaca      60
attcttgcaa ggtgcatgga actatgaacg tatgcaaaac ttgggttggg cttactcact     120
cattcctgct atcaaaaaac tttatactaa caaagaggac caagccgcag ctcttaaacg     180
tcacttggaa ttcttcaaca ctcacccctta cgtagctgct cctatcatag gggttacctt     240
agctcttgaa gaagaaaaag ctaatggtac tgaaatcgaa gatgcggcta tccaaggggt     300
taaaatcggt atgatgggtc cacttgccgg tatcggtgac cctgtcttct ggttcacaat     360
tcgtccaatt cttggtgccc ttggtgcatc attggcacaa gctggtaaca ttgctggtcc     420
acttatcttc ttcattggtt ggaaccttat ccgcatggcc ttcttgtggt acactcaaga     480
acttggttac aaagcaggtt cagaaatcac taaagacata tctggtggta tcttgaaaga     540
tattactaaa ggggcatcaa tacttggtat gttcatcttg gccgtcctcg ttaacgttg     600
ggtatctgtc gtcttcactg taaagcttcc aggtaaagtt ttgcctaaag gtgcttatat     660
tgaatggcca aaaggatatg ttactggtga ccaactaaaa actatccttg gtcaagtcaa     720
cgataagctt agctttgata agattcaagt cgataccccta caaaaacaat tggattcatt     780
aattccaggt ttgacgggac ttctccttac ttttgcatgt atgtggttgc ttaagaagaa     840
agtttcacca atcacaatca tcatcggact ctttgtagtt ggtattgttg caagcttctt     900
cggaatcatg taa                                                         913
```

<210> SEQ ID NO 207
<211> LENGTH: 28
<212> TYPE: PRT
<213> ORGANISM: Streptococcus thermophilus

<400> SEQUENCE: 207

```
Met Ala Glu Lys Ile Gln Leu Ser Gln Ala Asp Arg Lys Lys Gly Leu
1               5                   10                  15

Val Ala Leu Thr Ile Leu Ala Arg Cys Met Glu Leu
            20                  25
```

<210> SEQ ID NO 208
<211> LENGTH: 28
<212> TYPE: PRT
<213> ORGANISM: Streptococcus thermophilus

<400> SEQUENCE: 208

```
Met Ala Glu Lys Ile Gln Leu Ser Gln Ala Asp Arg Lys Lys Gly Leu
1               5                   10                  15

Val Ala Leu Thr Ile Leu Ala Arg Phe Met Glu Leu
```

20                  25

<210> SEQ ID NO 209
<211> LENGTH: 28
<212> TYPE: PRT
<213> ORGANISM: Streptococcus thermophilus

<400> SEQUENCE: 209

Met Ser Glu Lys Ile Gln Leu Ser Gln Ala Asp Arg Lys Lys Gly Leu
1               5                   10                  15

Val Ala Leu Thr Ile Leu Ala Arg Phe Met Glu Leu
            20                  25

<210> SEQ ID NO 210
<211> LENGTH: 28
<212> TYPE: PRT
<213> ORGANISM: Streptococcus thermophilus

<400> SEQUENCE: 210

Met Ala Glu Lys Ile Gln Leu Ser Gln Ala Asp Arg Arg Lys Gly Leu
1               5                   10                  15

Val Ala Leu Thr Ile Leu Ala Arg Phe Met Glu Leu
            20                  25

<210> SEQ ID NO 211
<211> LENGTH: 28
<212> TYPE: PRT
<213> ORGANISM: Streptococcus thermophilus

<400> SEQUENCE: 211

Met Ser Glu Lys Ile Gln Leu Ser Gln Ala Asp His Lys Lys Gly Leu
1               5                   10                  15

Val Ala Leu Thr Ile Leu Ala Arg Phe Met Glu Leu
            20                  25

<210> SEQ ID NO 212
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 212
caggtatgag tttagcaacg g                                                   21

<210> SEQ ID NO 213
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 213
agttcaatct tcatcatctc g                                                   21

<210> SEQ ID NO 214
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 214
gtagccacat tgttcctgac                                                     20

<210> SEQ ID NO 215
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 215
ttgctgaagc tacagtttcc                                               20

<210> SEQ ID NO 216
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 216
taagcaagac tagcagctcc                                               20

<210> SEQ ID NO 217
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 217
ttgcgtagtc gtgttgaagg                                               20

<210> SEQ ID NO 218
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 218
attgtccctt cataagcatc g                                             21

<210> SEQ ID NO 219
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 219
cgaactgggt gcagatgatg                                               20

<210> SEQ ID NO 220
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 220
attcaccacg gcctgagac                                                19

<210> SEQ ID NO 221
<211> LENGTH: 20
<212> TYPE: DNA
<213> ORGANISM: Artificial Sequence
<220> FEATURE:

```
<223> OTHER INFORMATION: Oligonucleotide primer

<400> SEQUENCE: 221
gaagcagttt ggggtagtag                                              20

<210> SEQ ID NO 222
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 222
gagttatcta caggagctgg                                              20
```

LACTIC ACID BACTERIA

CROSS-REFERENCE TO RELATED APPLICATIONS

This application is a U.S. national stage application under 35 U.S.C. § 371 of International Application No. PCT/EP2018/086681, filed on Dec. 21, 2018, entitled "NEW LACTIC ACID BACTERIA," the contents of which are incorporated by reference in their entirety.

INCORPORATION BY REFERENCE OF THE SEQUENCE LISTING

The present application is being filed with a Sequence Listing in electronic format. The Sequence Listing is provided as a file entitled NB41483USPCT_SeqList.txt, created on Jun. 15, 2021, which is 453,090 bytes in size. The information in the electronic format of the Sequence Listing is incorporated by reference in its entirety.

FIELD OF THE INVENTION

The invention relates to a lactose-positive, galactose-negative, *Streptococcus thermophilus* strain carrying a mutation in genes selected from the group consisting of 1) a gene encoding a protein of the mannose-glucose-specific PTS and a glcK gene, 2) a gene encoding a protein of the mannose-glucose-specific PTS and a ccpA gene, and 3) a gene encoding a protein of the mannose-glucose-specific PTS, a glcK gene and a ccpA gene, wherein said strain, when used to ferment milk, provides a low lactose fermented milk and/or a fermented milk not undergoing post-acidification when stored at fermentation temperature. The invention also concerns a composition comprising at least one, lactose-positive, galactose-negative, *Streptococcus thermophilus* strain of the invention, and the use of this strain or composition to manufacture a fermented dairy product

BACKGROUND TO THE INVENTION

The food industry uses bacteria in order to improve the taste and the texture of food or feed products. In the case of the dairy industry, lactic acid bacteria are commonly used in order to, for example, bring about the acidification of milk (by fermentation of lactose) and to texturize the product into which they are incorporated. For example, the lactic acid bacteria of the species *Streptococcus thermophilus* (*S. thermophilus*) are used extensively, alone or in combination with other bacteria, in the manufacture of fresh fermented dairy products, such as cheese or yoghurt.

One of the limitations of the use of lactic acid bacteria in dairy technology is post-acidification, i.e. the production of lactic acid by the lactic acid bacteria after the target pH (the one required by the technology) has been obtained [termination of fermentation]. Thus, the post-acidification phenomenon is not only an issue for the dairy product manufacturers (who would like to have flexible manufacturing process, without necessarily having a rapid cooling step right after the target pH is obtained) but also for the consumers (production of lactic acid bacteria leading to an elevated acidity and reduced shelf life of the fermented product).

In addition, there is a trend from dairy consumers to have fermented products with reduced or low content of lactose (lactose intolerance).

WO2015/193459 proposes several solutions to overcome these issues: controlling the concentration of lactose in the milk before fermentation for example by adding lactase, providing lactic acid bacteria which are not able to hydrolyse lactose (lactose-negative strains). These solutions are however not satisfactory for dairy product manufacturers, since they require either the addition of exogenous enzyme (such as lactase) in the milk before fermentation rendering the manufacturing process more complex and more expensive, or the addition of a carbohydrate into the milk (such as sucrose) what is not in agreement with the growing demand for healthier products with no additives.

Therefore, there is a need for improving methods for producing fermented dairy products, which are both satisfactory for the manufacturers and the consumers, not undergoing post-acidification and with a reduced lactose content.

DESCRIPTION OF THE DRAWINGS

FIG. 1: Alignment of the GlcK protein sequence of DGCC7710 (DSM28255), DSM32587 (SEQ ID NO: 22) and ST1m-glcK0-gal+ strains (SEQ ID NO: 23). Differences with the GlcK protein of DGCC7710 (SEQ ID NO:2) are boxed.

DETAILED DESCRIPTION

Figure 2:
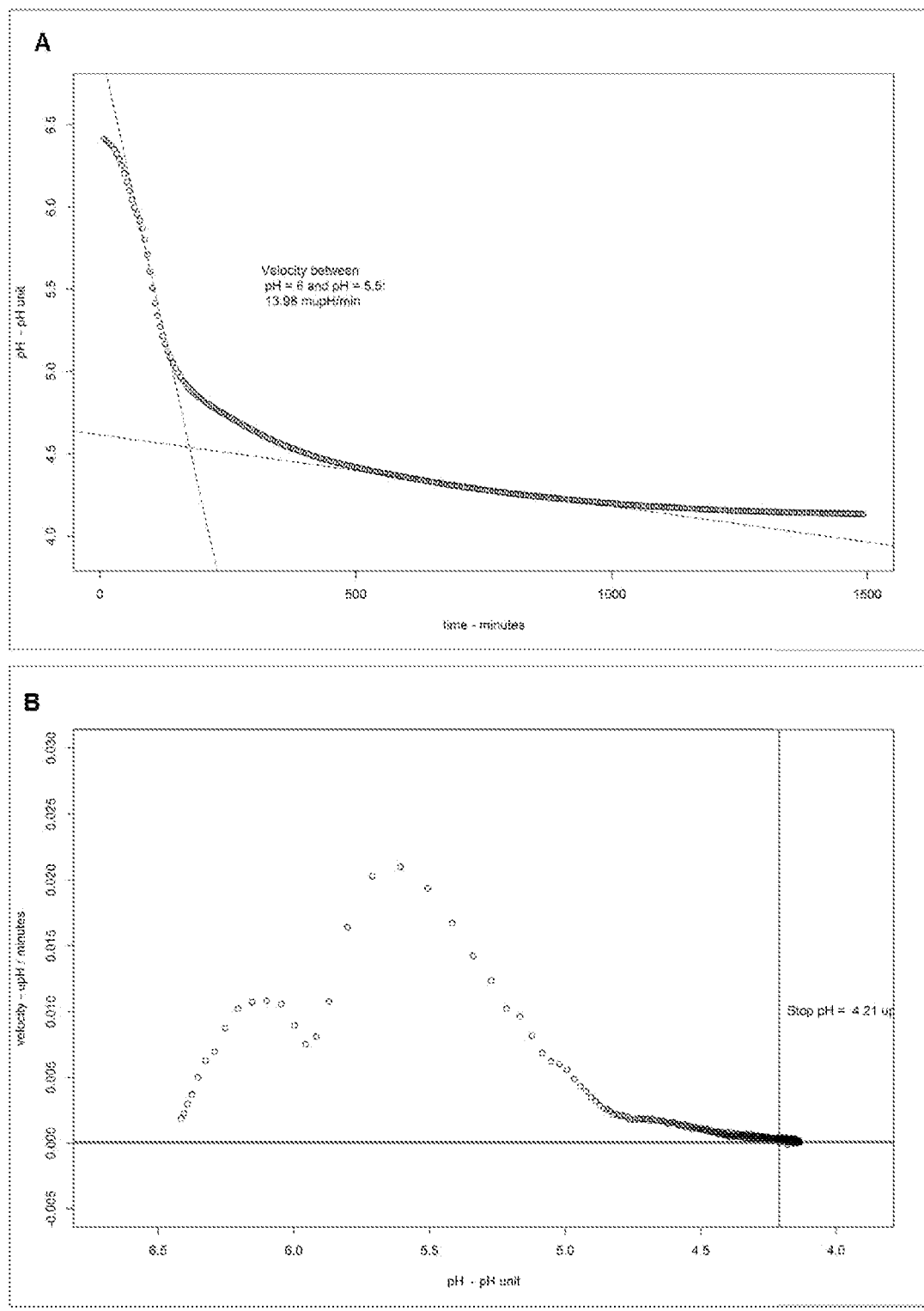
FIGS. 2 to 10 are graphs representing the evolution of the pH over time (A) and representing the velocity as a function of the pH (B) of a milk fermented respectively with the DGCC7710 (FIG. 2), ST1m-glcK+manM (FIG. 3), ST1m-ccpA+manL (FIG. 4), ST1m-ccpA+manM (FIG. 5), ST1m-ccpA+manN (FIG. 6), ST1m-glcK+ccpA+manM (FIG. 7), ST1.1 (FIG. 8), ST1.1m-glcK+manM (FIG. 9) or ST1.1m-ccpA+manL (FIG. 10) strain.
Figure 3:
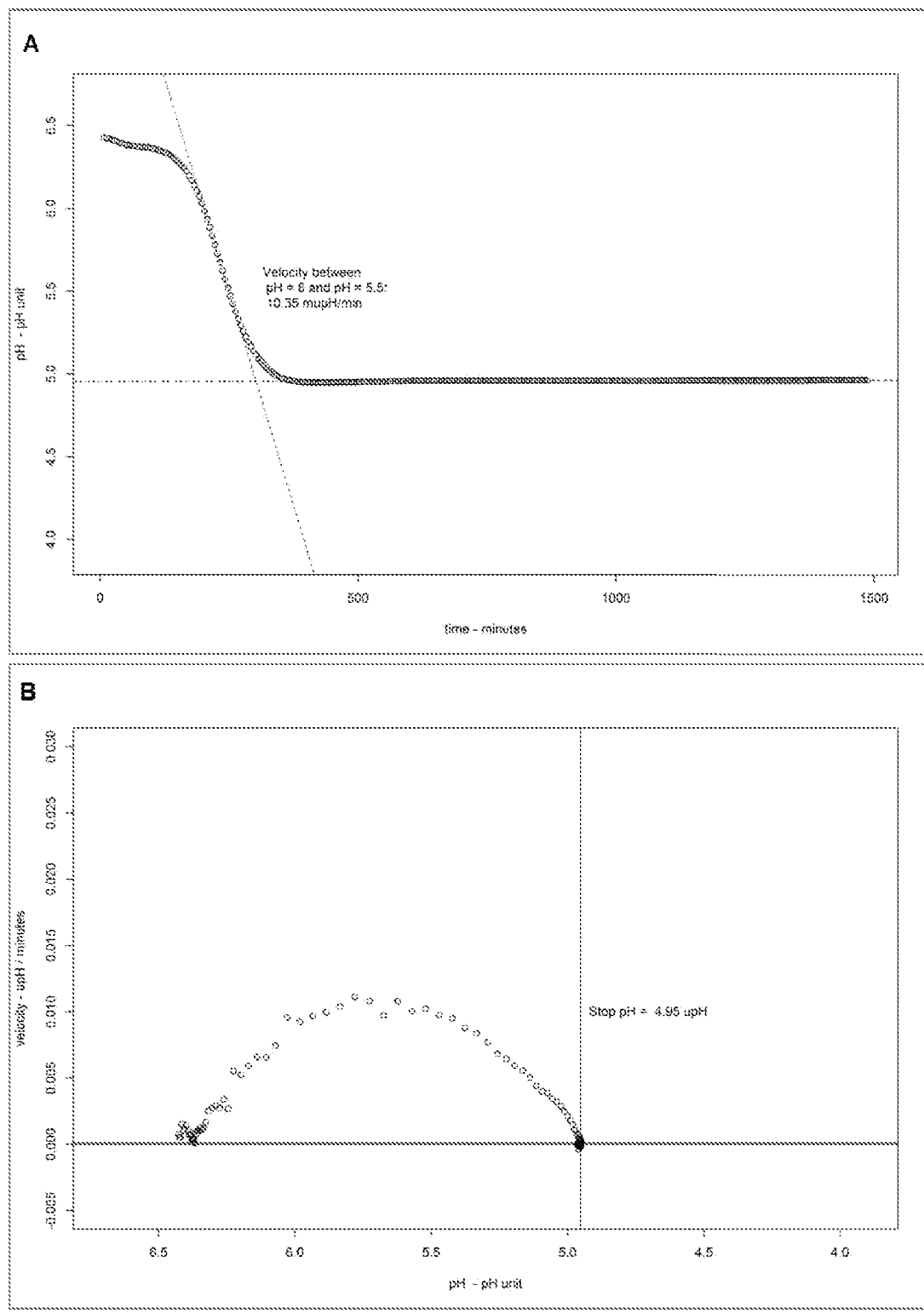
Figure 4:
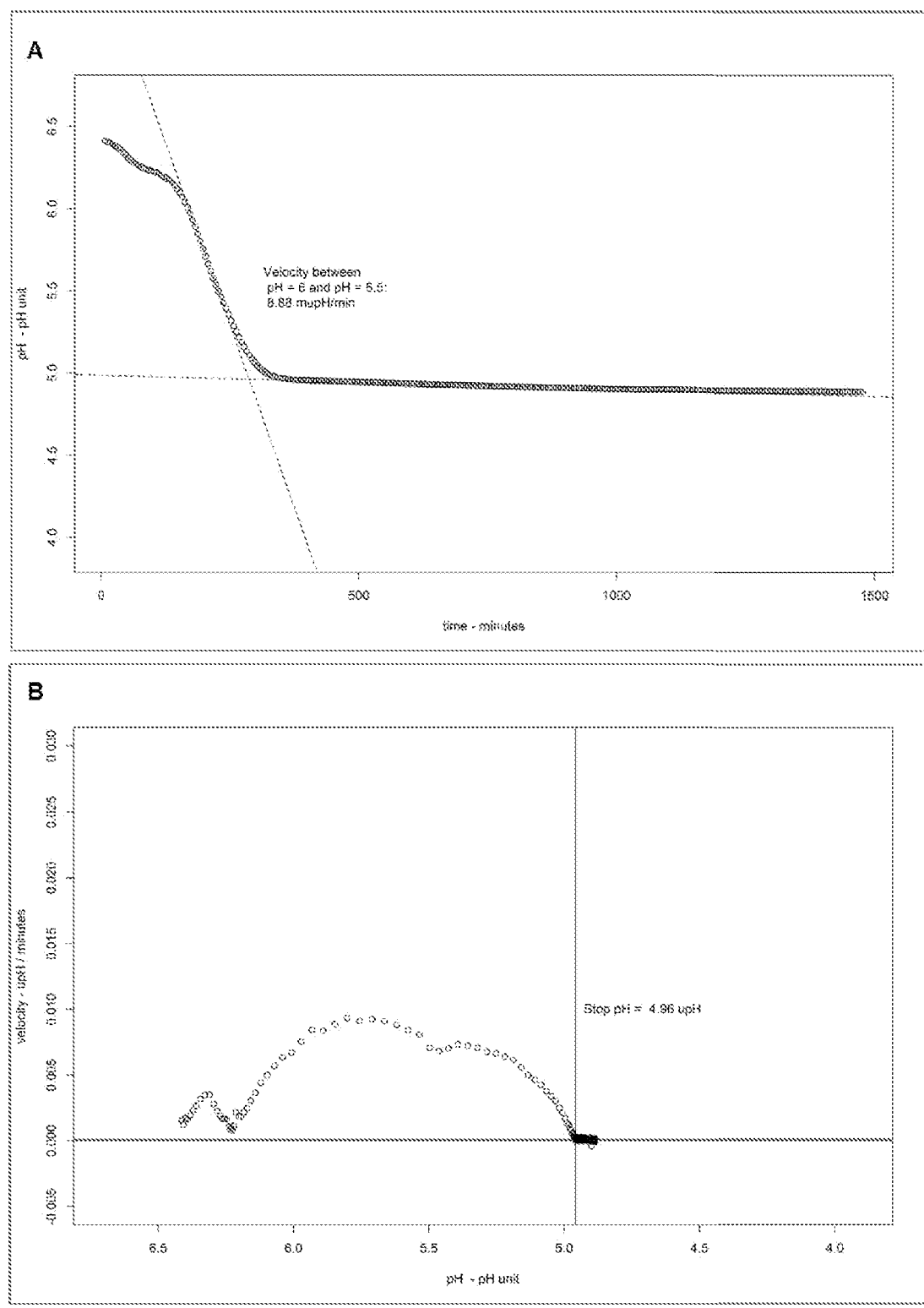
Figure 5:
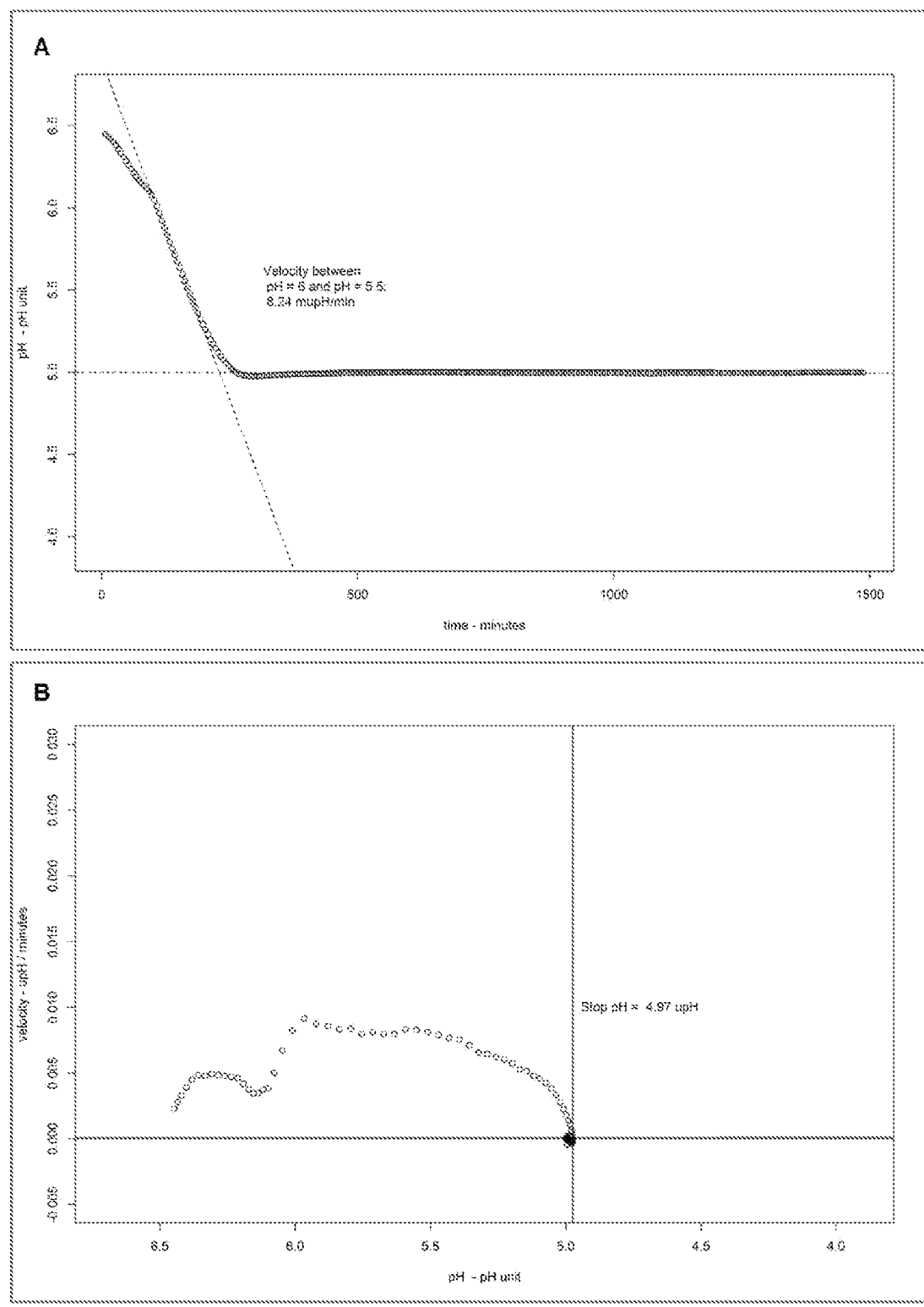
Figure 6:
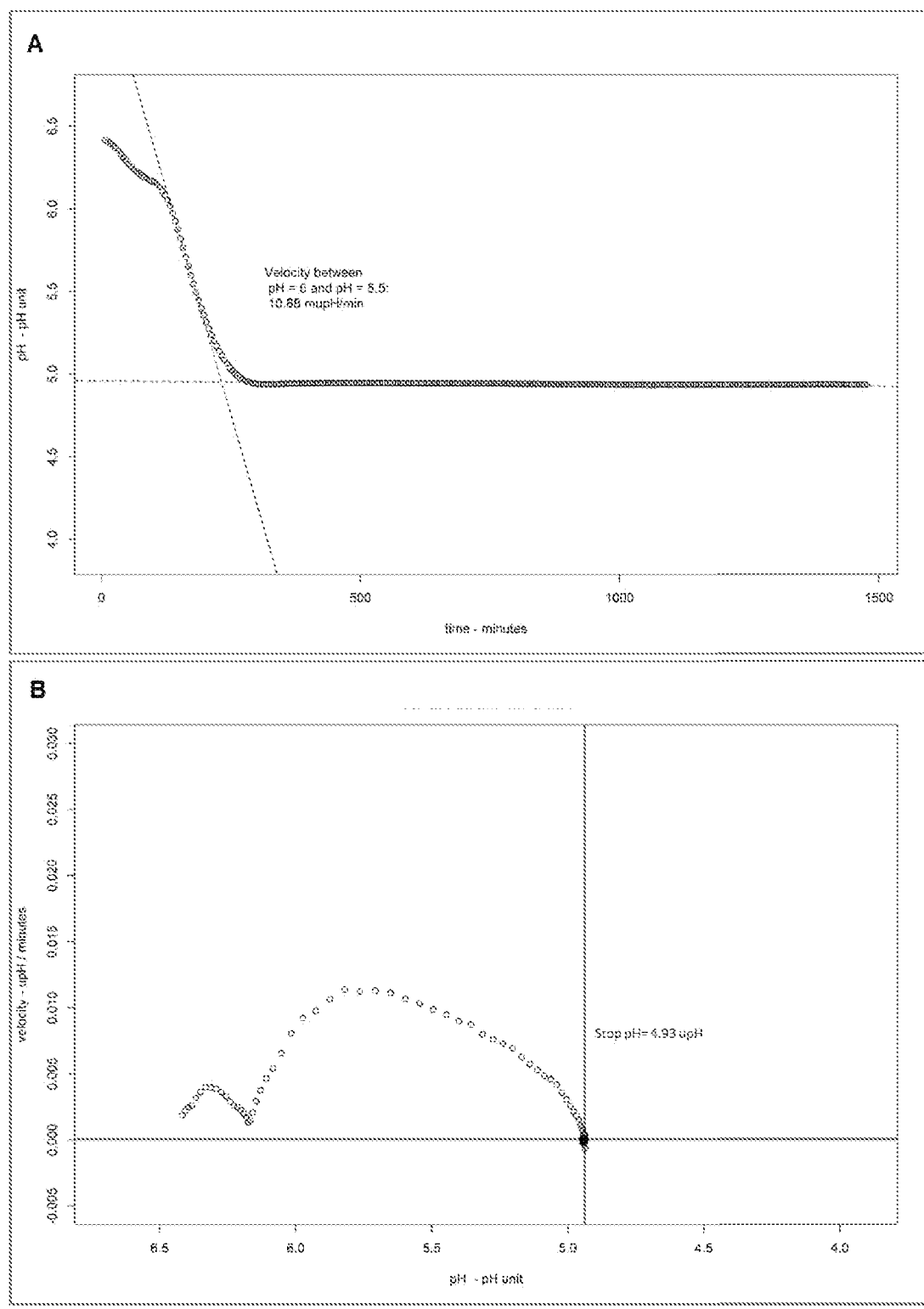
Figure 7:
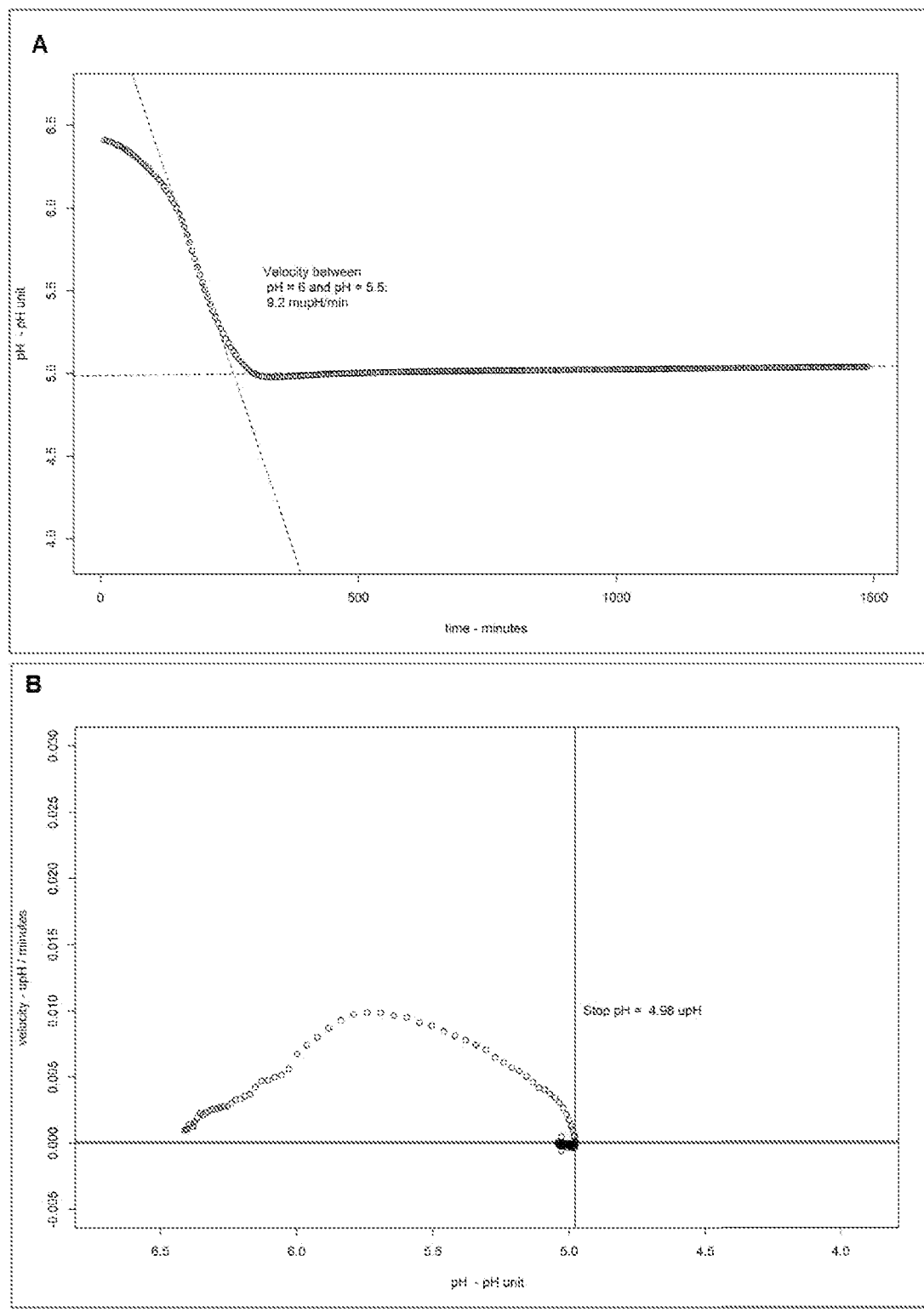

The present invention has put in evidence that mutations tightly deregulating sugar metabolism can be used to design *Streptococcus thermophilus* strains, which can be used to obtain low lactose fermented milk products and/or which can be used to produce fermented milk not undergoing post-acidification even when stored at fermentation temperature.

The inventors have nicely shown that such *Streptococcus thermophilus* strains can be characterized by the ratio of the amount of galactose released over the amount of lactose remaining in the fermented milk. This ratio translates the ability of the strain to consume lactose (uptake and hydrolysis) and to convert it into free galactose and glucose. Due to the galactose-negative phenotype of the *Streptococcus thermophilus* strains of the invention, the released galactose represents stoichiometrically the consumed lactose. It should be considered as the efficiency of the strain to over used lactose. Thus, the inventors have shown that in the galactose-negative strains of the invention, the catabolism of carbohydrates coming from lactose hydrolysis is tightly unregulated, such that the consumption of lactose is increased while the strain still keeps an acceptable growth for its use at an industrial level. The strains of the invention do not need to be galactose positive (phenotype which has been shown to be unstable on lactose).

The present invention is directed to a lactose-positive, galactose-negative, *Streptococcus thermophilus* strain, wherein, when said strain is used to ferment milk as assayed by test B, the ratio of the amount of galactose released (mM) over the amount of remaining lactose (mM) in said fermented milk is more than 1.2, more than 1.5, more than 2 or more than 3.

In an embodiment, the present invention is directed to a lactose-positive, galactose-negative, *Streptococcus thermophilus* strain carrying a mutation in genes selected from the group consisting of 1) a least one gene encoding a protein of the mannose-glucose-specific PTS and a glcK gene, 2) at least one gene encoding a protein of the mannose-glucose-specific PTS and a ccpA gene, and 3) a gene encoding a protein of the mannose-glucose-specific PTS, a glcK gene and a ccpA gene;

wherein, when said strain is used to ferment milk as assayed by test B, the ratio of the amount of galactose released (mM) over the amount of remaining lactose (mM) in said fermented milk is more than 1.2, more than 1.5, more than 2 or more than 3.

In an embodiment, the lactose-positive, galactose-negative, *Streptococcus thermophilus* strain carrying a mutation in one gene encoding a protein of the mannose-glucose-specific PTS and a glcK gene. In an embodiment, the gene encoding a protein of the mannose-glucose-specific PTS is selected from the group consisting of the manL gene, the manM gene, the manN gene and the manO gene. In an embodiment, the gene encoding a protein of the mannose-glucose-specific PTS is selected from the group consisting of the manL gene, the manM gene and the manN gene. In an embodiment, the lactose-positive, galactose-negative, *Streptococcus thermophilus* strain carrying a mutation in one gene selected from the group consisting of manL gene, the manM gene and the manN gene. In an embodiment, the lactose-positive, galactose-negative, *Streptococcus thermophilus* strain carrying a mutation in 2 genes selected from the group consisting of manL gene, the manM gene and the manN gene. In an embodiment, the lactose-positive, galactose-negative, *Streptococcus thermophilus* strain carrying a mutation in the manL gene, the manM gene and the manN gene.

In an embodiment, the present invention is directed to a lactose-positive, galactose-negative, *Streptococcus thermophilus* strain carrying a mutation in 2 or 3 genes selected from the group consisting of 1) a gene encoding a protein of the mannose-glucose-specific PTS and a glcK gene, 2) a gene encoding a protein of the mannose-glucose-specific PTS and a ccpA gene, and 3) a gene encoding a protein of the mannose-glucose-specific PTS, a glcK gene and a ccpA gene;

wherein, when said strain is used to ferment milk as assayed by test B, the ratio of the amount of galactose released (mM) over the amount of remaining lactose (mM) in said fermented milk is more than 1.2, more than 1.5, more than 2 or more than 3.

The Ratio of Amount of Galactose Released Over the Amount of Remaining Lactose by the Lactose-Positive, Galactose-Negative, *Streptococcus thermophilus* Strains of the Invention During Milk Fermentation.

In an embodiment, the lactose-positive, galactose-negative, *Streptococcus thermophilus* strain of the invention exhibit a ratio of the amount of galactose released (mM) over the amount of remaining lactose (mM) in said fermented milk which is more than 1.2. In an embodiment, the ratio of the amount of galactose released (mM) over the amount of remaining lactose (mM) in said fermented milk is selected from the group consisting of more than 1.2, more than 1.5, more than 2 and more than 3. In an embodiment, the ratio of the amount of galactose released (mM) over the amount of remaining lactose (mM) in said fermented milk is more than 1.5. In an embodiment, the ratio of the amount of galactose released (mM) over the amount of remaining lactose (mM) in said fermented milk is more than 2. In an embodiment, the ratio of the amount of galactose released (mM) over the amount of remaining lactose (mM) in said fermented milk is more than 3.

According to the invention, the amount of galactose released (mM) and the amount of remaining lactose (mM) during milk fermentation can be determined by methods well known in the art. In an embodiment, the concentration of galactose and lactose in a fermented milk is characterized by the Test B as defined below:

Test B:

UHT semi-skimmed milk "Le Petit Vendéen ("yoghurt milk") containing 3% (w/v) milk powder (BBA, Lactalis), previously pasteurized 10 min at 90° C., is inoculated at 1% (v/v, about $10^7$ CFU/ml) with a culture of the *S. thermophilus* strain to be assayed (M17-carbohydrate-free resuspended cells from overnight culture grown in M17 supplemented 3% sucrose). This milk is found to contain around 175 mM of lactose. The inoculated milk flasks are statically incubated in a water bath at 43° C. during 24 h, to obtain fermented milk. TO samples and samples of fermented milk (T24 h) (5 g) are diluted in 25 g 0.025 N $H_2SO_4$, before being centrifuged at 4600 rpm for 10 minutes at 4° C. The supernatant is filtered through a 0.2 μm Nylon filter (Phenomenex, Germany, Aschaffenburg) directly into a 2 ml HPLC vial. Samples are stored at −20° C. until further analysis. Carbohydrates [in particular galactose and lactose] are quantified by high performance liquid chromatography (Agilent 1200 HPLC) equipped with a refractive index detector using an AMINEX™ HPX-87H anion exchange column (Bio-Rad Laboratories Inc.) at 35° C., with 12.5 mM $H_2SO_4$ as the elution fluid and a flow rate of 0.6 ml min-1. The exploitation of results is made with CHEMSTATION® reprocessing software (Agilent).

For the avoidance of doubt, the *Streptococcus thermophilus* species is to be understood as a *Streptococcus salivarius* subsp. *thermophilus* strain.

By the expression "lactose-positive", it is meant a *Streptococcus thermophilus* strain which is able to grow on lactose as a sole source of carbohydrate source, in particular on a M17 medium supplemented with 2% lactose. In a particular embodiment, the "lactose-positive" phenotype is assayed by inoculating—into a M17 broth containing 2% lactose—an overnight culture of the *S. thermophilus* strain to be tested at a rate of 1%, and incubating for 20 hours at 37° C., and wherein a pH of 5.5 or lower at the end of incubation is indicative of a lactose-positive phenotype.

By the expression "galactose-negative", it is meant a *Streptococcus thermophilus* strain which is not able to grow on galactose as a sole source of carbohydrate source, in particular on a M17 medium supplemented with 2% galactose. In a particular embodiment, the "galactose-negative" phenotype is assayed by inoculating—into a M17 broth containing 2% galactose—an overnight culture of the *S. thermophilus* strain to be tested at 1% and incubating for 20 hours at 37° C., and wherein a pH of 6 or above at the end of incubation is indicative of a galactose-negative phenotype.

By the expression "derivative" in reference to an original strain (e.g. DGCC7710-derivative), it is meant a strain obtained from an original strain (e.g. from the DGCC7710 strain) by replacement of one of its genes (such as glcK, ccpA, . . . ) by another allele (in particular a mutated allele) of the same gene. In an embodiment, the derivative is obtained by the replacement of the full gene (coding sequence and promoter) of the original strain by another allele (coding sequence and promoter) of the same gene. In an embodiment, the derivative is obtained by the replacement of the coding sequence of a gene of the original strain by another allele (coding sequence) of the same gene.

Thus, the invention is directed to:
- a lactose-positive, galactose-negative, *Streptococcus thermophilus* strain carrying a mutation in at least one, in particular one, gene encoding a protein of the mannose-glucose-specific PTS and carrying a mutation in the glcK gene, wherein, when said strain is used to ferment milk as assayed by test B, the ratio of the amount of galactose released (mM) over the amount of remaining lactose (mM) in said fermented milk is more than 1.2, more than 1.5, more than 2 or more than 3. In an embodiment, the mutation in the gene encoding a protein of the mannose-glucose-specific PTS reduces or abolishes the import of glucose from the medium into the bacteria. In an embodiment, the mutated glcK gene encodes a glucokinase, the glucokinase activity of which in said strain is significantly reduced but not null. In an embodiment, said lactose-positive, galactose-negative, *Streptococcus thermophilus* strain carries a mutation in a gene encoding a protein of the mannose-glucose-specific PTS reducing or abolishing the import of glucose from the medium into the bacteria and carrying a mutation in the glcK gene encodes a glucokinase, such that the glucokinase activity of which in said strain is significantly reduced but not null in said strain. In any of these embodiments, the gene encoding a protein of the mannose-glucose-specific PTS is selected from the group consisting of the manL gene, the manM gene and the manN gene;
- a lactose-positive, galactose-negative, *Streptococcus thermophilus* strain carrying a mutation in at least one, in particular one, encoding a protein of the mannose-glucose-specific PTS and carrying a mutation in the ccpA gene, wherein, when said strain is used to ferment milk as assayed by test B, the ratio of the amount of galactose released (mM) over the amount of remaining lactose (mM) in said fermented milk is more than 1.2, more than 1.5, more than 2 or more than 3. In an embodiment, the mutation in the gene encoding a protein of the mannose-glucose-specific PTS reduces or abolishes the import of glucose from the medium into the bacteria. In an embodiment, the mutation in the ccpA gene leads to a lactose-positive, galactose-negative, *Streptococcus thermophilus* strain exhibiting a ratio of the beta-galactosidase activity of said strain as assayed by test D over the glucokinase activity of said strain as assayed by test E which is at least $4.10^{-6}$, at least $5.10^{-6}$, at least $6.10^{-6}$, at least $7.10^{-6}$ or at least $8.10^{-6}$. In an embodiment, said lactose-positive, galactose-negative, *Streptococcus thermophilus* strain carries a mutation in a gene encoding a protein of the mannose-glucose-specific PTS reducing or abolishing the import of glucose from the medium into the bacteria and carrying a mutation in the ccpA gene such that the ratio of the beta-galactosidase activity of said strain as assayed by test D over the glucokinase activity of said strain as assayed by test E which is at least $4.10^{-6}$. In any of these embodiments, the gene encoding a protein of the mannose-glucose-specific PTS is selected from the group consisting of the manL gene, the manM gene and the manN gene;
- a lactose-positive, galactose-negative, *Streptococcus thermophilus* strain carrying a mutation in at least one, in particular one, encoding a protein of the mannose-glucose-specific PTS, carrying a mutation in the glcK gene and carrying a mutation in the ccpA gene, wherein, when said strain is used to ferment milk as assayed by test B, the ratio of the amount of galactose released (mM) over the amount of remaining lactose (mM) in said fermented milk is more than 1.2, more than 1.5, more than 2 or more than 3. In an embodiment, the mutation in the gene encoding a protein of the mannose-glucose-specific PTS reduces or abolishes the import of glucose from the medium into the bacteria. In an embodiment, the mutated glcK gene encodes a glucokinase, the glucokinase activity of which in said strain is significantly reduced but not null in said strain. In an embodiment, the mutation in the ccpA gene leads to a lactose-positive, galactose-negative, *Streptococcus thermophilus* strain exhibiting a ratio of the beta-galactosidase activity of said strain as assayed by test D over the glucokinase activity of said strain as assayed by test E which is at least $4.10^{-6}$, at least $5.10_{-6}$, at least $6.10^{-6}$, at least $7.10^{-6}$ or at least $8.10^{-6}$. In an embodiment, said lactose-positive, galactose-negative, *Streptococcus thermophilus* strain carries a mutation in a gene encoding a protein of the mannose-glucose-specific PTS reducing or abolishing the import of glucose from the medium into the bacteria, carrying a mutation in the glcK gene encodes a glucokinase, such that the glucokinase activity of which in said strain is significantly reduced but not null in said strain and carrying a mutation in the ccpA gene, such that the ratio of the beta-galactosidase activity of said strain as assayed by test D over the glucokinase activity of said strain as assayed by test E which is at least $4.10_{-6}$. In any of these embodiments, the gene encoding a protein of the mannose-glucose-specific PTS is selected from the group consisting of the manL gene, the manM gene and the manN gene.

The following parts I to III describe respectively mutations of the glcK gene, mutations of the gene encoding a protein of the mannose-glucose-specific PTS (such as mutations of the manL, manM and manN genes) and mutations of the ccpA gene.

Though these mutations are disclosed herein separately (for sake of clarity), any embodiment of one part can be combined with any embodiment of another part or with any embodiment of the two other parts, to design a lactose-positive, galactose-negative, *Streptococcus thermophilus* strain as defined herein, which, when used to ferment milk as assayed by test B, the ratio of the amount of galactose released (mM) over the amount of remaining lactose (mM) in said fermented milk is more than 1.2, more than 1.5, more than 2 or more than 3.

For the avoidance of doubt, the present invention is directed to a lactose-positive, galactose-negative, *Streptococcus thermophilus* strain as defined herein, wherein, when said strain is used to ferment milk as assayed by test B, the ratio of the amount of galactose released (mM) over the amount of remaining lactose (mM) in said fermented milk is more than 1.2, more than 1.5, more than 2 or more than 3, wherein said strain carries:

1) a mutation in at least one, in particular one, gene encoding a protein of the mannose-glucose-specific PTS as defined in part II herein and a mutation in its glcK gene as defined in part I herein; or
2) a mutation in at least one, in particular one, gene encoding a protein of the mannose-glucose-specific PTS as defined in part II herein and a mutation in its ccpA gene as defined in part III herein; or
3) a mutation in at least one, in particular one, gene encoding a protein of the mannose-glucose-specific PTS as defined in part II herein, a a mutation in its glcK gene as defined in part I herein and a mutation in its ccpA gene as defined in part III herein;

I. Mutations of the glcK Gene

This part describes mutations of the glcK gene which can be used either in combination with a mutation of a gene encoding a protein of the mannose-glucose-specific PTS as defined herein, or in combination with a mutation of a gene encoding a protein of the mannose-glucose-specific PTS as defined herein and a mutation of the ccpA gene as defined herein, in the context of a lactose-positive, galactose-negative, Streptococcus thermophilus strain of the invention.

In an embodiment, the mutated glcK gene of the strain of the invention encodes a glucokinase, the glucokinase activity of which in said strain is significantly reduced but not null. Indeed, the inventors have put in evidence that some mutated alleles of the glcK gene codes for a glucokinase (GlcK), the glucokinase activity of which is significantly reduced but not null, when said mutated glcK gene is present in a lactose-positive galactose-negative Streptococcus thermophilus strain.

The expression "glcK gene encoding a glucokinase" means any DNA sequence of a Streptococcus thermophilus strain encoding the glucokinase enzyme which catalyses the conversion of glucose and ATP to glucose-6-phosphate (G6P) and ADP. Non-limitative examples of Streptococcus thermophilus glucokinase sequences are disclosed as SEQ ID Nos: 2, 4, 6, 8, 10 12, 14, 16, 18 and 20.

Within the invention, the glucokinase activity in a Streptococcus thermophilus strain is significantly reduced but not null as a consequence of a mutation in its glcK gene. In other words, the allele of the glcK gene carried by said strain is such that the glucokinase activity in said strain is significantly reduced but not null.

The expression "glucokinase activity in said strain is significantly reduced but not null" refers to a strain the glucokinase activity of which is both:
  significantly reduced in said strain, in particular as compared to the glucokinase activity in a strain carrying a non-mutated glcK gene; and
  not null, i.e., that an activity is detectable by test A as defined herein.

According to the invention, the feature "glucokinase activity in said strain is significantly reduced but not null" can be determined by methods well known in the art. Thus, methods for measuring the glucokinase activity in a Streptococcus thermophilus strain are known and include enzyme assays with commercially available reactants. Reference is made herein to the paragraph 2.4 of Pool et al. (2006. Metabolic Engineering 8 (5); 456-464) (incorporated herein by reference). In a particular embodiment, the glucokinase activity in a Streptococcus thermophilus strain of the invention is assayed by test A [i.e. the test A is carried out using the Streptococcus thermophilus strain of the invention] as defined below:

Test A:

A fresh overnight culture of the Streptococcus thermophilus strain to be assayed in M17 containing 30 g/L lactose is obtained and used to inoculate at 1% (vol/vol) 10 ml of fresh M17 30 g/L lactose. Cells are harvested by centrifugation (6000 g, 10 min, 4° C.) at a 600 nm optical density (OD600) of 0.8+/−0.2, washed in 5 ml cold GLCK buffer (5 mM MgCl2, 10 mM $K_2HPO_4/KH_2PO_4$ [pH 7.2]), and resuspended in 500 μl cold GLCK buffer. EDTA-free protease inhibitors "cOmplete™" (Roche, supplier reference 04693132001) is added in GLCK buffer as described by the provider. Cells are disrupted by the addition of 100 mg glass beads (150-212 μm, Sigma G1145) to 200 μl resuspended cells and oscillation at a frequency of 30 cycles/s for 6 min in a MM200 oscillating mill (Retsch, Haan, Germany). Cell debris and glass beads are removed by centrifugation (14000 g, 15 min, 4° C.), and supernatant transferred into a clean 1.5 mL centrifuge tube kept on ice. Total protein content is determined by using the FLUKA Protein Quantification Kit-Rapid (ref 51254). The glucokinase activity in the cell extracts is determined spectrophotometrically by a glucose-6-phosphate dehydrogenase (G-6PDH, EC1.1.1.49): NADPH-coupled assay (Porter et al., 1982), essentially as described by Pool et al. (2006). Each sample (5, 10 and 20 μL) is added to assay buffer (10 mM $K_2HPO_4/KH_2PO_4$ [pH 7.2], 5 mM MgCl2, 1 mM ATP, 20 mM glucose, 1 mM NADP, 1 U G-6PDH) in a 250 μL final volume, and the mixture was left for 5 min at 30° C. The optical density at 340 nm is measured for 5 minutes by using a Synergy HT multi-detection microplate reader (BIO-TEK). One unit of glucokinase corresponds to the amount of enzyme that catalyzes the phosphorylation of 1 μmole of D-glucose to D-Glucose 6-phosphate per minute under the assay conditions. Glucokinase activity is calculated as follows:

Glucokinase activity (μ/g of total protein extract)=dOD× V/[dt×l×x×ε×Qprot], wherein:
  dOD is the variation of optical density (OD) at 340 nm
  V is the volume of the reaction (herein 250 μL)
  dt=measurement time (in minutes)
  l=optical path length (herein 0.73 cm)
  ε=molar attenuation coefficient of nadph; h$^+$ (herein 6220 cm2/μmol)
  Qprot=quantity of protein in the cuvette (in g)

Measurements are triplicated for each sample, and the glucokinase specific activity values given herein under test A are the mean of three independent experiments.

In a first particular embodiment of the feature "glucokinase activity in said strain is significantly reduced but not null", the glucokinase activity in the Streptococcus thermophilus strain of the invention is between 200 and 1500 U/g of total protein extract, as assayed by test A. In a particular embodiment, the glucokinase activity in the Streptococcus thermophilus strain of the invention is between 300 and 1200 U/g of total protein extract, as assayed by test A. In a particular embodiment, the glucokinase activity in the Streptococcus thermophilus strain of the invention is between 400 and 1000 U/g of total protein extract, as assayed by test A. In a particular embodiment, the glucokinase activity in the Streptococcus thermophilus strain of the invention is between a minimal value selected from the group consisting of 200, 300 and 400 U/g of total protein extract and a maximal value selected from the group consisting of 1000, 1200 and 1500 U/g of total protein extract, as assayed by test A. It is noteworthy that, as mentioned in test A, the glucokinase activity values disclosed herein are the mean of three independent experiments (triplicates).

In a second particular embodiment of the feature "glucokinase activity in said strain is significantly reduced but not null", the glucokinase activity in the Streptococcus thermophilus strain of the invention is between 5 and 60% the activity of the glucokinase activity of the DGCC7710 strain deposited at the DSMZ under accession number DSM28255 on Jan. 14, 2014. By "glucokinase activity of the DGCC7710 strain", it is meant the activity of the DGCC7710 strain glucokinase (i.e., with SEQ ID NO:2) as assayed by test A in the DGCC7710 strain [i.e., the test A is carried out using the DGCC7710 strain]. The percentage value is calculated based on the glucokinase activity in the strain of the invention and the glucokinase activity of the DGCC7710 strain, both assayed by test A. In a particular embodiment, the glucokinase activity in the *Streptococcus thermophilus* strain of the invention is between 10 and 50% the glucokinase activity of the DGCC7710 strain. In a particular embodiment, the glucokinase activity in the *Streptococcus thermophilus* strain of the invention is between 15 and 40% the glucokinase activity of the strain DGCC7710. In a particular embodiment, the glucokinase activity of the *Streptococcus thermophilus* strain of the invention is between a minimal percentage selected from the group consisting of 5, 10 and 15% the glucokinase activity of the DGCC7710 strain and a maximal percentage selected from the group consisting of 40, 50 and 60% the glucokinase activity of the DGCC7710 strain. In a particular embodiment and whatever the range of percentages, the activity of the glucokinase activity is assayed by test A as described herein. It is noteworthy that the percentage values disclosed herein are calculated based on glucokinase activity values which are the mean of three independent experiments (triplicates) as assayed by test A.

In the first and second particular embodiments, the following strains can be used as controls in test A:
- as a positive control (i.e., a *Streptococcus thermophilus* strain, which is representative of strains carrying a non-mutated glcK gene): strain DGCC7710 deposited at the DSMZ under accession number DSM28255 on Jan. 14, 2014;
- as a negative control (i.e., a *Streptococcus thermophilus* strain having no detectable glucokinase activity): either a *Streptococcus thermophilus* the glcK gene of which is knocked-out or a *Streptococcus thermophilus* the glcK gene of which carries one of the mutations disclosed in WO2013/160413, WO2017/103051 or Sørensen et al. (2016) and summarized in Table 1 below:

TABLE 1 glcK mutations leading to a strain the glucokinase activity of which is not detectable

| Mutation at the glcK gene level | Change at the GlcK protein level | Mutation described in the deposited strain | Strains described in |
|---|---|---|---|
| T214C | S72P | DSM25851 | WO2013/160413 |
| C422T | T141I | DSM25850 | WO2013/160413 Sørensen (St1-GS-1) |
| G745A | G249R | DSM28889 | WO2017/103051 Sørensen (St2-GS-1) |

During milk fermentation, the lactose contained in the milk (as the main carbohydrate source in milk) is imported into *Streptococcus thermophilus* strains. The intracellular lactose is then cleaved into glucose and galactose by the beta-galactosidase enzyme (such that 1 mole of lactose gives 1 mole of glucose and 1 mole of galactose).

The feature "glucokinase activity in said strain is significantly reduced but null" can also be characterized by the maximum forward velocity of the glucokinase (herein called Vmax, and defined as the velocity of the Glucose+ATP conversion to G6P+ADP) or by the inverse of the affinity of the glucokinase (called Km) for one or two of its substrates, i.e., glucose and ATP. In an embodiment, the feature "glucokinase activity in said strain is significantly reduced but not null" for the strain of the invention is further characterized by the maximum forward velocity (Vmax) of its glucokinase in said strain.

Therefore, in combination with the first or second particular embodiment of the feature "glucokinase activity in said strain is significantly reduced but not null" defined herein, the maximum forward velocity (Vmax) of the glucokinase in the lactose-positive, galactose-negative, *Streptococcus thermophilus* strain of the invention is significantly reduced but not null. The feature "glucokinase Vmax in said strain is significantly reduced but not null" can be defined by one or two of these parameters:
- the Vmax is between 200 and 1500 U/g total protein extract, as assayed by test C.
- the Vmax is between 5 and 60% the Vmax of the glucokinase of the DGCC7710 strain deposited at the DSMZ under accession number DSM28255 on Jan. 14, 2014, when both assayed by test C.

In a particular embodiment, the mutated glcK gene of a lactose-positive, galactose-negative, *Streptococcus thermophilus* strain of the invention encodes a glucokinase, wherein the glucokinase activity in said strain is significantly reduced but not null (as defined herein), and wherein the maximum forward velocity (Vmax) of its glucokinase in said strain is significantly reduced but not null and defined by one or two of these parameters:
- the Vmax is between 200 and 1500 U/g total protein extract, as assayed by test C.
- the Vmax is between 5 and 60% the Vmax of the glucokinase of the DGCC7710 strain deposited at the DSMZ under accession number DSM28255 on Jan. 14, 2014, when both assayed by test C.

The glucokinase maximum forward velocity (Vmax) in a *Streptococcus thermophilus* of the invention is assayed by test C [i.e. the test C is carried out using the *Streptococcus thermophilus* strain of the invention] as defined below:

Test C:

The maximal forward velocity (Vmax) is determined by using various concentrations of glucose (0, 5, 10, 15, 20 mM) on crude extract prepared as described in test A. Measurements are triplicated for each sample, and the Vmax values given under test C are the mean of three independent experiments. The linear regression representing the inverse of the specific velocity in function of the inverse of the glucose concentration gives the inverse of the maximal forward velocity at the intersection with the Y-axis of the graphic.

In a particular embodiment of the maximum forward velocity of the glucokinase in the *Streptococcus thermophilus* strain of the invention, the Vmax is between 200 and 1500 U/g total protein extract, as assayed by test C. In a particular embodiment, the Vmax is between 300 and 1200 U/g total protein extract, as assayed by test C. In a particular embodiment, the Vmax is between 400 and 1000 U/g total protein extract. In a particular embodiment, the Vmax of the glucokinase in the *Streptococcus thermophilus* strain of the invention is between a minimal value selected from the group consisting of 200, 300 and 400 U/g of total protein extract and a maximal value selected from the group consisting of 1000, 1200 and 1500 U/g of total protein extract, as assayed by test C.

In a particular embodiment of the maximum forward velocity of the glucokinase in the *Streptococcus thermophilus* strain of the invention, the Vmax is between 5 and 60% the Vmax of the glucokinase of the DGCC7710 strain. By "Vmax of the glucokinase of the DGCC7710 strain", it is meant the Vmax of the DGCC7710 strain glucokinase (i.e., with SEQ ID NO:2) as assayed by test C in the DGCC 7710 strain [i.e., the test C is carried out using the DGCC7710 strain]. The percentage value is calculated based on the Vmax of the glucokinase in the strain of the invention and the Vmax of the DGCC7710 strain, both assayed by test C. In a particular embodiment, the glucokinase Vmax in the *Streptococcus thermophilus* strain of the invention is between 10 and 50% the Vmax of the glucokinase of the DGCC7710 strain, when both assayed by test C. In a particular embodiment, the glucokinase Vmax in the *Streptococcus thermophilus* strain of the invention is between 15 and 40% the Vmax of the glucokinase of the DGCC7710 strain. In a particular embodiment, the Vmax of the glucokinase in the *Streptococcus thermophilus* strain of the invention is between a minimal percentage selected from the group consisting of 5, 10 and 15% the Vmax of the glucokinase activity of the DGCC7710 strain and a maximal percentage selected from the group consisting of 40, 50 and 60% the Vmax of the glucokinase activity of the DGCC7710 strain.

The lactose-positive, galactose-negative *Streptococcus thermophilus* strain of the invention carries a mutation in the glcK gene encoding a glucokinase, the glucokinase activity of which in said strain is significantly reduced but not null as defined herein and optionally wherein the maximum forward velocity of the glucokinase in said strain is significantly reduced but not null as defined herein.

By "mutation in the glcK gene" within the present invention, it is meant any nucleotide variation within the glcK gene, wherein said variation at the nucleotide level leads to a glucokinase activity in a strain carrying this mutated glcK gene (as the sole glcK gene) which is significantly reduced but not null as defined herein and optionally leads to a maximum forward velocity of the glucokinase in said strain which is significantly reduced but not null as defined herein. In a particular embodiment, by "mutation in the glcK gene" within the present invention, it is meant any nucleotide variation within the open reading frame of the glcK gene, wherein said variation at the nucleotide level leads to a glucokinase activity in a strain carrying this mutated glcK gene (as the sole glcK gene) which is significantly reduced but not null as defined herein and optionally leads to a maximum forward velocity of the glucokinase in said strain which is significantly reduced but not null as defined herein.

Thus, though two *Streptococcus thermophilus* strains may differ by the sequence of their respective glcK gene, this does not necessarily mean that one of these two glcK genes is mutated in the sense of the invention. Indeed, are not considered as mutations within the present invention:
  variations at the nucleotide level which do not lead to any change at the protein level (silent variation) and which do not impact the translation of the glcK RNA; and
  variations at the nucleotide level which do lead to a change at the protein level, but wherein this change does not impact the glucokinase activity of the resulting GlcK protein and optionally the maximum forward velocity of the resulting GlcK protein, as defined herein. Indeed, such variations can be observed at the level of the glcK gene of the *Streptococcus thermophilus* of the invention without impacting the scope of protection.

Non-limitative examples of glcK genes which are not considered as mutated in the sense of the invention are:
  the polynucleotide encoding the glucokinase as defined in SEQ ID NO:2 (GlcK type ST1), in particular the polynucleotide as defined in SEQ ID NO:1; this GlcK type is the one of DGCC7710 strain deposited at the DSMZ under accession number DSM28255 on Jan. 14, 2014;
  the polynucleotide encoding the glucokinase as defined in SEQ ID NO:4 (GlcK type ST2), in particular the polynucleotide as defined in SEQ ID NO:3;
  the polynucleotide encoding the glucokinase as defined in SEQ ID NO:6 (GlcK type ST3), in particular the polynucleotide as defined in SEQ ID NO:5;
  the polynucleotide encoding the glucokinase as defined in SEQ ID NO:8 (GlcK type ST4), in particular the polynucleotide as defined in SEQ ID NO:7;
  the polynucleotide encoding the glucokinase as defined in SEQ ID NO:10 (GlcK type ST5), in particular the polynucleotide as defined in SEQ ID NO:9;
  the polynucleotide encoding the glucokinase as defined in SEQ ID NO:12 (GlcK type ST6), in particular the polynucleotide as defined in SEQ ID NO:11;
  the polynucleotide encoding the glucokinase as defined in SEQ ID NO:14 (GlcK type ST7), in particular the polynucleotide as defined in SEQ ID NO:13;
  the polynucleotide encoding the glucokinase as defined in SEQ ID NO:16 (GlcK type ST8), in particular the polynucleotide as defined in SEQ ID NO:15;
  the polynucleotide encoding the glucokinase as defined in SEQ ID NO:18 (GlcK type ST9), in particular the polynucleotide as defined in SEQ ID NO:17;
  the polynucleotide encoding the glucokinase as defined in SEQ ID NO:20 (GlcK type ST10), in particular the polynucleotide as defined in SEQ ID NO:19.

The amino acid differences at the level of the glucokinase together with the percentage of identity of each GlcK type to SEQ ID NO:2 are summarized in Table 3 (example 2). The glucokinase activity in strains of the GlcK types ST2 to ST10 is summarized in Table 4 (example 3).

Moreover, some nucleotide mutations within the glcK gene are not considered suitable for the purpose of the invention, because they lead to a glucokinase, the activity of which is null or is under the minimal value defined herein, as assayed by test A. Non-limitative examples of non-suitable mutations are described in Table 1. In an embodiment, the *Streptococcus thermophilus* of the invention does not carry a mutation selected from the group consisting of a mutation leading to the knock-out of the glcK gene and large deletions within the glcK gene.

In an embodiment, the lactose-positive, galactose-negative *Streptococcus thermophilus* strain of the invention carries a mutation in the open reading frame of the glcK gene leading to the substitution of an amino acid in the GlcK protein, the glucokinase activity of which in said strain carrying the mutated glcK gene is significantly reduced but not null (as defined herein) and optionally wherein the maximum forward velocity of the glucokinase in said strain is significantly reduced but not null as defined herein. In a particular embodiment, the lactose-positive, galactose-negative *Streptococcus thermophilus* strain of the invention carries a mutation in the glcK gene leading to the substitution of an amino acid in the GlcK protein, the glucokinase activity of which in said strain carrying the mutated glcK gene is significantly reduced but not null (as defined herein) and optionally wherein the maximum forward velocity of the glucokinase in said strain is significantly reduced but not null as defined herein. In a particular embodiment, the *Streptococcus thermophilus* strain of the invention carries a mutation in the glcK gene such that the GlcK protein is 322-amino acids in length and wherein the glucokinase activity in said strain is significantly reduced but not null as defined herein and optionally wherein the maximum forward velocity of the glucokinase in said strain is significantly reduced but not null as defined herein.

As discussed above, some DNA modifications can be observed at the level of the glcK gene of the *Streptococcus thermophilus* of the invention which do not impact the glucokinase activity of the strain. Based on test A defined herein together with the control strains defined herein, the person skilled in the art would know how to identify 1) a glcK gene encoding a glucokinase, the glucokinase activity of which in a strain carrying this glcK gene is significantly reduced but not null (as defined herein) and optionally wherein the maximum forward velocity of the glucokinase in a strain carrying this mutated glcK gene is significantly reduced but not null (as defined herein), 2) a glcK gene bearing a modification having no impact on the glucokinase activity in a strain carrying this modification or 3) a glcK gene encoding a glucokinase, the glucokinase activity of which in a strain carrying this glcK gene is null (as defined herein).

The DGCC7710 strain can be used as a control, by replacing its glcK gene by the glcK gene to be assayed to obtain a derivative of DGCC7710, and assaying the DGCC7710 derivative by test A (glucokinase activity) or test C (Vmax).

The inventors have identified two positions within the glucokinase, for which the amino acid nature has been shown to impact the activity of the glucokinase, such that the glucokinase activity is significantly reduced but not null as defined herein and to impact the Vmax of the glucokinase such that the Vmax is significantly reduced but not null as defined herein: position 144 and position 275 of the glucokinase (i.e., codon 144 and 275 of the glcK gene). It is noteworthy that based on tests A and C defined herein together with the control strains, the person skilled in the art would know how to identify other positions and appropriate amino acids within the glucokinase, to obtain a glucokinase activity significantly reduced but not null (as defined herein) and optionally a maximum forward velocity which is significantly reduced but not null, and thus the corresponding glcK gene.

In an embodiment, the amino acid at position 275 of the glucokinase (encoded by the glcK gene of the *Streptococcus thermophilus* strain of the invention) is not a glutamic acid (i.e., is any amino acid except a glutamic acid); thus, in an embodiment, the codon 275 of the glcK gene carried by the *Streptococcus thermophilus* strain of the invention is neither GAA nor GAG. In a particular embodiment, the amino acid at position 275 of the glucokinase is not an acidic amino acid (i.e., is any amino acid except an acidic amino acid); thus, in an embodiment, the codon 275 of the glcK gene carried by the *Streptococcus thermophilus* strain of the invention is a codon encoding a non-acidic amino acid. In a particular embodiment, the amino acid at position 275 of the glucokinase is selected from the group consisting of lysine and any of its conservative amino acids; thus, in an embodiment, the codon 275 of the glcK gene carried by the *Streptococcus thermophilus* strain of the invention is a codon encoding an amino acid selected from the group consisting of a lysine and any of its conservative amino acids. In a particular embodiment, the amino acid at position 275 of the glucokinase is a lysine; thus, in an embodiment, the codon 275 of the glcK gene carried by the *Streptococcus thermophilus* strain of the invention is either AAA or AAG. In a particular embodiment, the nucleotides 823-825 of the glcK gene carried by the *Streptococcus thermophilus* strain of the invention are AAA or AAG.

In a particular embodiment, the sequence of the GlcK protein of the lactose-positive, galactose-negative *Streptococcus thermophilus* strain of the invention is selected from the group consisting of:
a) a sequence as defined in SEQ ID NO:25, wherein the amino acid at position 275 is any amino acid except a glutamic acid, in particular is any amino acid except an acidic amino acid, in particular is a lysine; and
b) a Glck variant sequence having at least 90% similarity or identity with SEQ ID NO:25, wherein the amino acid of the glucokinase corresponding to position 275 of SEQ ID NO:25 (or the amino acid at position 275 of the glucokinase) is any amino acid except a glutamic acid, in particular is any amino acid except an acidic amino acid, in particular is a lysine. In a particular embodiment, the GlcK variant sequence is 322-amino acids in length.

In another embodiment, the amino acid at position 144 of the glucokinase (encoded by the glcK gene of the *Streptococcus thermophilus* strain of the invention) is not a glycine (i.e., is any amino acid except a glycine); thus, in an embodiment, the codon 144 of the glcK gene carried by the *Streptococcus thermophilus* strain of the invention is not GGT, GGC, GGA or GGG. In a particular embodiment, the amino acid at position 144 of the glucokinase is not an aliphatic amino acid (i.e., is any amino acid except an aliphatic amino acid). In a particular embodiment, the amino acid at position 144 of the glucokinase is selected from the group consisting of serine and any of its conservative amino acids; thus, in an embodiment, the codon 144 of the glcK gene carried by the *Streptococcus thermophilus* strain of the invention is a codon encoding an amino acid selected from the group consisting of a serine and any of its conservative amino acids. In a particular embodiment, the amino acid at position 144 of the glucokinase is a serine; thus, in an embodiment, the codon 144 of the glcK gene carried by the *Streptococcus thermophilus* strain of the invention is AGT, AGC, TCT, TCC, TCA or TCG. In a particular embodiment, the nucleotides 430-432 of the glcK gene carried by the *Streptococcus thermophilus* strain of the invention are AGT, AGC, TCT, TCC, TCA or TCG.

In a particular embodiment, the sequence of the GlcK protein of the lactose-positive, galactose-negative *Streptococcus thermophilus* strain of the invention is selected from the group consisting of:
a) a sequence as defined in SEQ ID NO:46, wherein the amino acid at position 144 is any amino acid except a glycine, in particular is any amino acid except an aliphatic amino acid, in particular is a serine; and
b) a GlcK variant sequence having at least 90% similarity or identity with SEQ ID NO:46, wherein the amino acid of the glucokinase corresponding to position 144 of SEQ ID NO:46 (or the amino acid at position 144 of the glucokinase) is any amino acid except a glycine, in particular is any amino acid except an aliphatic amino acid, in particular is a serine. In a particular embodiment, the GlcK variant sequence is 322-amino acids in length.

For the definition of the GlcK variant having at least 90% similarity or identity with SEQ ID NO: 25, the similarity or identity is calculated herein over the whole length of the 2 sequences after optimal alignment [i.e., number of similar or identical amino acid residues in the aligned parts(s) of the sequences]; the position 275 as defined in SEQ ID NO:25 is not considered for the calculation of the similarity or of the identity. In a particular embodiment, the GlcK variant sequence has at least 91, 92, 93, 94, 95, 96, 97, 98 or 99% similarity or identity with SEQ ID NO: 25, wherein the amino acid corresponding to position 275 of SEQ ID NO:25 (or the amino acid at position 275 of the glucokinase) is any amino acid except a glutamic acid, in particular is any amino acid except an acidic amino acid, in particular is a lysine. In an embodiment, the GlcK variant sequence has at least 95% similarity or identity with SEQ ID NO:25, wherein the amino acid corresponding to position 275 of SEQ ID NO:25 (or the amino acid at position 275 of the glucokinase) is any amino acid except a glutamic acid, in particular is any amino acid except an acidic amino acid, in particular is a lysine. In an embodiment, the GlcK variant sequence has at least 97% similarity or identity with SEQ ID NO:25, wherein the amino acid corresponding to position 275 of SEQ ID NO:25 (or the amino acid at position 275 of the glucokinase) is any amino acid except a glutamic acid, in particular is any amino acid except an acidic amino acid, in particular is a lysine.

In a particular embodiment, the GlcK variant sequence differs from SEQ ID NO:25 by from 1 to 30 amino acid substitutions wherein the amino acid at position 275 of said Glck variant is any amino acid except a glutamic acid, in particular is any amino acid except an acidic amino acid, in particular is a lysine (the position 275 is not considered for the calculation of the number of substitution(s)). In a particular embodiment, the GlcK variant sequence differs from SEQ ID NO: 25 by from 1 to 20 amino acid substitutions, wherein the amino acid at position 275 of said GlcK variant is any amino acid except a glutamic acid, in particular is any amino acid except an acidic amino acid, in particular is a lysine. In a particular embodiment, the GlcK variant sequence differs from SEQ ID NO: 25 by from 1 to 15 amino acid substitutions wherein the amino acid at position 275 of said GlcK variant is any amino acid except a glutamic acid, in particular is any amino acid except an acidic amino acid, in particular is a lysine. In a particular embodiment, the GlcK variant sequence differs from SEQ ID NO: 25 by from 1 to 10 amino acid substitutions wherein the amino acid at position 275 of said GlcK variant is any amino acid except a glutamic acid, in particular is any amino acid except an acidic amino acid, in particular is a lysine. In a particular embodiment, the GlcK variant sequence differs from SEQ ID NO: 25 by 1, 2, 3, 4, 5, 6, 7, 8, 9, 10, 11 or 12 amino acid substitutions, wherein the amino acid at position 275 of said GlcK variant is any amino acid except a glutamic acid, in particular is any amino acid except an acidic amino acid, in particular is a lysine.

For the definition of the Glck variant having at least 90% similarity or identity with SEQ ID NO: 46, the similarity or identity is calculated herein over the whole length of the 2 sequences after optimal alignment [i.e., number of similar or identical amino acid residues in the aligned parts(s) of the sequences]; the position 144 as defined in SEQ ID NO:46 is not considered for the calculation of the similarity or of the identity. In a particular embodiment, the GlcK variant sequence has at least 91, 92, 93, 94, 95, 96, 97, 98 or 99% similarity or identity with SEQ ID NO: 46, wherein the amino acid corresponding to position 144 of SEQ ID NO:46 (or the amino acid at position 144 of the glucokinase) is any amino acid except a glycine, in particular is any amino acid except an aliphatic amino acid, in particular is a serine. In an embodiment, the GlcK variant sequence has at least 95% similarity or identity with SEQ ID NO:46, wherein the amino acid corresponding to position 144 of SEQ ID NO:46 (or the amino acid at position 144 of the glucokinase) is any amino acid except a glycine, in particular is any amino acid except an aliphatic amino acid, in particular is a serine. In an embodiment, the GlcK variant sequence has at least 97% similarity or identity with SEQ ID NO:46, wherein the amino acid corresponding to position 144 of SEQ ID NO:46 (or the amino acid at position 144 of the glucokinase) is any amino acid except a glycine, in particular is any amino acid except an aliphatic amino acid, in particular is a serine.

In a particular embodiment, the GlcK variant sequence differs from SEQ ID NO:46 by from 1 to 30 amino acid substitutions wherein the amino acid at position 144 of said GlcK variant is any amino acid except a glycine, in particular is any amino acid except an aliphatic amino acid, in particular is a serine (the position 144 is not considered for the calculation of the number of substitution(s)). In a particular embodiment, the GlcK variant sequence differs from SEQ ID NO: 46 by from 1 to 20 amino acid substitutions, wherein the amino acid at position 144 of said GlcK variant is any amino acid except a glycine, in particular is any amino acid except an aliphatic amino acid, in particular is a serine. In a particular embodiment, the GlcK variant sequence differs from SEQ ID NO: 46 by from 1 to 15 amino acid substitutions wherein the amino acid at position 144 of said GlcK variant is any amino acid except a glycine, in particular is any amino acid except an aliphatic amino acid, in particular is a serine. In a particular embodiment, the GlcK variant sequence differs from SEQ ID NO: 46 by from 1 to 10 amino acid substitutions wherein the amino acid at position 144 of said GlcK variant is any amino acid except a glycine, in particular is any amino acid except an aliphatic amino acid, in particular is a serine. In a particular embodiment, the GlcK variant sequence differs from SEQ ID NO: 46 by 1, 2, 3, 4, 5, 6, 7, 8, 9, 10, 11 or 12 amino acid substitutions, wherein the amino acid at position 144 of said GlcK variant is any amino acid except a glycine, in particular is any amino acid except an aliphatic amino acid, in particular is a serine.

In an embodiment, the sequence of the GlcK protein of the lactose-positive, galactose-negative *Streptococcus thermophilus* strain of the invention is selected from the group consisting of SEQ ID NOs: 25, 26, 27, 28, 29, 30, 31, 32, 33 and 34, wherein the amino acid at position 275 of said variant is any amino acid except a glutamic acid, in particular is any amino acid except an acidic amino acid, in particular is a lysine; thus, in an embodiment, the glcK gene carried by the *Streptococcus thermophilus* strain of the invention encodes a GlcK protein, the sequence of which is selected from the group consisting of SEQ ID NOs: 25, 26, 27, 28, 29, 30, 31, 32, 33 and 34, wherein the amino acid at position 275 of the glucokinase is not a glutamic acid, in particular is not an acidic amino acid, in particular is a lysine respectively. In a particular embodiment, either as the SEQ ID NO:25 or any GlcK variant sequence having at least 90% similarity or identity with SEQ ID NO:25 as defined herein (in particular SEQ ID NO: 26, 27, 28, 29, 30, 31, 32, 33 or 34), the amino acid of the glucokinase corresponding to position 275 of SEQ ID NO:25 (or the amino acid at position 275 of the glucokinase) is not a glutamic acid; thus, in an embodiment, the codon 275 of the glcK gene carried by the *Streptococcus thermophilus* strain of the invention is neither GAA nor GAG; thus, in an embodiment, the glcK gene carried by the *Streptococcus thermophilus* strain of the invention encodes a GlcK protein, the sequence of which is selected from the group consisting of SEQ ID NO: 25 and any GlcK variant sequence having at least 90% similarity or identity with SEQ ID NO:25 as defined herein (in particular SEQ ID NO: 26, 27, 28, 29, 30, 31, 32, 33 or 34), wherein the amino acid of the glucokinase corresponding to position 275 of SEQ ID NO: 25 (or the amino acid at position 275 of the glucokinase) is not a glutamic acid.

In a particular embodiment, either as the SEQ ID NO:25 or any GlcK variant sequence having at least 90% similarity or identity with SEQ ID NO:25 as defined herein (in particular SEQ ID NO: 26, 27, 28, 29, 30, 31, 32, 33 or 34), the amino acid of the glucokinase corresponding to position 275 of SEQ ID NO:25 (or the amino acid at position 275 of the glucokinase) is not an acidic amino acid; thus, in an embodiment, the codon 275 of the glcK gene carried by the *Streptococcus thermophilus* strain of the invention is a codon which does not encode an acidic amino acid; thus, in an embodiment, the glcK gene carried by the *Streptococcus thermophilus* strain of the invention encodes a GlcK protein, the sequence of which is selected from the group consisting of SEQ ID NO: 25 and any Glck variant sequence having at least 90% similarity or identity with SEQ ID NO:25 as defined herein (in particular SEQ ID NO: 26, 27, 28, 29, 30, 31, 32, 33 or 34), wherein the amino acid of the glucokinase corresponding to position 275 of SEQ ID NO:25 (or the amino acid at position 275 of the glucokinase) is not an acidic amino acid.

In a particular embodiment, either as the SEQ ID NO:25 or any GlcK variant sequence having at least 90% similarity or identity with SEQ ID NO:25 as defined herein (in particular SEQ ID NO: 26, 27, 28, 29, 30, 31, 32, 33 or 34), the amino acid of the glucokinase corresponding to position 275 of SEQ ID NO:25 (or the amino acid at position 275 of the glucokinase) is selected from the group consisting of lysine and any of its conservative amino acids; thus, in an embodiment, the codon 275 of the glcK gene carried by the *Streptococcus thermophilus* strain of the invention is a codon encoding an amino acid selected from the group consisting of lysine and any of its conservative amino acids; thus, in an embodiment, the glcK gene carried by the *Streptococcus thermophilus* strain of the invention encodes a GlcK protein, the sequence of which is selected from the group consisting of SEQ ID NO: 25 and any GlcK variant sequence having at least 90% similarity or identity with SEQ ID NO:25 as defined herein (in particular SEQ ID NO: 26, 27, 28, 29, 30, 31, 32, 33 or 34), wherein the amino acid of the glucokinase corresponding to position 275 of SEQ ID NO:25 (or the amino acid at position 275 of the glucokinase) is a lysine and any of its conservative amino acids.

In a particular embodiment, either as the SEQ ID NO:25 or any GlcK variant sequence having at least 90% similarity or identity with SEQ ID NO:25 as defined herein (in particular SEQ ID NO: 26, 27, 28, 29, 30, 31, 32, 33 or 34), the amino acid of the glucokinase corresponding to position 275 of SEQ ID NO:25 (or the amino acid at position 275 of the glucokinase) is a lysine; thus, in an embodiment, the codon 275 of the glcK gene carried by the *Streptococcus thermophilus* strain of the invention is a codon encoding a lysine respectively, in particular is AAA or AAG, respectively; thus, in a particular embodiment, the sequence of the GlcK protein of the lactose-positive, galactose-negative *Streptococcus thermophilus* strain of the invention is selected from the group consisting of SEQ ID NOs: 22, 35, 36, 37, 38, 39, 40, 41, 42 and 43; thus, in an embodiment, the glcK gene carried by the *Streptococcus thermophilus* strain of the invention encodes a Glck protein, the sequence of which is selected from the group consisting of SEQ ID NOs: 22, 35, 36, 37, 38, 39, 40, 41, 42 and 43; in a particular embodiment, the glcK gene carried by the *Streptococcus thermophilus* strain of the invention is as defined in SEQ ID NO:21.

In another embodiment, the sequence of the GlcK protein of the lactose-positive, galactose-negative *Streptococcus thermophilus* strain of the invention is selected from the group consisting of SEQ ID NOs: 46, 47, 48, 49, 50, 51, 52, 53, 54 and 55, wherein the amino acid at position 144 of said variant is any amino acid except a glycine, in particular is any amino acid except an aliphatic amino acid, in particular is a serine; thus, in an embodiment, the glcK gene carried by the *Streptococcus thermophilus* strain of the invention encodes a GlcK protein, the sequence of which is selected from the group consisting of SEQ ID NOs: 46, 47, 48, 49, 50, 51, 52, 53, 54 and 55, wherein the amino acid at position 144 of the glucokinase is not a glycine, in particular is not an aliphatic amino acid, in particular is a serine.

In a particular embodiment, either as the SEQ ID NO:46 or any GlcK variant sequence having at least 90% similarity or identity with SEQ ID NO:46 as defined herein (in particular SEQ ID NO: 47, 48, 49, 50, 51, 52, 53, 54 or 55), the amino acid of the glucokinase corresponding to position 144 of SEQ ID NO:46 (or the amino acid at position 144 of the glucokinase) is not a glycine; thus, in an embodiment, the codon 144 of the glcK gene carried by the *Streptococcus thermophilus* strain of the invention is not GGT, GGC, GGA or GGG; thus, in an embodiment, the glcK gene carried by the *Streptococcus thermophilus* strain of the invention encodes a GlcK protein, the sequence of which is selected from the group consisting of SEQ ID NO: 46 and any GlcK variant sequence having at least 90% similarity or identity with SEQ ID NO:46 as defined herein (in particular SEQ ID NO: 47, 48, 49, 50, 51, 52, 53, 54 or 55), wherein the amino acid of the glucokinase corresponding to position 144 of SEQ ID NO: 46 (or the amino acid at position 144 of the glucokinase) is not a glycine.

In a particular embodiment, either as the SEQ ID NO:46 or any GlcK variant sequence having at least 90% similarity or identity with SEQ ID NO:46 as defined herein (in particular SEQ ID NO: 47, 48, 49, 50, 51, 52, 53, 54 or 55), the amino acid of the glucokinase corresponding to position 144 of SEQ ID NO:46 (or the amino acid at position 144 of the glucokinase) is not an aliphatic amino acid; thus, in an embodiment, the codon 144 of the glcK gene carried by the *Streptococcus thermophilus* strain of the invention is a codon which does not encode an aliphatic amino acid; thus, in an embodiment, the glcK gene carried by the *Streptococcus thermophilus* strain of the invention encodes a Glck protein, the sequence of which is selected from the group consisting of SEQ ID NO:46 and any GlcK variant sequence having at least 90% similarity or identity with SEQ ID NO:46 as defined herein (in particular SEQ ID NO: 47, 48, 49, 50, 51, 52, 53, 54 or 55), wherein the amino acid of the glucokinase corresponding to position 144 of SEQ ID NO:46 (or the amino acid at position 144 of the glucokinase) is not an aliphatic amino acid.

In a particular embodiment, either as the SEQ ID NO:46 or any GlcK variant sequence having at least 90% similarity or identity with SEQ ID NO:46 as defined herein (in particular SEQ ID NO: 47, 48, 49, 50, 51, 52, 53, 54 or 55), the amino acid of the glucokinase corresponding to position 144 of SEQ ID NO:46 (or the amino acid at position 144 of the glucokinase) is selected from the group consisting of serine and any of its conservative amino acids; thus, in an embodiment, the codon 144 of the glcK gene carried by the *Streptococcus thermophilus* strain of the invention is a codon encoding an amino acid selected from the group consisting of serine and any of its conservative amino acids; thus, in an embodiment, the glcK gene carried by the *Streptococcus thermophilus* strain of the invention encodes a GlcK protein, the sequence of which is selected from the group consisting of SEQ ID NO: 46 and any GlcK variant sequence having at least 90% similarity or identity with SEQ ID NO:46 as defined herein (in particular SEQ ID NO: 47, 48, 49, 50, 51, 52, 53, 54 or 55), wherein the amino acid of the glucokinase corresponding to position 144 of SEQ ID NO:46 (or the amino acid at position 144 of the glucokinase) is a serine and any of its conservative amino acids.

In a particular embodiment, either as the SEQ ID NO:46 or any GlcK variant sequence having at least 90% similarity or identity with SEQ ID NO:46 as defined herein (in particular SEQ ID NO: 47, 48, 49, 50, 51, 52, 53, 54 or 55), the amino acid of the glucokinase corresponding to position 144 of SEQ ID NO:46 (or the amino acid at position 144 of the glucokinase) is a serine; thus, in an embodiment, the codon 144 of the glcK gene carried by the Streptococcus thermophilus strain of the invention is a codon encoding a serine, in particular is AAA or AAG; thus, in a particular embodiment, the sequence of the GlcK protein of the lactose-positive, galactose-negative Streptococcus thermophilus strain of the invention is selected from the group consisting of SEQ ID NOs: 45, 56, 57, 58, 59, 60, 61, 62, 63 and 64; thus, in an embodiment, the glcK gene carried by the Streptococcus thermophilus strain of the invention encodes a GlcK protein, the sequence of which is selected from the group consisting of SEQ ID NOs: 45, 56, 57, 58, 59, 60, 61, 62, 63 and 64; in a particular embodiment, the glcK gene carried by the Streptococcus thermophilus strain of the invention is as defined in SEQ ID NO:44.

When defining the sequence of the GlcK protein of the lactose-positive, galactose-negative Streptococcus thermophilus strain of the invention, it is according to the teaching of this application that the glucokinase activity in the strain expressing this GlcK protein is significantly reduced but not null as defined herein and optionally that the Vmax of the glucokinase in this strain is significantly reduced but not null as defined herein.

II. Mutations of a Gene Encoding a Protein of the Mannose-Glucose-Specific PTS, in Particular Mutations of the ManL, ManM and ManN Genes This part describes mutations of a gene encoding a protein of the mannose-glucose-specific phosphotransferase system (mannose-glucose-specific PTS), mannose-glucose-specific PTS, in particular mutations of the manL, manM and manN genes, which can be used either in combination with a mutation of a glcK gene as defined herein, or in combination with a mutation of a ccpA gene as defined herein, or in combination with both a mutation of a glcK gene and a mutation of a ccpA gene as defined herein, in the context of a lactose-positive, galactose-negative, Streptococcus thermophilus strain of the invention.

Any mutation in a gene encoding a protein of the mannose-glucose-specific PTS is appropriate, as long as when combined with a mutated glcK gene as defined herein, or combined with a mutation of a ccpA gene as defined herein, or when combined with both a mutated glcK gene and a mutated ccpA gene as defined herein in a lactose-positive, galactose-negative Streptococcus thermophilus strain, the ratio of the amount of galactose released (mM) over the amount of remaining lactose (mM) in said fermented milk is more than 1.2 as defined herein, when said strain is used to ferment milk (by test B).

The inventors have shown that mutations in a gene encoding a protein of the mannose-glucose-specific PTS, in particular in a mutated manL gene, a mutated manM gene, a mutated manN gene or a mutated manO gene, which reduce or abolish the import of glucose from the medium in a lactose-positive, galactose-negative Streptococcus thermophilus strain, are particularly advantageous within the invention. In an embodiment, the mutation of the gene encoding a protein of the mannose-glucose-specific PTS leads to the reduction or abolition of the glucose import activity of the protein encoded by this gene. In an embodiment, the mutated gene is the manL gene and the mutation of the manL gene leads to the reduction or abolition of the glucose import activity of the IIAB$^{Man}$ protein. In an embodiment, the mutated gene is the manM gene and the mutation of the manM gene leads to the reduction or abolition of the glucose import activity of the IIC$^{Man}$ protein. In an embodiment, the mutated gene is the manN gene and the mutation of the manN gene leads to the reduction or abolition of the glucose import activity of the IID$^{Man}$ protein.

In an embodiment, the mutation of the gene encoding a protein of the mannose-glucose-specific PTS, in particular of the manL gene, manM gene or manN gene, is a mutation leading to the knock-out (i.e., the complete disruption) of the gene.

In an embodiment, the mutation of the gene encoding a protein of the mannose-glucose-specific PTS, in particular of the manL gene, manM gene or manN gene, is a mutation of the promoter of the gene, in particular a mutation of the promoter of the gene reducing or inhibiting the transcription of the gene.

In an embodiment, the mutation of the gene encoding a protein of the mannose-glucose-specific PTS, in particular of the manL gene, manM gene or manN gene, is a mutation introduced into the coding sequence of the gene, in particular a mutation leading to the reduction or abolition of the glucose import activity of the protein encoded by the mutated gene, in particular to the reduction or abolition of the glucose import activity of the IIAB$^{Man}$ protein, IIC$^{Man}$ protein or IID$^{Man}$ protein.

In an embodiment, the mutation of the gene encoding a protein of the mannose-glucose-specific PTS, in particular of the manL gene, manM gene or manN gene is a mutation in the coding sequence of the gene, leading to a truncated protein, in particular to a truncated IIAB$^{Man}$ protein, a truncated IIC$^{Man}$ protein or a truncated IID$^{Man}$ protein, in particular to a truncated protein (such as a truncated IIAB$^{Man}$ protein, a truncated IIC$^{Man}$ protein or a truncated IID$^{Man}$ protein) having a reduced or abolished glucose import activity. Whatever the position of the truncation, the mutation introduced into the gene is either a nucleotide substitution leading to a STOP codon or a deletion, insertion or deletion/insertion leading to a frameshift of the open reading frame and a premature STOP codon. In an embodiment, the mutation introduced into the gene is a nucleotide substitution leading to a STOP codon. In an embodiment, the mutation introduced into the gene is a deletion, insertion or deletion/insertion leading to a frameshift of the open reading frame and a premature STOP codon.

Though two Streptococcus thermophilus strains may differ by the sequence of their respective manL, manM or manN gene, this does not necessarily mean that one of these genes is mutated in the sense of the invention. Indeed, are not considered as mutations of the manL, manM or manN gene gene within the present invention:
  variations at the nucleotide level which do not lead to any change at the protein level (silent variation) and which do not impact the translation of the manL, manM or manN RNA; and
  variations at the nucleotide level which do lead to a change at the protein level, but wherein this change does not enable, when combined with a mutated glcK gene as defined herein, or combined with a mutation of a ccpA gene as defined herein, or when combined with both a mutated glcK gene and a mutated copA in a gene in a lactose-positive, galactose-negative *Streptococcus thermophilus* strain, to reach a ratio of the amount of galactose released (mM) over the amount of remaining lactose (mM) in said fermented milk more than 1.2 as defined herein, when said strain is used to ferment milk (by test B).

Non-limitative examples of manL, manM and manN genes (respectively encoding the IIAB$^{Man}$ protein, the IIC$^{Man}$ protein and the IID$^{Man}$ protein) which are not considered as mutated in the sense of the invention are:

the polynucleotide encoding the IIAB$^{Man}$ protein as defined in SEQ ID NO:78 (IIAB$^{Man}$ type ST1), in particular the polynucleotide as defined in SEQ ID NO:77; this IIAB$^{Man}$ type is the one of DGCC7710 strain;

the polynucleotide encoding the IIAB$^{Man}$ protein as defined in SEQ ID NO: 80, 82, 84, 86, 88, 90, 92, 94, 96, 98, 100, 102, 104, 106, 108 and 110 (IIAB$^{Man}$ type ST2 to ST17), in particular the polynucleotide as defined in SEQ ID NO: 79, 81, 83, 85, 87, 89, 91, 93, 95, 97, 99, 101, 103, 105, 107 and 109. The sequence of the IIAB$^{Man}$ proteins as defined in SEQ ID NO: 80, 82, 84, 86, 88, 90, 92, 94, 96, 98, 100, 102, 104, 106, 108 and 110 is from 98.4 to 99.6% identical to SEQ ID NO:78;

the polynucleotide encoding the IIC$^{Man}$ protein as defined in SEQ ID NO:130 (IIC$^{Man}$ type ST1), in particular the polynucleotide as defined in SEQ ID NO:129; this IIC$^{Man}$ type is the one of DGCC7710;

the polynucleotide encoding the IIC$^{Man}$ protein as defined in SEQ ID NO:132, 134, 136, 138, 140, 142, 144, 146, 148, 150, 152, 154 and 156 (IIC$^{Man}$ type ST2 to ST14), in particular the polynucleotide as defined in SEQ ID NO:131, 133, 135, 137, 139, 141, 143, 145, 147, 149, 151, 153 and 155. The sequence of the IIC$^{Man}$ proteins as defined in SEQ ID NO: 132, 134, 136, 138, 140, 142, 144, 146, 148, 150, 152, 154 and 156 is from 98.5 to 99.6% identical to SEQ ID NO:130;

the polynucleotide encoding the IID$^{Man}$ protein as defined in SEQ ID NO:167 (IID$^{Man}$ type ST1), in particular the polynucleotide as defined in SEQ ID NO:166; this IID$^{Man}$ type is the one of DGCC7710 strain;

the polynucleotide encoding the IID$^{Man}$ protein as defined in SEQ ID NO:169, 171, 173, 175, 177, 179, 181, 183, 185, 187, 189, 191, 193, 195, 197, 199, 201, 203 and 205 (IID$^{Man}$ type ST2 to ST20), in particular the polynucleotide as defined in SEQ ID NO: 168, 170, 172, 174, 176, 178, 180, 182, 184, 186, 188, 190, 192, 194, 196, 198, 200, 202 and 204. The sequence of the IID$^{Man}$ proteins as defined in SEQ ID NO: 169, 171, 173, 175, 177, 179, 181, 183, 185, 187, 189, 191, 193, 195, 197, 199, 201, 203 and 205 is from 97.3 to 99.6% identical to SEQ ID NO:167.

The inventors have identified at least one mutation in the manL gene, which when inserted into the manL gene of an original lactose-positive, galactose-negative, *Streptococcus thermophilus* strain [mutated in the glcK gene, the copA gene or both the glcK and ccpA genes as defined herein] enables, when said strain is used to ferment milk, to reach a ratio of the amount of galactose released (mM) over the amount of remaining lactose (mM) in said fermented milk which is more than 1.2 as defined herein (as assayed by test B).

In an embodiment, the mutation in the manL gene leads to the truncation of the IIAB$^{Man}$ protein at position 305. In an embodiment, the mutation in the manL gene is the substitution of the nucleotide G in the nucleotide T at position 916 (leading to a stop codon at position 306). A *Streptococcus thermophilus* IIAB$^{Man}$ protein truncated at position 305 is referred herein as IIAB$^{Man}$ 305.

In an embodiment, the sequence of said IIAB$^{Man}$ protein truncated in position 305 is selected from the group consisting of:
  a) a sequence as defined in SEQ ID NO:112; and
  b) a IIAB$^{Man}$ variant sequence having at least 90% similarity or identity with SEQ ID NO: 112, in particular being 305 amino acids in length.

For the definition of the IIAB$^{Man}$ variant having at least 90% similarity or identity with SEQ ID NO: 112, the similarity or identity is calculated herein over the whole length of the 2 sequences after optimal alignment [i.e., number of similar or identical amino acid residues in the aligned parts(s) of the sequences]. In a particular embodiment, the IIAB$^{Man}$ variant sequence has at least 91, 92, 93, 94, 95, 96, 97, 98 or 99% similarity or identity with SEQ ID NO: 112.

In a particular embodiment, the IIAB$^{Man}$ variant sequence differs from SEQ ID NO:112 by from 1 to 30 amino acid substitutions. In a particular embodiment, the IIAB$^{Man}$ variant sequence differs from SEQ ID NO: 112 by from 1 to 20 amino acid substitutions. In a particular embodiment, the IIAB$^{Man}$ variant sequence differs from SEQ ID NO: 112 by from 1 to 15 amino acid substitutions. In a particular embodiment, the IIAB$^{Man}$ variant sequence differs from SEQ ID NO: 112 by from 1 to 10 amino acid substitutions. In a particular embodiment, the IIAB$^{Man}$ variant sequence differs from SEQ ID NO: 112 by 1, 2, 3, 4, 5, 6, 7, 8, 9 or 10 amino acid substitutions. In an embodiment, the sequence of the IIAB$^{Man}$ protein of the lactose-positive, galactose-negative *Streptococcus thermophilus* strain of the invention is selected from the group consisting of SEQ ID NOs: 112 to 128.

In an embodiment, the manL gene carried by the *Streptococcus thermophilus* strain of the invention encodes a IIAB$^{Man}$ protein, the sequence of which is selected from the group consisting of SEQ ID NO: 112 and any IIAB$^{Man}$ variant sequence having at least 90% similarity or identity with SEQ ID NO: 112 as defined herein (in particular SEQ ID NO:113 to 128). In an embodiment, the manL gene carried by the *Streptococcus thermophilus* strain of the invention is as defined in SEQ ID NO:111.

The inventors have identified at least one mutation in the manM gene, which when inserted into the manL gene of an original lactose-positive, galactose-negative, *Streptococcus thermophilus* strain [mutated in the glcK gene, the ccpA gene or both the glcK and ccpA genes as defined herein] enables, when said strain is used to ferment milk, to reach a ratio of the amount of galactose released (mM) over the amount of remaining lactose (mM) in said fermented milk more than 1.2 as defined herein (as assayed by test B).

In an embodiment, the mutation in the manM gene leads to the truncation of the IIC$^{Man}$ protein at position 208. In an embodiment, the mutation in the manM gene is the substitution of the nucleotide G in the nucleotide T at position 625 (leading to a stop codon at position 209). A *Streptococcus thermophilus* IIC$^{Man}$ protein truncated at position 208 is referred herein as IIC$^{Man}$ 208.

In an embodiment, the sequence of said IIC$^{Man}$ protein truncated in position 208 is selected from the group consisting of:
  a) a sequence as defined in SEQ ID NO:158; and
  b) a IIC$^{Man}$ variant sequence having at least 90% similarity or identity with SEQ ID NO: 158, in particular being 208 amino acids in length.

For the definition of the IIC$^{Man}$ variant having at least 90% similarity or identity with SEQ ID NO: 158, the similarity or identity is calculated herein over the whole length of the 2 sequences after optimal alignment [i.e., number of similar or identical amino acid residues in the aligned parts(s) of the sequences]. In a particular embodiment, the IIC$^{Man}$ variant sequence has at least 91, 92, 93, 94, 95, 96, 97, 98 or 99% similarity or identity with SEQ ID NO: 158.

In a particular embodiment, the IIC$^{Man}$ variant sequence differs from SEQ ID NO:158 by from 1 to 30 amino acid substitutions. In a particular embodiment, the IIC$^{Man}$ variant sequence differs from SEQ ID NO:158 by from 1 to 20 amino acid substitutions. In a particular embodiment, the IIC$^{Man}$ variant sequence differs from SEQ ID NO:158 by from 1 to 15 amino acid substitutions. In a particular embodiment, the IIC$^{Man}$ variant sequence differs from SEQ ID NO: 158 by from 1 to 10 amino acid substitutions. In a particular embodiment, the IIC$^{Man}$ variant sequence differs from SEQ ID NO:158 by 1, 2, 3, 4, 5, 6, 7, 8, 9 or 10 amino acid substitutions. In an embodiment, the sequence of the IIC$^{Man}$ protein of the lactose-positive, galactose-negative *Streptococcus thermophilus* strain of the invention is selected from the group consisting of SEQ ID NO:158 to 165.

In an embodiment, the manM gene carried by the *Streptococcus thermophilus* strain of the invention encodes a IIC$^{Man}$ protein, the sequence of which is selected from the group consisting of SEQ ID NO: 158 and any IIC$^{Man}$ variant sequence having at least 90% similarity or identity with SEQ ID NO:158 as defined herein (in particular SEQ ID NO:159 to 165). In an embodiment, the manM gene carried by the *Streptococcus thermophilus* strain of the invention is as defined in SEQ ID NO:157.

The inventors have identified at least one mutation in the manN gene, which when inserted into the manN gene of an original lactose-positive, galactose-negative, *Streptococcus thermophilus* strain [mutated in the glcK gene, the ccpA gene or both the glcK and ccpA genes as defined herein] enables, when said strain is used to ferment milk, to reach a ratio of the amount of galactose released (mM) over the amount of remaining lactose (mM) in said fermented milk more than 1.2 as defined herein (as assayed by test B).

In an embodiment, the mutation in the manN gene leads to the truncation of the IID$^{Man}$ protein at position 28. In an embodiment, the mutation in the manN gene is an insertion of a nucleotide A in the stretch of 5 nucleotides A at positions 37-41 (leading to a stretch of 6 nucleotides A, a frameshift of the open reading frame and a truncation of the IID$^{Man}$ protein at position 28). This *Streptococcus thermophilus* IID$^{Man}$ protein truncated at position 28 is referred herein as IID$^{Man}_{28}$.

In an embodiment, the sequence of said IID$^{Man}$ protein truncated in position 28 is selected from the group consisting of:
  a) a sequence as defined in SEQ ID NO:207; and
  b) a IID$^{Man}$ variant sequence having at least 90% similarity or identity with SEQ ID NO:207, in particular being 28 amino acids in length.

For the definition of the IID$^{Man}$ variant having at least 90% similarity or identity with SEQ ID NO: 207, the similarity or identity is calculated herein over the whole length of the 2 sequences after optimal alignment [i.e., number of similar or identical amino acid residues in the aligned parts(s) of the sequences]. In a particular embodiment, the IIC$^{Man}$ variant sequence has at least 91, 92, 93, 94, 95, 96, 97, 98 or 99% similarity or identity with SEQ ID NO:207.

In a particular embodiment, the IID$^{Man}$ variant sequence differs from SEQ ID NO:207 by from 1 to 10 amino acid substitutions. In a particular embodiment, the IID$^{Man}$ variant sequence differs from SEQ ID NO:207 by 1, 2, 3, 4, 5, 6, 7, 8, 9 or 10 amino acid substitutions. In an embodiment, the sequence of the IID$^{Man}$ protein of the lactose-positive, galactose-negative *Streptococcus thermophilus* strain of the invention is selected from the group consisting of SEQ ID NO:207 to 211.

In an embodiment, the manN gene carried by the *Streptococcus thermophilus* strain of the invention encodes a IID$^{Man}$ protein, the sequence of which is selected from the group consisting of SEQ ID NO:207 and any IID$^{Man}$ variant sequence having at least 90% similarity or identity with SEQ ID NO:207 as defined herein (in particular SEQ ID NO: 208 to 211). In an embodiment, the manN gene carried by the *Streptococcus thermophilus* strain of the invention is as defined in SEQ ID NO:206.

Whatever the mutation of the glcK gene as defined herein and the mutation of the ccpA gene as defined herein (present alone or combined in a lactose-positive, galactose-negative, *Streptococcus thermophilus* strain of the invention), at least one gene encoding a protein of the mannose-glucose-specific PTS is mutated as defined herein. Whatever the embodiment, the invention encompasses a lactose-positive, galactose-negative, *Streptococcus thermophilus* strain carrying a mutation in one, two or three genes selected from the group consisting of the manL gene, the manM gene and the manN gene. In an embodiment, the lactose-positive, galactose-negative, *Streptococcus thermophilus* strain of the invention carries a mutation in manL. In an embodiment, the lactose-positive, galactose-negative, *Streptococcus thermophilus* strain of the invention carries a mutation in manM. In an embodiment, the lactose-positive, galactose-negative, *Streptococcus thermophilus* strain of the invention carries a mutation in manN. In an embodiment, the lactose-positive, galactose-negative, *Streptococcus thermophilus* strain of the invention carries a mutation in manL and a mutation in manM. In an embodiment, the lactose-positive, galactose-negative, *Streptococcus thermophilus* strain of the invention carries a mutation in manL and a mutation in manN. In an embodiment, the lactose-positive, galactose-negative, *Streptococcus thermophilus* strain of the invention carries a mutation in manM and a mutation in manN. In an embodiment, the lactose-positive, galactose-negative, *Streptococcus thermophilus* strain of the invention carries a mutation in manL, a mutation in manM and a mutation in manN.

Any method can be used to identify a mutation in a gene encoding a protein of the mannose-glucose-specific PTS, in particular in the manL gene, manM gene or manN gene suitable within the lactose-positive, galactose-negative, *Streptococcus thermophilus* strain of the invention.

As an example, to identify a suitable mutation in the manL gene, manM gene or manN gene, the person skilled in the art can proceed by the following method:
  a) provide the DSM32587 strain (mutated in its glcK gene)

b) carry out mutagenesis on the manL, manM or manN gene of the strain in a), for example by random or directed mutagenesis, to obtain a manL, manM or manN gene, the sequence of which is different from the sequence of the manL, manM or manN gene of DSM32587, to obtain a man-mutated DSM32587 strain;

c) determining by test B the ratio of the amount of galactose released (mM) over the amount of remaining lactose (mM) in milk fermented with the man-mutated DSM32587 strain of step b), wherein a ratio of more than 1.2 means that the mutated manL, manM or manN gene is according to the invention. In a particular embodiment, a mutated manL, manM or manN gene is considered to be according to the invention when the ratio of the amount of galactose released (mM) over the amount of remaining lactose (mM) in the fermented milk is more than 1.5, is more than 2 or is more than 3.

Alternatively, the person skilled in the art can proceed by the following method:

a) provide a DGCC7710 strain in which its ccpA gene has been replaced by the mutated ccpA gene as defined in SEQ ID NO:71 (ccpA$_{A14114-120}$), called herein DGCC7710-ccpA$_{A14114-120}$ strain;

b) carry out mutagenesis on the manL, manM or manN gene of the strain in a), for example by random or directed mutagenesis, to obtain a manL, manM or manN gene, the sequence of which is different from the sequence of the manL, manM or manN gene of the DGCC7710-ccpA$_{A14114-120}$ strain, to obtain a man-mutated DGCC7710-ccpA$_{A14114-120}$ strain;

c) determining by test B the ratio of the amount of galactose released (mM) over the amount of remaining lactose (mM) in milk fermented with the man-mutated DGCC7710-ccpA$_{A14114-120}$ strain of step b), wherein a ratio of more than 1.2 means that the mutated manL, manM or manN gene is according to the invention. In a particular embodiment, a mutated manL, manM or manN gene is considered to be according to the invention when the ratio of the amount of galactose released (mM) over the amount of remaining lactose (mM) in the fermented milk is more than 1.5, is more than 2 or is more than 3.

Once identified, the mutated manL, manM or manN gene according to the invention can be introduced in lieu of the manL, manM or manN of a lactose-positive, galactose-negative, *Streptococcus thermophilus* strain, to obtain a lactose-positive, galactose-negative, *Streptococcus thermophilus* strain of the invention.

III. Mutations of the ccpA Gene

This part describes mutations of the ccpA (Catabolite Control Protein A) gene which can be used either in combination with a mutation of a gene encoding a protein of the mannose-glucose-specific PTS as defined herein, or in combination with a mutation of a gene encoding a protein of the mannose-glucose-specific PTS as defined herein and a mutation of the glcK gene as defined herein, in the context of a lactose-positive, galactose-negative, *Streptococcus thermophilus* strain of the invention.

Any mutation in the ccpA gene is appropriate, as long as when combined with a mutated glcK gene as defined herein, or combined with a mutated gene encoding a protein of the mannose-glucose-specific PTS as defined herein, or when combined with both a mutated glcK gene and a mutated gene encoding a protein of the mannose-glucose-specific PTS as defined herein in a lactose-positive, galactose-negative *Streptococcus thermophilus* strain, the ratio of the amount of galactose released (mM) over the amount of remaining lactose (mM) in said fermented milk is more than 1.2 as defined herein, when said strain is used to ferment milk.

The inventors have shown that mutations of the ccpA gene, leading to a *Streptococcus thermophilus* strain of the invention, can be characterized by the ratio of the beta-galactosidase activity as assayed by test D over the glucokinase activity as assayed by test E, in a strain carrying this mutated ccpA. Thus, a ccpA mutation as defined herein is a mutation of the ccpA gene which leads to a lactose-positive, galactose-negative, *Streptococcus thermophilus* strain exhibiting a ratio of the beta-galactosidase activity as assayed by test D over the glucokinase activity as assayed by test E which is at least $4.10^{-6}$. In an embodiment, the ratio of the beta-galactosidase activity as assayed by test D over the glucokinase activity as assayed by test E is selected from the group consisting of at least $4.10^{-6}$, at least $5.10^{-6}$, at least $6.10^{-6}$, at least $7.10^{-6}$ or at least $8.10^{-6}$. In an embodiment, the ratio of the beta-galactosidase activity as assayed by test D over the glucokinase as assayed by test E is at least $5.10^{-6}$. In an embodiment, the ratio of the beta-galactosidase activity as assayed by test D over the glucokinase as assayed by test E is at least $6.10^{-6}$. In an embodiment, the ratio of the beta-galactosidase activity as assayed by test D over the glucokinase as assayed by test E is at least $7.10^{-6}$. In an embodiment, the ratio of the beta-galactosidase activity as assayed by test D over the glucokinase activity as assayed by test E is at least $8.10^{-6}$. Whatever the minimal value of the ratio as defined herein, the ratio of the beta-galactosidase activity as assayed by test D over the glucokinase activity as assayed by test E is no less than $8.10^{-3}$.

For the determination of the ratio of the beta-galactosidase activity over the glucokinase activity in the strain of the invention, test D and test E as described herein are used:

Test D:

The beta-galactosidase activity in a *Streptococcus thermophilus* strain of the invention is assayed by test D [i.e. the test D is carried out using the *Streptococcus thermophilus* strain of the invention].

A fresh overnight culture of the *Streptococcus thermophilus* strain to be assayed in M17 containing 30 g/L lactose is obtained and used to inoculate at 1% (vol/vol) 10 ml of fresh M17 30 g/L lactose. Cells are harvested by centrifugation (6000 g, 10 min, 4° C.) after 3 hours of growth on M17+30 g/l lactose at 42° C., washed in 1.5 ml cold lysis buffer (KPO4 0.1 M), and resuspended in 300 μl cold lysis buffer. EDTA-free protease inhibitors "cOmplete™" (Roche, supplier reference 04693132001) is added in lysis buffer as described by the provider. Cells are disrupted by the addition of 100 mg glass beads (150-212 μm, Sigma G1145) to 250 μl resuspended cells and oscillation at a frequency of 30 cycles/s for 6 min in a MM200 oscillating mill (Retsch, Haan, Germany). Cell debris and glass beads are removed by centrifugation (14000 g, 15 min, 4° C.), and supernatant transferred into a clean 1.5 mL centrifuge tube kept on ice. Total protein content is determined by using the FLUKA Protein Quantification Kit-Rapid (ref 51254). The beta-galactosidase activity in the cell extracts is determined spectrophotometrically by a monitoring of the hydrolysis of O-nitro-Phenol-Beta-Glactoside (ONPG) into galactose and O-nitro-phenol (ONP). 20 μL of the bacteria extract are mixed with 135 μL of React Buffer (NaPO$_4$ 0.1 M+KCl 0.01 M+MgSO$_4$ 0.001 M+ONPG 3 mM+Beta Mercapto Ethanol 60 mM, pH=6). The production of ONP leads to a yellow color into the tube. When this color appears, the reaction is block by adding 250 μL of Stopping buffer (Na$_2$CO$_3$ 1 M). The optical density at 420 nm is measured using a Synergy HT multi-detection microplate reader (BIO-TEK). One unit of galactosidase corresponds to the amount of enzyme that catalyzes the production of 1 μmole ONP per minute under the assay conditions. Beta-Galactosidase activity is calculated as follows:

Beta-Galactosidase activity (U/g of total protein extract)= dOD×V/[dt×l×ε×Qprot], wherein:
dOD is the variation of optical density (OD) at 420 nm between the blank and the tested sample
V is the volume of the reaction in which the optical density is measured (herein 250 μL)
dt=represent the duration in minutes between the addition of the 20 μL of bacterial extract and the addition of the 250 μL stopping buffer
l=optical path length (herein 0.73 cm)
ε=molar attenuation coefficient of ONP (herein 4500 cm$^2$/μmol)
Qprot=quantity of protein in the cuvette (in g)

Measurements are at least triplicated for each sample, and the beta-galactosidase specific activity values given herein under test D are the mean of three independent experiments.

Test E

The glucokinase activity in a *Streptococcus thermophilus* strain of the invention, for the determination of the ratio, is assayed by test E [i.e. the test E is carried out using the *Streptococcus thermophilus* strain of the invention].

A fresh overnight culture of the *Streptococcus thermophilus* strain to be assayed in M17 containing 30 g/L lactose is obtained and used to inoculate at 1% (vol/vol) 10 ml of fresh M17 30 g/L lactose. Cells are harvested by centrifugation (6000 g, 10 min, 4° C.) after 3 hour of growth on M17+30 g/L lactose at 42° C., washed in 1.5 ml cold GLCK buffer (5 mM MgCl2, mM K$_2$HPO$_4$/KH$_2$PO$_4$ [pH 7.2]), and resuspended in 300 μl cold GLCK buffer. EDTA-free protease inhibitors "cOmplete™" (Roche, supplier reference 04693132001) is added in GLCK 10 buffer as described by the provider. Cells are disrupted by the addition of 100 mg glass beads (150-212 μm, Sigma G1145) to 250 μl resuspended cells and oscillation at a frequency of 30 cycles/s for 6 min in a MM200 oscillating mill (Retsch, Haan, Germany). Cell debris and glass beads are removed by centrifugation (14000 g, 15 min, 4° C.), and supernatant transferred into a clean 1.5 mL centrifuge tube kept on ice. Total protein content is determined by using the FLUKA Protein Quantification Kit-Rapid (ref 51254). The glucokinase activity in the cell extracts is determined spectrophotometrically by a glucose-6-phosphate dehydrogenase (G-6PDH, EC1.1.1.49): NADPH-coupled assay (Porter et al., 1982), essentially as described by Pool et al. (2006). Each sample (5, 10 and 20 μL) is added to assay buffer (10 mM K$_2$HPO$_4$/KH$_2$PO$_4$ [pH 7.2], 5 mM MgCl2, 1 mM ATP, 20 mM glucose, 1 mM NADP, 1 U G-6PDH) in a 250 μL final volume, and the mixture was left for 5 min at 30° C. The optical density at 340 nm is measured for 5 minutes by using a Synergy HT multi-detection microplate reader (BIO-TEK). One unit of glucokinase corresponds to the amount of enzyme that catalyzes the phosphorylation of 1 μmole of D-glucose to D-Glucose 6-phosphate per minute under the assay conditions. Glucokinase activity is calculated as follows:

Glucokinase activity (U/g of total protein extract)=dOD× V/[dt×l×ε× Qprot], wherein:
dOD is the variation of optical density (OD) at 340 nm
V is the volume of the reaction (herein 250 μL)
dt=measurement time (in minutes)
l=optical path length (herein 0.73 cm)
ε=molar attenuation coefficient of NADPH; H$^+$ (herein 6220 cm2/μmol)
Qprot=quantity of protein in the cuvette (in g)

Measurements are triplicated for each sample, and the glucokinase specific activity values given herein under test E are the mean of three independent experiments.

In an embodiment, the ccpA gene mutation is not a mutation leading to the knock-out (i.e., the complete disruption) of the gene.

In an embodiment, the ccpA gene mutation is a mutation in the coding sequence of the ccpA gene, in particular in the first 270 nucleotides of the coding sequence of the ccpA gene. In an embodiment, the mutation is a mutation selected from the group consisting of:
a) a non-sense mutation (i.e. leading to a STOP codon) located between the nucleotide 1 and the nucleotide 270 of the coding sequence of the ccpA gene; and
b) a mutation, located in the first quarter of the coding sequence of the ccpA gene (i.e., between nucleotide 1 and the nucleotide 250), leading to a frameshift of the open reading frame of the ccpA gene.

In an embodiment, the mutation leading to a frameshift of the open reading frame of the ccpA gene is located between nucleotide 50 and the nucleotide 200 of the coding sequence of the ccpA gene. In an embodiment, the mutation leading to a frameshift of the open reading frame of the ccpA gene is located between nucleotide 100 and the nucleotide 150 of the coding sequence of the ccpA gene. Whatever the location of the mutation leading to a frameshift, the mutation is selected from the group consisting of a deletion, an insertion or a deletion/insertion (which all are not a multiple of 3).

Though two *Streptococcus thermophilus* strains may differ by the sequence of their respective ccpA gene, this does not necessarily mean that one of these two ccpA genes is mutated in the sense of the invention. Indeed, are not considered as mutations of the ccpA gene within the present invention:
variations at the nucleotide level which do lead to a change at the protein level, but wherein this change does not enable to obtain a ratio—of the beta-galactosidase activity as assayed by test D over the glucokinase activity as assayed by test E of the lactose-positive, galactose-negative, *Streptococcus thermophilus* strain encoding this modified protein—of at least $4.10^{-6}$ Non-limitative examples of ccpA genes which are not considered as mutated in the sense of the invention are:
the polynucleotide as defined in SEQ ID NO:65 (ccpA type ST1); this copA type is the one of the DGCC7710 strain;
the polynucleotide as defined in SEQ ID NO:66 (ccpA type ST2), which has 99.8% identity with SEQ ID NO:65;
the polynucleotide as defined in SEQ ID NO:67 (ccpA type ST3), which has 99.8% identity with SEQ ID NO:65;
the polynucleotide as defined in SEQ ID NO:68 (ccpA type ST4), which has 99.7% identity with SEQ ID NO:65;
the polynucleotide as defined in SEQ ID NO:69 (ccpA type ST5), which has 99.8% identity with SEQ ID NO:65; and
the polynucleotide as defined in SEQ ID NO:70 (ccpA type ST6), which has 99.7% identity with SEQ ID NO:65.

The inventors have identified at least one mutation, which when present into the ccpA gene of a lactose-positive, galactose-negative, *Streptococcus thermophilus* strain enables this strain to exhibit a ratio of the beta-galactosidase activity in said strain as assayed by test D over the glucokinase activity in said strain as assayed by test E of at least 4.106 as defined herein. Thus, the invention is directed to a lactose-positive, galactose-negative, *Streptococcus thermophilus* strain carrying a mutation in the ccpA gene selected from the group consisting of a non-sense mutation located between the nucleotide 1 and the nucleotide 270 of the coding sequence of the ccpA gene and a mutation, located in the first quarter of the coding sequence of the ccpA gene, leading to a frameshift of the open reading frame of the ccpA gene, wherein the ratio of the beta-galactosidase activity in said strain as assayed by test D over the glucokinase activity in said strain as assayed by test E is at least 4.106 as defined herein.

In an embodiment, the mutation of the ccpA gene is a deletion of a nucleotide A in the stretch of 7 nucleotides A at positions 114-120 (leading to a frameshift of the open reading frame of the ccpA gene). Such *Streptococcus thermophilus* mutated ccpA gene is referred herein as $ccpA_{\Delta A114-120}$.

In an embodiment, the sequence of said ccpA gene with a STOP codon at codon 66 is selected from the group consisting of:
a) a sequence as defined in SEQ ID NO:71; and
b) a ccpA variant sequence having at least 90% identity with SEQ ID NO:71. The ccpA variant as defined herein carries a mutation as defined above, i.e., is selected from the group consisting of a non-sense mutation located between the nucleotide 1 and the nucleotide 270 of the coding sequence of the ccpA gene and a mutation, located in the first quarter of the coding sequence of the ccpA, leading to a frameshift of the open reading frame of the ccpA gene.

For the definition of the ccpA variant having at least 90% identity with SEQ ID NO:71, the identity is calculated herein over the whole length of the 2 sequences after optimal alignment [i.e., number of identical nucleotides in the aligned parts(s) of the sequences]. In a particular embodiment, the ccpA variant sequence has at least 91, 92, 93, 94, 95, 96, 97, 98 or 99% identity with SEQ ID NO:71. In a particular embodiment, the ccpA variant sequence differs from SEQ ID NO:71 by from 1 to 30 nucleotide substitutions. In a particular embodiment, the ccpA variant sequence differs from SEQ ID NO:71 by from 1 to 20 nucleotide substitutions. In a particular embodiment, the ccpA variant sequence differs from SEQ ID NO:71 by from 1 to 15 nucleotide substitutions. In a particular embodiment, the ccpA variant sequence differs from SEQ ID NO:71 by from 1 to 10 nucleotide substitutions. In a particular embodiment, the copA variant sequence differs from SEQ ID NO:71 by 1, 2, 3, 4, 5, 6, 7, 8, 9 or 10 nucleotide substitutions. In an embodiment, the sequence of the ccpA gene of the lactose-positive, galactose-negative *Streptococcus thermophilus* strain of the invention is selected from the group consisting of SEQ ID NOs: 71, 72, 73, 74, 75 and 76.

The person skilled in the art is given, in this part of the application, guidance on how to identify mutations of the ccpA gene other than the one specifically disclosed. Based on the ratio defined above [of the amount of galactose released (mM) over the amount of remaining lactose (mM) in the fermented milk as defined herein] together with a reference strain defined herein, the person skilled in the art would know how to identify a mutated ccpA gene according to the invention and to obtain a *Streptococcus thermophilus* strain of the invention.

Thus, the person skilled in the art can proceed by the following method:
a) provide a DGCC7710 strain in which its manL gene has been replaced by the mutated manL gene as defined in SEQ ID NO:111 (manL gene encoding the $IIAB^{Man}_{305}$ protein), called herein DGCC7710-$IIAB^{Man}_{305}$ strain;
b) carry out mutagenesis on the ccpA gene of the strain in a), for example by random or directed mutagenesis, to obtain a ccpA the sequence of which is different from the sequence of the ccpA gene of the DGCC7710-$IIAB^{Man}_{305}$ strain, to obtain a ccpA-mutated DGCC7710-$IIAB^{Man}_{305}$ strain;
c) determining by test B the ratio of the amount of galactose released (mM) over the amount of remaining lactose (mM) of a milk fermented by the ccpA-mutated DGCC7710-$IIAB^{Man}_{305}$ strain of step b), wherein a ratio of more than 1.2 means that the mutated ccpA is according to the invention. In a particular embodiment, a mutated ccpA gene is considered to be according to the invention when the ratio of the amount of galactose released (mM) over the amount of remaining lactose (mM) in the fermented milk is more than 1.5, is more than 2 or is more than 3.

Alternatively, the person skilled in the art can proceed by the following method:
a) provide a DGCC7710 strain in which its manM gene has been replaced by the mutated manM gene as defined in SEQ ID NO:157 (manM gene encoding the $IIC^{Man}_{208}$ protein), called herein DGCC7710-$IIC^{Man}_{208}$ strain;
b) carry out mutagenesis on the ccpA gene of the strain in a), for example by random or directed mutagenesis, to obtain a ccpA the sequence of which is different from the sequence of the ccpA gene of the DGCC7710-$IIC^{Man}_{208}$ strain, to obtain a ccpA-mutated DGCC7710-$IIC^{Man}_{208}$ strain;
c) determining by test B the ratio of the amount of galactose released (mM) over the amount of remaining lactose (mM) of a milk fermented by the ccpA-mutated DGCC7710-$IIC^{Man}_{208}$ strain of step b), wherein a ratio of more than 1.2 means that the mutated ccpA is according to the invention. In a particular embodiment, a mutated ccpA gene is considered to be according to the invention when the ratio of the amount of galactose released (mM) over the amount of remaining lactose (mM) in the fermented milk is more than 1.5, is more than 2 or is more than 3.

The person skilled in the art can also proceed by the following method:
a) provide a DGCC7710 strain in which its manN gene has been replaced by the mutated manN gene as defined in SEQ ID NO:206 (manN gene encoding the $IID^{Man}_{28}$ protein), called herein DGCC7710-$IID^{Man}_{28}$ strain;
b) carry out mutagenesis on the ccpA gene of the strain in a), for example by random or directed mutagenesis, to obtain a copA the sequence of which is different from the sequence of the ccpA gene of the DGCC7710-$IID^{Man}_{28}$ strain, to obtain a ccpA-mutated DGCC7710-$IID^{Man}_{28}$ strain;
c) determining by test B the ratio of the amount of galactose released (mM) over the amount of remaining lactose (mM) of a milk fermented by the ccpA-mutated DGCC7710-$IID^{Man}_{28}$ strain of step b), wherein a ratio of more than 1.2 means that the mutated ccpA is according to the invention. In a particular embodiment, a mutated ccpA gene is considered to be according to the invention when the ratio of the amount of galactose released (mM) over the amount of remaining lactose (mM) in the fermented milk is more than 1.5, is more than 2 or is more than 3.

Once identified, a mutated ccpA gene—as identified herein—can be introduced in lieu of the ccpA gene of a lactose-positive, galactose-negative, *Streptococcus thermophilus* strain, to obtain a lactose-positive, galactose-negative, *Streptococcus thermophilus* strain of the invention.

Further Characterization of the Strains of the Invention

It is part of the invention that the lactose-positive, galactose-negative, *Streptococcus thermophilus* strain defined herein, when used to ferment milk by test B, exhibits a ratio of the amount of galactose released (mM) over the amount of remaining lactose (mM) which is more than 1.2, more than 1.5, more than 2 or more than 3. This feature can be used as described herein to design and identify strains of the invention. The inventors have shown that strains exhibiting this ratio (as a consequence of a mutation in a gene encoding a protein of the mannose-glucose-specific PTS and a mutation in the glcK gene and/or the ccpA gene) enable, when they are used to ferment milk:
1) to obtain a low lactose fermented milk; and/or
2) to obtain a fermented milk not undergoing post-acidification, even when stored at fermentation temperature.

Thus, if needed, these 2 advantages can be used to further characterize the strains of the invention, in addition to the ratio of the amount of galactose released (mM) over the amount of remaining lactose (mM) as assayed by test B, and the mutations defined herein for the gene encoding a protein of the mannose-glucose-specific PTS, the glcK gene and the ccpA gene.

In an embodiment, the lactose-positive, galactose-negative, *Streptococcus thermophilus* strain of the invention—in addition to exhibit, when used to ferment milk by test B, a ratio of the amount of galactose released (mM) over the amount of remaining lactose (mM) which is more than 1.2, more than 1.5, more than 2 or more than 3—is characterized by the fact that it leads to a low lactose fermented milk, when used to ferment milk by test B.

In an embodiment, the lactose-positive, galactose-negative, *Streptococcus thermophilus* strain of the invention—in addition to exhibit, when used to ferment milk by test B, a ratio of the amount of galactose released (mM) over the amount of remaining lactose (mM) which is more than 1.2, more than 1.5, more than 2 or more than 3—is characterized by the fact that it leads to a fermented milk, not undergoing post-acidification when stored at fermentation temperature.

In an embodiment, the lactose-positive, galactose-negative, *Streptococcus thermophilus* strain of the invention—in addition to exhibit, when used to ferment milk by test B, a ratio of the amount of galactose released (mM) over the amount of remaining lactose (mM) which is more than 1.2, more than 1.5, more than 2 or more than 3—is characterized by the fact that it leads to a low lactose fermented milk not undergoing post-acidification when stored at fermentation temperature (when used to ferment milk by test B).

The expression "low lactose fermented milk" means a fermented milk which has an amount of remaining lactose in the fermented milk, at the end of the fermentation by test B, which is less than 60 mM, less than 50 mM, less than 45 mM, less than 40 mM, less than 35 mM or less than 30 mM. In an embodiment, the concentration of remaining lactose in a fermented milk obtained by test B using a strain of the invention is less than 60 mM. In an embodiment, the concentration of remaining lactose in a fermented milk obtained by test B using a strain of the invention is less than 50 mM. In an embodiment, the concentration of remaining lactose in a fermented milk obtained by test B using a strain of the invention is less than 45 mM. In an embodiment, the concentration of remaining lactose in a fermented milk obtained by test B using a strain of the invention is less than 40 mM. In an embodiment, the concentration of remaining lactose in a fermented milk obtained by test B using a strain of the invention is less than 35 mM. In an embodiment, the concentration of remaining lactose in a fermented milk obtained by test B using a strain of the invention is less than 30 mM. In an embodiment, the concentration of remaining lactose in a fermented milk obtained by test B using a strain of the invention is selected from the group consisting of a concentration which is less than 60 mM, less than 50 mM, less than 45 mM, less than 40 mM, less than 35 mM and less than 30 mM. It is noteworthy that the amount of lactose in the milk provided in test B is before fermentation about 300 mM (60 g/L).

The expression "not undergoing post-acidification" means a milk product which, when inoculated with a strain of the invention and fermented by test B, has its pH decreased to a pH at which the speed of acidification definitively becomes less than 0.1 mUpH/min (defined herein as $pH_{STOP}$), wherein said $pH_{STOP}$ is comprised between 4.6 and 5.3, and optionally the slope between pH 6 and pH 5.5 is at least −0.008 UpH/min.

Thus, the absence of post-acidification is characterized by the fact that the pH of the fermented milk stops between 4.6 and 5.3 when using test B. The pH is considered to be stopped ($pH_{STOP}$), when the speed of acidification ($\Delta pH/\Delta time$) definitively becomes less than 0.1 mUpH/min (less than 0.0001 UpH/min). By "definitively becomes", it is meant that the speed of acidification stays less than 0.1 mUpH/min for the remaining time of the test B (i.e. up to 24 h at fermentation temperature), once the $pH_{STOP}$ is obtained.

In an embodiment, the $pH_{STOP}$ obtained using a strain of the invention by test B is comprised between 4.7 and 5.2. In an embodiment, the $pH_{STOP}$ obtained using a strain of the invention by test B is comprised between 4.8 and 5.1. In an embodiment, the $pH_{STOP}$ obtained using a strain of the invention by test B is comprised between a minimal value selected from the group consisting of 4.6, 4.7 and 4.8 and a maximal value selected from the group consisting of 5.1, 5.2 and 5.3.

In an embodiment, the fermented milk not undergoing post-acidification is also characterized by the slope between pH 6 and pH 5.5. The slope represents the inverse of the velocity (speed of acidification). In an embodiment, the slope is at least −0.009 UpH/min. In an embodiment, the slope is at least −0.01 UpH/min.

Examples of Some Strains of the Invention

The invention is also directed to the following lactose-positive, galactose-negative *Streptococcus thermophilus* strains:

a strain corresponding to the DSM32587 strain (deposited at the DSMZ on Aug. 15, 2017) into which the coding sequence of the manL gene is replaced by the sequence as set forth in SEQ ID NO:111 (encoding $IIAB^{Man}_{305}$) and its variants; a variant is defined herein as a lactose-positive, galactose-negative *Streptococcus thermophilus* strain bearing the same mutated manL gene, and which, when used to ferment milk as assayed by test B, the ratio of the amount of galactose released (mM) over the amount of remaining lactose (mM) in said fermented milk is more than 1.2;

a strain corresponding to the DSM32587 strain into which the coding sequence of the manM gene is replaced by the sequence as set forth in SEQ ID NO:157 (encoding $IIC^{Man}_{208}$) and its variants; a variant is defined herein as a lactose-positive, galactose-negative *Streptococcus thermophilus* strain bearing the same mutated manM gene, and which, when used to ferment milk as assayed by test B, the ratio of the amount of galactose released (mM) over the amount of remaining lactose (mM) in said fermented milk is more than 1.2;

a strain corresponding to the DSM32587 strain into which the coding sequence of the manN gene is replaced by the sequence as set forth in SEQ ID NO:206 (encoding $IID^{Man}_{28}$) and its variants; a variant is defined herein as a lactose-positive, galactose-negative *Streptococcus thermophilus* strain bearing the same mutated manN gene, and which, when used to ferment milk as assayed by test B, the ratio of the amount of galactose released (mM) over the amount of remaining lactose (mM) in said fermented milk is more than 1.2;

a strain corresponding to the DSM32587 strain into which the coding sequence of the ccpA gene is replaced by the sequence as set forth in SEQ ID NO:71 ($ccpA_{\Delta 14114-120}$) and the coding sequence of the manL gene is replaced by the sequence as set forth in SEQ ID NO:111 (encoding $IIAB^{Man}_{305}$) and its variants; a variant is defined herein as a lactose-positive, galactose-negative *Streptococcus thermophilus* strain bearing the same mutated ccpA gene and same mutated manL gene, and which, when used to ferment milk as assayed by test B, the ratio of the amount of galactose released (mM) over the amount of remaining lactose (mM) in said fermented milk is more than 1.2;

a strain corresponding to the DSM32587 strain into which the coding sequence of the ccpA gene is replaced by the sequence as set forth in SEQ ID NO:71 ($ccpA_{\Delta 14114-120}$) and the coding sequence of the manM gene is replaced by the sequence as set forth in SEQ ID NO:157 (encoding $IIC^{Man}_{208}$) and its variants; a variant is defined herein as a lactose-positive, galactose-negative *Streptococcus thermophilus* strain bearing the same mutated ccpA gene and same mutated manM gene, and which, when used to ferment milk as assayed by test B, the ratio of the amount of galactose released (mM) over the amount of remaining lactose (mM) in said fermented milk is more than 1.2;

a strain corresponding to the DSM32587 strain into which the coding sequence of the ccpA gene is replaced by the sequence as set forth in SEQ ID NO:71 ($ccpA_{\Delta 14114-120}$) and the coding sequence of the manN gene is replaced by the sequence as set forth in SEQ ID NO:206 (encoding $IID^{Man}_{28}$) and its variants; a variant is defined herein as a lactose-positive, galactose-negative *Streptococcus thermophilus* strain bearing the same mutated ccpA gene and same mutated manN gene, and which, when used to ferment milk as assayed by test B, the ratio of the amount of galactose released (mM) over the amount of remaining lactose (mM) in said fermented milk is more than 1.2;

a strain corresponding to the DSM28255 strain into which the coding sequence of the ccpA gene is replaced by the sequence as set forth in SEQ ID NO:71 ($ccpA_{\Delta 14114-120}$) and the coding sequence of the manL gene is replaced by the sequence as set forth in SEQ ID NO:111 (encoding $IIAB^{Man}_{305}$) and its variants; a variant is defined herein as a lactose-positive, galactose-negative *Streptococcus thermophilus* strain bearing the same mutated ccpA gene and same mutated manL gene, and which, when used to ferment milk as assayed by test B, the ratio of the amount of galactose released (mM) over the amount of remaining lactose (mM) in said fermented milk is more than 1.2.

a strain corresponding to the DSM28255 strain into which the coding sequence of the ccpA gene is replaced by the sequence as set forth in SEQ ID NO:71 ($ccpA_{\Delta 14114-120}$) and the coding sequence of the manM gene is replaced by the sequence as set forth in SEQ ID NO:157 (encoding $IIC^{Man}_{208}$) and its variants; a variant is defined herein as a lactose-positive, galactose-negative *Streptococcus thermophilus* strain bearing the same mutated ccpA gene and same mutated manM gene, and which, when used to ferment milk as assayed by test B, the ratio of the amount of galactose released (mM) over the amount of remaining lactose (mM) in said fermented milk is more than 1.2;

a strain corresponding to the DSM28255 strain into which the coding sequence of the ccpA gene is replaced by the sequence as set forth in SEQ ID NO:71 ($ccpA_{\Delta 14114-120}$) and the coding sequence of the manN gene is replaced by the sequence as set forth in SEQ ID NO:206 (encoding $IID^{Man}_{28}$) and its variants; a variant is defined herein as a lactose-positive, galactose-negative *Streptococcus thermophilus* strain bearing the same mutated ccpA gene and same mutated manN gene, and which, when used to ferment milk as assayed by test B, the ratio of the amount of galactose released (mM) over the amount of remaining lactose (mM) in said fermented milk is more than 1.2.

In a particular embodiment, the genome sequence of the strain variant as defined herein has an identity of at least 90%, with the genome sequence of the strain the variant is obtained from, in particular an identity of at least 90%, at least 91%, at least 95%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, at least 99.92%, at least 99.94%, at least 99.96%, at least 99.98%, or at least 99.99% with the genome sequence of the strain the variant is obtained from. The identity is described in comparing the two genome sequences over their full-length (global alignment), and may be calculated using any program based on the Needleman-Wunsch algorithm.

Composition, Method and Use with Strains the Lactose-Positive, Galactose-Negative *Streptococcus thermophilus* Strains of the Invention The invention is also directed to a bacterial composition comprising or consisting of at least one, in particular one, lactose-positive, galactose-negative *Streptococcus thermophilus* strain of the invention. In a particular embodiment, the bacterial composition is a pure culture, i.e., comprises or consists of a single bacterium strain. In another embodiment, the bacterial composition is a mixed culture, i.e., comprises or consists of the lactose-positive, galactose-negative *Streptococcus thermophilus* strain(s) of the invention and at least one other bacterium strain. By "at least" (in reference to a strain or bacterium), it is meant 1 or more, and in particular 1, 2, 3, 4 or 5 strains.

Thus, in an embodiment, a bacterial composition of the invention comprises or consists of the lactose-positive, galactose-negative *Streptococcus thermophilus* strain(s) of the invention and at least one lactic acid bacterium of the species selected from the group consisting of a *Lactococcus* species, a *Streptococcus* species, a *Lactobacillus* species including *Lactobacillus acidophilus*, an *Enterococcus* species, a *Pediococcus* species, a *Leuconostoc* species, a *Bifidobacterium* species and an *Oenococcus* species or any combination thereof. *Lactococcus* species include *Lactobacillus acidophilus* and *Lactococcus lactis*, including *Lactococcus lactis* subsp. *lactis, Lactococcus lactis* subsp. *cremoris* and *Lactococcus lactis* subsp. *lactis* biovar diacetylactis. *Bifidobacterium* species includes *Bifidobacterium animalis*, in particular *Bifidobacterium animalis* subsp *lactis*. Other lactic acid bacteria species include *Leuconostoc* sp., *Streptococcus thermophilus, Lactobacillus delbrueckii* subsp. *bulgaricus*, and *Lactobacillus helveticus*.

In an embodiment, the bacterial composition comprises or consists of the lactose-positive, galactose-negative *Streptococcus thermophilus* strain(s) of the invention, and at least one *Streptococcus thermophilus* strain, different from the *S. thermophilus* strain(s) of the invention and/or at least one strain of the *Lactobacillus* species, and/or any combination thereof. In a particular embodiment, the bacterial composition comprises or consists of the *Streptococcus thermophilus* strain(s) of the invention, one or several strain(s) of the species *Lactobacillus delbrueckii* subsp. *bulgaricus* and/or one or several strain(s) of the species *Lactobacillus helveticus* and/or any combination thereof, and optionally at least one *Streptococcus thermophilus* strain, different from the *S. thermophilus* strain(s) of the invention. In a particular embodiment, the bacterial composition comprises or consists of the *Streptococcus thermophilus* strain(s) of the invention, at least one strain of species *Streptococcus thermophilus*, different from the *S. thermophilus* strain(s) of the invention, and a strain of the species *Lactobacillus delbrueckii* subsp. *bulgaricus*. In another particular embodiment, the bacterial composition comprises or consists of the *Streptococcus thermophilus* strain(s) of the invention, and a strain of the species *Lactobacillus delbrueckii* subsp. *bulgaricus*.

In an embodiment, the bacterial composition comprises or consists of the *Streptococcus thermophilus* strain(s) of the invention, a *Lactococcus lactis* subsp. *lactis* and/or a *Lactococcus lactis* subsp. *cremoris*.

In a particular embodiment of any bacterial composition defined herein, either as a pure or mixed culture, the bacterial composition further comprises at least one probiotic strain such as *Bifidobacterium animalis* subsp. *lactis, Lactobacillus acidophilus, Lactobacillus paracasei*, or *Lactobacillus casei*.

In a particular embodiment, the bacterial composition, either as a pure or mixed culture as defined above is under frozen, dried, freeze-dried, liquid or solid format, in the form of pellets or frozen pellets, or in a powder or dried powder. In a particular embodiment, the bacterial composition of the invention is in a frozen format or in the form of pellets or frozen pellets, in particular contained into one or more box or sachet. In another embodiment, the bacterial composition as defined herein is under a powder form, such as a dried or freeze-dried powder, in particular contained into one or more box or sachet.

In a particular embodiment, the bacterial composition of the invention, either as a pure culture or mixed culture as defined above, and whatever the format (frozen, dried, freeze-dried, liquid or solid format, in the form of pellets or frozen pellets, or in a powder or dried powder) comprises the lactose-positive, galactose-negative *Streptococcus thermophilus* strain(s) of the invention in a concentration comprised in the range of $10^5$ to $10^{12}$ cfu (colony forming units) per gram of the bacterial composition. In a particular embodiment, the concentration of the lactose-positive, galactose-negative *Streptococcus thermophilus* strain(s) within the bacterial composition of the invention is in the range of $10^7$ to $10^{12}$ cfu per gram of the bacterial composition, and in particular at least $10^7$, at least $10^8$, at least $10^9$, at least $10^{10}$ or at least $10^{11}$ CFU/g of the bacterial composition. In a particular embodiment, when in the form of frozen or dried concentrate, the concentration of the lactose-positive, galactose-negative *Streptococcus thermophilus* strain(s)—as pure culture or as a mixed culture-within the bacterial composition is in the range of $10^8$ to $10^{12}$ cfu/g of frozen concentrate or dried concentrate, and more preferably at least $10^8$, at least $10^9$, at least $10^{10}$, at least $10^{11}$ or at least $10^{12}$ cfu/g of frozen concentrate or dried concentrate.

The invention also concerns a method for manufacturing a fermented product, comprising a) inoculating a substrate with the lactose-positive, galactose-negative *Streptococcus thermophilus* strain(s) of the invention and b) fermenting said inoculated substrate, to obtain a fermented product. In a particular embodiment, the lactose-positive, galactose-negative *Streptococcus thermophilus* strain(s) of the invention is inoculated as a bacterial composition as defined herein, such as a pure culture or a mixed culture. In an embodiment, the substrate into which the *S. thermophilus* strain(s) or bacterial composition of the invention is added to is milk substrate. By "milk substrate", it is meant milk of animal and/or plant origin. In a particular embodiment, the milk substrate is of animal origin, such as cow, goat, sheep, buffalo, zebra, horse, donkey, or camel, and the like. The milk may be in the native state, a reconstituted milk, a skimmed milk, or a milk supplemented with compounds necessary for the growth of the bacteria or for the subsequent processing of fermented milk. Therefore, in a particular embodiment, the invention also provides a method for manufacturing a fermented dairy product, comprising a) inoculating a milk substrate with the lactose-positive, galactose-negative *Streptococcus thermophilus* strain(s) or bacterial composition of the invention and b) fermenting said inoculated milk substrate, to obtain a fermented dairy product.

The invention is also directed to the use of the lactose-positive, galactose-negative, *Streptococcus thermophilus* strain(s) of the invention or a composition of the invention, to manufacture a fermented dairy product.

The invention is also directed to a fermented dairy product, which is obtained using the lactose-positive, galactose-negative *Streptococcus thermophilus* strain(s) of the invention or a bacterial composition of the invention, in particular obtained or obtainable by the method of the invention. Thus, the invention is directed to a fermented dairy product comprising the lactose-positive, galactose-negative *Streptococcus thermophilus* strain(s) of the invention. In a particular embodiment, the fermented dairy food product of the invention is fresh fermented milk. In a particular embodiment, the fermented dairy product of the invention—in particular the fresh fermented milk as defined herein-contains the DSM32587 strain deposited at the DSMZ on Aug. 15, 2017 or any variant thereof as defined herein.

Proteins, Nucleic Acids, Vectors, Constructs and their Uses

The invention is directed to a polynucleotide encoding a *Streptococcus thermophilus* glucokinase, the glucokinase activity of which is significantly reduced but not null. In an embodiment, the reduced but not null glucokinase activity is determined in a DGCC7710 derivative, i.e., a DGCC7710 strain into which its glcK gene has been replaced by the glcK polynucleotide to be assayed. To test that a polynucleotide encoding a glucokinase fulfils the "significantly reduced but not null" glucokinase activity feature in a DGCC7710 derivative, the glcK gene of the DGCC7710 strain is replaced by the glcK gene encoding the *Streptococcus thermophilus* glucokinase to be assayed to obtain the derivative of DGCC7710, and the DGCC7710 derivative is assayed by test A (see example 4).

A *Streptococcus thermophilus* glucokinase (encoded by a polynucleotide of the invention) fulfils the "significantly reduced but not null" glucokinase activity feature in a DGCC7710 derivative, when:
a) either the glucokinase activity of said *Streptococcus thermophilus* glucokinase in a DGCC7710 derivative is between 200 and 1500 U/g of total protein extract, as assayed by test A, in particular between 300 and 1200 U/g or between 400 and 1000 U/g of total protein extract, as assayed by test A, or
b) the glucokinase activity of said *Streptococcus thermophilus* glucokinase in a DGCC7710 derivative is between 5 and 60% the glucokinase activity of the DGCC7710 strain deposited at the DSMZ under accession number DSM28255 on Jan. 14, 2014, when both assayed by test A, in particular between 10 and 50% or between 15 and 40% the glucokinase activity of the DGCC7710 strain, wherein the glucokinase activity in said DG7710 derivative and the glucokinase activity of the DGCC7710 strain are assayed by test A.

In a particular embodiment, the glucokinase activity of the *Streptococcus thermophilus* glucokinase in a DGCC7710 derivative is between 200 and 1500 U/g of total protein extract, as assayed by test A. In a particular embodiment, the glucokinase activity of the *Streptococcus thermophilus* glucokinase in a DGCC7710 derivative is between 300 and 1200 U/g of total protein extract, as assayed by test A. In a particular embodiment, the glucokinase activity of the *Streptococcus thermophilus* glucokinase in a DGCC7710 derivative is between 400 and 1000 U/g of total protein extract, as assayed by test A. In a particular embodiment, the glucokinase activity of the *Streptococcus thermophilus* glucokinase in a DGCC7710 derivative is between a minimal value selected from the group consisting of 200, 300 and 400 U/g of total protein extract and a maximal value selected from the group consisting of 1000, 1200 and 1500 U/g of total protein extract, as assayed by test A. It is noteworthy that, as mentioned in test A, the glucokinase activity values disclosed herein are the mean of three experiments (triplicates).

In a particular embodiment, the glucokinase activity of the *Streptococcus thermophilus* glucokinase (encoded by a polynucleotide of the invention) in a DGCC7710 derivative is between 5 and 60% the activity of the glucokinase activity of the DGCC7710 strain deposited at the DSMZ under accession number DSM28255 on Jan. 14, 2014. By "glucokinase activity of the DGCC7710 strain" it is meant the activity of the DGCC7710 strain glucokinase (i.e., with SEQ ID NO:2) as assayed by test A in the DGCC7710 strain [i.e., the test A is carried out using the DGCC7710 strain]. The percentage value is calculated based on the glucokinase activity of the *Streptococcus thermophilus* glucokinase in a DGCC7710 derivative and the glucokinase activity of the DGCC7710 strain, both assayed by test A.

In a particular embodiment, the glucokinase activity of the *Streptococcus thermophilus* glucokinase in a DGCC7710 derivative is between 5 and 60% the glucokinase activity of the DGCC7710 strain. In a particular embodiment, the glucokinase activity of the *Streptococcus thermophilus* glucokinase in a DGCC7710 derivative is between 10 and 50% the glucokinase activity of the DGCC7710 strain. In a particular embodiment, the glucokinase activity of the *Streptococcus thermophilus* glucokinase in a DGCC7710 derivative is between 15 and 40% the glucokinase activity of the strain DGCC7710. In a particular embodiment, the glucokinase activity of the *Streptococcus thermophilus* glucokinase in a DGCC7710 derivative is between a minimal percentage selected from the group consisting of 5, 10 and 15% the glucokinase activity of the DGCC7710 strain and a maximal percentage selected from the group consisting of 40, 50 and 60% the glucokinase activity of the DGCC7710 strain. In a particular embodiment and whatever the range of percentages, the glucokinase activity of the *Streptococcus thermophilus* glucokinase is assayed in a DGCC7710 derivative by test A as described herein. It is noteworthy that the percentage values disclosed herein are calculated based on glucokinase activity values which are the mean of three independent experiments (triplicates) as assayed by test A.

The feature "glucokinase activity in a DGCC7710 derivative is significantly reduced but not null" can also be characterized, in a DGCC7710 derivative, by the maximum forward velocity of the glucokinase (Vmax) or by the affinity of the glucokinase (called Km) for one or two of its substrates, i.e., glucose and ATP. In an embodiment, the feature "significantly reduced but not null glucokinase activity in a DGCC7710 derivative" of the *Streptococcus thermophilus* glucokinase (encoded by a polynucleotide of the invention) is further characterized by the maximum forward velocity of this glucokinase in a DGCC7710 derivative.

Therefore, in combination with the embodiment of the feature "glucokinase activity in a DGCC7710 derivative is significantly reduced but not null" defined herein, the maximum forward velocity (Vmax) of the *Streptococcus thermophilus* glucokinase is significantly reduced but not null in a DGCC7710 derivative. To test that a glucokinase fulfils the "significantly reduced but not null" Vmax feature in a DGCC7710 derivative, the open reading frame of the glcK gene of the DGCC7710 strain is replaced by the open reading frame of the glcK gene encoding the *Streptococcus thermophilus* glucokinase to be assayed (i.e., the polynucleotide of the invention) to obtain a derivative of DGCC7710, and the DGCC7710 derivative is assayed by test C (see example 4). The expression "DGCC7710 derivative" is as defined above.

The "significantly reduced but not null in a DGCC7710 derivative" feature of the Vmax of the glucokinase can be defined by one or two of these parameters:
the Vmax of the *Streptococcus thermophilus* glucokinase in a DGCC7710 derivative is between 200 and 1500 U/g total protein extract, as assayed by test C;
the Vmax of the *Streptococcus thermophilus* glucokinase in a DGCC7710 derivative is between 5 and 60% the Vmax of the glucokinase of the DGCC7710 strain deposited at the DSMZ under accession number DSM28255 on Jan. 14, 2014, when both assayed by test C.

In a particular embodiment, the invention relates to a polynucleotide encoding a *Streptococcus thermophilus* glucokinase, the glucokinase activity of which in a DGCC7710 derivative is significantly reduced but not null (as defined herein) and wherein the maximum forward velocity (Vmax) of said glucokinase in a DGCC7710 derivative is significantly reduced but not null, and defined by one or two of these parameters:

the Vmax of the *Streptococcus thermophilus* glucokinase in a DGCC7710 derivative is between 200 and 1500 U/g total protein extract, as assayed by test C;

the Vmax of the *Streptococcus thermophilus* glucokinase in a DGCC7710 derivative is between 5 and 60% the Vmax of the glucokinase of the DGCC7710 strain deposited at the DSMZ under accession number DSM28255 on Jan. 14, 2014, when both assayed by test C.

In a particular embodiment, the Vmax of the *Streptococcus thermophilus* glucokinase in a DGCC7710 derivative is between 200 and 1500 U/g total protein extract, as assayed by test C. In a particular embodiment, the Vmax of the *Streptococcus thermophilus* glucokinase in a DGCC7710 derivative is between 300 and 1200 U/g total protein extract, as assayed by test C. In a particular embodiment, the Vmax of the *Streptococcus thermophilus* glucokinase in a DGCC7710 derivative is between 400 and 1000 U/g total protein extract. In a particular embodiment, the Vmax of the *Streptococcus thermophilus* glucokinase in a DGCC7710 derivative is between a minimal value selected from the group consisting of 200, 300 and 400 U/g of total protein extract and a maximal value selected from the group consisting of 1000, 1200 and 1500 U/g of total protein extract, as assayed by test C.

In a particular embodiment, the Vmax of the *Streptococcus thermophilus* glucokinase in a DGCC7710 derivative is between 10 and 50% the Vmax of the glucokinase of the DGCC7710 strain, when both assayed by test C. By "Vmax of the glucokinase of the DGCC7710 strain" it is meant the Vmax of the DGCC7710 strain glucokinase (i.e., with SEQ ID NO:2) as assayed by test C in the DGCC7710 strain [i.e., the test C is carried out using the DGCC7710 strain]. The percentage value is calculated based on the Vmax of the *Streptococcus thermophilus* glucokinase in a DGCC7710 derivative and the Vmax of the glucokinase of DGCC7710 strain, both assayed by test C. In a particular embodiment, the Vmax of the *Streptococcus thermophilus* glucokinase in a DGCC7710 derivative is between 15 and 40% the Vmax of the glucokinase of the DGCC7710 strain. In a particular embodiment, the Vmax of the *Streptococcus thermophilus* glucokinase in a DGCC7710 derivative is between a minimal percentage selected from the group consisting of 5, 10 and 15% the Vmax of the glucokinase activity of the DGCC7710 strain and a maximal percentage selected from the group consisting of 40, 50 and 60% the Vmax of the glucokinase activity of the DGCC7710 strain.

In an embodiment, the polynucleotide of the invention encodes a *Streptococcus thermophilus* glucokinase having a significantly reduced but not null glucokinase activity in a DGCC7710 derivative and optionally a significantly reduced but not null Vmax in a DGCC7710 derivative, the sequence of which has at its position 275 (numbering based on the sequence as defined in SEQ ID NO:25) an amino acid which is not a glutamic acid (i.e., is any amino acid except a glutamic acid). In an embodiment, the polynucleotide of the invention encodes a *Streptococcus thermophilus* glucokinase having a significantly reduced but not null glucokinase activity in a DGCC7710 derivative and optionally a significantly reduced but not null in a DGCC7710 derivative, the sequence of which has at its position 275 (numbering based on the sequence as defined in SEQ ID NO:25) an amino acid which is not an acidic amino acid (i.e., is any amino acid except an acidic amino acid). In an embodiment, the polynucleotide of the invention encodes a *Streptococcus thermophilus* glucokinase having a significantly reduced but not null glucokinase activity in a DGCC7710 derivative and optionally a significantly reduced but not null Vmax in a DGCC7710 derivative, the sequence of which has at its position 275 (numbering based on the sequence as defined in SEQ ID NO:25) an amino acid which is selected from the group consisting of a lysine and any of its conservative amino acids. In an embodiment, the polynucleotide of the invention encodes a *Streptococcus thermophilus* glucokinase having a significantly reduced but not null glucokinase activity in a DGCC7710 derivative and optionally a significantly reduced but not null in a DGCC7710 derivative, the sequence of which has at its position 275 (numbering based on the sequence as defined in SEQ ID NO:25) an amino acid which is a lysine. In a particular embodiment, the polynucleotide of the invention encodes a *Streptococcus thermophilus* which is 322 amino acids in length.

In another embodiment, the polynucleotide of the invention encodes a *Streptococcus thermophilus* glucokinase having a significantly reduced but not null glucokinase activity in a DGCC7710 derivative and optionally a significantly reduced but not null Vmax in a DGCC7710 derivative, the sequence of which has at its position 144 (numbering based on the sequence as defined in SEQ ID NO:25) an amino acid which is not a glycine (i.e., is any amino acid except a glycine). In an embodiment, the polynucleotide of the invention encodes a *Streptococcus thermophilus* glucokinase having a significantly reduced but not null glucokinase activity in a DGCC7710 derivative and optionally a significantly reduced but not null in a DGCC7710 derivative, the sequence of which has at its position 144 (numbering based on the sequence as defined in SEQ ID NO:25) an amino acid which is not an aliphatic amino acid (i.e., is any amino acid except an aliphatic amino acid). In an embodiment, the polynucleotide of the invention encodes a *Streptococcus thermophilus* glucokinase having a significantly reduced but not null glucokinase activity in a DGCC7710 derivative and optionally a significantly reduced but not null Vmax in a DGCC7710 derivative, the sequence of which has at its position 144 (numbering based on the sequence as defined in SEQ ID NO:25) an amino acid which is selected from the group consisting of a serine and any of its conservative amino acids. In an embodiment, the polynucleotide of the invention encodes a *Streptococcus thermophilus* glucokinase having a significantly reduced but not null glucokinase activity in a DGCC7710 derivative and optionally a significantly reduced but not null in a DGCC7710 derivative, the sequence of which has at its position 144 (numbering based on the sequence as defined in SEQ ID NO:25) an amino acid which is a serine. In a particular embodiment, the polynucleotide of the invention encodes a *Streptococcus thermophilus* glucokinase which is 322 amino acids in length.

In a particular embodiment, the polynucleotide of the invention encodes a *Streptococcus thermophilus* glucokinase having a significantly reduced but not null glucokinase activity in a DGCC7710 derivative and optionally a significantly reduced but not null in a DGCC7710 derivative is selected from the group consisting of:
  a) a sequence as defined in SEQ ID NO:25, wherein the amino acid at position 275 is any amino acid except a glutamic acid, in particular is any amino acid except an acidic amino acid, in particular is a lysine; and
  b) a Glck variant sequence having at least 90% similarity or identity with SEQ ID NO:25, wherein the amino acid of the glucokinase corresponding to position 275 of SEQ ID NO:25 (or the amino acid at position 275 of the glucokinase) is any amino acid except a glutamic acid, in particular is any amino acid except an acidic amino acid, in particular is a lysine. In a particular embodiment, the GlcK variant sequence is 322-amino acids in length. In an embodiment, said Glck variant has an arginine at its position 278 and/or a serine at its position 279.
c) a sequence as defined in SEQ ID NO:46, wherein the amino acid at position 144 is any amino acid except a glycine, in particular is any amino acid except an aliphatic amino acid, in particular is a serine; and
d) a GlcK variant sequence having at least 90% similarity or identity with SEQ ID NO:46, wherein the amino acid of the glucokinase corresponding to position 144 of SEQ ID NO:46 (or the amino acid at position 144 of the glucokinase) is any amino acid except a glycine, in particular is any amino acid except an aliphatic amino acid, in particular is a serine. In a particular embodiment, the GlcK variant sequence is 322-amino acids in length.

For the definition of the GlcK variant having at least 90% similarity or identity with SEQ ID NO: 25, the similarity or identity is calculated herein over the whole length of the 2 sequences after optimal alignment [i.e., number of similar or identical amino acid residues in the aligned parts(s) of the sequences]; the position 275 as defined in SEQ ID NO:25 is not considered for the calculation of the similarity or identity. In a particular embodiment, the GlcK variant sequence has at least 91, 92, 93, 94, 95, 96, 97, 98 or 99% similarity or identity with SEQ ID NO: 25, wherein the amino acid of the glucokinase corresponding to position 275 of SEQ ID NO: 25 (or the amino acid at position 275 of the glucokinase) is any amino acid except a glutamic acid, in particular is any amino acid except an acidic amino acid, in particular is a lysine. In an embodiment, the GlcK variant sequence has at least 95% similarity or identity with SEQ ID NO:25, wherein the amino acid corresponding to position 275 of SEQ ID NO:25 (or the amino acid at position 275 of the glucokinase) is any amino acid except a glutamic acid, in particular is any amino acid except an acidic amino acid, in particular is a lysine. In an embodiment, the GlcK variant sequence has at least 97% similarity or identity with SEQ ID NO: 25, wherein the amino acid corresponding to position 275 of SEQ ID NO:25 (or the amino acid at position 275 of the glucokinase) is any amino acid except a glutamic acid, in particular is any amino acid except an acidic amino acid, in particular is a lysine.

In a particular embodiment, the GlcK variant sequence differs from SEQ ID NO:25 by from 1 to 30 amino acid substitutions wherein the amino acid at position 275 of said GlcK variant is any amino acid except a glutamic acid, in particular is any amino acid except an acidic amino acid, in particular is a lysine (the position 275 is not considered for the calculation of the number of substitution(s)). In a particular embodiment, the GlcK variant sequence differs from SEQ ID NO: 25 by from 1 to 20 amino acid substitutions, wherein the amino acid at position 275 of said GlcK variant is any amino acid except a glutamic acid, in particular is any amino acid except an acidic amino acid, in particular is a lysine. In a particular embodiment, the GlcK variant sequence differs from SEQ ID NO:25 by from 1 to 15 amino acid substitutions wherein the amino acid at position 275 of said GlcK variant is any amino acid except a glutamic acid, in particular is any amino acid except an acidic amino acid, in particular is a lysine. In a particular embodiment, the GlcK sequence differs from SEQ ID NO:25 by from 1 to 10 amino acid substitutions wherein the amino acid at position 275 of said GlcK variant is any amino acid except a glutamic acid, in particular is any amino acid except an acidic amino acid, in particular is a lysine. In a particular embodiment, the GlcK sequence differs from SEQ ID NO:25 by 1, 2, 3, 4, 5, 6, 7, 8, 9, 10, 11 or 12 amino acid substitutions wherein the amino acid at position 275 of said GlcK variant is any amino acid except a glutamic acid, in particular is any amino acid except an acidic amino acid, in particular is a lysine.

In a particular embodiment, the sequence of the *Streptococcus thermophilus* glucokinase (encoded by a polynucleotide of the invention) is selected from the group consisting of SEQ ID NOs: 25, 26, 27, 28, 29, 30, 31, 32, 33 and 34, wherein the amino acid at position 275 of said variant is any amino acid except a glutamic acid, in particular is any amino acid except an acidic amino acid, in particular is a lysine. In a particular embodiment, either as the SEQ ID NO: 25 or any GlcK variant sequence having at least 90% similarity or identity with SEQ ID NO: 25 as defined herein (in particular SEQ ID NO: 26, 27, 28, 29, 30, 31, 32, 33 or 34), the amino acid of the glucokinase corresponding to position 275 of SEQ ID NO:25 (or the amino acid at position 275 of the glucokinase) is not a glutamic acid.

In a particular embodiment, either as the SEQ ID NO:25 or any GlcK variant sequence having at least 90% similarity or identity with SEQ ID NO:25 as defined herein (in particular SEQ ID NO: 26, 27, 28, 29, 30, 31, 32, 33 or 34), the amino acid of the glucokinase (encoded by a polynucleotide of the invention) corresponding to position 275 of SEQ ID NO:25 (or the amino acid at position 275 of the glucokinase) is not an acidic amino acid. In a particular embodiment, either as the SEQ ID NO:25 or any GlcK variant sequence having at least 90% similarity or identity with SEQ ID NO:25 as defined herein (in particular SEQ ID NO: 26, 27, 28, 29, 30, 31, 32, 33 or 34), the amino acid of the glucokinase corresponding to position 275 of SEQ ID NO:25 (or the amino acid at position 275 of the glucokinase) is selected from the group consisting of a lysine and any of its conservative amino acids. In a particular embodiment, either as the SEQ ID NO:25 or any GlcK variant sequence having at least 90% similarity or identity with SEQ ID NO:25 as defined herein (in particular SEQ ID NO: 26, 27, 28, 29, 30, 31, 32, 33 or 34), the amino acid of the glucokinase corresponding to position 275 of SEQ ID NO:25 (or the amino acid at position 275 of the glucokinase) is a lysine; thus, in a particular embodiment, the sequence of the *Streptococcus thermophilus* glucokinase (encoded by a polynucleotide of the invention) is selected from the group consisting of SEQ ID NOs: 22, 35, 36, 37, 38, 39, 40, 41, 42 and 43.

For the definition of the GlcK variant having at least 90% similarity or identity with SEQ ID NO: 46, the similarity or identity is calculated herein over the whole length of the 2 sequences after optimal alignment [i.e., number of similar or identical amino acid residues in the aligned parts(s) of the sequences]; the position 144 as defined in SEQ ID NO:46 is not considered for the calculation of the similarity or identity. In a particular embodiment, the GlcK variant sequence has at least 91, 92, 93, 94, 95, 96, 97, 98 or 99% similarity or identity with SEQ ID NO: 46, wherein the amino acid of the glucokinase corresponding to position 144 of SEQ ID NO: 46 (or the amino acid at position 144 of the glucokinase) is any amino acid except a glycine, in particular is any amino acid except an aliphatic amino acid, in particular is a serine. In an embodiment, the GlcK variant sequence has at least 95% similarity or identity with SEQ ID NO: 46, wherein the amino acid corresponding to position 144 of SEQ ID NO:46 (or the amino acid at position 144 of the glucokinase) is any amino acid except a glycine, in particular is any amino acid except an aliphatic amino acid, in particular is a serine. In an embodiment, the GlcK variant sequence has at least 97% similarity or identity with SEQ ID NO:46, wherein the amino acid corresponding to position 144 of SEQ ID NO:46 (or the amino acid at position 144 of the glucokinase) is any amino acid except a glycine, in particular is any amino acid except an aliphatic amino acid, in particular is a serine.

In a particular embodiment, the GlcK variant sequence differs from SEQ ID NO:46 by from 1 to 30 amino acid substitutions wherein the amino acid at position 144 of said GlcK variant is any amino acid except a glycine, in particular is any amino acid except an aliphatic amino acid, in particular is a serine (the position 144 is not considered for the calculation of the number of substitution(s)). In a particular embodiment, the GlcK variant sequence differs from SEQ ID NO: 46 by from 1 to 20 amino acid substitutions, wherein the amino acid at position 144 of said Glck variant is any amino acid except a glycine, in particular is any amino acid except an aliphatic amino acid, in particular is a serine. In a particular embodiment, the GlcK variant sequence differs from SEQ ID NO:46 by from 1 to 15 amino acid substitutions wherein the amino acid at position 144 of said GlcK variant is any amino acid except a glycine, in particular is any amino acid except an aliphatic amino acid, in particular is a serine. In a particular embodiment, the GlcK sequence differs from SEQ ID NO:46 by from 1 to 10 amino acid substitutions wherein the amino acid at position 144 of said GlcK variant is any amino acid except a glycine, in particular is any amino acid except an aliphatic amino acid, in particular is a serine. In a particular embodiment, the GlcK sequence differs from SEQ ID NO:46 by 1, 2, 3, 4, 5, 6, 7, 8, 9, 10, 11 or 12 amino acid substitutions wherein the amino acid at position 144 of said GlcK variant is any amino acid except a glycine, in particular is any amino acid except an aliphatic amino acid, in particular is a serine.

In a particular embodiment, the sequence of the *Streptococcus thermophilus* glucokinase (encoded by a polynucleotide of the invention) is selected from the group consisting of SEQ ID NOs: 46, 47, 48, 49, 50, 51, 52, 53, 54 and 55, wherein the amino acid at position 144 of said variant is any amino acid except a glycine, in particular is any amino acid except an aliphatic amino acid, in particular is a serine. In a particular embodiment, either as the SEQ ID NO: 46 or any GlcK variant sequence having at least 90% similarity or identity with SEQ ID NO: 46 as defined herein (in particular SEQ ID NO: 47, 48, 49, 50, 51, 52, 53, 54 or 55), the amino acid of the glucokinase corresponding to position 144 of SEQ ID NO:46 (or the amino acid at position 144 of the glucokinase) is not a glycine.

In a particular embodiment, either as the SEQ ID NO:46 or any GlcK variant sequence having at least 90% similarity or identity with SEQ ID NO:46 as defined herein (in particular SEQ ID NO: 47, 48, 49, 50, 51, 52, 53, 54 or 55), the amino acid of the glucokinase (encoded by a polynucleotide of the invention) corresponding to position 144 of SEQ ID NO:46 (or the amino acid at position 144 of the glucokinase) is not an aliphatic amino acid. In a particular embodiment, either as the SEQ ID NO:46 or any GlcK variant sequence having at least 90% similarity or identity with SEQ ID NO:46 as defined herein (in particular SEQ ID NO: 47, 48, 49, 50, 51, 52, 53, 54 or 55), the amino acid of the glucokinase corresponding to position 144 of SEQ ID NO:46 (or the amino acid at position 144 of the glucokinase) is selected from the group consisting of a serine and any of its conservative amino acids. In a particular embodiment, either as the SEQ ID NO:46 or any GlcK variant sequence having at least 90% similarity or identity with SEQ ID NO:46 as defined herein (in particular SEQ ID NO: 47, 48, 49, 50, 51, 52, 53, 54 or 55), the amino acid of the glucokinase corresponding to position 144 of SEQ ID NO:46 (or the amino acid at position 144 of the glucokinase) is a serine; thus, in a particular embodiment, the sequence of the *Streptococcus thermophilus* glucokinase (encoded by a polynucleotide of the invention) is selected from the group consisting of SEQ ID NOs: 45, 56, 57, 58, 59, 60, 61, 62, 63 and 64.

When defining the sequence of the *Streptococcus thermophilus* glucokinase (encoded by a polynucleotide of the invention), it is according to the teaching of this application that the glucokinase activity in a DGCC7710 derivative expressing this glucokinase is significantly reduced but not null as defined herein and optionally that the Vmax of this glucokinase in a DGCC7710 derivative is significantly reduced but not null as defined herein.

The invention is also directed to a polynucleotide encoding a 322-amino acid glucokinase. In a particular embodiment, said polynucleotide is from a *Streptococcus thermophilus* strain. Based on the genetic code, the person skilled in the art knows whether a polynucleotide encodes a *Streptococcus thermophilus* glucokinase as defined herein. In a particular embodiment, when the encoded glucokinase is 322 amino acids in length, the polynucleotide of the invention is 969 nucleotides in length.

A non-limitative example of a polynucleotide of the invention is disclosed in SEQ ID NO:21. Another non-limitative example of a polynucleotide of the invention is disclosed in SEQ ID NO: 44. Other non-limitative examples of polynucleotides of the invention are the sequences as defined in SEQ ID Nos: 1, 3, 5, 7, 9, 11, 13, 15, 17 and 19, but into which the codon 144 or 275 encodes any amino acid except a glycine or glutamic acid respectively, in particular encodes any amino acid except an aliphatic or acidic amino acid respectively, in particular encodes a serine or lysine respectively. In particular, non-limitative examples of polynucleotides of the invention are the sequences as defined in SEQ ID Nos: 1, 3, 5, 7, 9, 11, 13, 15, 17 and 19, but into which the codon 275 is AAA or AAG. In particular, non-limitative examples of polynucleotides of the invention are the sequences as defined in SEQ ID Nos: 1, 3, 5, 7, 9, 11, 13, 15, 17 and 19, but into which the codon 144 is AGT, AGC, TCT, TCC, TCA or TCG.

The invention also concerns the use a polynucleotide of the invention (or a construct, plasmid or vector) to design a bacterial cell, in particular a gram-positive bacterial cell, in particular a *Streptococcus thermophilus* cell. In a particular embodiment, the polynucleotide of the invention (or a construct, plasmid or vector) is used to replace the glcK gene of a *Streptococcus thermophilus* strain, such that the *Streptococcus thermophilus* strain expresses a glucokinase as defined herein. In a particular embodiment, the only glucokinase expressed by said obtained *Streptococcus thermophilus* is a glucokinase as defined herein. In a particular embodiment, the polynucleotide of the invention (or a construct, plasmid or vector) is used to replace the glcK gene of a lactose-positive *Streptococcus thermophilus* strain. In an embodiment, the polynucleotide of the invention (or a construct, plasmid or vector) is used to replace the glcK gene of a lactose-positive, galactose-negative *Streptococcus thermophilus* strain.

The invention is also directed to a (mutated) *Streptococcus thermophilus* ccpA polynucleotide, as defined or as identified above. In an embodiment, the invention is directed to a (mutated) *Streptococcus thermophilus* ccpA polynucleotide selected from the group consisting of:

a) a ccpA polynucleotide, which when inserted in lieu of the ccpA gene of the DGCC7710 strain, leads to a DGCC7710 derivative exhibiting a ratio of beta-galactosidase activity as assayed by test D over the glucokinase activity as assayed by test E of at least $4.10^{-6}$ as defined herein.

b) a ccpA polynucleotide, which when inserted in lieu of the ccpA gene of a DGCC7710 strain into which the manL gene has previously been replaced by a manL gene as defined in SEQ ID NO:111 (i.e., of the DGCC7710-IIAB$^{Man}_{305}$ strain) leads to a DGCC7710-IIAB$^{Man}_{305}$ derivative, which, when used to ferment milk as assayed by test B, exhibits a ratio of the amount of galactose released (mM) over the amount of remaining lactose (mM) in said fermented milk which is more than 1.2, more than 1.5, more than 2, more than 2.5 or more than 3 c) a ccpA polynucleotide, which when inserted in lieu of the ccpA gene of a DGCC7710 strain into which the manM gene has previously been replaced by a manM gene as defined in SEQ ID NO:157 (i.e., of the DGCC7710-IIC$^{Man}_{208}$ strain) leads to a DGCC7710-IIC$^{Man}_{208}$ derivative, which, when used to ferment milk as assayed by test B, exhibits a ratio of the amount of galactose released (mM) over the amount of remaining lactose (mM) in said fermented milk which is more than 1.2, more than 1.5, more than 2, more than 2.5 or more than 3;

d) a ccpA polynucleotide, which when inserted in lieu of the ccpA gene of a DGCC7710 strain into which the manN gene has previously been replaced by a manN gene as defined in SEQ ID NO:206 (i.e., of the DGCC7710-IID$^{Man}_{28}$ strain) leads to a DGCC7710-IID$^{Man}_{28}$ derivative, which, when used to ferment milk as assayed by test B, exhibits a ratio of the amount of galactose released (mM) over the amount of remaining lactose (mM) in said fermented milk which is more than 1.2, more than 1.5, more than 2, more than 2.5 or more than 3.

For any of b) to d), the DGCC7710-IIAB$^{Man}_{305}$ derivative, the DGCC7710-IIC$^{Man}_{208}$ derivative or the DGCC7710-IID$^{Man}_{28}$ derivative can further be characterized by the fact it exhibits a ratio of beta-galactosidase activity as assayed by test D over the glucokinase activity as assayed by test E of at least 4.106 as defined herein.

In this context, the term "derivative" when applied to the DGCC7710-IIAB$^{Man}_{305}$ strain, the DGCC7710-IIC$^{Man}_{208}$ strain and the DGCC7710-IID$^{Man}_{28}$ strain means the DGCC7710-IIAB$^{Man}_{305}$ strain, the DGCC7710-IIC$^{Man}_{208}$ strain and the DGCC7710-IID$^{Man}_{28}$ strain into which the original ccpA gene (the one of the DGCC7710 strain) has been replaced by the mutated ccpA gene to be assayed.

In this context, DGCC7710-IIAB$^{Man}_{305}$ strain means a DGCC7710 strain into which its manL gene is replaced by a manL gene as defined in SEQ ID NO:111. Similarly, DGCC7710-IIC$^{Man}_{208}$ strain means a DGCC7710 strain into which its manM gene is replaced by a manM gene as defined in SEQ ID NO: 157. Similarly, DGCC7710-IID$^{Man}_{28}$ strain means a DGCC7710 strain into which its manN gene is replaced by a manN gene as defined in SEQ ID NO:206.

In an embodiment, the mutated ccpA polynucleotide is not a knocked-out allele (i.e., a disrupted allele) of the ccpA gene.

In an embodiment, the ccpA gene mutation is a mutation in the coding sequence of the ccpA gene, in particular in the first 270 nucleotides of the coding sequence of the ccpA gene. In an embodiment, the mutation is a mutation selected from the group consisting of:

a) a non-sense mutation (i.e. leading to a STOP codon) located between the nucleotide 1 and the nucleotide 270 of the coding sequence of the copA gene; and b) a mutation, located in the first quarter of the coding sequence of the ccpA gene (i.e., between nucleotide 1 and the nucleotide 250), leading to a frameshift of the open reading frame of the ccpA gene.

In an embodiment, the mutation leading to a frameshift of the open reading frame of the ccpA gene is located between nucleotide 50 and the nucleotide 200 of the coding sequence of the ccpA gene. In an embodiment, the mutation leading to a frameshift of the open reading frame of the ccpA gene is located between nucleotide 100 and the nucleotide 150 of the coding sequence of the ccpA gene. Whatever the location of the mutation leading to a frameshift, the mutation is selected from the group consisting of a deletion, an insertion or a deletion/insertion (which all are not a multiple of 3).

In an embodiment, the sequence of the mutated ccpA polynucleotide is selected from the group consisting of a) a sequence as defined in SEQ ID NO:71; and b) a ccpA variant sequence having at least 90% identity with SEQ ID NO:71. The definition of the ccpA variant having at least 90% identity is as detailed under the paragraph "µl. Mutations of the ccpA gene" above.

The (mutated) glcK polynucleotide as defined herein [encoding a mutated Streptococcus thermophilus glucokinase as defined herein] and the (mutated) ccpA polynucleotide as defined herein can be used to design a Streptococcus thermophilus strain, in particular a lactose-positive, galactose-negative, Streptococcus thermophilus strain. The use consists in substituting the glcK gene and/or the ccpA gene of an original Streptococcus thermophilus strain by a mutated glcK polynucleotide and/or a mutated ccpA polynucleotide as defined herein, to design a Streptococcus thermophilus strain having its original gene(s) replaced by the (mutated) one(s) as defined herein. The invention is also directed to a method to design a Streptococcus thermophilus strain, comprising 1) substituting the glcK gene and/or the ccpA gene of an original Streptococcus thermophilus strain by a mutated glcK polynucleotide and/or a mutated ccpA polynucleotide as defined herein, and 2) obtaining a Streptococcus thermophilus strain having its original gene(s) replaced by the (mutated) one(s) as defined herein.

In an embodiment of the use or the method, the original Streptococcus thermophilus strain carries a mutation in at least one, in particular one, gene encoding a protein of the mannose-glucose-specific PTS, in particular in its manL gene, in its manM gene and/or in its manN gene as defined herein; thus, the substitution of the glcK gene and/or the copA gene of this original Streptococcus thermophilus strain by a mutated glcK polynucleotide and/or a mutated ccpA polynucleotide as defined herein will lead to a lactose-positive, galactose-negative, Streptococcus thermophilus strain of the invention. In another embodiment of the use or the method, the original Streptococcus thermophilus strain does not carry a mutation in a gene encoding a protein of the mannose-glucose-specific PTS; thus, the substitution of the glcK gene and/or the ccpA gene of this original Streptococcus thermophilus strain by a mutated glcK polynucleotide and/or a mutated ccpA polynucleotide as defined herein will lead to an intermediate lactose-positive, galactose-negative, Streptococcus thermophilus strain, which can be used as a starting strain to mutate at least one, in particular one, gene encoding a protein of the mannose-glucose-specific PTS, in particular the manL gene, manM gene and/or manN gene, to design a lactose-positive, galactose-negative, *Streptococcus thermophilus* strain of the invention.

The invention is also directed to the use of a mutated gene (or polynucleotide) encoding a protein of the mannose-glucose-specific PTS, in particular a mutated manL gene, a mutated manM gene or a mutated manN gene to design a *Streptococcus thermophilus* strain, in particular a lactose-positive, galactose-negative, *Streptococcus thermophilus* strain. In an embodiment, the use consists in substituting [or replacing] the manL gene, manM gene or manN gene of an original *Streptococcus thermophilus* strain respectively by a mutated manL, manM or manN polynucleotide as defined herein, to design a *Streptococcus thermophilus* strain having its original gene replaced by the (mutated) one as defined herein. By "respectively", it is meant that the original manL is replaced by the mutated manL, the original manM is replaced by the mutated manM and/or the original manN is replaced by the mutated manN. The invention is also directed to a method to design a *Streptococcus thermophilus* strain, comprising 1) substituting [or replacing] the manL gene, manM gene or manN gene of an original *Streptococcus thermophilus* strain respectively by a mutated manL, manM or manN polynucleotide as defined herein, and 2) obtaining a *Streptococcus thermophilus* strain having its original gene replaced by the (mutated) one as defined herein.

In an embodiment of the use or the method, the original *Streptococcus thermophilus* strain carries a mutation in its glcK gene. In an embodiment of the use or the method, the original *Streptococcus thermophilus* strain carries a mutation in its ccpA gene. In an embodiment of the use or the method, the original *Streptococcus thermophilus* strain carries a mutation in its glcK gene and a mutation in its ccpA gene. It is the aim of the invention that the substitution of the manL gene, manM gene or manN gene in an original *Streptococcus thermophilus* strain [carrying a mutation in its glcK gene and/or a mutation in its copA gene] respectively by a mutated manL, manM or manN polynucleotide as defined herein, will lead to a lactose-positive, galactose-negative, *Streptococcus thermophilus* strain as defined in the invention, i.e., a lactose-positive, galactose-negative, *Streptococcus thermophilus* strain exhibiting a ratio of the amount of galactose released (mM) over the amount of remaining lactose (mM) which is more than 1.2, more than 1.5, more than 2 or more than 3 as defined herein.

In an embodiment of the use or the method, the original *Streptococcus thermophilus* strain carries a mutation in its glcK gene as defined under part I above. In an embodiment of the use or the method, the original *Streptococcus thermophilus* strain carries a mutation in its ccpA gene as defined under part III above. In an embodiment of the use or the method, the original *Streptococcus thermophilus* strain carries a mutation in its glcK gene as defined under part I above and a mutation in its ccpA gene as defined under part III above.

In an embodiment, the mutated *Streptococcus thermophilus* manL gene, manM gene or manN gene encodes respectively a IIAB$^{Man}$ protein, a IIC$^{Man}$ protein or IID$^{Man}$ protein, the glucose import activity of which is decreased or abolished.

In an embodiment, the mutated *Streptococcus thermophilus* manL gene, manM gene or manN gene is characterized by the fact that, when individually inserted in lieu of the manL gene, manM gene or manN gene of the DSM32587 strain:

the DSM32587 derivative, which, when used to ferment milk as assayed by test B, exhibits a ratio of the amount of galactose released (mM) over the amount of remaining lactose (mM) in said fermented milk which is more than 1.2. In a particular embodiment, a mutated manL, manM or manN gene is considered to be according to the invention when the ratio of the amount of galactose released (mM) over the amount of remaining lactose (mM) in the fermented milk is more than 1.5, is more than 2 or is more than 3.

In this context, the term "derivative" when applied to the DSM32587 strain, means the DSM32587 strain into which the original manL, manM or manN gene has been replaced by the mutated manL, manM or manN gene to be assayed.

In an embodiment, the mutated *Streptococcus thermophilus* manL gene, manM gene or manN gene is characterized by the fact that, when individually inserted in lieu of the manL gene, manM gene or manN gene of the a DGCC7710 strain into which the ccpA gene has previously been replaced by the ccpA gene as defined in SEQ ID NO:71 (i.e., of the DGCC7710-ccpA$_{A1A114-120}$ strain):

the DGCC7710-ccpA$_{A1A114-120}$ derivative, which, when used to ferment milk as assayed by test B, exhibits a ratio of the amount of galactose released (mM) over the amount of remaining lactose (mM) in said fermented milk which is more than 1.2. In a particular embodiment, a mutated manL, manM or manN gene is considered to be according to the invention when the ratio of the amount of galactose released (mM) over the amount of remaining lactose (mM) in the fermented milk is more than 1.5, is more than 2 or is more than 3.

In this context, the expression "DGCC7710-ccpA$_{A1A114-120}$ derivative" when applied to the DGCC7710-ccpA$_{A1A114-120}$ strain, means the DGCC7710-ccpA$_{A1A114-120}$ strain into which the original manL, manM or manN gene has been replaced by the mutated manL, manM or manN gene to be assayed. In this context, DGCC7710-ccpA$_{A1A114-120}$ strain is the DGCC7710 strain into which its ccpA gene has previously been replaced by the ccpA gene as defined in SEQ ID NO: 71.

By "individually inserted", it is meant that, for characterization of the mutated man gene, only one man gene of the DSM32587 strain or of the DGCC7710-ccpA$_{A1A114-120}$ strain is replaced (or substituted) by the respective mutated man gene to be characterized.

In an embodiment, the mutated gene encoding a protein of the mannose-glucose-specific PTS is a mutated manL gene. In an embodiment, the mutated *Streptococcus thermophilus* manL codes for a *Streptococcus thermophilus* IIAB$^{Man}$ protein, the glucose import activity of which is decreased or abolished, in particular a *Streptococcus thermophilus* IIAB$^{Man}$ protein truncated in position 305 (IIAB$^{Man}_{305}$). In an embodiment, the mutated *Streptococcus thermophilus* manL codes for a truncated *Streptococcus thermophilus* IIAB$^{Man}$ protein, the sequence of which is selected from the group consisting of a) a sequence as defined in SEQ ID NO: 112 and b) a IIAB variant sequence having at least 90% similarity or identity with SEQ ID NO: 112, in particular being 305 amino acids in length. In an embodiment, the mutated manL gene encodes a IIAB$^{Man}$ protein, the sequence of which is selected from the group consisting of SEQ ID NO: 112 to 128. In an embodiment, the mutated *Streptococcus thermophilus* manL gene is as defined in SEQ ID NO:111. The expression "IIAB$^{Man}$ variant having at least 90% similarity or identity" is a defined in "II. Mutations of a gene encoding a protein of the mannose-glucose-specific PTS, in particular mutations of the manL, manM and manN genes" above.

In an embodiment, the mutated gene encoding a protein of the mannose-glucose-specific PTS is a mutated manM gene. In an embodiment, the mutated *Streptococcus thermophilus* manM codes for a *Streptococcus thermophilus* IIC$^{Man}$ protein, the glucose import activity of which is decreased or abolished, in particular a *Streptococcus thermophilus* IIC$^{Man}$ protein truncated in position 208 (IIC$^{Man}_{208}$). In an embodiment, the mutated *Streptococcus thermophilus* manM codes for a truncated *Streptococcus thermophilus* IIC$^{Man}$ protein, the sequence of which is selected from the group consisting of a) a sequence as defined in SEQ ID NO: 158 and b) a IIC$^{Man}$ variant sequence having at least 90% similarity or identity with SEQ ID NO: 158, in particular being 208 amino acids in length. In an embodiment, the mutated manM gene encodes a IIC$^{Man}$ protein, the sequence of which is selected from the group consisting of SEQ ID NO:158 to 165. In an embodiment, the mutated *Streptococcus thermophilus* manM gene is as defined in SEQ ID NO:157. The expression "IIC$^{Man}$ variant having at least 90% similarity or identity" is a defined in "II. Mutations of a gene encoding a protein of the mannose-glucose-specific PTS, in particular mutations of the manL, manM and manN genes" above.

In an embodiment, the mutated gene encoding a protein of the mannose-glucose-specific PTS is a mutated manN gene. In an embodiment, the mutated *Streptococcus thermophilus* manN codes for a *Streptococcus thermophilus* IID$^{Man}$ protein, the glucose import activity of which is decreased or abolished, in particular a *Streptococcus thermophilus* IID$^{Man}$ protein truncated in position 28 (IID$^{Man}_{28}$). In an embodiment, the mutated *Streptococcus thermophilus* manN codes for a truncated *Streptococcus thermophilus* IID$^{Man}$ protein, the sequence of which is selected from the group consisting of a) a sequence as defined in SEQ ID NO: 207; and b) a IID$^{Man}$ variant sequence having at least 90% similarity or identity with SEQ ID NO: 207, in particular being 28 amino acids in length. In an embodiment, the mutated manN gene encodes a IID$^{Man}$ protein, the sequence of which is selected from the group consisting of SEQ ID NO: 207 to 211. In an embodiment, the mutated *Streptococcus thermophilus* manN gene is as defined in SEQ ID NO:206. The expression "IID$^{Man}$ variant having at least 90% similarity or identity" is a defined in "II. Mutations of a gene encoding a protein of the mannose-glucose-specific PTS, in particular mutations of the manL, manM and manN genes" above.

In an embodiment, the polynucleotide as defined herein is provided under an isolated form. An "isolated" polynucleotide, is substantially or essentially free from components that normally accompany or interact with the gene as found in its naturally occurring environment. Thus, an isolated polynucleotide is substantially free of other cellular material, or culture medium when produced by recombinant techniques, or substantially free of chemical precursors or other chemicals when chemically synthesized.

The invention is also directed to a construct comprising a polynucleotide as defined herein. In an embodiment, the present invention covers a construct comprising a polynucleotide of the invention operably linked to a regulatory sequence. The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences. The term "regulatory sequences" includes promoters and/or enhancers and other expression regulation signals. The term "promoter" is used in the normal sense of the art, e.g. an RNA polymerase binding site. In an embodiment, independently or in combination with the "regulatory sequence" embodiment, the construct contains or expresses another gene, such as a marker allowing for the selection of the construct. Various markers exist which may be used, for example those markers that provide for antibiotic resistance—e.g. resistance to bacterial antibiotics-such as Erythromycin, Ampicillin, Streptomycin and Tetracycline.

Thus, in a further aspect, there is provided a vector comprising a polynucleotide or a construct as defined herein. As used herein, the term "vector" refers to any nucleic acid molecule into which another nucleic acid (e.g., the polynucleotide of the invention) can be inserted and which can be introduced into and replicate within bacterial strain such as *Streptococcus thermophilus* strain. Thus, the term refers to any nucleic acid construct (and, if necessary, any associated delivery system) capable of use for introducing genetic material into a bacterial strain, in particular a *Streptococcus thermophilus* strain. Selection of appropriate vectors is within the knowledge of those having skill in the art. In an embodiment, the vector is a plasmid. As used herein, the term "plasmid" refers to a circular double-stranded (ds) DNA construct that can be used as a vector for introducing DNA into a bacterial strain, in particular a *Streptococcus thermophilus* strain. The constructs or the vectors may be introduced into a bacterial strain as described herein, such as the DGCC7710 strain.

The polynucleotide, construct, vector or plasmid of the invention disclosed herein can be introduced into a *Streptococcus thermophilus* strain, using any method available.

"Introducing" (and "introduced") is intended to mean presenting to the *Streptococcus thermophilus* strain, the polynucleotide, construct, vector or plasmid of the invention as defined herein, in such a manner that the component(s) gains access to the interior of the *Streptococcus thermophilus* strain. The methods and compositions do not depend on a particular method for introducing a sequence into a *Streptococcus thermophilus* strain, only that the polynucleotide, construct, vector or plasmid of the invention gains access to the interior of the *Streptococcus thermophilus* strain. Introducing includes the incorporation of a polynucleotide, construct, vector or plasmid of the invention into the *Streptococcus thermophilus* strain where polynucleotide or construct of the invention may be incorporated into the genome of the *Streptococcus thermophilus* strain, and includes the transient (direct) provision of a polynucleotide or construct to the *Streptococcus thermophilus* strain.

Introducing a polynucleotide, construct, vector or plasmid of the invention into a *Streptococcus thermophilus* strain can be carried out by several methods, including transformation, conjugation, transduction or protoplast fusion. Methods for introducing polynucleotide, construct, vector or plasmid of the invention by transformation into a *Streptococcus thermophilus* strain, include, but are not limited to, microinjection, electroporation, stable transformation methods, transient transformation methods [such as induced competence using chemical (e.g. divalent cations such as CaCl$_2$)) or mechanical (electroporation) means], ballistic particle acceleration (particle bombardment), direct gene transfer, viral-mediated introduction, cell-penetrating peptides or mesoporous silica nanoparticle (MSN)-mediated direct protein delivery. Introducing a polynucleotide, construct, vector or plasmid of the invention into a *Streptococcus thermophilus* strain can be carried out by conjugation, which is a specific method of natural DNA exchange requiring physical cell-to-cell contact. Introducing a polynucleotide, construct, vector or plasmid of the invention into a *Streptococcus thermophilus* strain can be carried out by transduction, which is the introduction of DNA via a virus (e.g. phage) infection which is also a natural method of DNA exchange. Generally, such methods involve incorporating a polynucleotide within a viral DNA or RNA molecule.

The invention is also directed to the following mutated man genes as such and their corresponding encoded proteins:

the mutated *Streptococcus thermophilus* manL coding for a *Streptococcus thermophilus* truncated IIAB$^{Man}$ protein, the sequence of which is selected from the group consisting of a) a sequence as defined in SEQ ID NO:112 and b) a IIAB variant sequence having at least 90% similarity or identity with SEQ ID NO:112, in particular being 305 amino acids in length. In an embodiment, the mutated *Streptococcus thermophilus* manL gene encodes a IIAB$^{Man}$ protein, the sequence of which is selected from the group consisting of SEQ ID NO: 112 to 128. In an embodiment, the mutated *Streptococcus thermophilus* manL gene is as defined in SEQ ID NO:111.

the mutated *Streptococcus thermophilus* manN coding for a *Streptococcus thermophilus* truncated IID$^{Man}$ protein, the sequence of which is selected from the group consisting of a) a sequence as defined in SEQ ID NO:207; and b) a IID$^{Man}$ variant sequence having at least 90% similarity or identity with SEQ ID NO:207, in particular being 28 amino acids in length. In an embodiment, the mutated *Streptococcus thermophilus* manN gene encodes a IID$^{Man}$ protein, the sequence of which is selected from the group consisting of SEQ ID NO: 207 to 211. In an embodiment, the mutated *Streptococcus thermophilus* manN gene is as defined in SEQ ID NO:206.

The expression "IIAB$^{Man}$ variant and IID$^{Man}$ variant having at least 90% similarity or identity" is a defined in "II. Mutations of a gene encoding a protein of the mannose-glucose-specific PTS, in particular mutations of the manL and manN genes" above.

The invention is also directed to a method to design a lactose-positive, galactose-negative, *Streptococcus thermophilus* strain:
a) providing a lactose-positive, galactose-negative, *Streptococcus thermophilus* strain, carrying a glcK gene encoding a glucokinase, the activity of which is reduced but not null as defined herein, and optionally carrying a mutated ccpA gene;
b) mutating at least one, in particular one, gene encoding a protein of the mannose-glucose-specific PTS, in particular a manL gene, a manM gene and/or a manN gene; and
c) selecting a lactose-positive, galactose-negative, *Streptococcus thermophilus* strain, which, when used to ferment milk as assayed by test B, exhibiting a ratio of the amount of galactose released (mM) over the amount of remaining lactose (mM) in said fermented milk is more than 1.2.

In an embodiment, the strain selected in step c) exhibits a ratio of the amount of galactose released (mM) over the amount of remaining lactose (mM) in said fermented milk which is more than 1.5, more than 2, more than 2.5 or more than 3, when assayed by test B.

In an embodiment, the at least one gene encoding a protein of the mannose-glucose-specific PTS, in particular a manL, manM or manN gene, is mutated such as encoding a protein, in particular a truncated protein, the glucose import activity of which is decreased or abolished.

The invention is also directed to a method to design a lactose-positive, galactose-negative, *Streptococcus thermophilus* strain:
a) providing a lactose-positive, galactose-negative, *Streptococcus thermophilus* strain, carrying at least one gene, in particular one gene, encoding at least one mutated protein, in particular one protein, of the mannose-glucose-specific PTS, in particular a mutated IIAB$^{Man}$ protein, a mutated IIC$^{Man}$ protein and/or a mutated IID$^{Man}$ protein, the glucose import activity of which is decreased or abolished;
b) mutating a glcK gene encoding a glucokinase, the activity of which is reduced but not null as defined herein, and/or mutating a ccpA gene;
c) selecting a lactose-positive, galactose-negative, *Streptococcus thermophilus* strain, which, when used to ferment milk as assayed by test B, exhibiting a ratio of the amount of galactose released (mM) over the amount of remaining lactose (mM) in said fermented milk is more than 1.2.

In an embodiment, the strain selected in step c) exhibits a ratio of the amount of galactose released (mM) over the amount of remaining lactose (mM) in said fermented milk which is more than 1.5, more than 2, more than 2.5 or more than 3, when assayed by test B.

In an embodiment, the gene encoding a mutated protein of the mannose-glucose-specific PTS the glucose import activity of which is decreased or abolished, encodes a truncated protein, in particular a truncated IIAB$^{Man}$ protein, a truncated IIC$^{Man}$ protein or a truncated IID$^{Man}$ protein.

In an embodiment of the 2 methods defined above, the method further comprises:
d) selecting a strain, which when used for fermenting milk by test B, provides a low lactose fermented milk, in particular a fermented milk, the amount of remaining lactose of which is less than 60 mM, less than 50 mM, less than 45 mM, less than 40 mM, less than 35 mM or less than 30 mM In an embodiment of the 2 methods defined above, the method further comprises
d) selecting a strain which, when inoculated to a milk which is then fermented by test B, the pH of the milk decreases to a pH at which the speed of acidification definitively becomes less than 0.1 mUpH/min, wherein said pH$_{STOP}$ is comprised between 4.6 and 5.3, and optionally the slope between pH6 and pH5.5 is at least-0.008 UpH/min. In an embodiment, the strain is selected when the pH$_{STOP}$ is comprised between a minimal value selected from the group consisting of 4.6, 4.7 and 4.8 and a maximal value selected from the group consisting of 5.1, 5.2 and 5.3. In an embodiment, the strain is selected when the slope between pH6 and pH5.5 is at least 0.009 or at least 0.01 UpH/min.

Various preferred features and embodiments of the present invention will now be described by way of non-limiting examples.

Material and Methods

Strains and Growth Conditions

The *S. thermophilus* strains (ST) disclosed in the present application were grown at 37° C. in M17 broth (Oxoïd, supplier reference CM0817) supplemented with 30 g/L of appropriate carbohydrate and if necessary, addition of 15 g/L Agar bacteriologic Type A (Biokar, supplier reference #A1010HA), or at 43° C. in milk (UHT semi-skimmed milk "Le Petit Vendéen"+3% milk powder BBA Lactalis). Autoclaved M17 broth was supplemented with 0.2 µm filtered lactose, sucrose, galactose or glucose. Frozen stocks of ST strains were obtained by half-diluting an overnight culture in M17 supplemented with 5 g/L lactose, and 10% glycerol, and stored at −20° C.

Quantification of Carbohydrate Catabolism During Milk Fermentation [Test B]

UHT semi-skimmed milk "Le Petit Vendéen ("yoghurt milk") containing 3% (w/v) milk powder (BBA, Lactalis), previously pasteurized 10 min at 90° C., was inoculated at 1% (v/V, about $10^7$ CFU/ml) with a culture of the S. thermophilus strain to be assayed (M17-carbohydrate-free resuspended cells from overnight culture grown in M17 supplemented 3% sucrose). This milk was found to contain around 175 mM of lactose. The inoculated milk flasks were statically incubated in a water bath at 43° C. during 24 h, to obtain fermented milk. T0 samples and samples of fermented milk (T24 h) (5 g) were diluted in 25 g 0.025 N $H_2SO_4$, before being centrifuged at 4600 rpm for 10 minutes at 4° C. The supernatant was filtered through a 0.2 µm Nylon filter (Phenomenex, Germany, Aschaffenburg) directly into a 2 ml HPLC vial. Samples were stored at −20° C. until further analysis. Carbohydrates were quantified by high performance liquid chromatography (Agilent 1200 HPLC) equipped with a refractive index detector using an AMINEX™ HPX-87H anion exchange column (Bio-Rad Laboratories Inc.) at 35° C., with 12.5 mM $H_2SO_4$ as the elution fluid and a flow rate of 0.6 ml min-1. The exploitation of results was made with CHEMSTATION® reprocessing software (Agilent).

glcK Sequencing

PCR amplification of the glucokinase gene was performed using primers GlcK-F4 (5'-CAGGTATGAGTT-TAGCAACGG-3') (SEQ ID NO: 212) and GlcK-R12 (5' ATTCACCACGGCCTGAGAC-3') (SEQ ID NO: 220), [incubation step at 98° C., 5 min, followed by 33 cycles of 98° C., 45 s; 58° C., 30 s; 68° C., 3 min, with a final extension step at 72° C., 7 min]. The PCR products of 2788 bp were then treated with Illustra™ ExoProStar™ according to the manufacturer's instructions (GE Healthcare). Sequencing reactions were performed by using the BigDye® Terminator v3.1 Cycle Sequencing kit (Life Technologies) according to the manufacturer's instructions using an AB3500 (Applied Biosystems™), and primers listed in Table 2.

TABLE 2

Listing of primers for sequencing glcK.

| Primers | Sequences |
| --- | --- |
| GlcK-F4 | CAGGTATGAGTTTAGCAACGG |
| GlcK-R8 | AGTTCAATCTTCATCATCTCG |
| GlcK-F5 | GTAGCCACATTGTTCCTGAC |
| GlcK-R6 | TTGCTGAAGCTACAGTTTCC |
| GlcK-R4 | TAAGCAAGACTAGCAGCTCC |
| GlcK-F7 | TTGCGTAGTCGTGTTGAAGG |
| GlcK-R10 | ATTGTCCCTTCATAAGCATCG |

TABLE 2-continued

Listing of primers for sequencing glcK.

| Primers | Sequences |
| --- | --- |
| GlcK-F11 | CGAACTGGGTGCAGATGATG |
| GlcK-R12 | ATTCACCACGGCCTGAGAC |

Glucokinase Activity [Test A]

A fresh overnight culture of a Streptococcus thermophilus strain in M17 containing 30 g/L lactose was obtained and used to inoculate at 1% (vol/vol) 10 ml of fresh M17 30 g/L lactose. Cells were harvested by centrifugation (6000 g, 10 min, 4° C.) at a 600 nm optical density (OD600) of 0.8, washed in 5 ml cold GLCK buffer (5 mM MgCl2, 10 mM $K_2HPO_4/KH_2PO_4$ [pH 7.2]), and resuspended in 500 µl cold GLCK buffer. EDTA-free protease inhibitors "cOmplete™" (Roche, supplier reference 04693132001) was added in GLCK buffer as described by the provider. Cells were disrupted by the addition of 100 mg glass beads (150-212 µm, Sigma G1145) to 200 µl resuspended cells and oscillation at a frequency of 30 cycles/s for 6 min in a MM200 oscillating mill (Retsch, Haan, Germany). Cell debris and glass beads were removed by centrifugation (14000 g, 15 min, 4° C.), and supernatant transferred into a clean 1.5 mL centrifuge tube kept on ice. Total protein content was determined by using the FLUKA Protein Quantification Kit-Rapid (ref 51254). The glucokinase activity in the cell extracts was determined spectrophotometrically by a glucose-6-phosphate dehydrogenase (G-6PDH, EC1.1.1.49): NADPH-coupled assay (Porter et al., 1982), essentially as described by Pool et al. (2006). Each sample (5, 10 and 20 µL) was added to assay buffer (10 mM $K_2HPO_4/KH_2PO_4$ [pH 7.2], 5 mM MgCl2, 1 mM ATP, 20 mM glucose, 1 mM NADP, 1 U G-6PDH) in a 250 µL final volume, and the mixture was left for 5 min at 30° C. The optical density at 340 nm was measured for 5 minutes by using a Synergy HT multi-detection microplate reader (BIO-TEK). One unit of glucokinase corresponds to the amount of enzyme that catalyzes the phosphorylation of 1 µmole of D-glucose to D-Glucose 6-phosphate per minute under the assay conditions. Glucokinase activity was calculated as follows:

Glucokinase activity (U/g of total protein extract)= $dOD \times V/[dt \times l \times \epsilon \times Qprot]$, wherein:

dOD is the variation of optical density (OD) at 340 nm
V is the volume of the reaction (herein 250 µL)
dt=measurement time (in minutes)
l=optical path length (herein 0.73 cm)
ε=molar attenuation coefficient of NADPH; $H^+$ (herein 6220 cm2/µmol)
Qprot=quantity of protein in the cuvette (in g)

Measurements were triplicated for each sample, and the glucokinase specific activity values given herein under test A are the mean of three independent experiments.

Maximal Forward Velocity of GlcK [Test C]

The maximal forward velocity (Vmax) of GlcK was determined by using various concentrations of glucose (0, 5, 10, 15, 20 mM) on crude extract prepared as described in the "glucokinase activity" (test A). Measurements were triplicated for each sample, and the Vmax values given herein under test C are the mean of three independent experiments. The linear regression representing the inverse of the specific velocity in function of the inverse of the glucose concentration gives the inverse of the maximal forward velocity at the intersection with the Y-axis of the graphic.

Milk Acidifying Performance

The acidifying properties of *S. thermophilus* strains were evaluated by recording the pH over time, during milk fermentation as described in test B. The pH was monitored for 24 hours using the CINAC system (Alliance Instruments, France; pH electrode Mettler 405 DPAS SC, Toledo, Spain) as previously described. The pH was measured and recorded every 5 minutes. Using the CINAC v2.07 software, the slope between pH 6.0 and pH 5.5 (UpH/minute) [Slope pH6-5.5] was calculated.

Transfer of the glcK Allele of the ST0 Strain into the Genome of 3 Other *S. thermophilus* Strains A 1889 bp PCR product bearing the glcK gene of the ST0 strain was obtained using primers GlcK-F1 (5'-GAAGCAGTTTGGGGTAGTAG-3') (SEQ ID NO: 221) and GlcK-R2 (5'-GAGTTATCTACAGGAGCTGG-3') (SEQ ID NO: 222). The PCR product was then purified using QIAquick® PCR Purification Kit (Qiagen), and eluted in RNase free water. The concentration of the PCR product was determined using NanoDrop™ 2000 spectrophotometer (Thermo Scientific, Wilmington, MA). The size and the purity of the PCR product were verified by gel-based capillary electrophoresis QIAxcel® system (Qiagen, Hilden, Germany). Strains DGCC7710, ST1.1 and ST1.2 were transformed with the 1889 bp PCR product and mutants having their glcK gene replaced by the glcK allele of the ST0 strain were selected (the presence of the glcK allele of the ST0 strain was checked by sequencing).

RESULTS

Example 1: Screening of a *Streptococcus thermophilus* Collection for Glucose-Excreting Strains The inventors of the present application, with a wish to select strains secreting glucose, used another approach. A *Streptococcus thermophilus* collection was screened by test B for strains able to excrete glucose in the fermented milk. An amount of 10 mM of glucose was used as the minimal threshold for selection. One strain, ST0, releasing 30 mM of glucose in fermented milk using test B, was selected.

Example 2. Identification of a Mutation in the glcK Gene

Sequencing of several genes—of the ST0 strain—known to be involved in the catabolism of carbohydrates in *S. thermophilus* was carried out and aligned with the corresponding gene sequences of other *Streptococcus thermophilus* of our collection.

A non-conservative amino acid difference, E275K, was identified in the GlcK sequence of the ST0 strain, which was not found in any of the GlcK sequence of the other *S. thermophilus* strains of the collection; this amino acid difference is the result of a A at position 823 of the glcK gene instead of a G. Further comparison of the glucokinase encoded by the glcK gene of other *S. thermophilus* strains confirmed that a lysine at position 275 (instead of a glutamic acid) was unique to ST0 and was not found in any of the 107 other strains.

Other amino acid differences identified in the deduced glucokinase from these 108 strains are represented in Table 3. Thus, 10 different glucokinase types could be distinguished (GlcK type 1 to GlcK type 10, as set forth respectively in SEQ ID NOs: 2, 4, 6, 8, 10, 12, 14, 16, 18 and 20). For the next experiments, 10 strains, ST1 to ST10, each expressing a unique glucokinase were selected. SEQ ID NO:2 was taken as a reference sequence, because this GlcK type was found in about 70% of the 108 analysed strains. In particular, the DGCC7710 strain, deposited at the DSMZ under accession number DSM28255 on Jan. 14, 2014, encodes a glucokinase as defined in SEQ ID NO:2. It is noteworthy that the only amino acid difference between the sequence of the glucokinase encoded by the ST0 strain and SEQ ID NO: 2 is the amino acid difference in position 275.

TABLE 3

GlcK protein differences identified by comparison of the GlcK protein sequence encoded by 108 *S. thermophilus*, and GlcK protein sequence encoded by ST0. The listed amino acid positions indicate all the amino acid differences between the GlcK proteins. GlcK protein sequence from ST1 (SEQ ID NO: 2) was chosen as a reference sequence. The amino acid positions not listed in this Table are identical for all the glucokinases from this study. "aa diff" column gives the number of amino acid differences as compared to SEQ ID NO: 2. "% id" column gives the percentage of identity to SEQ ID NO: 2

| aa position | 21 | 33 | 38 | 49 | 64 | 100 | 131 | 133 | 137 | 141 | 144 | 149 | 152 |
|---|---|---|---|---|---|---|---|---|---|---|---|---|---|
| ST1 | T | E | E | E | D | V | N | N | I | T | G | A | N |
| ST2 | — | — | — | — | — | — | — | — | V | — | — | — | — |
| ST3 | N | G | — | — | — | — | — | — | V | — | — | V | K |
| ST4 | — | — | — | — | A | — | — | — | — | — | — | — | — |
| ST5 | — | — | — | — | — | — | — | — | — | — | — | — | — |
| ST6 | — | — | — | — | — | — | — | — | — | — | — | — | — |
| ST7 | — | — | — | D | — | — | — | — | V | — | — | — | — |
| ST8 | N | G | — | — | — | — | — | — | V | — | — | V | K |
| ST9 | — | — | D | — | — | — | S | D | V | — | — | — | — |
| ST10 | — | — | D | — | — | I | — | D | V | — | — | — | — |
| ST0 | — | — | — | — | — | — | — | — | — | — | — | — | — |
| ST20 | — | — | — | — | — | — | — | — | — | — | S | — | — |

| aa position | 182 | 188 | 197 | 198 | 209 | 220 | 227 | 252 | 265 | 275 | aa diff. | % id. |
|---|---|---|---|---|---|---|---|---|---|---|---|---|
| ST1 | K | V | V | A | S | F | I | T | V | E | / | / |
| ST2 | — | — | — | — | — | — | — | — | — | — | 1 | 99.7 |
| ST3 | — | — | I | — | — | — | L | — | — | — | 7 | 97.8 |
| ST4 | — | — | — | — | — | — | — | — | — | — | 1 | 99.7 |
| ST5 | — | A | — | — | — | — | — | — | — | — | 1 | 99.7 |
| ST6 | N | — | — | T | — | — | — | — | — | — | 2 | 99.4 |
| ST7 | — | — | — | — | — | L | L | I | — | — | 5 | 98.4 |

TABLE 3-continued

GlcK protein differences identified by comparison of the GlcK protein sequence encoded by 108 S. thermophilus, and GlcK protein sequence encoded by ST0. The listed amino acid positions indicate all the amino acid differences between the GlcK proteins. GlcK protein sequence from ST1 (SEQ ID NO: 2) was chosen as a reference sequence. The amino acid positions not listed in this Table are identical for all the glucokinases from this study. "aa diff" column gives the number of amino acid differences as compared to SEQ ID NO: 2. "% id" column gives the percentage of identity to SEQ ID NO: 2

| Strain | | | | | | | | | | | aa diff | % id |
|---|---|---|---|---|---|---|---|---|---|---|---|---|
| ST8 | — | — | I | — | — | — | — | — | — | — | 6 | 98.1 |
| ST9 | — | — | — | — | — | L | L | I | — | — | 7 | 97.8 |
| ST10 | — | — | — | — | — | L | L | I | I | — | 8 | 97.5 |
| ST0 | — | — | — | — | — | — | — | — | — | K | 1 | 99.7 |
| ST20 | — | — | — | — | — | — | — | — | — | — | 1 | 99.7 |

Example 3. Measurement of the Glucokinase Activity of the ST0 Strain and Comparison with Other Strains (ST1 to ST10)

The glucokinase activity of the ST0 strain was compared with the glucokinase activity of the ST1 to ST10 strains selected as reported in example 2, using test A. The results are summarized in Table 4.

TABLE 4

Glucokinase specific activity of 11 strains: 10 strains-ST1 to ST10-each representing a different GlcK protein variant, and ST0 identified in example 1; ND: not determined

| Strain | Glucokinase specific activity (U/g total protein extract) | | relative activity (% DGCC7710) |
|---|---|---|---|
| | Average | STD | |
| DGCC7710 (ST1 type) | 2756 | 140 | 100 |
| ST2 | 2250 | 381 | 82 |
| ST3 | 2595 | 173 | 94 |
| ST4 | 2014 | 105 | 73 |
| ST5 | ND | ND | ND |
| ST6 | 2892 | 354 | 105 |
| ST7 | 2791 | 104 | 101 |
| ST8 | 2471 | 293 | 90 |
| ST9 | 2553 | 337 | 93 |
| ST10 | 2718 | 280 | 99 |
| ST0 | 977 | 29 | 35 |

These data show that the glucokinase activity of strains ST1 to ST10 is comprised from 2014 to 2791 U/g total protein extract as assayed by test A. A glucokinase activity above 1800 U/g total protein extract was considered to represent a normal glucokinase activity. The glucokinase activity of the DGCC7710 strain was considered as a reference glucokinase activity (since expressing the most frequent GlcK type, defined as SEQ ID NO:2).

In contrast, the ST0 strain, expressing a Glck protein bearing a lysine at position 275 has a glucokinase activity which is around 977 U/g total protein extract as assayed by test A, i.e. is about 3 times less the glucokinase activity of the DGCC7710 strain (35%).

These data show that the approach retained by the inventors enabled to select for the first time a galactose-negative S. thermophilus strain expressing a glucokinase, the activity of which is significantly reduced but not null.

Example 4: Comparison of the Glucokinase Activity, Vmax and Km, of the DGCC7710 Strain, a DGCC7710 Derivative Bearing the E275K Difference and a Galactose-Positive Variant of DGCC7710 Bearing a Glucokinase Null Amino Acid Change A derivative of the DGCC7710 strain was designed, into which the glcK gene encodes a glucokinase with the glutamic acid (E) at position 275 was replaced by the amino acid lysine (K). This derivative (DGCC12534) was deposited at the DSMZ on Aug. 15, 2017 under accession number DSM32587. The sequence of its GlcK protein is as defined in SEQ ID NO: 22.

In parallel, a mutant of DGCC7710 was generated, into which the serine(S) at position 72 was replaced by a proline (P), to give a GlcK protein with a sequence as defined in SEQ ID NO: 23 [S72P amino acid substitution; reported in strain DSM25851 of application WO2013/160413]. Because the S72P amino acid substitution leads to a null glucokinase activity (i.e. a strain which is not able to use glucose via the glucokinase), the mutant was previously rendered galactose positive (in order to be able to use galactose, because a galactose-negative S. thermophilus strain displaying a null glucokinase activity is expected to be non-viable on lactose). Thus, the gal operon promoter of the DGCC7710 strain was previously mutated according to application WO2011/026863 to give a gal operon promoter having the sequence as defined in SEQ NO: 24. A galactose-positive mutant bearing the S72P amino acid substitution in the GlcK protein was obtained and called ST1m-glcK0-gal+.

An alignment of the protein sequence of the glucokinase of DGCC7710, DSM32587 and ST1m-glcK0-gal+ strains is disclosed in FIG. 1.

The glucokinase activity, the Vmax and Km of the glucokinase of DGCC7710, of DSM32587 and of ST1m-glcK0-gal+ strains were determined as described in the Material and Methods. The results obtained are disclosed in Tables 5 and 6.

TABLE 5

Glucokinase specific activity of DGCC7710 strain, and in DSM32587 and ST1m-glcK0-gal+ strains and % of activity as compared to the glucokinase activity of DGCC7710 strain

| Strain | Glucokinase specific activity (U/g total protein extract) | | relative activity (% DGCC7710) |
|---|---|---|---|
| | Average | STD | |
| DGCC7710 | 2756 | 140 | 100 |
| DSM32587 | 907 | 32 | 33 |
| ST1m-glK0-gal+ | 0 | / | 0 |

TABLE 6

Vmax of glucokinase of DGCC7710 strain and in DSM32587 and ST1m0gal+ strains and % of Vmax glucokinase as compared to the Vmax of glucokinase of DGCC7710 strain, and Km activity of glucokinase of DGCC7710, DSM32587 and ST1m-g/cK0-gal+ strains; ND: not determined.

| Strain | Vmax Glucokinase (U/g total protein extract) | | | Km Glucokinase (mM) | |
|---|---|---|---|---|---|
| | average | STD | % DGCC7710 | average | STD |
| DGCC7710 | 2855 | 178 | 100 | 1319 | 73 |
| DSM32587 | 914 | 21 | 32 | 1328 | 56 |
| ST1m-gkK0-gal+ | ND | / | ND | ND | / |

The data of Table 5 nicely shown that replacing the glutamic acid (E) at position 275 of the GlcK protein by a lysine (K) is sufficient alone to significantly decrease the glucokinase activity from 2756 to 907 U/g (i.e., 33% of DGCC7710 activity) in the DGCC7710 derivative (DSM32587). The data obtained for the ST1m-glcK0-gal+ mutant confirm that the S72P amino acid change is sufficient to totally abolish the glucokinase activity. Together with the glucokinase activity, the inventors also studied whether the observed decrease of glucokinase activity in the DSM32587 strain was a consequence of a decrease of the affinity (Km) of the glucokinase for its substrate (glucose) and/or a decrease in the maximum forward velocity (Vmax) of the glucokinase. The data of Table 6 confirm that replacing the glutamic acid (E) at position 275 of the GlcK protein by a lysine (K) is sufficient alone to significantly decrease the Vmax of the glucokinase from 2855 to 914 U/g (i.e., 32% of DGCC7710 Vmax) in the DGCC7710 derivative (DSM32587). In absence of a functional glucokinase in the ST1m-glcK0-gal+ mutant, the Vmax could not be determined.

Example 5: Identification of a Further GlcK Mutated Protein

A *Streptococcus thermophilus* strain (ST20) was identified, the glcK gene of which contains a non-conservative amino acid difference, G144S. This amino acid change was not found in any of the GlcK sequence of the other *S. thermophilus* strains of the collection (GlcK types ST1 to ST10). It is noteworthy that the only amino acid difference between the sequence of the glucokinase encoded by the ST20 strain and SEQ ID NO:2 is the amino acid difference in position 144 (Table 3).

Example 6: Comparison of Sugar Catabolism and Acidification Kinetics of the DGCC7710 Strain, the DSM32587 Strain, the ST20 Strain, the ST1m-glcK0-Gal+ Strain, the ST1.1 Strain and a glcK-Mutated ST1.1 Strain, During Milk Fermentation Considering, on the one hand, the impact of the mutations E275K and G144S on the activity of glucokinase (reduced but not null), and on the other hand, the role of the glucokinase in glucose metabolism, the DGCC7710 strain, the DSM32587 strain, the ST20 strain, the ST1m-glcK0-gal+ strain (all described above), as well as a second parental strain (ST1.1 strain, encoding a glucokinase as defined in SEQ ID NO:22) and its glcK-mutated ST1.1 strain (having the E275K substitution; ST1.1m-glcK strain) were used to ferment milk by test B and the concentration of glucose, galactose and lactose present in the fermented milk was determined (see material and methods). The results are summarized in Table 7 below.

TABLE 7

Carbohydrate catabolism in milk fermented (24 h) with DGCC7710, DSM32587, ST20 and ST1m-g/cK0-gal+, strains

| Strain | Glucose released (mM) | Galactose released (mM) | Lactose remaining (mM) | slope pH 6-5.5 (UpH/min) |
|---|---|---|---|---|
| DGCC7710 | <0.1 | 53 | 116 | −0.0140 |
| DSM32587 | 32 | 73 | 95 | −0.0148 |
| ST20 | 49 | 62 | 101 | −0.0124 |
| ST1m-gkK0-gal+ | 109 | 88 | 17 | −0.0077 |
| ST.1.1 | <0.1 | 44 | 119 | −0.0180 |
| ST1.1m-gkK | 35 | 65 | 96 | −0.0168 |

The data of Table 7 show that:
the DSM32587 strain and ST20 strain release 32 mM and 49 mM of glucose respectively after milk fermentation, whereas the DGCC7710 strain having a high glucokinase activity does not release detectable amount of glucose. This difference is also seen between the ST1.1 strain and its glcK mutant (ST1.1m-glcK). As far as ST1m-glcK0-gal+ mutant is concerned, this galactose-positive mutant excretes 109 mM of glucose;
the DSM32587 strain and ST20 strain releases 73 mM and 62 mM of galactose respectively after milk fermentation, whereas the DGCC7710 strain releases 53 mM. This slight difference is also seen between the ST1.1 strain and its glcK mutant (ST1.1m-glcK);
with regards to the lactose remaining in the fermented milk, the ST1m-glcK0-gal+ mutant consumes almost all the lactose present in milk (158 mM out of about 175 mM), such that the concentration of remaining lactose in the fermented milk is 17 mM. In contrast, with the DSM32587 strain or the ST20 strain, the concentration of remaining lactose is in the same range as for the DGCC7710 strain [95 and 101 versus 116]. This is also seen between the ST1.1m-glcK strain and the ST1.1 strain [96 versus 119].
These data show that almost all the galactose moiety (coming from the lactose hydrolysis) is released in the fermented milk when using the DGCC7710, the DSM32587, ST20, ST1.1 and ST1.1m-glcK strains (59 mM, 80 mM, 66 mM, 56 mM and 79 mM of lactose consumed for 53 mM, 73 mM, 62 mM, 44 mM and 65 mM of galactose released). It is reminded that 1 mole of lactose gives after hydrolysis 1 mole of glucose and 1 mole of galactose. The glucose moiety was partially consumed by the strain Thus, in a milk containing 175 mM of lactose (test B), this means that there is more lactose remaining in the milk than lactose consumed by the strain.

This behaviour can also be translated by determining the ratio galactose released (mM) in the fermented milk over lactose remaining (mM) in the fermented milk, when assayed by test B. This ratio is 0.452 in DGCC7710, 0.775 in DSM32587, 0.544 in ST20 strain, 0.373 in ST1.1 and 0.672 in ST1.1m-glcK, i.e., below 1 in the above glcK-mutated strains and their parental strains. This ratio represents the efficiency of lactose uptake and hydrolysis in a galactose-negative strain.

Example 7: Determination of Sugar Catabolism and Acidification Kinetics in Lactose-Positive Galactose-Negative ccpA-Mutated and Man-Mutated *S. thermophilus* Strains Based on the observations done in example 6, the inventors have determined the sugar catabolismand acidification kinetics of *S. thermophilus* strains mutated in the ccpA gene or mutated in a gene encoding a protein of the mannose-glucose-specific PTS (manL, manM or manN gene). The following mutants have been designed in the background of DGCC7710 (ST1) and ST1.1, and used for fermentation by test B:

- a DGCC7710 derivative, into which the ccpA gene was replaced by the ccpA gene having a deletion of a nucleotide A in the stretch of 7 nucleotides A at positions 114-120 (SEQ ID NO: 71), leading to a frameshift of the open reading frame of the ccpA gene (ST1m-ccpA);
- a DGCC7710 derivative, having a knocked-out ccpA gene (ST1m-KOccpA);
- a DGCC7710 derivative, into which the man gene was replaced by a manL gene with the substitution of the nucleotide G in the nucleotide T at position 916 (SEQ ID NO:111), leading to a stop codon at position 306 of the IIAB$^{Man}$ protein (ST1m-manL);
- a DGCC7710 derivative, into which the manM gene was replaced by a manM gene with a substitution of the nucleotide G in the nucleotide T at position 625 (SEQ ID NO:157), leading to a stop codon at position 209 of the IIC$^{Man}$ protein (ST1m-manM);
- a DGCC7710 derivative, into which the manN gene was replaced by a manN gene with an insertion of a nucleotide A in the stretch of 5 nucleotides A at positions 37-41 (SEQ ID NO: 206), leading to a frameshift of the open reading frame and a truncation of the IID$^{Man}$ protein at position 28 (ST1m-manN);
- a ST1.1 derivative, into which the copA gene was replaced by a copA gene having a deletion of a nucleotide A in the stretch of 7 nucleotides A at positions 114-120 (SEQ ID NO: 71) (ST1.1m-ccpA); and
- a ST1.1 derivative, into which the manL gene was replaced by a manL gene with the substitution of the nucleotide G in the nucleotide T at position 916 (SEQ ID NO:111) (ST1.1m-manL).

The results are summarized in Table 8 below.

TABLE 8

Carbohydrate catabolism in milk fermented (24 h) with ccpA-mutated and man-mutated strains and their parental strains

| Strain | Galactose released (mM) | Lactose remaining (mM) | Ratio galactose released/lactose remaining | slope pH 6-5.5 (UpH/min) |
|---|---|---|---|---|
| DGCC7710 | 53 | 116 | 0.452 | −0.0140 |
| ST1m-ccpA | 60 | 109 | 0.544 | −0.0125 |
| ST1m-KOccpA | 66 | 96 | 0.686 | −0.0084 |
| ST1m-manL | 65 | 101 | 0.643 | −0.0104 |
| ST1m-manM | 68 | 100 | 0.678 | −0.0089 |
| ST1m-manN | 63 | 102 | 0.615 | −0.0095 |
| ST1.1 | 44 | 119 | 0.373 | −0.0180 |
| ST1.1m-ccpA | 51 | 110 | 0.465 | −0.0160 |
| ST1.1m-manL | 50 | 113 | 0.445 | −0.0123 |

These data show that none of the ccpA-mutated and man-mutated strains are suitable to remove lactose during milk fermentation (lactose concentration between 96 and 113 mM).

These data confirm that the values of the ratio galactose released over lactose remaining in the fermented milk obtained with strains mutated in the ccpA gene or in a gene encoding a protein of the mannose-glucose-specific PTS and with their parental strains, are in agreement with the values reported in example 6 above (i.e., a ratio which is less than 1).

Example 8: Determination of Sugar Catabolism and Acidification Kinetics in Lactose-Positive Galactose-Negative *S. thermophilus* Strains Both Mutated in a Gene Encoding a Protein of the Mannose-Glucose-Specific PTS and Mutated in a glcK Gene and/or ccpA Gene The inventors have then designed strains mutated in a gene encoding a protein of the mannose-glucose-specific PTS (manL, manM or manN) and mutated in a glcK gene and/or ccpA gene. Thus, the double-mutated and triple-mutated strains, based on the following mutated genes, were designed, in the background of DGCC7710 (ST1) or in the background of ST1.1.

- ST1m-glcK+manM: DSM32587 derivative (carrying the glcK gene encoding a glucokinase with the substitution E275K; example 2), into which the manM gene was replaced by the mutated manM gene as defined in SEQ ID NO:157;
- ST1m-ccpA+manL: ST1m-ccpA derivative (DGCC7710 carrying the mutated ccpA gene as defined in SEQ ID NO:71), into which the manL gene was replaced by the mutated manM gene as defined in SEQ ID NO:111;
- ST1m-ccpA+manM: ST1m-ccpA derivative (DGCC7710 carrying the mutated ccpA gene as defined in SEQ ID NO:71), into which the manM gene was replaced by the mutated manM gene as defined in SEQ ID NO:157;
- ST1m-ccpA+manN: ST1m-ccpA derivative, into which the manN gene was replaced by the mutated manN gene as defined in SEQ ID NO:206;
- ST1m-glcK+ccpA+manM: DSM32587 derivative, into which the ccpA gene was replaced by the mutated ccpA gene as defined in SEQ ID NO:71 and the manM gene was replaced by the mutated manM gene as defined in SEQ ID NO:157;
- ST1.1m-glcK+manM: ST1.1m-glcK derivative (ST1.1 strain carrying the glcK gene encoding a glucokinase with the substitution E275K), into which the manM gene was replaced by the mutated manM gene as defined in SEQ ID NO:157; and ST1.1m-ccpA+manL: ST1.1m-ccpA derivative (ST1.1 carrying the mutated ccpA gene as defined in SEQ ID NO:71), into which the manL gene was replaced by the mutated manL gene as defined in SEQ ID NO:111.

The results are summarized in Table 9 below.

TABLE 9

Carbohydrate catabolism in milk fermented (24 h) with double and triple mutated strains and their parental strains

| Strain | Galactose released (mM) | Lactose remaining (mM) | Ratio galactose released/ lactose remaining | slope pH 6-5.5 (UpH/min) |
|---|---|---|---|---|
| DGCC7710 | 53 | 116 | 0.452 | −0.0140 |
| DSM32587 | 73 | 95 | 0.775 | −0.0148 |
| ST1m-glcK+ manM | 117 | 33 | 3.500 | −0.0104 |
| ST1m-ccpA+ manL | 131 | 25 | 5.252 | −0.0089 |
| ST1m-ccpA+ manM | 129 | 31 | 4.207 | −0.0082 |
| ST1m-ccpA+ manN | 128 | 28 | 4.606 | −0.0109 |
| ST1m-glcK+ ccpA+ manM | 129 | 29 | 4.431 | −0.0092 |
| ST1.1 | 44 | 119 | 0.373 | −0.0180 |
| ST1.1m-glcK+ manM | 98 | 55 | 1.780 | −0.0140 |
| ST1.1m-ccpA+ manL | 117 | 34 | 3.460 | −0.0091 |

Surprisingly, whereas all the galactose-negative single-mutated strains (mutated in one gene among the glcK gene, the ccpA, the manL gene, the manM gene and the manN gene) show lactose concentration around or more than 100 mM by test B (between 95 and 113) [see tables 7 and 8], the introduction of 2 or 3 mutated genes (a mutated gene encoding a protein of the mannose-glucose-specific PTS, and a mutated glcK gene and/or a mutated ccpA gene) leads to strains which when used to ferment milk by test B remove between 68% and 85% of the lactose originally contained in the milk (i.e., a lactose concentration between 25 and 55 mM).

Interestingly, the ratio galactose released over lactose remaining in the fermented milk defined above is dramatically increased as compared to, not only the non-mutated strains but also the single-mutated strains. Thus, this ratio is comprised between 1.780 and 5.252. This demonstrates that more than the lactose concentration remaining in the fermented milk, the ratio galactose released over lactose remaining in the fermented milk is an excellent parameter to distinguish galactose-negative strains which are suitable for removing lactose during milk fermentation from strains which are not suitable for removing lactose. This shows the interest of the double or triple mutant strains for manufacturing producers desiring to obtain low lactose fermented milk products (with less than 60 mM).

Example 9: pH Stop in Milk Fermented with the Double or Triple Mutants of the Invention The DGCC7710, ST1m-glcK+manM, ST1m-ccpA+manL, ST1m-ccpA+manM, ST1m-ccpA+manN, ST1m-glcK+ccpA+manM, ST1.1, ST1.1m-glcK+manM and ST1.1m-ccpA+manL strains (all described above) were used to ferment milk by test B [24 hours at fermentation temperature].

The pH was recorded using a CINAC device. The evolution of the pH over time is represented in FIGS. 2A, 3A, 4A, 5A, 6A, 7A, 8A, 9A and 10A. The velocity between pH 6 and pH 5.5 was calculated as the slope of the linear model deduced from the evolution of the pH as a function of time for value of pH between 6 and 5.5. The slope value is the opposite of the velocity (Table 10). The evolution of the velocity as a function of the pH was also represented (FIGS. 2B, 3B, 4B, 5B, 6B, 7B, 8B, 9B and 10B). Velocity is determined as the instantaneous derivative of the pH evolution as a function of time. The $pH_{STOP}$ was characterized as the pH value at which the speed decrease became non-detectable (below 0.1 mupH/minutes) (Table 10). The time corresponding to the $pH_{STOP}$ ($TpH_{STOP}$) was also determined (Table 10).

TABLE 10

Acidification kinetics obtained with double and triple mutated strains and their parental strains

| Strain | $pH_{STOP}$ | Slope pH 6-5.5 (UpH/min) | $TpH_{STOP}$ (min) |
|---|---|---|---|
| DGCC7710 | 4.21 | −0.0140 | 952 |
| ST1m-glcK+ manM | 4.95 | −0.0104 | 392 |
| ST1m-ccpA+ manL | 4.96 | −0.0089 | 388 |
| ST1m-ccpA+ manM | 4.97 | −0.0082 | 298 |
| ST1m-ccpA+ manN | 4.93 | −0.0109 | 312 |
| ST1m-glcK+ ccpA+ manM | 4.98 | −0.0092 | 328 |
| ST1.1 | 4.31 | −0.0180 | 602 |
| ST1.1m-glcK+ manM | 4.74 | −0.0140 | 458 |
| ST1.1m-ccpA+ manL | 4.66 | −0.0091 | 512 |

Figure 8:
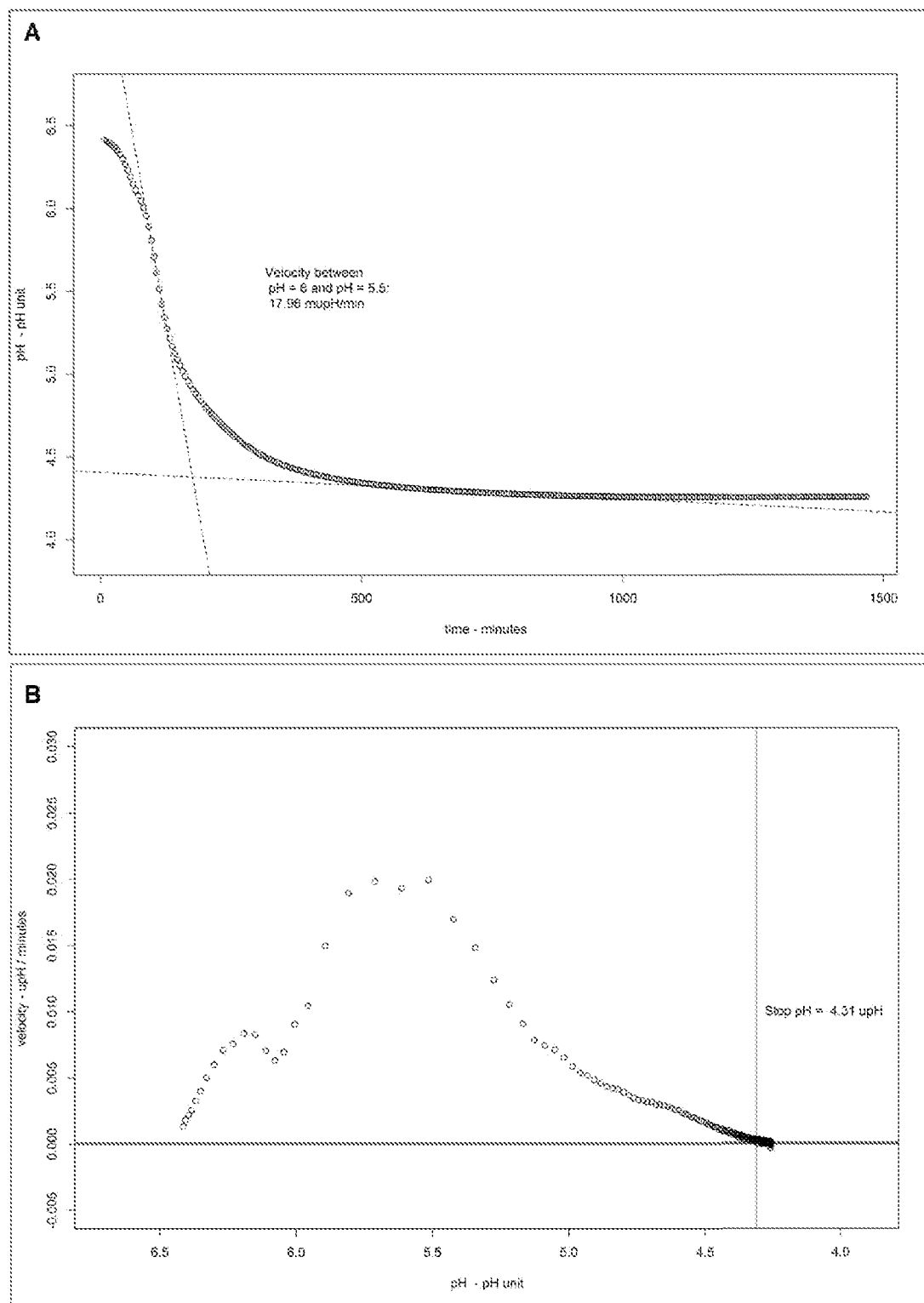
Figure 9:
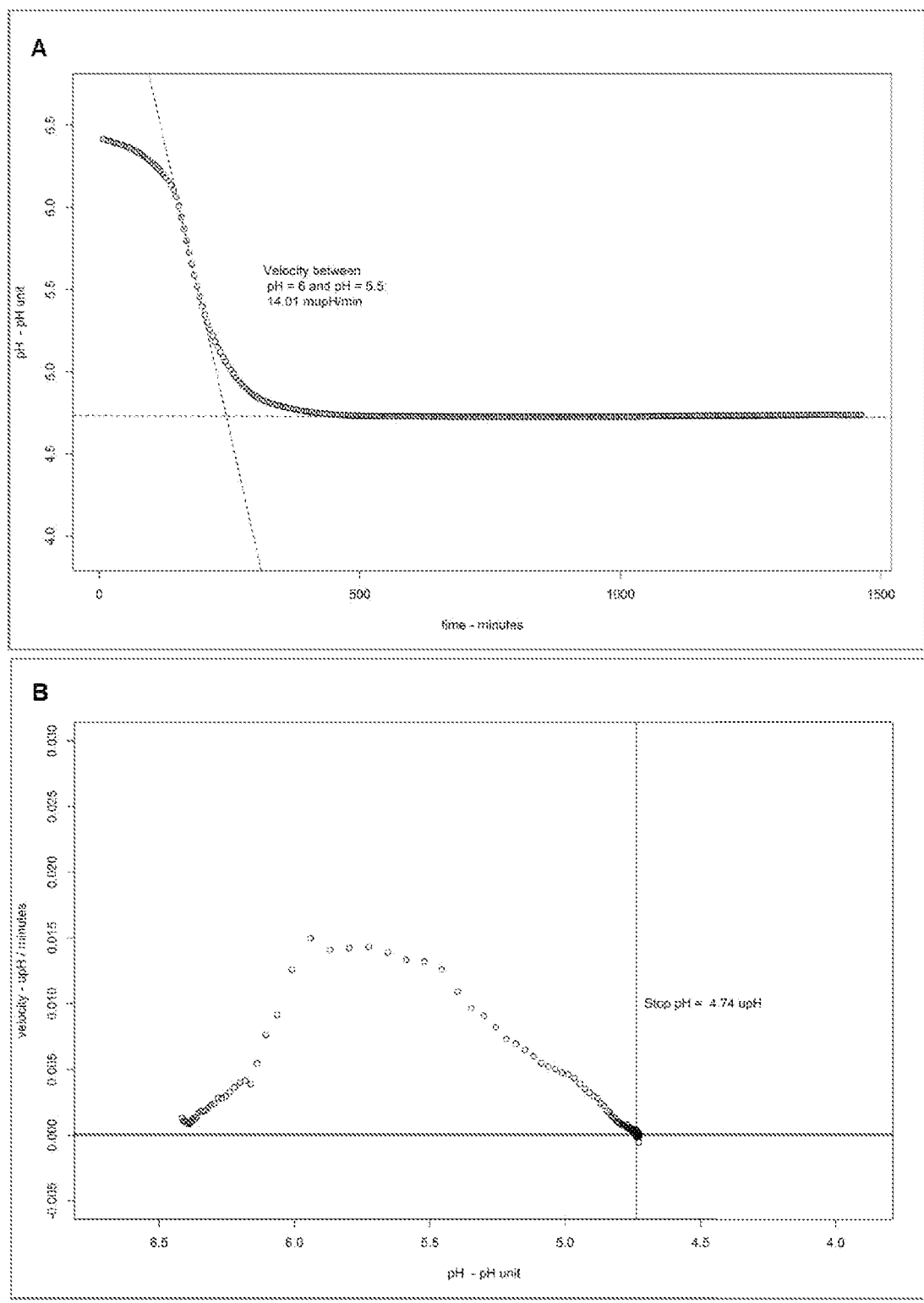
Figure 10:
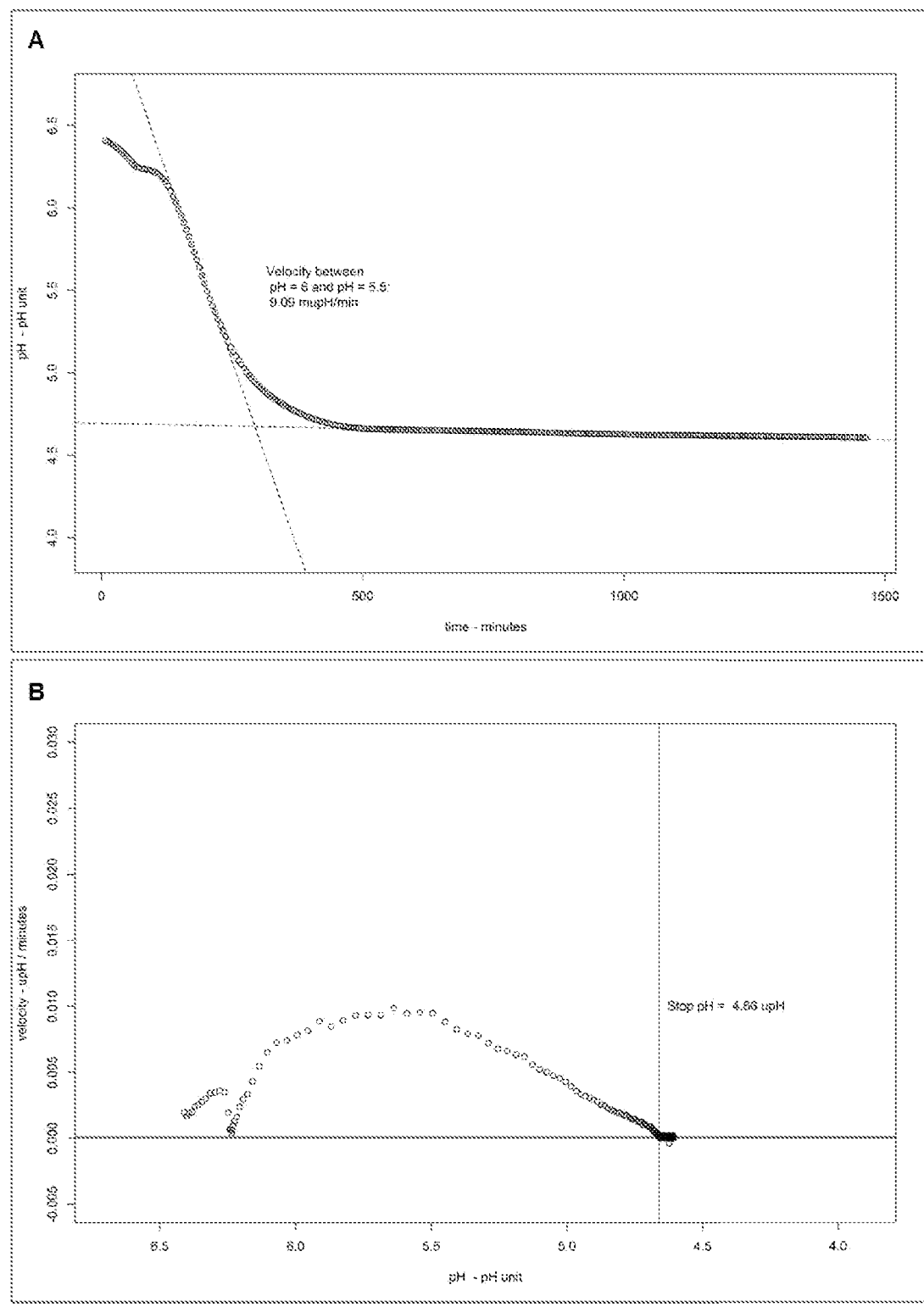

The data of Table 10 show that a milk fermented with the double or triple mutant strains (of the invention) has a higher $pH_{STOP}$ (between 4.66 and 4.98) than a milk fermented with the parental strains (4.21 and 4.31). In other words, this means that the pH obtained at the end of the test B (24 h at fermentation temperature) is higher using the double or triple mutant strains (of the invention) than the parental strains. This Table also shows that the $pH_{STOP}$ is obtained between 298 and 512 minutes after inoculation and maintained until 24 hours (i.e., more than 15 hours). FIGS. 3A, 4A, 5A, 6A, 7A, 9A and 10A show the stability of the pH of the fermented milk over time, once the $pH_{STOP}$ was obtained (with the double or triple mutant strains), as compared to a pH regularly decreasing when using the parental strains (FIGS. 2A and 8A). FIGS. 3B, 4B, 5B, 6B, 7B, 9B and 10B show that the speed of acidification (velocity) stops at a high pH between 4.6 and 5 with the double or triple mutant strains, whereas the speed of acidification stops at a low pH (4.21 and 4.31) when using the parental strains (FIGS. 2B and 8B). Altogether, these results show the absence of post-acidification of milk fermented with the double or triple mutant strains of the invention.

These data also show that the acidification kinetics (slope between pH 6 and 5.5) is acceptable at the industrial level to manufacture fermented dairy products.

Altogether, these results show the interest of the double or triple mutant strains for manufacturing producers desiring, not only to obtain fermented products the pH of which is stopped at a higher range (4.6-5.3), but also to maintain their process at fermentation temperature without impacting the pH of the fermented dairy products.

SEQUENCES

SEQ ID NO: 2
MSKKLLGIDLGGTTVKFGILTADGEVQEKWAIETNTFENGSHIVPDIVESLKHRLELYGLTAEDFIGIGMGSPGA
VDRENKTVTGAFNLNWAETQEVGSVIEKELGIPFAIDNDANVAALGERWVGAGANNRNVVFITLGTGVGGGVIAD
GNLIHGVAGAGGEIGHIIVEPDTGFECTCGNKGCLETVASATGIVRVAHHLAEKYEGNSSIKAAVDNGEFVTSKD
IIVAATEGDKFADSIVDKVSKYLGLATANISNILNPDSVVIGGGVSAAGEFLRSRVEGYFTRYAFPQVRRTTKVK
LAELGNDAGIIGAASLAYSIDK

SEQ ID NO: 22
MSKKLLGIDLGGTTVKFGILTADGEVQEKWAIETNTFENGSHIVPDIVESLKHRLELYGLTAEDFIGIGMGSPGA
VDRENKTVTGAFNLNWAETQEVGSVIEKELGIPFAIDNDANVAALGERWVGAGANNRNVVFITLGTGVGGGVIAD
GNLIHGVAGAGGEIGHIIVEPDTGFECTCGNKGCLETVASATGIVRVAHHLAEKYEGNSSIKAAVDNGEFVTSKD
IIVAATEGDKFADSIVDKVSKYLGLATANISNILNPDSVVIGGGVSAAGKFLRSRVEGYFTRYAFPQVRRTTKVK
LAELGNDAGIIGAASLAYSIDK

SEQ ID NO: 45
MSKKLLGIDLGGTTVKFGILTADGEVQEKWAIETNTFENGSHIVPDIVESLKHRLELYGLTAEDFIGIGMGSPGA
VDRENKTVTGAFNLNWAETQEVGSVIEKELGIPFAIDNDANVAALGERWVGAGANNRNVVFITLGTGVSGGVIAD
GNLIHGVAGAGGEIGHIIVEPDTGFECTCGNKGCLETVASATGIVRVAHHLAEKYEGNSSIKAAVDNGEFVTSKD
IIVAATEGDKFADSIVDKVSKYLGLATANISNILNPDSVVIGGGVSAAGEFLRSRVEGYFTRYAFPQVRRTTKVK
LAELGNDAGIIGAASLAYSIDK

SEQ ID NO: 23
MSKKLLGIDLGGTTVKFGILTADGEVQEKWAIETNTFENGSHIVPDIVESLKHRLELYGLTAEDFIGIGMGPPGA
VDRENKTVTGAFNLNWAETQEVGSVIEKELGIPFAIDNDANVAALGERWVGAGANNRNVVFITLGTGVGGGVIAD
GNLIHGVAGAGGEIGHIIVEPDTGFECTCGNKGCLETVASATGIVRVAHHLAEKYEGNSSIKAAVDNGEFVTSKD
IIVAATEGDKFADSIVDKVSKYLGLATANISNILNPDSVVIGGGVSAAGEFLRSRVEGYFTRYAFPQVRRTTKVK
LAELGNDAGIIGAASLAYSIDK

SEQ ID NO: 65
ATGAATACTGATGAAACAATCACAATTTATGATGTAGCGCGTGAAGCTGGAGTATCGATGGCAACTGTTTCTCGT
GTTGTAAATGGTAACAAAAACGTAAAAGAAAACACCCGAAAAAAGTGCTCGAAGTCATTGATCGTTTGGATTAC
CGTCCAAATGCGGTTGCGCGTGGCTTGGCAAGTAAAAAAACAACTACTGTAGGAGTTGTCATTCCAAATATTGTA
AATAGCTATTTTGCTACTCTAGCTAAAGGTATTGATGACATTGCAACCATGTATAAGTATAATATTGTTCTTGCT
TCCAGTGATGATAATGAGGATCATGAAGTTACAGTCATTCATTCTCTAATTTCTAAACAAGTTGATGGTATTATT
TTTATGGGACACCATCTGACAGAAAAAATCCGTGCAGAATTCTCTCGTACCCGTACACCGATTGTTCTAGCAGGA
ACAGTTGATCTCGAACACCAATTACCAAGTGTTAACATCGACTATAAAGCTGCCGTTGAGGATTGTGTAACGCAA
CTTGCTAAAAATAATGAAAAGGTTGCCTTTGTATCAGGACCACTAATTGATGATATTAATGGCAAACTACGTTTG
GCCGGGTATAAGTCTGGACTTGAAAAGAATAATTTGAGCTACAACGAAGGACTTGTCTTTGAAGCTAAATATAGC
TATAAAGACGGCTTTGAGTTAGCACAACGTGTCTTGAACTCTGGTGCCACTGCTGCCTATGTTGGGGAAGATGAA
TTGGCTGCAGGTCTCTTGAATGGCCTCTTTGCTGCAGGCAAATCAGTTCCAGAAGATTTCGAAATCATCACAAGC
AATGATTCACCGGTTACAAGCTACACACGTCCAAACCTTTCTAGTATAAACCATCCTCTCTATGATTTAGGGGCA
GTTAGCATGCGTATGTTGACTAAAATTATGCATAAGGAAGAACTTGAAGATAAAGACGTTATTCTTAATCATGGT
CTAACTTTACGCCAGTCAACAAAATAA

SEQ ID NO: 71
ATGAATACTGATGAAACAATCACAATTTATGATGTAGCGCGTGAAGCTGGAGTATCGATGGCAACTGTTTCTCGT
GTTGTAAATGGTAACAAAAACGTAAAAGAAAACACCCGAAAAAAGTGCTCGAAGTCATTGATCGTTTGGATTACC
GTCCAAATGCGGTTGCGCGTGGCTTGGCAAGTAAAAAAACAACTACTGTAGGAGTTGTCATTCCAAATATTGTAA
ATAGCTATTTTGCTACTCTAGCTAAAGGTATTGATGACATTGCAACCATGTATAAGTATAATATTGTTCTTGCTT
CCAGTGATGATAATGAGGATCATGAAGTTACAGTCATTCATTCTCTAATTTCTAAACAAGTTGATGGTATTATTT
TTATGGGACACCATCTGACAGAAAAAATCCGTGCAGAATTCTCTCGTACCCGTACACCGATTGTTCTAGCAGGAA
CAGTTGATCTCGAACACCAATTACCAAGTGTTAACATCGACTATAAAGCTGCCGTTGAGGATTGTGTAACGCAAC
TTGCTAAAAATAATGAAAAGGTTGCCTTTGTATCAGGACCACTAATTGATGATATTAATGGCAAACTACGTTTGG
CCGGGTATAAGTCTGGACTTGAAAAGAATAATTTGAGCTACAACGAAGGACTTGTCTTTGAAGCTAAATATAGCT
ATAAAGACGGCTTTGAGTTAGCACAACGTGTCTTGAACTCTGGTGCCACTGCTGCCTATGTTGGGGAAGATGAAT
TGGCTGCAGGTCTCTTGAATGGCCTCTTTGCTGCAGGCAAATCAGTTCCAGAAGATTTCGAAATCATCACAAGCA
ATGATTCACCGGTTACAAGCTACACACGTCCAAACCTTTCTAGTATAAACCATCCTCTCTATGATTTAGGGGCAG
TTAGCATGCGTATGTTGACTAAAATTATGCATAAGGAAGAACTTGAAGATAAAGACGTTATTCTTAATCATGGTC
TAACTTTACGCCAGTCAACAAAATAA

SEQ ID NO: 78
MGIGIIIASHGRFAEGIHQSGSMIFGDQEKVQVVTFMPSEGPDDLYAHFNNAIAQFDVDDEILVLADLWSGSPFN
QASRIARENPDRKIAIITGLNLPMLIQAYTERMMDANATVEQVAANIIKEAKGGIKALPEELNPAEETTAAPVEA
AAPQGAIPEGTVIGDGKLKINLARLDTRLLHGQVVTNWVPYSKADRIIVASDDVAKDELRKELIKQAAPNGIKVN
VVPIQKLIDASKDPRFGNTHALVLFETVQDALRAIEGGVPIKELNVGSMAHSTGKTMVNNVLSMDKDDVACFEKL
RDLGVEFDVRKVPNDSKKDLFELIKKANVQ

SEQ ID NO: 111
ATGGGTATCGGTATTATTATTGCCAGCCATGGTAGGTTCGCTGAAGGAATCCACCAATCAGGCTCTATGATTTTT
GGGGACCAAGAGAAAGTTCAAGTTGTGACTTTCATGCCAAGTGAAGGTCCTGATGATTTGTACGCTCACTTCAAC
AACGCCATTGCACAATTCGATGTTGATGATGAAATTCTTGTTTTGGCTGACCTTTGGAGTGGTTCACCATTTAAC
CAAGCTAGTCGAATCGCTAGGGAAAATCCAGATCGCAAGATTGCTATCATCACAGGACTTAACTTGCCAATGCTA
ATCCAAGCATACACTGAACGTATGATGGATGCTAACGCTACTGTAGAGCAAGTTGCTGCTAATATCATCAAGGAA
GCTAAGGGTGGTATCAAGGCACTTCCAGAAGAGCTAAATCCAGCTGAGGAAACAACTGCAGCTCCTGTAGAAGCT
GCAGCACCTCAAGGAGCTATCCCTGAAGGAACAGTCATCGGAGATGGAAACTCAAGGATTAACTTGGCACGTTTG
GACACACACGTCTCTTGCATGGTCAAGTAGTAACTAACTGGGTACCTTATTCTAAAGCAGACCGTATTATTGTTGCT
TCGGATGACGTTGCCAAAGATGAGCTTCGTAAGGAATTGATCAAACAGGCTGCACCAAACGGTATTAAAGTAAAC
GTTGTTCCGATTCAAAAATTAATTGATGCTTCTAAAGACCCACGTTTTGGAAATACACATGCGCTTGTCTTGTTC
GAAACTGTTCAAGACGCACTTCGTGCTATCGAAGGTGGCGTGCCAATAAAAGAACTTAACGTTGGTTCTATGGCT

SEQUENCES

```
CACTCAACTGGTAAAACAATGGTTAACAACGTTTTGTCTATGGATAAAGATGATGTTGCTTGTTTTGAAAAATTA
CGTGACCTTGGCGTTTAATTTGACGTCCGTAAGGTTCCAAACGATTCTAAGAAAGATTTGTTTGAGCTTATCAAG
AAAGCTAACGTTCAATAA

SEQ ID NO: 112
MGIGIIIASHGRFAEGIHQSGSMIFGDQEKVQVVTFMPSEGPDDLYAHFNNAIAQFDVDDEILVLADLWSGSPFN
QASRIARENPDRKIAIITGLNLPMLIQAYTERMMDANATVEQVAANIIKEAKGGIKALPEELNPAEETTAAPVEA
AAPQGAIPEGTVIGDGKLKINLARLDTRLLHGQVVTNWVPYSKADRIIVASDDVAKDELRKELIKQAAPNGIKVN
VVPIQKLIDASKDPRFGNTHALVLFETVQDALRAIEGGVPIKELNVGSMAHSTGKTMVNNVLSMDKDDVACFEKL
RDLGV

SEQ ID NO: 130
MSDMSIISAILVVAVAFLAGLESILDQFQFHQPLVACTLIGAATGNLTAGIMLGGSLQMITLAWANIGAAVAPDV
ALASVAAAIILVKGGKFTAEGIGVAIAIAILLAVAGLFLTMPVRTASIAFVHAADKAAEHGNIAGVERAYYLALL
LQGLRIAVPAALLLAIPAQSVQHALGLMPDWLTHGLVVGGGMVVAVGYAMIINMMATREVWPFFAIGFALAAISQ
LTLIALSTIGVAIAFIYLNLSKQGGGNGGGNGGGTSSGSGDPIGDILEDY

SEQ ID NO: 157
ATGTCAGATATGTCAATTATTTCTGCGATTTTGGTCGTAGCTGTTGCCTTCCTTGCTGGTCTTGAAAGTATCCTT
GACCAATTCCAATTCCACCAACCACTTGTTGCATGTACCCTCATCGGTGCTGCCACAGGTAACCTCACTGCAGGT
ATCATGCTTGGTGGTTCTCTTCAAATGATTACCCTTGCTTGGGCAAACATCGGTGCTGCCGTAGCTCCTGACGTT
GCCCTTGCATCTGTTGCCGCTGCCATCATTTTGGTTAAAGGTGGTAAATTTACAGCTGAAGGTATCGGTGTTGCG
ATTGCAATAGCTATCCTGCTTGCAGTTGCAGGTCTCTTCCTAACTATGCCTGTTCGTACAGCATCTATTGCCTTT
GTTCATGCTGCAGATAAAGCTGCAGAACACGGAAACATCGCTGGTGTTGAACGTGCATACTACCTCGCTCTCCTT
CTTCAAGGTTTGCGTATTGCTGTGCCAGCAGCCCTTCTTCTTGCCATCCCGGCCCAATCTGTTCAACATGCCCTT
GGCTTGATGCCTGACTGGCTCACCCATGGTTTGGTTGTCGGTGGTGGTATGGTCGTAGCCGTTGGTTACGCCATG
ATTATCAATATGATGGCTACTCGTTAAGTTTGGCCATTCTTCGCCATTGGTTTTGCTTTGGCAGCAATTAGCCAA
TTGACACTTATCGCTCTTAGTACCATTGGTGTTGCCATCGCCTTCATCTACCTCAACCTTTCTAAACAAGGTGGC
GGAAATGGTGGCGGAAATGGTGGCGGAACTTCATCTGGTTCAGGCGACCCAATCGGCGATATCTTGGAAGACTAC
TAG

SEQ ID NO: 158
MSDMSIISAILVVAVAFLAGLESILDQFQFHQPLVACTLIGAATGNLTAGIMLGGSLQMITLAWANIGAAVAPDV
ALASVAAAIILVKGGKFTAEGIGVAIAIAILLAVAGLFLTMPVRTASIAFVHAADKAAEHGNIAGVERAYYLALL
LQGLRIAVPAALLLAIPAQSVQHALGLMPDWLTHGLVVGGGMVVAVGYAMIINMMATR

SEQ ID NO: 166
MAEKIQLSQADRKKVWWRSQFLQGAWNYERMQNLGWAYSLIPAIKKLYTNKEDQAAALKRHLEFFNTHPYVAAPI
IGVTLALEEEKANGTEIEDAAIQGVKIGMMGPLAGIGDPVFWFTIRPILGALGASLAQAGNIAGPLIFFIGWNLI
RMAFLWYTQELGYKAGSEITKDISGGILKDITKGASILGMFILAVLVERWVSVVFTVKLPGKVLPKGAYIEWPKG
YVTGDQLKTILGQVNDKLSFDKIQVDTLQKQLDSLIPGLTGLLLTFACMWLLKKKVSPITIIIGLFVVGIVASFF
GIM

SEQ ID NO: 206
ATGGCTGAAAAAATTCAATTATCTCAAGCGGATCGTAAAAAAGGTTTGGTGGCGCTCACAATTCTTGCAAGGTGC
ATGGAACTATGAACGTATGCAAAACTTGGGTTGGGCTTACTCACTCATTCCTGCTATCAAAAAACTTTATACTAA
CAAAGAGGACCAAGCCGCAGCTCTTAAACGTCACTTGGAATTCTTCAACACTCACCCTTACGTAGCTGCTCCTAT
CATAGGGGTTACCTTAGCTCTTGAAGAAGAAAAGCTAATGGTACTGAAATCGAAGATGCGGCTATCCAAGGGGT
TAAAATCGGTATGATGGGTCCACTTGCCGGTATCGGTGACCCTGTCTTCTGGTTCACAATTCGTCCAATTCTTGG
TGCCCTTGGTGCATCATTGGCACAAGCTGGTAACATTGCTGGTCCACTTATCTTCTTCATTGGTTGGAACCTTAT
CCGCATGGCCTTCTTGTGGTACACTCAAGAACTTGGTTACAAAGCAGGTTCAGAAATCACTAAAGACATATCTGG
TGGTATCTTGAAAGATATTACTAAAGGGGCATCAATACTTGGTATGTTCATCTTGGCCGTCCTCGTTGAACGTTG
GGTATCTGTCGTCTTCACTGTAAAGCTTCCAGGTAAAGTTTTGCCTAAAGGTGCTTATATTGAATGGCCAAAAGG
ATATGTTACTGGTGACCAACTAAAAACTATCCTTGGTCAAGTCAACGATAAGCTTAGCTTTGATAAGATTCAAGT
CGATACCCTACAAAAACAATTGGATTCATTAATTCCAGGTTTGACGGGACTTCTCCTTACTTTTGCATGTATGTG
GTTGCTTAAGAAGAAAGTTTCACCAATCACAATCATCATCGGACTCTTTGTAGTTGGTATTGTTGCAAGCTTCTT
CGGAATCATGTAA

SEQ ID NO: 207
MAEKIQLSQADRKKGLVALTILARCMEL
```

Strains

DGCC numbers are internal references to DuPont Danisco collection; DSM numbers are the numbers assigned by the Leibniz-Institut DSMZ-Deutsche Sammlung von Mikroorganismen und Zellkulturen, GmbH (Inhoffenstr. 7B, D-38124 Braunschweig), following deposit under the Budapest Treaty.

As far as the *Streptococcus thermophilus* strain DGCC7710 deposited under the Budapest Treaty at the Leibniz-Institut DSMZ-Deutsche Sammlung von Mikroorganismen und Zellkulturen, GmbH, on Jan. 14, 2014 under number DSM28255 is concerned, we hereby confirm that the depositor, Danisco Deutschland GmbH (of Busch-Johannsen-Strasse 1, D-25899 Niebüll, Germany) has authorised the Applicant (DuPont Nutrition Biosciences ApS) to refer to the deposited biological material in this application. The expressions "DGCC7710 strain" and "DGCC7710 derivative" are used interchangeably with the expressions "DSM28255 strain" and "DSM28255 derivative".

The *Streptococcus thermophilus* strain deposited under the Budapest Treaty at the Leibniz-Institut DSMZ-Deutsche Sammlung von Mikroorganismen und Zellkulturen, GmbH, on Aug. 15, 2017 under number DSM32587 has been deposited by DuPont Nutrition Biosciences ApS.

The applicant requests that a sample of the deposited micro-organisms stated herein may only be made available to an expert, until the date on which the patent is granted.

In respect to those designations in which a European Patent is sought, a sample of these deposited microorganisms will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies.

The invention claimed is:

1. A lactose-positive, galactose-negative, *Streptococcus thermophilus* strain comprising:
   at least one mutated gene encoding a protein of the mannose-glucose-specific phosphotransferase system (mannose-glucose-specific PTS), the glucose import activity of which is decreased or abolished, and
   at least one mutated gene selected from the group consisting of:
   a) a mutation in a glucokinase (glcK) gene such that the glucokinase activity of said strain is reduced but not null,
      wherein the protein sequence of said glucokinase is a glcK variant sequence having at least 90% identity with SEQ ID NO:25 or SEQ ID NO:46,
      wherein the amino acid of the glucokinase corresponding to position 275 of SEQ ID NO: 25 is not a glutamic acid, and/or the amino acid of the glucokinase corresponding to position 144 of SEQ ID NO:46 is not a glycine;
   b) a mutation in a catabolite control protein A (ccpA) gene, wherein the sequence of said mutated ccpA gene is selected from the group consisting of:
      i) a sequence comprising SEQ ID NO:71, and
      ii) a ccpA variant sequence having at least 90% identity with SEQ ID NO:71; and
   c) a combination thereof.

2. The lactose-positive, galactose-negative, *Streptococcus thermophilus* strain according to claim 1, carrying a mutation in at least one gene encoding a protein of the mannose-glucose-specific PTS, the glucose import activity of which is decreased or abolished, and carrying a mutation in a glcK gene such that the glucokinase activity of said strain is reduced but not null,
   wherein the protein sequence of said glucokinase is a glcK variant sequence having at least 90% identity with SEQ ID NO:25 or SEQ ID NO:46,
   wherein the amino acid of the glucokinase corresponding to position 275 of SEQ ID NO: 25 is not a glutamic acid, and/or the amino acid of the glucokinase corresponding to position 144 of SEQ ID NO:46 is not a glycine.

3. The lactose-positive, galactose-negative, *Streptococcus thermophilus* strain according to claim 2, wherein the protein sequence of said glucokinase is a glcK variant sequence having at least 90% similarity or identity with SEQ ID NO:25, wherein the amino acid of the glucokinase corresponding to position 275 of SEQ ID NO:25 is not a glutamic acid.

4. The lactose-positive, galactose-negative, *Streptococcus thermophilus* strain according to claim 2, wherein the protein sequence of said glucokinase is a glcK variant sequence having at least 90% similarity or identity with SEQ ID NO:46, wherein the amino acid of said glucokinase corresponding to position 144 of SEQ ID NO:46 is not a glycine.

5. The lactose-positive, galactose-negative, *Streptococcus thermophilus* strain according to claim 2, further carrying a mutation in the ccpA gene.

6. The lactose-positive, galactose-negative, *Streptococcus thermophilus* strain according to claim 1, carrying a mutation in at least one gene encoding a protein of the mannose-glucose-specific PTS, the glucose import activity of which is decreased or abolished, and carrying a mutation in a catabolite control protein A (ccpA) gene,
   wherein the sequence of said mutated ccpA gene is selected from the group consisting of:
   i) a sequence comprising SEQ ID NO:71, and
   ii) a ccpA variant sequence having at least 90% identity with SEQ ID NO:71.

7. The lactose-positive, galactose-negative, *Streptococcus thermophilus* strain according to claim 6, wherein the ccpA gene comprises a mutation selected from the group consisting of:
   a non-sense mutation located between the nucleotide 1 and the nucleotide 270 of the coding sequence of the ccpA gene, and
   a mutation located in the first quarter of the coding sequence of the ccpA gene leading to a frameshift of the open reading frame of the ccpA gene.

8. The lactose-positive, galactose-negative, *Streptococcus thermophilus* strain according to claim 1, wherein the at least one gene encoding a protein of the mannose-glucose-specific PTS is selected from the group consisting of the manL gene, the manM gene and the manN gene.

9. The lactose-positive, galactose-negative, *Streptococcus thermophilus* strain according to claim 1, wherein the mutated gene encoding a protein of the recite—mannose-glucose-specific PTS, the glucose import activity of which is decreased or abolished, is selected from the group consisting of:
   a) a *Streptococcus thermophilus* IIAB$^{Man}$ protein truncated in position 305 (IIAB$^{Man}_{305}$);
   b) a *Streptococcus thermophilus* IIC$^{Man}$ protein truncated in position 208 (IIC$^{Man}_{208}$); and
   c) a *Streptococcus thermophilus* IID$^{Man}$ protein truncated in position 28 (IID$^{Man}_{28}$).

10. The lactose-positive, galactose-negative, *Streptococcus thermophilus* strain according to claim 9, wherein the protein sequence of said IIAB$^{Man}_{305}$ protein is selected from the group consisting of:
a) a sequence as defined in SEQ ID NO:112; and
b) a IIAB$^{Man}$ variant sequence having at least 90% sequence similarity or identity with SEQ ID NO:112; wherein the protein sequence of said IIC$^{Man}_{208}$ is selected from the group consisting of:
a) a sequence as defined in SEQ ID NO:158; and
b) a IIC$^{Man}$ variant sequence having at least 90% sequence similarity or identity with SEQ ID NO: 158;
wherein the protein sequence of said IID$^{Man}_{28}$ protein is selected from the group consisting of:
a) a sequence as defined in SEQ ID NO:207; and
b) a IID$^{Man}$ variant sequence having at least 90% sequence similarity or identity with SEQ ID NO: 207.

11. A composition comprising at least one lactose-positive, galactose-negative, *Streptococcus thermophilus* strain according to claim 1 in combination with one or more strain(s) selected from the group consisting of a strain of the *Lactobacillus* genus, a strain of the *Lactococcus* genus, or a strain of the *Bifidobacterium* genus.

12. A method for manufacturing a fermented dairy product comprising:
inoculating a milk substrate with the lactose-positive, galactose-negative, *Streptococcus thermophilus* strain according to claim 1 or a composition comprising at least one lactose-positive, galactose-negative, *Streptococcus thermophilus* strain according to claim 1; and
fermenting said inoculated milk, to obtain a fermented dairy product.

13. A fermented dairy product comprising at least one lactose-positive, galactose-negative, *Streptococcus thermophilus* strain according to claim 1.

14. The composition of claim 11, wherein the strain of the *Lactobacillus* genus is *Lactobacillus delbrueckii* subsp *bulgaricus* strain.

15. The composition of claim 11, wherein the strain of the *Lactococcus* genus is a *Lactococcus lactis* strain.

* * * * *